US011535878B2

(12) United States Patent
Beauprez et al.

(10) Patent No.: US 11,535,878 B2
(45) Date of Patent: Dec. 27, 2022

(54) IN VIVO SYNTHESIS OF SIALYLATED COMPOUNDS

(71) Applicant: INBIOSE N.V., Ghent (BE)

(72) Inventors: Joeri Beauprez, Bredene (BE); Pieter Coussement, Gentebrugge (BE); Dries Van Herpe, Wondelgem (BE); Gert Peters, Ghent (BE); Annelies Vercauteren, Eke (BE)

(73) Assignee: INBIOSE N.V., Ghent (BE)

( * ) Notice: Subject to any disclaimer, the term of this patent is extended or adjusted under 35 U.S.C. 154(b) by 375 days.

(21) Appl. No.: 16/473,932

(22) PCT Filed: Dec. 26, 2017

(86) PCT No.: PCT/EP2017/084593
§ 371 (c)(1),
(2) Date: Jun. 26, 2019

(87) PCT Pub. No.: WO2018/122225
PCT Pub. Date: Jul. 5, 2018

(65) Prior Publication Data
US 2019/0338328 A1 Nov. 7, 2019

(30) Foreign Application Priority Data

Dec. 27, 2016 (EP) .................................... 16206916

(51) Int. Cl.
  *C12P 19/16* (2006.01)
  *C12P 19/04* (2006.01)
  *C12N 1/20* (2006.01)
  *C12P 19/18* (2006.01)
  *C12N 9/10* (2006.01)
  *C12N 9/12* (2006.01)
  *C12N 9/16* (2006.01)
  *C12N 9/80* (2006.01)
  *C12N 9/88* (2006.01)
  *C12N 9/90* (2006.01)
  *C12N 15/52* (2006.01)
  *C12P 19/26* (2006.01)

(52) U.S. Cl.
CPC ............ *C12P 19/18* (2013.01); *C12N 9/1029* (2013.01); *C12N 9/1085* (2013.01); *C12N 9/1205* (2013.01); *C12N 9/16* (2013.01); *C12N 9/80* (2013.01); *C12N 9/88* (2013.01); *C12N 9/90* (2013.01); *C12N 15/52* (2013.01); *C12P 19/26* (2013.01)

(58) Field of Classification Search
CPC ......... C12P 21/005; C12P 19/26; C12P 19/44; C12N 9/1081; C12N 9/1051; C12N 9/1048; C12Y 205/01057
USPC .... 435/100, 72, 101, 190, 194, 252.3, 320.1
See application file for complete search history.

(56) References Cited

FOREIGN PATENT DOCUMENTS

| EP | 1484406 | 12/2004 |
| EP | 2927316 | 10/2015 |
| WO | WO 2007/101862 | 9/2007 |
| WO | WO 2008/097366 | 8/2008 |
| WO | WO 2012/083329 | 6/2012 |

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
Zhu etal, "EfficientWhole-Cell . . . " Biotechnology Letters, vol. 39, No. 1, 2016, pp. 55-63.
Ishikawa etal, "Microbial Production . . . " Carbohydrate Research, vol. 345, No. 18, 2010, pp. 2605-2609.
Fierfort et al., "Genetic Engineering . . . " J ournal ofTechnology, vol. 134, No. 3-4, 2008, pp. 261-265.
Hamamoto, et al., "Enzymatic Synthesis . . . " Bioscience Biotechnology Biochemistry, vol. 69, No. 10, 2005, pp. 1944-1950.

(Continued)

*Primary Examiner* — Tekchand Saidha
*Assistant Examiner* — Mohammad Y Meah
(74) *Attorney, Agent, or Firm* — Barbara E. Johnson, Esq.

(57) ABSTRACT

The present invention is in the technical field of synthetic biology and metabolic engineering. More particularly, the present invention is in the technical field of fermentation of metabolically engineered microorganisms. The present invention describes engineered microorganisms able to synthesize sialylated compounds via an intracellular biosynthesis route. These microorganisms can dephosphorylate N-acetylglucosamine-6-phosphate to N-acetylglucosamine and convert the N-acetylglucosamine to N-acetylmannosamine. These microorganisms also have the ability to convert N-acetylmannosamine to N-acetyl-neuraminate. Furthermore, the present invention provides a method for the large scale in vivo synthesis of sialylated compounds, by culturing a microorganism in a culture medium, optionally comprising an exogenous precursor such as, but not limited to lactose, lactoNbiose, N-acetyllactosamine and/or an aglycon, wherein said microorganism intracellularly dephosphorylates N-acetylglucosamine-6-phosphate to N-acetylglucosamine, converts N-acetylglucosamine to N-acetylmannosamine and convert the latter further to N-acetyl-neuraminate.

12 Claims, 8 Drawing Sheets

Specification includes a Sequence Listing.

(56) References Cited

OTHER PUBLICATIONS

Chen et al., "Advances in the Biology . . . " ACS Chemical Biology, vol. 5, No. 2, 2009, pp. 163-176.
Li et at, "S ialic Acid Metabolism . . . " Applied Microbiology and Technology, vol. 94, No. 4, 2012, pp. 887-905.
Tao et al., "Biotechnological production . . . " Applied Microbiology and Biotechnology, vol. 87, No. 4, 2012, pp. 1281-1289.
Wang, "S ialic Acid is An Essential . . . " Annual Review of Nutrition, vol. 29, No. 1, 2009, pp. 177-222.
Lee, et al., "A synthetic suicide riboswitch . . . " Metabolic Engineering, vol. 28, 2015, pp. 143-150.
Kuznetsova et al., "Genome-wide Analysis . . . " J ournal of Biological Chemistry, vol. 281, No. 47, 2006, pp. 36149-36161.
Borisova et al., "The N-Acetylmuramic Acid . . . " MBIO, vol. 8:e00092-17, 2017, pp. 1-12.
Koonin et al., "Computer Analysis . . . " J ournal of Molecular Biology, vol. 244, No. 1, 1994, pp. 125-132.

* cited by examiner

Fig. 6:

```
                          120           130           140           150
EcAppA/1-432   GCPQSGQ.....VAII...ADVDERTRKTG........EAFAAGLAP.
EcYfbR/1-199   NRKFGGNVNAERIALL..AMYHDA....S........EVL........
EcAphA/1-237   TQAISAV.....CLLFALNSSAVALASSP............SPLNPG
EcYfgL/1-604   EVLNTWR.....VGMNDFARIAGGQDNRR...........NILSPG
EcYfbL/1-188   ................................................
EcSerB/1-322   AAWCVED.....YQVI...RLAGSLTARATRLAHEAQ......LDV.
EcYbiV/1-271   ...MSVK.....VIVT...DMDGTFLNDAKTYNQ..........P.
EcYidA/1-270   ...MAIK.....LIAI...DMDGTLLLPDHTIS............P.
EcCof/1-272    .....MAR.....LAAF...DMDGTLLMPDHHLG............E.
EcYbhA/1-272   ...MTTR.....VIAL...DLDGTLLTPKKTLL.............P.
EcYaed/1-191   .MAKSVP.....AIFL...DRDGTINVDHGY...VHEIDNFEFID.
EcHisB/1-355   ...MSQK.....YLFI...DRDGTLISEPPSDFQVDRFDKLAFEP.
EcNagD/1-250   ...MTIK.....NVIC...DIDGVLMHDNVAVPGAAEFLHGIMDK.
BsAraL/1-272   DTPVSPA.....GILI...DLDGTVFRGNELIEGAREAIKTLRRM.
EcYedP/1-271   ..MFSIQ.....QPLLVFSDLDGTLLDSHSYDWQPAAPWLTRLRE.
EcOtsB/1-266   PELSAKY.....AWFF...DLDGTLAEIKPHPDQVV..VPDNILQ.
EcYihX/1-199   ................................................
EcYigL/1-561   LCLGKLR.....LGSIQLGNSIGVLVVSLLLGQQHFSINTDALNL.
EcSurE/1-253   ......MR.....ILLS...NDDGVHAPGI.............QTLAK.
EcYfjG/1-225   ...MKWD.....WIFF...DADETLFTFD............S..FT.
EcYdfG/1-222   ..WGDVD.....TVLL...DMDGTLLDLA.............FDNY..
EcYfgB/1-239   ..LGRIS.....ALTF...DLDDTYDNR.............PVILR.
EcYniC/1-222   ..PRQIL.....AAIF...DMDGLLIDSE.............PLWDR.
EcYigU/1-219   ...MKLQ.....GVIF...DLDGVITDTA.............HLHFQ.
EcYqaB/1-188   ..YERYA.....GLIF...DMDGTILDTE.............PTHRK.
EcYieH/1-221   ..MSRIE.....AVFF...DCDGTLVDSE.............VICSR.
PsNupP/1-223   ...MRLR.....AVLF...DMDGTLLDTA.............PDFIA.
EcGph/1-252    ..FEDIR.....GVAF...DLDGTLVDSA.............PGLAA.
EcYbiT/1-216   ...MRCK.....GFLF...DLDGTLVDSL.............PAVER.
ScDOG1/1-246   ..EFSAD.....LCLF...DLDGTIVSTT.............VAAEK.
                                    Motif 1
```

Fig. 6 cont.:

```
                         460           470          480           490          500
                          |             |            |             |            |
EcAppA/1-432    HPPQKQAYGVTLPTSVLFIAGHDTN...LAN.........LGGALEL....
EcYfbR/1-199    RRSQEMDYFME.....IFVPSF..........................
EcAphA/1-237    ..........QDKNIRIFYGDSDND...ITA......ARDVGARGIRILRAS
EcYjgL/1-604    ...NSQDLNNS.KVSCTVSVDSTIT..GLLKEPLNNALLAIRNEHLLLM...
EcYmbL/1-188    .....EKLAIA.PENVAYGDDLIDWPVMEK.........VGLSVAVADAHF
EcSerB/1-322    .....QEYEIP.LAQTVAIGDGANDLPMIKA.........AGLGIAYHA.KF
EcYbiV/1-271    .....KRWDLS.PQNVVAIGDSGNDAEMLKM.........ARYSFAMGNAAE
EcYidA/1-270    .....DVLGIK.PEEIMAI GRGEND IAMIEY.........AGVGVAMDNAIF
EcCof/1-272     .....QHLGLS.LRDCMAF GDAMND REMLVS.........VGSGFIMGNAMF
EcYbhA/1-272    .....EAQGWS.MENVVAF GDNFND SMLEA.........AGTGVAMGNADD
EcYaed/1-191    .......LHID.MAASYMV GDKLE. .DMQA.........AVAANVGTKVLVRTG
EcHisB/1-355    .......QAMD.RANSYVI GDRAT. .DIQL.........AENMGITG..LRY..
EcNagD/1-250    .......MQAH.SEETVIV GDNLRT .DILA.........GFQAGLETILVLSGV
BsAraL/1-272    .......MGLS.AHECMII GDSIES .DIAM.........GKLYGMKSALVLTGE
EcYedP/1-271    .....QLSQK.RPTTLGLGDOPNDAPLLEV.MDYAVIVKGLNREGVHLHG
EcOtsB/1-266    ......APFI.GRTPVFL GDDLTD ESGFAV.........VNRLGGMSVKIGTGA
EcYihX/1-199    .....EGFS.PSDTVFFDDNAD...NIEG.........ANGLGITSILVKDKT
EcYigL/1-561    ..NLRELGIY.RQTGCYIERIRRN..GILANPDGAVLQMGDEIALVGYPC
EcSurE/1-253    .......MRPR........PDIVVS..GINA.........GPNLGDDVIYSGTVA
EcYfjG/1-225    .......AGNPDRSRVLMV GDTAES .DILG.........GINAGLATCWLNAHF
EcYfhG/1-323    ........TGLK.AERTLFI DDSEA...ILDA.........AAGFGIRYCLGVTN.
EcYigB/1-238    .......LNVP.IGEILHV GDDLTT .DVGG.........AIRSGMQACWIRPEN
EcYniC/1-222    .......LGVD.PLTCVAL EDSVN...GMIA.........SKAARMRSIVVPAPE
EcYqjU/1-219    .......LGVP.PQACIGI EDAQA...GIDA.........INASGMRSVGIGAGL
EcYqaB/1-199    .......MGVQ.PTQCVVF EDADF...GIQA.........ARAAGMDAVDVRLL.
EcYieH/1-221    .......MNVN.VENCILV DDSVA...GAQS.........GIDAGMEVFYFCADF
PsMupP/1-223    .......LNLD.PASVLFV GDDLR...DIES.........GRDAGTRTAAVRYG.
EcGph/1-252     .......MGIA.PQQMLFV GDSRN...DIQA.........AKAAGCPSVGLTYG.
EcYbiT/1-216    .......LGLA.PQECVVV EDAPA...GVLS.........GLAAGCHVIAVNAF.
ScDOG1/1-246    LRGDLQLTGKQ.DLKYVVF EDAPV...GIKA.........GKAMGAITVGITSS.

Motif 2
```

IN VIVO SYNTHESIS OF SIALYLATED COMPOUNDS

The present invention is in the technical field of synthetic biology and metabolic engineering. More particularly, the present invention is in the technical field of fermentation of metabolically engineered microorganisms. The present invention describes engineered micro-organisms able to synthesize sialylated compounds via an intracellular biosynthesis route. These micro-organisms can dephosphorylate N-acetylglucosamine-6-phosphate to N-acetyl glucosamine and convert the N-acetylglucosamine to N-acetylmannosamine. These micro-organisms also have the ability to convert N-acetylmannosamine to N-acetyl-neuraminate. Furthermore, the present invention provides a method for the large scale in vivo synthesis of sialylated compounds, by culturing a microorganism in a culture medium, optionally comprising an exogenous precursor such as, but not limited to lactose, lacto-N-biose, N-acetyllactosamine and/or an aglycon, wherein said microorganism intracellularly dephosphorylates N-acetylglucosamine-6-phosphate to N-acetylglucosamine, converts N-acetylglucosamine to N-acetylmannosamine and convert the latter further to N-acetyl-neuraminate.

BACKGROUND

Sialylated compounds such as sialic acid and sialylated oligosaccharides have gained attention the last years, because of their broad application range. For example, sialic acid is considered as an anti-viral precursor. Sialylated oligosaccharides form an essential part of human milk and are ascribed anti-adhesive and immunomodulatory properties; others described them to be involved in brain development. Sialylation, in general, of proteins, lipids or aglycons are used in anti-cancer medicine and in the treatment of neurological diseases.

Sialic acid is a general term used to describe a large family of acidic sugars that are predominantly found on the cell surface of eukaryotic cells. The most common sialic acid is N-acetylneuraminic acid or Neu5Ac, an acidic nine-carbon sugar that undergoes several modifications to generate the members of the sialic acid family. As seen in e.g. FIG. 1 of WO2008097366, the diversity of the sialic acid family is represented with over 50 known members. Sialic acid represents a large family of cell-surface carbohydrates that are derived from an acidic, nine-carbon parent compound called N-acetylneuraminic acid or Neu5Ac. Neu5Ac is often decorated with acetyl, phosphate, methyl, sulfate and lactyl groups, which are described to be required for desirable cell signalling and cell adhesion events mediated by sialic acid.

Sialic acids and sialylated compounds are common in higher eukaryotic organisms which produce them in a conserved biosynthetic route. This route starts from endogenic UDP-N-acetylglucosamine which is converted to sialic acid through the action of a UDP-N-acetylglucosamine 2-epimerase (hydrolysing) (EC 3.2.1.183), a N-acylmannosamine kinase (EC 2.7.1.60), a N-acylneuraminate-9-phosphate synthase (EC 2.5.1.57) and a Neu5Ac-9-P phosphatase (EC 3.1.3.29). This sialic acid can subsequently be activated and transferred to the desired acceptor via a CMP-sialic acid synthase (EC 2.7.7.43) and e.g. a sialyltransferase. Efforts have been made to express this biosynthetic route in other eukaryotic organisms, whereas prokaryotic systems were not reported. The pathway was functionally expressed in yeast (*Pichia pastoris*) and plant (*Arabidopsis thaliana*) to produce sialylated N-glycans. However, large scale production of sialylated oligosaccharides was never reported. The functional overexpression of eukaryotic genes in prokaryotic systems remains a daunting task without certain outcome due to the lack of specific chaperones, faulty enzyme folding and missing cell organelles. On top of that remains the huge energy requirement of the pathway and the depletion of intercellular UDP-GlcNAc (UDP-N-acetylglucosamine), necessary for cell growth.

Processes based on enzymatic, chemical as well as fermentative production of sialylated compounds exist. However, all of them have significant disadvantages. For instance, chemical synthesis requires many sequential chemical steps and enzymatic synthesis requires expensive precursors, whereas the fermentative process is still under heavy development. Nonetheless, the latter has the highest industrial production potential.

One type of described fermentative production process uses a biosynthesis route that originates from prokaryotes like *Campylobacter jejuni* that naturally produces sialic acid or sialylated compounds. This biosynthesis route starts from endogenous UDP-N-acetylglucosamine which cells use for their cell wall. This is converted to N-acetylmannosamine and N-acetylneuraminate by the action of an UDP-N-acetylglucosamine epimerase (generally named neuC) and a sialic acid synthase (generally named neuB).

Using only part of this prokaryotic biosynthesis route, Priem et al. (*Glycobiology* 12, 2002, 235-240) describe the use of living bacterial cells to produce sialyloligosaccharides. In this method, sialyllactose was directly produced by growing cells of metabolically engineered *Escherichia coli* strains which overexpressed the *Neisseria meningitidis* genes for alpha-2,3-sialyltransferase and for CMP-Neu5Ac synthase, these strains were further devoid of beta-galactosidase and N-acetylneuraminic acid (Neu5Ac) aldolase activities. These microorganisms were grown at high cell density with glycerol as the carbon and energy source, while exogenous lactose and Neu5Ac were supplied as precursors for sialyllactose synthesis. During the growth, lactose and Neu5Ac were internalized by the induction of the expression of an *E. coli* galactoside and an exogenous Neu5Ac permease. Lactose and Neu5Ac accumulate in the cytoplasm where Neu5Ac was then converted into CMP-Neu5Ac to be further transferred on lactose to form sialyllactose. Large scale production of sialyloligosaccharides by this microbiological method requires important amounts of Neu5Ac as a precursor.

Another microbial system was developed for production of sialyloligosaccharides without the need of an exogenous supply of sialic acid. WO2007101862 describes such method for producing sialylated oligosaccharides with microorganisms comprising heterologous genes encoding a CMP-Neu5Ac synthetase, a sialic acid synthase, an UDP-GlcNAc-6-phosphate 2-epimerase and a sialyltransferase, and wherein the endogenous genes coding for sialic acid aldolase (NanA) and for ManNAc kinase (NanK) have been deleted or inactivated. The use of this prokaryotic biosynthesis route is very energy intensive for the cell. Furthermore, the described route for producing the sialylated oligosaccharides competes for the UDP-GlcNAc which is essential for the cells own peptidoglycan synthesis. Building on this concept, Kang et al. have created a production host that does not use a sialic acid synthase, but the endogenous sialic acid aldolase, which has a less favourable chemical equilibrium (*Metabolic engineering* 14, 2012, 623-629).

EP1484406 describes the production of Neu5Ac using *E. coli* overexpressing N-acetylglucosamine 2-epimerase and Neu5Ac synthase, but needs N-acetylglucosamine (GlcNAc) as external precursor. In the described method, GlcNAc needs to be used as such. Therefore, the cells in EP1484406 need to be disrupted such that the GlcNAc can be used directly by the GlcNAc-2-epimerase. As described by Lundgren et al. (Org. Biomol. Chem., 2007, 5, 1903-1909) intact cells will convert the incoming GlcNAc to N-acetylglucosamine-6-phosphate (GlcNAc-6-P) which will be used by the cell for cell growth. This GlcNAc-6-P is not available intercellular and can therefore not be used for the GlcNAc-2-epimerase which needs a non-phosphorylated GlcNAc for epimerisation to ManNAc. This explains why permeabilization of the cells of EP1484406 is necessary. As explained by Lundgren et al., the GlcNAc-6-P can be used for making Neu5Ac but this requires another synthesis pathway comprising UDP-GlcNAc as an intermediate, which is described above in WO2007101862. The resulting pathway further increases energy demand compared to the one described in the latter patent because uridylation of GlcNAc requires an extra ATP.

Deng et al. (Metabolic Engineering 7 (2005), 201-214) describes the production of GlcNAc via intracellular production of GlcNAc-6-P which is then efficiently dephosphorylated and secreted into the medium as GlcNAc. According to Deng et al., this dephosphorylation happens upon export, more specifically in the periplasm of *Escherichia coli*. The extracellular produced GlcNAc described in this method, is not available for intracellular conversion. This method to produce GlcNAc requires a two-phase fed batch process, i.e. a cell growth phase followed by a GlcNAc production phase which is only induced after the culture had reached a high cell density, to minimize inhibitory effects of phosphorylated amino sugars.

Others have attempted the same by heterologously expressing phosphatases and encountered the problem of reduced growth and strong metabolic burden (Lee and Oh, *Metabolic engineering*, 2015, 143-150). The main reason for said reduction in growth/biomass formation is the non-specificity of the phosphatase that is introduced, which dephosphorylates other essential phosphorylated compounds. Such modifications hence lead to reduced fitness and lower specific productivity. It furthermore leads to selective pressure to mutate the production pathway during production, which reduces the overall process stability.

The production pathways of sialic acid and sialylated oligosacharides require the formation of high level of phosphorylated (e.g. GlcNAc-6-P) and nucleotide pathway intermediates. It is commonly understood that such formation leads to aspecific degradation of these intermediates by activation of aspecific phosphatases, which in turn leads to reduced fitness. In order to circumvent the effect of the expression of metabolic pathways on the growth of the production hosts, it is standard to use inducible expression systems. In this method first biomass is formed and later in the production process the production pathway is activated by for instance IPTG. This was applied by others for the production of sialic acid and sialylated oligosaccharides (WO2007101862; Priem et al. *Glycobiology* 12, 2002, 235-240; Kang et al., *Metabolic engineering* 14, 2012, 623-629; Yang et al., *Metabolic engineering* 43, 2017, 21-28). Apart from losing productivity and titer, another downside in the use of inducible systems is the excretion of intermediate pathway metabolites such as GlcNAc and ManNAc. This leads to the requirement of extra downstream processing steps for the purification, hence a higher production cost in the production of sialic acid, sialyllactose or other sialylated compounds.

The methods for producing sialylated compounds, discussed hereabove, are still insufficient in meeting the large demand of the biotechnological, pharmaceutical and medical industries. A metabolic engineering approach that successfully overcomes the problems referred to above, would represent a significant and long awaited advance in the field.

SUMMARY

Surprisingly, we have been able to create a production pathway that does not require induction, and does not require a UDP-GlcNAc epimerase, but allows constitutive expression which also allows better tuning of the metabolic pathway improving production and reducing byproduct formation during the production process.

According to one embodiment of the present invention, there is provided a method for sialylated compound production with microorganisms which does not require induction.

According to a further embodiment of the present invention, there is provided a production pathway that does not require a UDP-GlcNAc epimerase, and comprising modulating expression of phosphatase which does not pose a metabolic burden to the cell as was shown previously in the art. Said further embodiment of the present invention provides also an increased sialylated compound production by modulating the expression of phosphatase.

In another further embodiment, the above method, when combined with the constitutive expression of the genes of the metabolic pathway, also allows better tuning of the metabolic pathway reducing byproduct formation during the production process.

DESCRIPTION

The present invention describes an economical, more efficient and alternative biosynthesis route for the production of sialylated compounds using micro-organisms.

The present invention provides a method of producing sialylated compounds by fermentative growth of microorganisms.

In particular, the invention relates to a method for the production of sialylated compounds, wherein the method comprises culturing a microorganism in a culture medium. The microorganism intracellularly converts following reactions: N-acetylglucosamine-6-phosphate to N-acetylglucosamine, N-acetylglucosamine to N-acetylmannosamine, and N-acetylmannosamine to N-acetyl-neuraminate. Furthermore, this microorganism is unable to: i) convert N-acetylglucosamine-6-P to glucosamine-6-P, ii) convert N-acetylglucosamine to N-acetylglucosamine-6-P, and iii) convert N-acetyl-neuraminate to N-acetyl-mannosamine.

Preferably, the conversion of N-acetylglucosamine-6-phosphate to N-acetylglucosamine is obtained by the action of an intracellularly expressed phosphatase. In another preferred embodiment the N-acetylglucosamine is converted to N-acetylmannosamine by an intracellularly expressed N-acetylmannosamine epimerase. In an alternative preferred embodiment the N-acetylmannosamine is converted by an intracellular expressed sialic acid synthase to N-acetyl-neuraminate. Even more preferably, the microorganism comprises all three enzymes such that the microorganism converts i) N-acetylglucosamine-6-phosphate to N-acetylglucosamine by action of an intracellularly expressed phosphatase, ii) the N-acetylglucosamine to N-acetylmannosamine by an intracellularly expressed N-acetylmannosamine epimerase; and iii) the N-acetylmannosamine to N-acetyl-neuraminate by an intracellular expressed sialic acid synthase.

Preferably, the microorganism used in the method of the invention is unable to produce following enzymes i) a N-acetylglycosamine-6-phosphate deacetylase, ii) a N-acetylglucosamine kinase, and iii) a N-acetylneuraminate aldolase.

The present invention also provides a microorganism which expresses i) a phosphatase to dephosphorylate N-acetylglucosamine-6-phosphate to N-acetylglucosamine (EC 3.1.3.), ii) a GlcNAc 2-epimerase to convert N-acetylglucosamine (GlcNAc) to N-acetylmannosamine (manNac) (EC 5.1.3.8), and iii) a sialic acid synthetase to synthesise N-acetyl-neuraminate (Neu5Ac) from N-acetylmannosamine (ManNAc) (EC 2.5.1.56). Furthermore, this microorganism is unable to: i) convert N-acetylglucosamine-6-P to glucosamine-6-P, ii) convert N-acetyl-glucosamine to N-acetyl-glucosamine-6-P, and iii) convert N-acetyl-neuraminate to N-acetyl-mannosamine.

In one aspect, the invention provides a micro-organism that is enabled to catalyse the following reactions: the intracellular conversion of N-acetylglucosamine-6-phosphate to N-acetylglucosamine, the intracellular conversion of N-acetylglucosamine to N-acetylmannosamine and, the intracellular conversion of N-acetylmannosamine to sialic acid.

It is generally accepted that N-acetylglucosamine-6-phosphate is naturally efficiently excreted out of the cell and meanwhile dephosphorylated by phosphatases in the periplasm (see p. 212, second column, Deng et al., Metabolic Engineering 7 (2005), 201-214). Therefore, without the present invention, this excreted product would be unavailable for conversion to sialic acid. Furthermore, re-internalization occurs through transport proteins which phosphorylate the N-acetylglucosamine.

The use of an intracellular N-acetylglucosamine-2-epimerase ensures lower energy (ATP) consumption than the classical prokaryotic route (via UDP-N-acetylglucosamine). This enables a more efficient production of sialic acid, sialylated oligosaccharides and/or sialylated products with a healthier and more efficient strain. By optimizing expression levels, the unfavourable chemical equilibrium is overcome and no need of large amounts of free N-acetylglucosamine are necessary, as is in literature. Indeed, in the art, this enzyme is solely used in enzymatic reactions which use high concentrations of N-acetylglucosamine to produce N-acetylmannosamine. It would be hence logical that the use of an epimerase would require large amounts of intracellular formed GlcNAc which is shown to be released in the medium (see Deng as described supra), however, the present invention has proven this can be avoided. Another advantage of the present invention over enzymatic methods, is that inexpensive substrates can be used in the present invention, as for example a monosaccharide such as for example glucose, galactose or fructose, a disaccharide such as for example sucrose or maltose or a polyol, such as, but not limited to, glycerol. This enables an economic production method by fermentation. Different phosphatases (EC 3.1.3.) that convert N-acetylglucosamine-6-phosphate into N-acetylglucosamine are described in the art and can be used in the present invention. Phosphatases from the HAD superfamily and the HAD-like family are described in the art. Examples from these families can be found in the enzymes expressed from genes yqaB, inhX, yniC, ybiV, yidA, ybjI, yigL or cof from *Escherichia coli*. One phosphatase that catalyzes this reaction is identified in *Blastocladiella emersonii*. Phosphatases are generally aspecific and the activity is generally not related to the family or structure. Other examples can thus be found in all phosphatase families. Specific phosphatases are easily identified and screened by well-known methods as described by Fahs et al. (*ACS Chem. Biol.*, 2016, 11 (11), 2944-2961).

Preferably, the phosphatase of the present invention is a HAD-alike phosphatase. A HAD-alike phosphatase as defined herein refers to any phosphatase polypeptide which comprises: any one or more of the following motifs as defined below:

Motif 1: hDxDx[TV] (SEQ ID NO: 73), or
Motif 2: [GSTDE][DSEN]x(1-2)[hP]x(1-2) [DGTS] (SEQ ID NOs: 74, 75, 76, 77) wherein h means a hydrophobic amino acid (A, I, L, M, F, V, P, G) and x can be any distinct amino acid.

In another preferred embodiment, HAD-alike polypeptides typically have in increasing order of preference at least 80%, 81%, 82%, 83%, 84%, 85%, 86%, 87%, 88%, 89%, 90%, 91%, 92%, 93%, 94%, 95%, 96%, 97%, 98%, or 99% overall sequence identity to any one of the polypeptides represented by SEQ ID NOs: 43, 44, 45, 47, 48, 50, 51, 52, 54, 55 or 57. Preferably, those polypeptides also comprise at least one of the above identified Motifs. More preferably, they comprise both motifs.

The overall sequence identity is determined using a global alignment algorithm, such as the Needleman Wunsch algorithm in the program GAP (GCG Wisconsin Package, Accelrys), preferably with default parameters and preferably with sequences of mature proteins (i.e. without taking into account secretion signals or transit peptides). Compared to overall sequence identity, the sequence identity will generally be higher when only conserved domains or motifs are considered.

In a preferred embodiment, the HAD-alike polypeptide comprises any one of SEQ ID NOs: 43, 44, 45, 47, 48, 50, 51, 52, 54, 55 or 57.

In another preferred embodiment, the phosphatase is chosen from the HAD superfamily or the HAD-like phosphatase family. More preferably, the phosphatase is chosen from the group comprising: i) enzymes expressed by the genes yqaB, inhX, yniC, ybiV, yidA, ybjI, yigL or cof from *Escherichia coli*, ii) the phosphatase of *Blastocladiella emersonii* and iii) other phosphatase families.

Examples of N-acetyl-D-glucosmine-2-epimerase (EC 5.1.3.8) can be found in prokaryotes and eukaryotes. Examples for prokaryotes are found in cyanobacteria like for example *Acaryochloris marina, Anabaena variabilis, Anabaena marina, Nostoc punctiforme, Acaryochloris* species, *Anabaena* species, *Nostoc* species and *Synechocystis* species. They are also found in *Bacteroides* species like for example *Bacteroides ovatus* and *Bacteroides thetaiotaomicron* and in *Capnocytophaga canimorsus* and *Mobiluncus mulieris*. In eukaryotics, N-acetyl-D-glucosmine-2-epimerase is found in *Glycin max, Mus musculus, Homo sapiens, Rattus norvegicus, Bos Taurus, Sus scrofa, Canis lupus*. Preferably, in the method and microorganism of the present invention, N-acetylmannosamine-2-epimerase is chosen from the group comprising i) N-acetylmannosamine-2-epimerase from cyanobacteria, more in particular from *Acaryochloris marina, Anabaena variabilis, Anabaena marina, Nostoc punctiforme, Acaryochloris* species, *Anabaena species, Nostoc* species and *Synechocystis* species; ii) N-acetylmannosamine-2-epimerase from *Bacteroides* species, more in particular from *Bacteroides ovatus, Bacteroides thetaiotaomicron, Capnocytophaga canimorsus* and *Mobiluncus mulieris*; iii) N-acetyl-D-glucosmine-2-epimerase from *Glycin max, Mus musculus, Homo sapiens, Rattus norvegicus, Bos Taurus, Sus scrofa* or *Canis lupus*.

N-acetyl neuraminate synthase (also called sialic acid synthase in the art) (EC 2.5.1.56) activity is found in several prokaryotic organisms like for example *Streptococcus agalatiae, Bacillus subtilis, Legionella pneumophilla, Campylobacter jejuni, Idiomarina loihiensis, Moritella viscosa, Aliivibrio salmonicida, Escherichia coli, Methanocaldococcus jannaschi, Clostridium sordellii, Butyrivibrio proteoclasticus, Micromonas commoda* or *Neisseria meningitis*. Preferably, in the method and microorganism of the invention, the sialic acid (or N-acetyl neuraminate) synthase is chosen from the group comprising: sialic acid synthase from *Streptococcus agalatiae, Bacillus subtilis, Legionella pneumophilla, Campylobacter jejuni, Idiomarina loihiensis, Moritella viscosa, Aliivibrio salmonicida, Escherichia coli, Methanocaldococcus jannaschi, Clostridium sordellii, Butyrivibrio proteoclasticus, Micromonas commoda* or *Neisseria meningitis*.

In one preferred aspect, any one or more of the phosphatase, N-acetylmannosamine epimerase and sialic acid synthase is overexpressed in the microorganism. In an alternative preferred aspect, any one or more of the phosphatase, N-acetylmannosamine epimerase and sialic acid synthase is introduced and expressed in the microorganism.

In another aspect, the microorganism lacks the genes encoding for following enzymes i) a N-acetylglycosamine-6-phosphate deacetylase, ii) a N-acetylglucosamine kinase, and iii) a N-acetylneuraminate aldolase. In another preferred aspect, the genes encoding for following enzymes i) a N-acetylglycosamine-6-phosphate deacetylase, ii) a N-acetylglucosamine kinase, and iii) a N-acetylneuraminate aldolase are reduced in activity, preferably said genes are deleted or knocked-out, in the microorganism.

In another preferred aspect, the microorganism further encodes a protein that facilitates uptake of lactose and lacks enzymes that metabolize lactose. Methods to produce microorganisms which resist lactose killing and the resulting microorganisms are described in WO2016/075243 which is herein incorporated by reference.

In a preferred aspect the microorganisms of, and used in the method of, the invention also express a CMP-sialic acid synthase (EC 2.7.7.43) and a sialyltransferase (EC 2.4.99.1) in order to activate the sialic acid and transfer it to a desired compound.

In a preferred aspect, the N-acetylglucosamine-6-phosphate is obtained by introducing a glucosamine-phosphate N-acetyltransferase (EC 2.3.1.4) which uses intracellular glucosamine-6-phosphate as a substrate. In most microorganisms, glucosamine-6-phosphate is naturally present in the cell, but the intracellular production can be elevated by expressing a L-glutamine:D-fructose-6-phosphate aminotransferase without inhibition, obtained either through protein engineering or by screening natural enzymes, such as present in gram positive bacteria (Deng et al., Metabolic Engineering 7 (2005), 201-214).

In the present invention, the expression of the genes to convert N-acetylglucosamine-6-phosphate to N-acetyl-neuraminate or sialic acid are optimized in a way that enables intracellular dephosphorylation of N-acetylglucosamine-6-phosphate, prevents toxic accumulation of N-acetylglucosamine-6-phosphate and prevents excretion of N-acetylglucosamine and/or N-acetylmannosamine. Said optimization is the result of the use of constitutive expression of the genes of the production pathway. In a preferred embodiment, the present invention prevents the excretion of at least 10%, 20%, 30%, 35%, 40%, 45%, 50%, or 60% of the formed N-acetylglucosamine and/or N-acetylmannosamine. In a further preferred embodiment, the microorganism produces less extracellular N-acetylglucosamine and/or N-acetylmannosamine than sialylated compound. More preferably, the microorganism produces less than 50%, 40%, 30%, 20%, 10%, 5%, 2% extracellular N-acetylglucosamine and/or N-acetylmannosamine than sialylated compound. In another preferred embodiment of the present invention the microorganism produces equal or more than 50%, 60%, 70%, 80%, 90%, 95%, 98% extracellular sialylated compound on total extracellular carbohydrate.

In a particular aspect, the invention relates to a method for synthesis of sialylated compounds, without any exogenous sialic acid addition to the culture medium.

The sialylated compound can be N-acetylneuramic acid, a sialylated oligosaccharide, a sialylated lipid, sialylated glycolipids (such as, but not limited to gangliosides, ceramides), a sialylated protein or a sialylated aglycon.

A sialylated oligosaccharide is a charged sialic acid containing oligosaccharide, i.e. an oligosaccharide having a sialic acid residue. It has an acidic nature. Some examples are 3-SL (3-sialyllactose), 3-sialyllactosamine, 6-SL (6-sialyllactose or n-acetylneuraminate alfa 2,6 galactosyl beta 1,4 Glucose), 6-sialyllactosamine, oligosaccharides comprising 6-sialyllactose, SGG hexasaccharide (Neu5Ac alfa-2,3Gal beta-1,3GalNac beta-1,3Gala-1,4Gal beta-1, 4Gal), sialylated tetrasaccharide (Neu5Ac-alfa-2,3Gal beta-1,4GlcNAc beta-14GlcNAc), pentasaccharide LSTD (Neu5Ac alfa-2,3Gal beta-1,4GlcNAc beta-1,3Gal beta-1, 4Glc), sialylated lacto-N-triose, sialylated lacto-N-tetraose, sialyllacto-N-neotetraose, monosialyllacto-N-hexaose, disialyllacto-N-hexaose I, monosialyllacto-N-neohexaose I, monosialyllacto-N-neohexaose II, disialyllacto-N-neohexaose, disialyllacto-N-tetraose, disialyllacto-N-hexaose II, sialyllacto-N-tetraose a, disialyllacto-N-hexaose I, sialyllacto-N-tetraose b, 3-sialyl-3-fucosyllactose, disialomonofucosyllacto-N-neohexaose, monofucosylmonosialyllacto-N-octaose (sialyl Lea), sialyllacto-N-fucohexaose II, disialyllacto-N-fucopentaose II, monofucosyldisialyllacto-N-tetraose and oligosaccharides bearing one or several sialic acid residu(s), including but not limited to: oligosaccharide moieties of the gangliosides selected from GM3 (3sialyllactose, Neu5Aca-2,3Gal beta-4Glc) and oligosaccharides comprising the GM3 motif, GD3 Neu5Aca-2,8Neu5Aca-2, 3Gal beta-1,4Glc GT3 (Neu5Aca-2,8Neu5Aca-2, 8Neu5Aca-2,3Gal beta-1,4Glc); GM2 GalNAc beta-1,4 (Neu5Aca-2,3)Gal beta-1,4Glc, GM1 Gal beta-1,3GalNAc beta-1,4(Neu5Aca-2,3)Gal beta-1,4Glc, GD1a Neu5Aca-2, 3Gal beta-1,3GalNAc beta-1,4(Neu5Aca-2,3)Gal beta-1, 4Glc GT1a Neu5Aca-2,8Neu5Aca-2,3Gal beta-1,3GalNAc beta-1,4(Neu5Aca-2,3)Gal beta-1,4Glc GD2 GalNAc beta-1,4(Neu5Aca-2,8Neu5Aca2,3)Gal beta-1,4Glc GT2 Gspal-NAc beta-1,4(Neu5Aca-2,8Neu5Aca-2,8Neu5Aca2,3)Gal beta-1,4Glc GD1b, Gal beta-1,3GalNAc beta-1,4(Neu5Aca-2,8Neu5Aca2,3)Gal beta-1,4Glc GT1b Neu5Aca-2,3Gal beta-1,3GalNAc beta-1,4(Neu5Aca-2,8Neu5Aca2,3)Gal beta-1,4Glc GQ1b Neu5Aca-2,8Neu5Aca-2,3Gal beta-1, 3GalNAc beta-1,4Neu5Ac beta-1,4(Neu5Aca-2, 8Neu5Aca2,3)Gal beta-1,4Glc GT1c Gal beta-1,3GalNAc beta-1,4(Neu5Aca-2,8Neu5Aca-2,8Neu5Aca2,3)Gal beta-1,4Glc GQ1c, Neu5Aca-2,3Gal beta-1,3GalNAc beta-1,4 (Neu5Aca-2,8Neu5Aca-2,8Neu5Aca2,3)Gal beta-1,4Glc GP1c Neu5Aca-2,8Neu5Aca-2,3Gal beta-1,3GalNAc beta-1,4(Neu5Aca-2,8Neu5Aca-2,8Neu5Aca2,3)Gal beta-1,4Glc GD1a Neu5Aca-2,3Gal beta-1,3(Neu5Aca-2,6)GalNAc beta-1,4Gal beta-1,4Glc Fucosyl-GM1 Fuca-1,2Gal beta-1, 3GalNAc beta-1,4(Neu5Aca-2,3)Gal beta-1,4Glc; all of which may be extended to the production of the corresponding gangliosides by reacting the above oligosaccharide moieties with ceramide or synthetizing the above oligosaccharides on a ceramide.

The term micro-organism or organism or cell as indicated above refers to a microorganism chosen from the list comprising a bacterium, a yeast, or a fungus, or, refers to a plant or animal cell. The latter bacterium preferably belongs to the phylum of the Proteobacteria or the phylum of the Firmicutes or the phylum of the Cyanobacteria or the phylum Deinococcus-Thermus. The latter bacterium belonging to the phylum Proteobacteria belongs preferably to the family Enterobacteriaceae, preferably to the species *Escherichia coli*. The latter bacterium preferably relates to any strain belonging to the species *Escherichia coli* such as but not limited to *Escherichia coli* B, *Escherichia coli* C, *Escherichia coli* W, *Escherichia coli* K12, *Escherichia coli* Nissle. More specifically, the latter term relates to cultivated *Escherichia coli* strains—designated as *E. coli* K12 strains—which are well-adapted to the laboratory environment, and, unlike wild type strains, have lost their ability to thrive in the intestine. Well-known examples of the *E. coli* K12 strains are K12 Wild type, W3110, MG1655, M182, MC1000, MC1061, MC4100, JM101, NZN111 and AA200. Hence, the present invention specifically relates to a mutated and/or transformed *Escherichia coli* strain as indicated above wherein said *E. coli* strain is a K12 strain. More specifically, the present invention relates to a mutated and/or transformed *Escherichia coli* strain as indicated above wherein said K12 strain is *E. coli* MG1655. The latter bacterium belonging to the phylum Firmicutes belongs preferably to the Bacilli, preferably Lactobacilliales, with members such as *Lactobacillus lactis, Leuconostoc mesenteroides*, or Bacillales with members such as from the species *Bacillus, Bacillus subtilis* or, *B. amyloliquefaciens*. The latter Bacterium belonging to the phylum Actinobacteria, preferably belonging to the family of the Corynebacteriaceae, with members *Corynebacterium glutamicum* or *C. afermentans*, or belonging to the family of the of the Streptomycetaceae with members *Streptomyces griseus* or *S. fradiae*. The latter yeast preferably belongs to the phylum of the Ascomycota or the phylum of the Basidiomycota or the phylum of the Deuteromycota or the phylum of the Zygomycetes. The latter yeast belongs preferably to the genus *Saccharomyces, Pichia, Hansenula, Kluyveromyces, Yarrowia* or *Starmerella*. The latter fungus belongs preferably to the genus *Rhizopus, Dictyostelium, Penicillium, Mucor* or *Aspergillus*.

The culture medium for the production host can optionally comprise an exogenous precursor or this precursor can be produced by the strain itself, such as a glycan like for example lactose, lactosamine, lacto-N-triose, lacto-N-tetraose, lacto-N-neotetraose; an oligosaccharide; a peptide; a lipid or an aglycon. In one particular aspect, the process of the invention is based on the active uptake of an exogenous precursor, such as for example a mono, di or tri-saccharide, more particularly an exogenous precursor selected from lactose, N-acetyllactosamine, lacto-N-biose, galactose, beta-galactoside, and alpha-galactoside such as but not limited to globotriose (Gal-alpha-1,4Gal-beta-1,4Glc), while the microorganisms are growing on an inexpensive carbon substrate, such as a disaccharide such as sucrose or maltose. Moreover, these microorganisms are also able to grow on glucose, fructose or glycerol. The expression exogenous precursor is intended to denote a compound involved in the biosynthetic pathway of the product according to the invention that is internalized by the microorganism.

In one aspect, the invention provides for method for production of sialylated forms of lacto-N-triose, lacto-N-tetraose or lacto-N-neotetraose. Any one of these three molecules are synthetized by the micro-organism via the activity of a galactosyltransferase (EC 2.4.1.38), preferably originating from the group comprising *Homo sapiens, Bos taurus, Mus mulatta, Gallus gallus, Danio rerio, Helicobacter pylori* and *Haemophilus ducrey* and/or a N-acetyl-glucosaminyltransferase (EC 2.4.1.90) preferably originating from the group comprising *Bos Taurus, Homo Sapiens* and *Mus Musculus*. To enhance the formation of these oligosaccharides the genes coding for UDP sugar hydrolase and galactose-1-phosphate uridylyltransferase are lacking, reducing in activity or knocked out in the microorganism.

In another aspect a method for producing a sialylated oligosaccharide is provided in which the method comprises culturing a microorganism as described above and wherein the microorganism produces internally, activated N-acetyl-neuraminate as donor substrate for a sialyltransferase; and wherein the method further comprises culturing the microorganism in a culture medium which comprises an exogenous precursor selected from the group consisting of lactose, N-acetyllactosamine, lacto-N-biose, galactose, beta-galactoside, and alpha-galactoside such as but not limited to globotriose (Gal-alpha-1,4Gal-beta-1,4Glc)galactose. The exogenous precursor is actively taken up into the microorganism and the exogenous precursor is the acceptor substrate for the sialytransferase for producing the sialylated oligosaccharide.

In a further aspect, the method according to the invention provides for the production of 3sialyllactose or 6sialyllactose. In this method the microorganism is cultivated at high cell density on a carbon substrate, such as glucose or glycerol, and fed with lactose. The lactose is internalized by the lactose permease and sialylated by the recombinant sialyltransferase using the CMP-N-acetyl-neuraminate endogenously generated from N-acetylglucosamine.

The microorganism or cell of the invention is capable to grow on a monosaccharide, disaccharide, oligosaccharide, polysaccharide, polyol, a complex medium or a mixture thereof as the main carbon source. With the term main is meant the most important carbon source for biomass formation, carbon dioxide and/or by-products formation (such as acids and/or alcohols, such as acetate, lactate, and/or ethanol), i.e. 20, 30, 40, 50, 60, 70, 75, 80, 85, 90, 95, 98, 99% of all the required carbon is derived from the above-indicated carbon source. In one embodiment of the invention, said carbon source is the sole carbon source for said organism, i.e. 100% of all the required carbon is derived from the above-indicated carbon source.

In a further preferred embodiment, the microorganism or cell of the invention is using a split metabolism having a production pathway and a biomass pathway as described in WO2012/007481, which is herein incorporated by reference. Said organism can, for example, be genetically modified to accumulate fructose-6-phosphate by altering the genes selected from the phosphoglucoisomerase gene, phosphofructokinase gene, fructose-6-phosphate aldolase gene, fructose isomerase gene, and/or fructose:PEP phosphotransferase gene.

With the term monosaccharide is meant a sugar that is not decomposable into simpler sugars by hydrolysis, is classed as either an aldose or ketose, and contains one or more hydroxyl groups per molecule. Examples are glucose, fructose, galactose, mannose, ribose and/or arabinose.

With the term disaccharide is meant a sugar that is composed of two monosaccharides that are chemically bound. Examples are maltose, sucrose, lactose, trehalose, cellobiose and/or chitobiose.

With the term oligosaccharide is meant a sugar that is composed of three to ten monosaccharides that are chemically bound. Examples are maltotriose, fructo-oligosaccharides, galacto-oligosaccharides, mannan oligosaccharides, isomaltooligosaccharide, human milk oligosaccharides and/or glucooligosaccharides.

With the term polyol is meant an alcohol containing multiple hydroxyl groups. For example glycerol, sorbitol, or mannitol.

With the term complex medium is meant a medium for which the exact constitution is not determined. Examples are molasses, corn steep liquor, peptone, tryptone or yeast extract.

Production of sialylated compounds can be increased by adding precursors to the medium, such as N-acetylglusosamine, N-acetylmannosamine, glutamine, glutamate, phosphoenolpyruvate and/or pyruvate.

The sialylated compounds produced in the method of the invention as described above may be recovered using various methods, or a combination thereof, known in the art. Depending on the produced sialylated compound, the compound is available in the extracellular fraction or retained in the cells. When the produced sialylated compound is retained in the cells, the sialylated compound will first be released from the cells by cell disruption. Again depending on the produced sialylated compound, the cells may be separated from the extracellular fraction. In the other case, cells are disrupted without first separation from the extracellular fraction, wherein cells are disrupted by techniques such as, but not limited to, heating, freeze thawing and/or shear stress through sonication, mixing and/or French press. The extracellular and/or intracellular fraction may be separated from the cells and/or cell debris by centrifugation, filtration, microfiltration, and nanofiltration. Flocculating agents may be used to aid in product separation. The sialylated compounds in the extracellular or intracellular fraction may be extracted by ion exchange, ultra- or nanofiltration or electrodialysis, chromatography such as size exclusion, ion chromatography and simulated moving bed. Another example of filtering the sialylated compounds from liquid phase is by filtration using a deep bed filter with cotton and activated carbon or carbon filter, where after the permeate is passed through a carbon polisher followed by e.g. a 0.2 micron microfiltration membrane system to remove color, micro-organisms and suspended carbon particles. Thereafter the sialylated compound may be concentrated in a vacuum evaporator to obtain a concentrate. The concentrate can be precipitated and/or dried through heat drying, spray drying and/or lyophilization to obtain high purity sialylated compound. An amorphous form powder can then be obtained. This amorphous powder may further be crystallised to obtain crystalline sialylated compound.

In exemplary embodiment, sialylated compounds may be isolated from the culture medium using methods known in the art for fermentations. For example, cells may be removed from the culture medium by centrifugation, filtration, flocculation, decantation, or the like. Then, the sialylated compounds may be isolated from the extracellular fraction using methods such as ion-exchange. A further purification of said sialylated compounds may be accomplished, for example, by nanofiltration or ultrafiltration or ion exchange to remove any remaining DNA, protein, LPS (endotoxins), or other impurity.

In another exemplary embodiment, sialyllactose may be isolated from the culture medium using methods known in the art for fermentations. For example, cells may be removed from the culture medium by centrifugation, filtration, flocculation, decantation, or the like. Then, the sialyllactose may be isolated from the extracellular fraction using methods such as ion-exchange. A further purification of said sialyllactose may be accomplished, for example, by nanofiltration or ultrafiltration or ion exchange to remove any remaining DNA, protein, LPS (endotoxins), or other impurity. Another purification and formulation step is accomplished by crystallization or precipitation of the product. Another formulation step is to spray dry or lyophilize sialyllactose.

The sialylated compound may contain a counter ion, such as, a monovalent ion, such as a proton, sodium ion, potassium, a divalent ion, such as calcium magnesium, iron, or, a trivalent ion such as iron, or a combination of ions.

Throughout the disclosure of the present disclosure the term sialic acid, N-acetyl neuraminate and N-acetyl neuraminic acid are used interchangeably.

As used herein, the term intracellular or intracellularly in e.g. intracellularly converting, intracellularly production, intracellularly expressed, intracellular formed must be understood to mean within the cell of the microorganism. The term extracellular must be understood to mean outside of the cell.

Further definitions used throughout the present specification

Homologue(s)

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

A deletion refers to removal of one or more amino acids from a protein.

An insertion refers to one or more amino acid residues being introduced into a predetermined site in a protein. Insertions may comprise N-terminal and/or C-terminal fusions as well as intra-sequence insertions of single or multiple amino acids. Generally, insertions within the amino acid sequence will be smaller than N- or C-terminal fusions, of the order of about 1 to 10 residues. Examples of N- or C-terminal fusion proteins or peptides include the binding domain or activation domain of a transcriptional activator as used in the yeast two-hybrid system, phage coat proteins, (histidine)-6-tag, glutathione S-transferase-tag, protein A, maltose-binding protein, dihydrofolate reductase, Tag>>100 epitope, c-myc epitope, FLAG(R)-epitope, lacZ, CMP (calmodulin-binding peptide), HA epitope, protein C epitope and VSV epitope.

A substitution refers to replacement of amino acids of the protein with other amino acids having similar properties (such as similar hydrophobicity, hydrophilicity, antigenicity, propensity to form or break a-helical structures or beta-sheet structures). Amino acid substitutions are typically of single residues, but may be clustered depending upon functional constraints placed upon the polypeptide and may range from 1 to 10 amino acids; insertions will usually be of the order of about 1 to 10 amino acid residues. The amino acid substitutions are preferably conservative amino acid substitutions. Conservative substitution tables are well known in the art (see for example Creighton (1984) Proteins. W.H. Freeman and Company (Eds) and Table 1 below).

TABLE 1

Examples of conserved amino acid substitutions

| Residue | Conservative Substitutions | Residue | Conservative Substitutions |
|---|---|---|---|
| Ala | Ser | Leu | Ile; Val |
| Arg | Lys | Lys | Arg; Gln |
| Asn | Gln; His | Met | Leu; Ile |
| Asp | Glu | Phe | Met; Leu; Tyr |
| Gln | As, | Ser | Thr; Gly |
| Cys | Ser | Thr | Ser; Val |
| Glu | Asp | Trp | Tyr |
| Gly | Pro | Tyr | Trp; Phe |
| His | Asn; Gln | Val | Ile; Leu |
| Ile | Leu; Val | | |

Amino acid substitutions, deletions and/or insertions may readily be made using peptide synthetic techniques well known in the art, such as solid phase peptide synthesis and the like, or by recombinant DNA manipulation. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

Derivatives

"Derivatives" include peptides, oligopeptides, polypeptides which may, compared to the amino acid sequence of the naturally-occurring form of the protein, such as the protein of interest, comprise substitutions of amino acids with non-naturally occurring amino acid residues, or additions of non-naturally occurring amino acid residues. "Derivatives" of a protein also encompass peptides, oligopeptides, polypeptides which comprise naturally occurring altered (glycosylated, acylated, prenylated, phosphorylated, myristoylated, sulphated etc.) or non-naturally altered amino acid residues compared to the amino acid sequence of a naturally-occurring form of the polypeptide. A derivative may also comprise one or more non-amino acid substituents or additions compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein. Furthermore, "derivatives" also include fusions of the naturally-occurring form of the protein with tagging peptides such as FLAG, HIS6 or thioredoxin (for a review of tagging peptides, see Terpe, Appl. Microbiol. Biotechnol. 60, 523-533, 2003).

Orthologue(s)/Paralogue(s)

Orthologues and paralogues encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene.

Domain, Motif/Consensus Sequence/Signature

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein. Identified by their high degree of conservation in aligned sequences of a family of protein homologues, they can be used as identifiers to determine if any polypeptide in question belongs to a previously identified polypeptide family.

The term "motif or "consensus sequence" or "signature" refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32:D134-D137, (2004)), or Pfam (Bateman et al., Nucleic Acids Research 30(1): 276-280 (2002)). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788 (2003)). Domains or motifs may also be identified using routine techniques, such as by sequence alignment.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters. For local alignments, the Smith-Waterman algorithm is particularly useful (Smith T F, Waterman M S (1981) J. Mol. Biol 147(1); 195-7).

Reciprocal BLAST

Typically, this involves a first BLAST involving BLASTing a query sequence (for example using any of the sequences listed in Table A of the Examples section) against any sequence database, such as the publicly available NCBI database. BLASTN or TBLASTX (using standard default values) are generally used when starting from a nucleotide sequence, and BLASTP or TBLASTN (using standard default values) when starting from a protein sequence. The BLAST results may optionally be filtered. The full-length sequences of either the filtered results or non-filtered results are then BLASTed back (second BLAST) against sequences from the organism from which the query sequence is derived. The results of the first and second BLASTs are then compared. A paralogue is identified if a high-ranking hit from the first blast is from the same species as from which the query sequence is derived, a BLAST back then ideally results in the query sequence amongst the highest hits; an orthologue is identified if a high-ranking hit in the first BLAST is not from the same species as from which the query sequence is derived, and preferably results upon BLAST back in the query sequence being among the highest hits.

High-ranking hits are those having a low E-value. The lower the E-value, the more significant the score (or in other words the lower the chance that the hit was found by chance). Computation of the E-value is well known in the art. In addition to E-values, comparisons are also scored by percentage identity. Percentage identity refers to the number of identical nucleotides (or amino acids) between the two compared nucleic acid (or polypeptide) sequences over a particular length. In the case of large families, ClustalW may be used, followed by a neighbour joining tree, to help visualize clustering of related genes and to identify orthologues and paralogues.

Construct

Additional regulatory elements may include transcriptional as well as translational enhancers. Those skilled in the art will be aware of terminator and enhancer sequences that may be suitable for use in performing the invention. An intron sequence may also be added to the 5 untranslated region (UTR) or in the coding sequence to increase the amount of the mature message that accumulates in the cytosol, as described in the definitions section. Other control sequences (besides promoter, enhancer, silencer, intron sequences, 3UTR and/or 5UTR regions) may be protein and/or RNA stabilizing elements. Such sequences would be known or may readily be obtained by a person skilled in the art.

The genetic constructs of the invention may further include an origin of replication sequence that is required for maintenance and/or replication in a specific cell type. One example is when a genetic construct is required to be maintained in a bacterial cell as an episomal genetic element (e.g. plasmid or cosmid molecule).

For the detection of the successful transfer of the nucleic acid sequences as used in the methods of the invention and/or selection of transgenic microorganisms comprising these nucleic acids, it is advantageous to use marker genes (or reporter genes). Therefore, the genetic construct may optionally comprise a selectable marker gene. The marker genes may be removed or excised from the transgenic cell once they are no longer needed. Techniques for marker removal are known in the art, useful techniques are described above in the definitions section.

Regulatory Element/Control Sequence/Promoter

The terms "regulatory element", "control sequence" and "promoter" are all used interchangeably herein and are to be taken in a broad context to refer to regulatory nucleic acid sequences capable of effecting expression of the sequences to which they are ligated. The term "promoter" typically refers to a nucleic acid control sequence located upstream from the transcriptional start of a gene and which is involved in recognising and binding of RNA polymerase and other proteins, thereby directing transcription of an operably linked nucleic acid. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative that confers, activates or enhances expression of a nucleic acid molecule in a cell, tissue or organ.

Constitutive Promoter

A "constitutive promoter" refers to a promoter that is transcriptionally active during most, but not necessarily all, phases of growth and development and under most environmental conditions, in at least one cell, tissue or organ.

Transgenic/Transgene/Recombinant

For the purposes of the invention, "transgenic", "transgene" or "recombinant" means with regard to, for example, a nucleic acid sequence, an expression cassette, gene construct or a vector comprising the nucleic acid sequence or an organism transformed with the nucleic acid sequences, expression cassettes or vectors according to the invention, all those constructions brought about by recombinant methods in which either (a) the nucleic acid sequences encoding proteins useful in the methods of the invention, or
(b) genetic control sequence(s) which is operably linked with the nucleic acid sequence according to the invention, for example a promoter, or
(c) a) and b) are not located in their natural genetic environment or have been modified by recombinant methods, it being possible for the modification to take the form of, for example, a substitution, addition, deletion, inversion or insertion of one or more nucleotide residues. The natural genetic environment is understood as meaning the natural genomic or chromosomal locus in the original microorganism or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences with the corresponding nucleic acid sequence encoding a polypeptide useful in the methods of the present invention, as defined above—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815.

A transgenic microorganism for the purposes of the invention is thus understood as meaning, as above, that the nucleic acids used in the method of the invention are not present in, or originating from, the genome of said microorganism, or are present in the genome of said microorganism but not at their natural locus in the genome of said microorganism, it being possible for the nucleic acids to be expressed homologously or heterologously. However, as mentioned, transgenic also means that, while the nucleic acids according to the invention or used in the inventive method are at their natural position in the genome of a microorganism, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, preferably, heterologous expression of the nucleic acids takes place. Preferred transgenic microorganism are mentioned herein.

It shall further be noted that in the context of the present invention, the term "isolated nucleic acid" or "isolated polypeptide" may in some instances be considered as a synonym for a "recombinant nucleic acid" or a "recombinant polypeptide", respectively and refers to a nucleic acid or polypeptide that is not located in its natural genetic environment and/or that has been modified by recombinant methods.

Modulation

The term "modulation" means in relation to expression or gene expression, a process in which the expression level is changed by said gene expression in comparison to the control microorganism, the expression level may be increased or decreased. The original, unmodulated expression may be of any kind of expression of a structural RNA (rRNA, tRNA) or mRNA with subsequent translation. For the purposes of this invention, the original unmodulated expression may also be absence of any expression. The term "modulating the activity" shall mean any change of the expression of the inventive nucleic acid sequences or encoded proteins, which leads to increased production yield and/or increased growth of the microorganisms. The expression can increase from zero (absence of, or immeasurable expression) to a certain amount, or can decrease from a certain amount to immeasurable small amounts or zero.

Expression

The term "expression" or "gene expression" means the transcription of a specific gene or specific genes or specific genetic construct. The term "expression" or "gene expression" in particular means the transcription of a gene or genes or genetic construct into structural RNA (rRNA, tRNA) or mRNA with or without subsequent translation of the latter into a protein. The process includes transcription of DNA and processing of the resulting mRNA product.

Increased Expression/Overexpression

The term "increased expression" or "overexpression" as used herein means any form of expression that is additional to the original wild-type expression level. For the purposes of this invention, the original wild-type expression level might also be zero, i.e. absence of expression or immeasurable expression.

Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the polypeptide of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a microorganism cell in the proper orientation and distance from a gene of the present invention so as to control the expression of the gene.

If polypeptide expression is desired, it is generally desirable to include a polyadenylation region at the 3-end of a polynucleotide coding region. The polyadenylation region can be derived from the natural gene, from a variety of other microorganism genes, or from T-DNA.

Moreover, the present invention relates to the following specific embodiments:

1. Method for the production of sialylated compounds, the method comprising:
   culturing a microorganism in a culture medium, said culture medium optionally comprising an exogenous precursor,
   wherein said microorganism intracellularly converts N-acetylglucosamine-6-phosphate to N-acetylglucosamine, said N-acetylglucosamine to N-acetylmannosamine and said N-acetylmannosamine to N-acetylneuraminate; and
   wherein said microorganism is unable to i) convert N-acetylglucosamine-6-P to glucosamine-6-P, ii) convert N-acetyl-glucosamine to N-acetyl-glucosamine-6-P, and iii) convert N-acetyl-neuraminate to N-acetylmannosamine.

2. The method according to embodiment 1 wherein:
   i) said conversion of N-acetylglucosamine-6-phosphate to N-acetylglucosamine is obtained by the action of an intracellularly expressed phosphatase,
   ii) said N-acetylglucosamine to N-acetylmannosamine conversion is performed by an intracellularly expressed N-acetylmannosamine epimerase; and
   iii) intracellular expressed sialic acid synthase converts said N-acetylmannosamine to N-acetyl-neuraminate.

3. The method according to any one of embodiment 1 or 2 wherein said organism is unable to produce following enzymes i) a N-acetylglycosamine-6-phosphate deacetylase, ii) a N-acetylglucosamine kinase, and iii) a N-acetylneuraminate aldolase.

4. The method according to any one of embodiment 1 to 3, wherein all said conversions are catalysed by enzymes encoded by constitutively expressed genes.

5. The method according to embodiment 2 wherein the phosphatase is chosen from the HAD superfamily or the HAD-like phosphatase family, preferably said phosphatase is chosen from the group comprising: i) enzymes expressed by the genes yqaB, inhX, yniC, ybiV, yidA, ybjI, yigL or cof from *Escherichia coli*, ii) the phosphatase of *Blastocladiella emersonii* and iii) other phosphatase families, more preferably said phosphatase is a HAD-alike phosphatase polypeptide as defined in the claims.

6. The method according to any one of the embodiments 2, 3, 4 or 5, wherein the N-acetylmannosamine-2-epimerase is chosen from the group comprising i) N-acetylmannosamine-2-epimerase from cyanobacteria, more in particular from *Acaryochloris marina, Anabaena variabilis, Anabaena marina, Nostoc punctiforme, Acaryochloris* species, *Anabaena* species, *Nostoc* species and *Synechocystis* species; ii) N-acetylmannosamine-2-epimerase from *Bacteroides* species, more in particular from *Bacteroides ovatus, Bacteroides thetaiotaomicron, Capnocytophaga canimorsus* and *Mobiluncus mulieris*; iii) N-acetyl-D-glucosmine-2-epimerase from *Glycin max, Mus musculus, Homo sapiens, Rattus norvegicus, Bos Taurus, Sus scrofa* or *Canis lupus*.

7. The method according to any one of the embodiments 2, 3, 4, 5 or 6, wherein the sialic acid synthase is chosen from the group comprising: sialic acid synthase from *Streptococcus agalatiae, Bacillus subtilis, Legionella pneumophilla, Campylobacter jejuni, Idiomarina loihiensis, Moritella viscosa, Aliivibrio salmonicida, Escherichia coli, Methanocaldococcus jannaschi, Clostridium sordellii, Butyrivibrio proteoclasticus, Micromonas commoda* or *Neisseria meningitis*.

8. The method according to any one of the preceding embodiments, wherein said sialylated compound is selected from the group consisting of N-acetylneuramic acid, sialylated oligosaccharide, sialylated lipids, sialylated protein, sialylated aglycon.

9. The method according to the previous embodiment, wherein said sialylated compound is a sialylated oligosaccharide.

10. The method according to embodiment 9, wherein said sialylated oligosaccharide is sialyllactose, preferably any one of 3-SL or 6-SL.

11. The method according to embodiment 9, wherein said sialylated oligosaccharide is disialyl lacto-N-tetraose.

12. The method according to embodiment 8, wherein said sialylated compound is N-acetylneuraminic acid.

13. The method according to any one of embodiment 1 to 10 wherein said sialylated compound is a sialylated lacto-N-triose, lacto-N-tetraose or a lacto-N-neotetraose, and wherein said microorganism further comprises the activity of a galactosyltransferase (EC 2.4.1.38), preferably said galactosyltransferase originates from the group comprising *Homo sapiens, Bos taurus, Mus mulatta, Gallus gallus, Danio rerio, Helicobacter pylori* and *Haemophilus ducrey*; and/or said microorganism comprises the activity of a N-acetylglucosaminyltransferase (EC 2.4.1.90), preferably said N-acetylglucosaminyltransferase originates from the group comprising *Bos taurus, Homo sapiens* and *Mus musculus*.

14. The method according to embodiment 13 wherein said microorganism is unable to express the genes coding for UDP sugar hydrolase and galactose-1-phosphate uridylyl-transferase.

15. The method according to any one of embodiments 1 to 14, wherein said microorganism produces less than 50%, 40%, 30%, 20%, 10%, 5%, 2% extracellular N-acetylglucosamine and/or N-acetylmannosamine than sialylated compound and/or said micro-organism produces equal or more than 50%, 60%, 70%, 80%, 90%, 95%, 98% sialylated compound on total carbohydrate 16. A method for producing a sialylated oligosaccharide, comprising:
   a) culturing a microorganism according to the method of any one of embodiments 1 to 7, 14 and 15, and wherein said microorganism produces internally, activated N-acetylneuraminate as donor substrate for a sialyltransferase; and
   b) culturing said microorganism in a culture medium comprising an exogenous precursor selected from the group consisting of lactose, N-acetyllactosamine, lacto-N-biose, galactose, beta-galactoside, and alpha-galactoside such as but not limited to globotriose (Gal-alpha-1,4Gal-beta-1,4Glc)galactose, wherein active uptake into the microorganism of said exogenous precursor occurs and wherein said exogenous precursor is the acceptor substrate for said sialytransferase for producing the sialylated oligosaccharide.

17. The method according to embodiment 2, wherein any one or more of said phosphatase, N-acetylmannosamine epimerase and sialic acid synthase is overexpressed in the microorganism.

18. The method according to embodiment 2, wherein any one or more of said phosphatase, N-acetylmannosamine epimerase and sialic acid synthase is introduced and expressed in the microorganism.

19. The method according to embodiment 3, wherein said microorganism lacks the genes encoding for following enzymes i) a N-acetylglycosamine-6-phosphate deacetylase, ii) a N-acetylglucosamine kinase, and iii) a N-acetylneuraminate aldolase.

20. The method according to embodiment 3, wherein in said microorganism the genes encoding for following enzymes i) a N-acetylglycosamine-6-phosphate deacetylase, ii) a N-acetylglucosamine kinase, and iii) a N-acetylneuraminate aldolase are reduced in activity, preferably said genes are deleted or knocked-out.

21. The method according to any one of the embodiments 1 to 20, wherein said microorganism further encodes a protein that facilitates uptake of lactose and lacks enzymes that metabolize lactose.

22. The method according to any one of embodiments 1 to 21, wherein said microorganism is a bacteria, preferably an *Escherichia coli* strain, more preferably an *Escherichia coli* strain which is a K12 strain, even more preferably the *Escherichia coli* K12 strain is *Escherichia coli* MG1655.

23. The method according to any one of embodiments 1 to 21, wherein said microorganism is a yeast.

24. The method according to any one of embodiments 1 to 23, wherein the exogenous precursor is chosen from the group comprising lactose, galactose, beta-galactoside, and alpha-galactoside, such as globotriose (Gal-alpha-1,4Gal-beta-1,4Glc).

25. A microorganism for the production of sialylated compounds, said microorganism-intracellularly converts N-acetylglucosamine-6-phosphate to N-acetylglucosamine, said N-acetylglucosamine to N-acetylmannosamine and said N-acetylmannosamine to N-acetyl-neuraminate; and
   is unable to i) convert N-acetylglucosamine-6-P to glucosamine-6-P, ii) convert N-acetyl-glucosamine to N-acetyl-glucosamine-6-P, and iii) convert N-acetyl-neuraminate to N-acetyl-mannosamine.

26. A microorganism for the production of a sialylated compound, said microorganism being defined in any one of embodiments 2 to 24.

27. A cell culture medium comprising lactose as precursor and the microorganism of any one of embodiments 25 or 26.

28. The method according to one of embodiments 1 to 24, for the production of 3sialyllactose or 6sialyllactose, wherein the microorganism is cultivated at high cell density on a carbon substrate, such as glucose or glycerol, and fed with lactose which is internalized by the lactose permease and sialylated by said recombinant sialyltransferase using the CMP-N-acetyl-neuraminate endogenously generated from N-acetylglucosamine.

29. The method according to any one of embodiments 1 to 24, wherein said sialylated compound is isolated from said culture medium by means of a unit operation selected from the group centrifugation, filtration, microfiltration, ultrafiltration, nanofiltration, ion exchange, electrodialysis, chromatography, simulated moving bed, evaporation, precipitation, crystallization, lyophilization and/or spray drying 30. A sialylated compound produced according to the method described in any one of embodiments 1 to 24, wherein said sialylated compound is purified by centrifugation and/or filtration, ion-exchange, concentration through evaporation or nanofiltration, formulation through crystallization or spraydrying or lyophilization.

31. A sialylated compound produced according to the method described in any one of embodiments 1 to 24, wherein said sialylated compound is added to food formulation, feed formulation, pharmaceutical formulation, cosmetic formulation, or agrochemical formulation.

32. The method according to any one of embodiments 1 to 24, wherein said culture medium comprises any one or more of the following: a monosaccharide, disaccharide, oligosaccharide, polysaccharide, polyol, a complex medium as the main carbon source.

33. The method according to embodiment 32, wherein said main carbon source provides at least 20%, 30%, 40%, 50%, 60%, 70%, 75%, 80%, 85%, 90%, 95%, 98%, 99% or 100% of all required carbon for the growth of said microorganism.

34. The method according to embodiment 32, wherein said monosaccharide is chosen from the group comprising glucose, fructose, galactose, mannose, ribose or arabinose.

35. The method according to embodiment 32, wherein said disaccharide is chosen from the group comprising maltose, sucrose, lactose, trehalose, cellobiose or chitobiose.

36. The method according to embodiment 32, wherein said oligosaccharide is chosen from the group comprising maltotriose, fructo-oligosaccharides, galacto-oligosaccharides, mannan oligosaccharides, isomaltooligosaccharide or glucooligosaccharides.

37. The method according to embodiment 32, wherein said polyol is chosen from the group comprising glycerol.

38. The method according to embodiment 32, wherein said complex medium is chosen from the group comprising molasses, corn steep liquor, peptone, tryptone or yeast extract.

In a preferred aspect, the present invention relates to the following preferred specific embodiments:
1. A method for the production of a sialylated compound in a microorganism, the method comprising:
culturing a microorganism in a culture medium, said culture medium optionally comprising an exogenous precursor,
wherein said microorganism comprises at least one nucleic acid encoding a phosphatase, at least one nucleic acid encoding an N-acetylmannosamine epimerase; and at least one nucleic acid encoding a sialic acid synthase, and wherein said microorganism is unable to i) convert N-acetyl-glucosamine-6-P to glucosamine-6-P, ii) convert N-acetyl-glucosamine to N-acetyl-glucosamine-6-P, and iii) convert N-acetyl-neuraminate to N-acetyl-mannosamine; and
modulating expression in said microorganism of a nucleic acid encoding a HAD-alike phosphatase polypeptide, wherein said HAD-alike phosphatase polypeptide comprises:
at least one of the following motifs:
Motif 1: hDxDx[TV] (SEQ ID NO: 73), or
Motif 2: [GSTDE][DSEN]x(1-2)[hP] x(1-2) [DGTS] (SEQ ID NOs: 74, 75, 76, 77) wherein h means a hydrophobic amino acid (A, I, L, M, F, V, P, G) and x can be any distinct amino acid;
or a homologue or derivative of any one of SEQ ID NOs: 43, 44, 45, 47, 48, 50, 51, 52, 54, 55 or 57 having at least 80%, 81%, 82%, 83%, 84%, 85%, 86%, 87%, 88%, 89%, 90%, 91%, 92%, 93%, 94%, 95%, 96%, 97%, 98%, or 99% overall sequence identity to said polypeptide.

2. The method according to preferred embodiment 1, wherein said HAD-alike polypeptide comprises any one of SEQ ID NOs: 43, 44, 45, 47, 48, 50, 51, 52, 54, 55, 57.

3. Method according to preferred embodiment 1, wherein said modulated expression is effected by introducing and expressing in a microorganism a nucleic acid encoding a HAD-alike polypeptide.

4. Method according to preferred embodiment 1, wherein said modulated expression is effected by the action of a constitutive promoter.

5. The method according to any one of the preceding preferred embodiments, wherein said sialylated compound is selected from the group consisting of N-acetylneuramic acid, sialylated oligosaccharide, sialylated lipids, sialylated protein, sialylated aglycon.

6. The method according to the previous preferred embodiment, wherein said sialylated compound is a sialylated oligosaccharide.

7. The method according to preferred embodiment 8, wherein said sialylated oligosaccharide is sialyllactose.

8. The method according to preferred embodiment 8, wherein said sialylated oligosaccharide is disialyl lacto-N-tetraose.

9. The method according to preferred embodiment 7, wherein said sialylated compound is N-acetylneuraminic acid.

10. The method according to any one of preferred embodiment 1 to 9 wherein said sialylated compound is a sialylated lacto-N-triose, lacto-N-tetraose or a lacto-N-neotetraose, and wherein said microorganism further comprises the activity of a galactosyltransferase (EC 2.4.1.38), preferably said galactosyltransferase originates from the group comprising *Homo sapiens, Bos taurus, Mus mulatta, Gallus gallus, Danio rerio, Helicobacter pylori* and *Haemophilus ducreyi*; and/or said microorganism comprises the activity of a N-acetylglucosaminyltransferase (EC 2.4.1.90), preferably said N-acetylglucosaminyltransferase originates from the group comprising *Bos taurus, Homo sapiens* and *Mus musculus*.

11. The method according to preferred embodiment 12 wherein said microorganism is unable to express the genes coding for UDP sugar hydrolase and galactose-1-phosphate uridylyltransferase.

12. The method according to any one of preferred embodiments 1 to 13, wherein said microorganism produces less than 50%, 40%, 30%, 20%, 10%, 5%, 2% extracellular N-acetylglucosamine and/or N-acetylmannosamine than sialylated compound and/or said micro-organism produces equal or more than 50%, 60%, 70%, 80%, 90%, 95%, 98% sialylated compound on total carbohydrate 13. A method for producing a sialylated oligosaccharide, comprising:
a) culturing a microorganism according to the method of any one of preferred embodiments 1 to 12, and wherein said microorganism produces internally, activated N-acetylneuraminate as donor substrate for a sialyltransferase; and
b) culturing said microorganism in a culture medium comprising an exogenous precursor selected from the group consisting of lactose, N-acetyllactosamine, lacto-N-biose, galactose, beta-galactoside, and alpha-galactoside such as but not limited to globotriose (Gal-alpha-1,4Gal-beta-1, 4Glc)galactose, wherein active uptake into the microorganism of said exogenous precursor occurs and wherein said exogenous precursor is the acceptor substrate for said sialytransferase for producing the sialylated oligosaccharide.

14. The method according to preferred embodiment 1, wherein any one or more of said N-acetylmannosamine epimerase and sialic acid synthase is overexpressed in the microorganism.

15. The method according to preferred embodiment 1, wherein any one or more of said N-acetylmannosamine epimerase and sialic acid synthase is introduced and expressed in the microorganism.

16. The method according to preferred embodiment 1, wherein said microorganism lacks the genes encoding for following enzymes i) a N-acetylglycosamine-6-phosphate deacetylase, ii) a N-acetylglucosamine kinase, and iii) a N-acetylneuraminate aldolase.

17. The method according to preferred embodiment 1, wherein in said microorganism the genes encoding for following enzymes i) a N-acetylglycosamine-6-phosphate deacetylase, ii) a N-acetylglucosamine kinase, and iii) a N-acetylneuraminate aldolase are reduced in activity, preferably said genes are deleted or knocked-out.

18. The method according to any one of the preferred embodiments 1 to 17, wherein said microorganism further encodes a protein that facilitates uptake of lactose and lacks enzymes that metabolize lactose.

19. The method according to any one of preferred embodiments 1 to 18, wherein said microorganism is a bacterium, preferably an *Escherichia coli* strain, more preferably an *Escherichia coli* strain which is a K12 strain, even more preferably the *Escherichia coli* K12 strain is *Escherichia coli* MG1655.

20. The method according to any one of preferred embodiments 1 to 18, wherein said microorganism is a yeast.

21. The method according to any one of preferred embodiments 1 to 20, wherein the exogenous precursor is chosen from the group comprising lactose, galactose, beta-galactoside, and alpha-galactoside, such as globotriose (Gal-alpha-1,4Gal-beta-1,4Glc).

22. Microorganism, obtainable by a method according to any one of claims 1 to 21, wherein said microorganism comprises a recombinant nucleic acid encoding a HAD-alike polypeptide.

23. A microorganism for the production of sialylated compounds wherein said microorganism comprises at least one nucleic acid encoding a phosphatase, at least one nucleic acid encoding an N-acetylmannosamine epimerase; and at least one nucleic acid encoding a sialic acid synthase, and wherein said microorganism is unable to i) convert N-acetyl-glucosamine-6-P to glucosamine-6-P, ii) convert N-acetyl-glucosamine to N-acetyl-glucosamine-6-P, and iii) convert N-acetyl-neuraminate to N-acetyl-mannosamine; characterised in that said microorganism comprises a modulated expression of a nucleic acid encoding a HAD-alike phosphatase polypeptide as defined in preferred embodiment 1.

24. Construct comprising:
(i) nucleic acid encoding a HAD-alike polypeptide as defined in preferred embodiment 1 or 2;
(ii) one or more control sequences capable of driving expression of the nucleic acid sequence of (i); and optionally
(iii) a transcription termination sequence.

25. Construct according to preferred embodiment 24, wherein one of said control sequences is a constitutive promoter.

26. Use of a construct according to preferred embodiment 24 or 25 in a method for producing sialylated compounds.

27. A sialylated compound produced according to the method described in any one of preferred embodiments 1 to 21, wherein said sialylated compound is added to food formulation, feed formulation, pharmaceutical formulation, cosmetic formulation, or agrochemical formulation.

28. A microorganism for the production of a sialylated compound, said microorganism being defined in any one of embodiments 2 to 21.

29. A cell culture medium comprising lactose as precursor and the microorganism of any one of embodiments 22, 23 or 28.

30. The method according to one of embodiments 1 to 21, for the production of 3sialyllactose or 6sialyllactose, wherein the microorganism is cultivated at high cell density on a carbon substrate, such as glucose or glycerol or sucrose, and fed with lactose which is internalized by the lactose permease and sialylated by said recombinant sialyltransferase using the CMP-N-acetyl-neuraminate endogenously generated from N-acetylglucosamine.

31. The method according to any one of embodiments 1 to 21, wherein said sialylated compound is isolated from said culture medium by means of a unit operation selected from the group centrifugation, filtration, microfiltration, ultrafiltration, nanofiltration, ion exchange, electrodialysis, chromatography, simulated moving bed, evaporation, precipitation, crystallization, lyophilization and/or spray drying 32. A sialylated compound produced according to the method described in any one of embodiments 1 to 21, wherein said sialylated compound is purified by centrifugation and/or filtration, ion-exchange, concentration through evaporation or nanofiltration, formulation through crystallization or spraydrying or lyophilization.

33. A sialylated compound produced according to the method described in any one of embodiments 1 to 21, wherein said sialylated compound is added to food formulation, feed formulation, pharmaceutical formulation, cosmetic formulation, or agrochemical formulation.

34. The method according to any one of embodiments 1 to 21, wherein said culture medium comprises any one or more of the following: a monosaccharide, disaccharide, oligosaccharide, polysaccharide, polyol, a complex medium as the main carbon source.

35. The method according to embodiment 34, wherein said main carbon source provides at least 20%, 30%, 40%, 50%, 60%, 70%, 75%, 80%, 85%, 90%, 95%, 98%, 99% or 100% of all required carbon for the growth of said microorganism.

36. The method according to embodiment 34, wherein said monosaccharide is chosen from the group comprising glucose, fructose, galactose, mannose, ribose or arabinose.

37. The method according to embodiment 34, wherein said disaccharide is chosen from the group comprising maltose, sucrose, lactose, trehalose, cellobiose or chitobiose.

38. The method according to embodiment 34, wherein said oligosaccharide is chosen from the group comprising maltotriose, fructo-oligosaccharides, galacto-oligosaccharides, mannan oligosaccharides, isomaltooligosaccharide or glucooligosaccharides.

39. The method according to embodiment 34, wherein said polyol is chosen from the group comprising glycerol.

40. The method according to embodiment 34, wherein said complex medium is chosen from the group comprising molasses, corn steep liquor, peptone, tryptone or yeast extract.

The following drawings and examples will serve as further illustration and clarification of the present invention and are not intended to be limiting.

BRIEF DESCRIPTION OF THE DRAWINGS

FIG. 1 shows an exemplary pathway as used in example 2 for the production of sialic acid according to the present invention.

FIG. 6 shows the parts of an alignment of the phosphatases tested in the examples.

Example 1: Materials and Methods

Figure 1A:
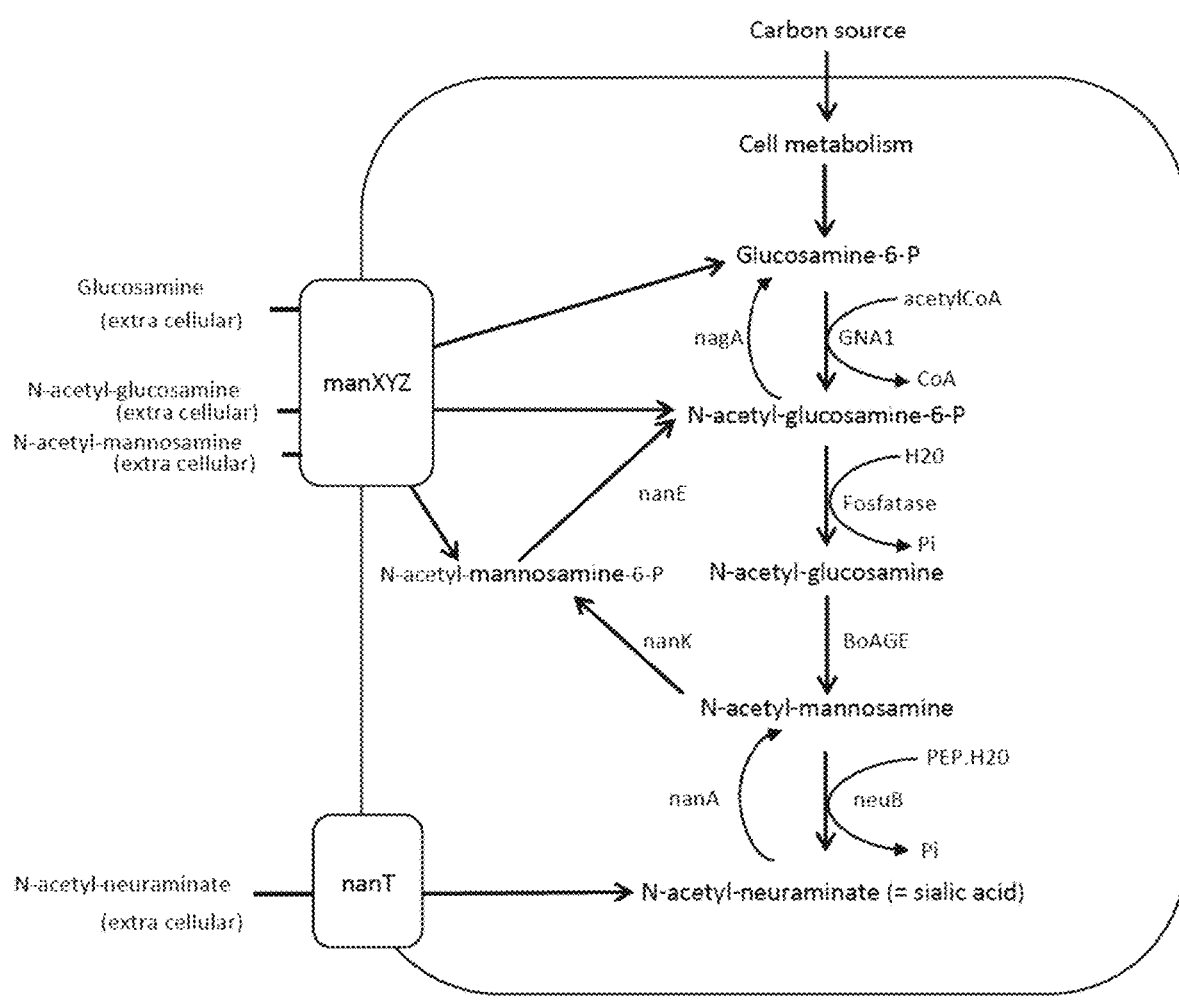
FIG. 1A shows the pathway without all KO and overexpression signs.

Method and Materials *Escherichia coli*
Media

Three different media were used, namely a rich Luria Broth (LB), a minimal medium for shake flask (MMsf) and a minimal medium for fermentation (MMf). Both minimal media use a trace element mix.

Trace element mix consisted of 3.6 g/L FeCl2.4H20, 5 g/L CaCl2.2H20, 1.3 g/L MnCl2.2H20, 0.38 g/L CuCl2.2H20, 0.5 g/L CoCl2.6H20, 0.94 g/L ZnCl2, 0.0311 g/L H3B04, 0.4 g/L Na2EDTA.2H20 and 1.01 g/L thiamine.HCl. The molybdate solution contained 0.967 g/L Na2Mo04.2H20. The selenium solution contained 42 g/L Se02.

The Luria Broth (LB) medium consisted of 1% tryptone peptone (Difco, Erembodegem, Belgium), 0.5% yeast extract (Difco) and 0.5% sodium chloride (VWR, Leuven, Belgium).

Luria Broth agar (LBA) plates consisted of the LB media, with 12 g/L agar (Difco, Erembodegem, Belgium) added.

Minimal medium for shake flask experiments (MMsf) contained 2.00 g/L NH4Cl, 5.00 g/L (NH4)2S04, 2.993 g/L KH2PO4, 7.315 g/L K2HP04, 8.372 g/L MOPS, 0.5 g/L NaCl, 0.5 g/L MgSO4.7H20. A carbon source chosen from, but not limited to glucose, fructose, maltose, glycerol and maltotriose, was used. The concentration was default 15 g/L, but this was subject to change depending on the experiment. 1 mL/L trace element mix, 100 μL/L molybdate solution, and 1 mL/L selenium solution. The medium was set to a pH of 7 with 1M KOH. Depending on the experiment lactose could be added as a precursor.

The minimal medium for fermentations contained 6.75 g/L NH4Cl, 1.25 g/L (NH4)2S04, 1.15 g/L KH2PO4 (low phosphate medium) or 2.93 g/L KH2PO4 and 7.31 g/L KH2PO4 (high phosphate medium), 0.5 g/L NaCl, 0.5 g/L MgSO4.7H20, a carbon source including but not limited to glucose, sucrose, fructose, maltose, glycerol and maltotriose, 1 mL/L trace element mix, 100 μL/L molybdate solution, and 1 mL/L selenium solution with the same composition as described above.

Complex medium, e.g. LB, was sterilized by autoclaving (121° C., 21) and minimal medium (MMsf and MMf) by filtration (0.22 μm Sartorius). If necessary the medium was made selective by adding an antibiotic (e.g. ampicillin (100 mg/L), chloramphenicol (20 mg/L), carbenicillin (100 mg/L), spectinomycin (40 mg/L) and/or kanamycin (50 mg/L)).

Strains

*Escherichia coli* MG1655 [lambda⁻, F⁻, rph-1] was obtained from *Coli* Genetic Stock Center (US), CGSC Strain #: 7740 in March 2007. Mutant strains were constructed using the homologous recombination, as described by Datsenko and Wanner (PNAS 97 (2000), 6640-6645).

Plasmids pKD46 (Red helper plasmid, Ampicillin resistance), pKD3 (contains an FRT-flanked chloramphenicol resistance (cat) gene), pKD4 (contains an FRT-flanked kanamycin resistance (kan) gene), and pCP20 (expresses FLP recombinase activity) plasmids were obtained from Prof. R. Cunin (Vrije Universiteit Brussel, Belgium in 2007).

Plasmid pCX-CjneuB was constructed using Gibson assembly. The gene CjneuB1 was expressed using the expression vector as described by Aerts et. al (Eng. Life Sci. 2011, 11, No. 1, 10-19).

Plasmid pCX-CjneuB-NmneuA-Pdbst was constructed using Gibson assembly. The genes CjneuB1, NmneuA and Pdbst were expressed using the expression vector as described by Aerts et. al (Eng. Life Sci. 2011, 11, No. 1, 10-19).

Plasmids for phosphatase expression were constructed using Golden Gate assembly. The phosphatases (EcAphA, EcCof, EcHisB, EcOtsB, EcSurE, EcYaed, EcYcjU, EcYedP, EcYfbT, EcYidA, EcYigB, EcYihX, EcYniC, EcYqaB, EcYrbL and PsMupP) were expressed using promoters apFAB87 and apFAB346 and UTRs gene10_SD2-junction_HisHA and UTR1 AATTCGCCGGAGGGATAT-TAAAAtgaatggaaaattgAAACATCTTAATCATGCTA-AGGAGGTTTTCTAATG (SEQ ID NO: 41). All promoters and UTRs except UTR1 are described by Mutalik et. al (Nat. Methods 2013, No. 10, 354-360). Also phosphatases EcAppA, EcGph, EcSerB, EcNagD, EcYbhA, EcYbiV, EcYbjL, EcYfbR, EcYieH, EcYjgL, Ec YjjG, EcYrfG, EcYbiU, ScDOG1 and BsAraL are expressed using the same promoters and UTRs.

Plasmid pBR322-NmneuB was constructed using a pBR322 vector via Golden Gate assembly. The promoter and UTR used for the expression of NmNeuB are promoter apFAB299 and UTR galE_SD2-junction_BCD12. Plasmid pSC101-NmneuA-Pdbst was constructed using a pSC101 vector via Golden Gate assembly. The promoters and UTRs used for the expression of NmneuA are promoter apFAB37 and UTR galE_SD2-junction_BCD18. The promoters and UTRs used for the expression of Pdbst are promoter apFAB339 and UTR galE_SD2-junction_BCD12. All promoters and UTRs are described by Mutalik et. al (Nat. Methods 2013, No. 10, 354-360).

Plasmids were maintained in the host *E. coli* DH5alpha (F, phi80dlacZdeltaM15, delta(lacZYA-argF) U169, deoR, recA1, endA1, hsdR17(rk⁻, mk⁺), phoA, supE44, lambda, thi-1, gyrA96, relA1). Bought from Invitrogen.

Gene Disruptions

Gene disruptions as well as gene introductions were performed using the technique published by Datsenko and Wanner (PNAS 97 (2000), 6640-6645). This technique is based on antibiotic selection after homologous recombination performed by lambda Red recombinase. Subsequent catalysis of a flippase recombinase ensures removal of the antibiotic selection cassette in the final production strain.

In Table A the necessary primers for the construction of the gene disruption cassette are listed.

TABLE A

Lists of primers to construct disruption cassette for the target gene.

| Gene target | Fw primer | Rv primer |
|---|---|---|
| lacZYA | GCTGAACTTGTAGGCCTGATAAGCGCAGCGTATCAGGCAATTTTTATAATCTTCATTTAAATGGCGCGC (SEQ ID NO: 1) | GCGCAACGCAATTAATGTGAGTTAGCTCACTCATTAGGCACCCCAGGCTTCGCCTACCTGTGACGGAAG (SEQ ID NO: 2) |
| nagABCDE | CGCTTAAAGATGCCTAATCCGCCAACGGCTTACATTTTACTTATTGAGGTGAATAGTGTAGGCTGGAGCTGCTTC (SEQ ID NO: 3) | GGCGTTTGTCATCAGAGCCAACCACGTCCGCAGACGTGGTTGCTATCATATGAATATCCTCCTTAG (SEQ ID NO: 4) |
| nanATEK | TAATGCGCCGCCAGTAAATCAACATGAAATGCCGCTGGCTCCGTGTAGGCTGGAGCTGCTTC (SEQ ID NO: 5) | CCAACAACAAGCACTGGATAAAGCGAGTCTGCGTCGCCTGGTTCAGTTCACATATGAATATCCTCCTTAG (SEQ ID NO: 6) |
| manXYZ | AAAATACATCTGGCACGTTGAGGTGTTAACGATAATAAGGAGGTAGCAAGTGTAGGCTGGAGCTGCTTC (SEQ ID NO: 7) | CCTCCAGATAAAAAAACGGGGCCAAAAGGCCCCGGTAGTGTACAACAGTCCATATGAATATCCTCCTTAG (SEQ ID NO: 8) |

For the genomic integration of the necessary genes into the production hosts genome based on the same technique used for the gene disruption, discussed before, with specific alterations to the disruption cassette. Between a homology site and the FRT site of the disruption cassette, the to be integrated constructed is located. This allows for elegant integration of the constructed in the region dictated by the homology sites.

Using this workflow, a direct gene disruption and genomic integration is possible. Primers that were used for target integration are at specific sites are listed in Table B.

TABLE B

Primers used for genomic integration

| Integration location | Fw primer | Rv primer |
|---|---|---|
| nagABCDE | GTTTGGCGTTTGTCATCAGAGCCAACCACGTCCGCAGACGTGGTTGCTATGTGTAGGCTGGAGCTGCTTC (SEQ ID NO: 9) | TTGTCATTGTTGGATGCGACGCTCAAGCGTCGCATCAGGCATAAAGCAGACTTAAGCGACTTCATTCACC (SEQ ID NO: 10) |
| nanATEK | CATGGCGGTAATGCGCCGCCAGTAAATCAACATGAAATGCCGCTGGCTCCGTGTAGGCTGGAGCTGCTTC (SEQ ID NO: 11) | CCAACAACAAGCACTGGATAAAGCGAGTCTGCGTCGCCTGGTTCAGTTCACTTAAGCGACTTCATTCACC (SEQ ID NO: 12) |
| manXYZ | AAAATACATCTGGCACGTTGAGGTGTTAACGATAATAAAGGAGGTAGCAAGTGTAGGCTGGAGCTGCTTC (SEQ ID NO: 13) | CCTCCAGATAAAAAAACGGGGCCAAAAGGCCCCGGTAGTGTACAACAGTCCTTAAGCGACTTCATTCACC (SEQ ID NO: 14) |
| lacZYA | GCGCAACGCAATTAATGTGAGTTAGCTCACTCATTAGGCACCCCAGGCTTGTGTAGGCTGGAGCTGCTTC (SEQ ID NO: 15) | GCTGAACTTGTAGGCCTGATAAGCGCAGCGTATCAGGCAATTTTTATAATCTTAAGCGACTTCATTCACC (SEQ ID NO: 16) |
| atpI-gidB | CAAAAAGCGGTCAAATTATACGGTGCGCCCCCGTGATTTCAAACAATAAGGTGTAGGCTGGAGCTGCTTC (SEQ ID NO: 17) | ATAACGTGGCTTTTTTTGGTAAGCAGAAAAATAAGTCATTAGTGAAAATATCTTAAGCGACTTCATTCACC (SEQ ID NO: 18) |

Clones carrying the temperature sensitive pKD46 helper plasmid were grown in 10 mL LB media with ampicillin (100 mg/L) and L-arabinose (10 mM) at 30° C. to an $OD_{600nm}$ of 0.6. The cells were made electro competent by sequential washing, once with 50 mL, and once with 1 mL ice-cold deionized water. Next, the cells were resuspended in 50 μL of ice-cold water. Finally, 10-100 ng of disruption/integration cassette was added to 50 μL of the washed cell solution for electroporation. Electroporation was performed using a Gene Pulser (trademark of BioRad) (600 Ohm 25 μFD, and 250 V).

After electroporation, cells were resuscitated in 1 mL LB media for 1 h at 37° C., and finally plated out onto LB-agar containing 25 mg/L of chloramphenicol or 50 mg/L of kanamycin to select antibiotic resistant transformants. The selected mutants were verified by PCR with primers upstream and downstream of the modified region and were subsequently grown on LB-agar at 42° C. for the loss of the pKD46 helper plasmid. The mutants were finally tested for ampicillin sensitivity.

The selected mutants (chloramphenicol or kanamycin resistant) were transformed with pCP20 plasmid, which is an ampicillin and chloramphenicol resistant plasmid that shows temperature-sensitive replication and thermal induction of FLP synthesis. The ampicillin-resistant transformants were selected at 30° C., after which a few were colony purified in LB at 42° C. and then tested for loss of all antibiotic resistances and thus also of the FLP helper plasmid. The gene disruptions and/or gene integration are checked with control primers and sequenced. These primers are listed in Table C.

TABLE C

Primers to validate either gene disruption and/or genomic integration for specific gene targets.

| Gene targets | Fw primer | Rv primer |
|---|---|---|
| lacZYA | CAGGTTTCCCGACTGGAAAG (SEQ ID NO: 19) | TGTGCGTCGTTGGGCTGATG (SEQ ID NO: 20) |
| nagABCDE | CGCTTGTCATTGTTGGATGC (SEQ ID NO: 21) | GCTGACAAAGTGCGATTTGTTC (SEQ ID NO: 22) |
| nanATEK | GTCGCCCTGTAATTCGTAAC (SEQ ID NO: 23) | CTTTCGGTCAGACCACCAAC (SEQ ID NO: 24) |
| manXYZ | ACGCCTCTGATTTGGCAAAG (SEQ ID NO: 25) | AGCCAGTGCGCTTAATAACC (SEQ ID NO: 26) |
| atpl-gidB | GCTGAACAGCAATCCACTTG (SEQ ID NO: 27) | TGAACGATATGGTGAGCTGG (SEQ ID NO: 28) |

Heterologous and Homologous Expression

Genes that needed to be expressed, be it from a plasmid or from the genome were synthetically synthetized with one of the following companies: DNA2.0, Gen9 or IDT.

*Escherichia coli* native genes, as e.g., phosphatases, were picked from the *E. coli* K-12 MG1655 genome. The origin of other genes are indicated in the relevant table.

Expression could be further facilitated by optimizing the codon usage to the codon usage of the expression host. Gene were optimized using the tools of the supplier.

Cultivation Conditions

A preculture of 96 well microtiter plate experiments was started from single colony on a LB plate, in 175 µL and was incubated for 8 h at 37° C. on an orbital shaker at 800 rpm. This culture was used as inoculum for a 96 well microtiter plate, with 175 µL MMsf medium by diluting 300×. These cultures in turn, were used as a preculture for the final experiment in a 96 well plate, again by diluting 300×. The 96 well plate can either be microtiter plate, with a culture volume of 175 µL or a 24 well deepwell plate with a culture volume of 3 mL.

A preculture for shake flask experiments was started from a single colony on a LB-plate, in 5 mL LB medium and was incubated for 8 h at 37° C. on an orbital shaker at 200 rpm. From this culture, 1 mL was transferred to 100 mL minimal medium (MMsf) in a 500 mL shake flask and incubated at 37° C. on an orbital shaker at 200 rpm. This setup is used for shake flask experiments.

A shake flask experiment grown for 16 h could also be used as an inoculum for a bioreactor. 4% of this cell solution was to inoculate a 2 L Biostat Dcu-B with a 4 L working volume, controlled by MFCS control software (Sartorius Stedim Biotech, Melsungen, Germany). Culturing condition were set to 37° C., 800 rpm stirring, and a gas flow rate of 1.5 L/min. The pH was controlled at 7 using 0.5 M H2SO4 and 25% NH$_4$OH. The exhaust gas was cooled. 10% solution of silicone antifoaming agent was added when foaming raised during the fermentation (approximately 10 6 L). The use of an inducer is not required as all genes are constitutively expressed.

Material and Methods *Saccharomyces cerevisae*

Media

Strains are grown on Synthetic Defined yeast medium with Complete Supplement Mixture (SD CSM) or CSM drop-out (SD CSM-Ura) containing 6.7 g/L Yeast Nitrogen Base without amino acids (YNB w/o AA, Difco), 20 g/L agar (Difco) (solid cultures), 22 g/L glucose monohydrate or 20 g/L lactose and 0.79 g/L CSM or 0.77 g/L CSM-Ura (MP Biomedicals).

Strains

*Saccharomyces cerevisiae* BY4742 created by Bachmann et al. (Yeast (1998) 14:115-32) was used available in the Euroscarf culture collection. All mutant strains were created by homologous recombination or plasmid transformation using the method of Gietz (Yeast 11:355-360, 1995). *Kluyveromyces marxianus lactis* is available at the LMG culture collection (Ghent, Belgium).

Plasmids

Yeast expression plasmid p2a_2µ_sia_GFA1 (Chan 2013 (Plasmid 70 (2013) 2-17)) was used for expression of foreign genes in *Saccharomyces cerevisiae*. This plasmid contains an ampicillin resistance gene and a bacterial origin of replication to allow for selection and maintenance in *E. coli*. The plasmid further contains the 2p yeast ori and the Ura3 selection marker for selection and maintenance in yeast. Finally, the plasmid can contain a beta-galactosidase expression cassette. Next, this plasmid also contains a N-acetylglucosamine-2-epimerase (for example from *Bacteroides ovatus* (BoAGE)) and a sialic acid synthase (for example from *Campylobacter jejuni* (CjneuB)). Finally, it also contains the fructose-6-P-aminotransferase from *Saccharomyces cerevisiae*, ScGFA1.

Yeast expression plasmid p2a_2µ_sia_glmS is based on p2a_2µ_sia but modified in a way that also glmS*54 (fructose-6-P-aminotransferase from *Escherichia coli*) is expressed.

Yeast expression plasmids p2a_2µ_sia_glmS_phospha is based on p2a_2µ_sia_glmS but modified in a way that also EcAphA (SEQ ID NO: 42), EcCof (SEQ ID NO: 43), EcHisB (SEQ ID NO: 44), EcOtsB (SEQ ID NO: 45), EcSurE (SEQ ID NO: 46), EcYaed (SEQ ID NO: 47), EcYcjU (SEQ ID NO: 48), EcYedP (SEQ ID NO: 49), EcYfbT (SEQ ID NO: 50), EcYidA (SEQ ID NO: 51), EcYigB (SEQ ID NO: 52), EcYihX (SEQ ID NO: 53), EcYniC (SEQ ID NO: 54), EcYqaB (SEQ ID NO: 55), EcYrbL (SEQ ID NO: 56), PsMupP (SEQ ID NO: 57), EcAppA (SEQ ID NO: 58), EcGph (SEQ ID NO: 59), EcSerB (SEQ ID NO: 60), EcNagD (SEQ ID NO: 61), EcYbhA (SEQ ID NO: 62), EcYbiV (SEQ ID NO: 63), EcYbjL (SEQ ID NO: 64), EcYfbR (SEQ ID NO: 65), EcYieH (SEQ ID NO: 66), EcYjgL (SEQ ID NO: 67), Ec YjjG (SEQ ID NO: 68), EcYrfG (SEQ ID NO: 69), EcYbiU (SEQ ID NO: 70), ScDOG1 (SEQ ID NO: 71) and BsAraL (SEQ ID NO: 72) are expressed.

Yeast expression plasmid p2a_21_SL-glmS is based on p2a_21_sia but modified in a way that also KlLAC12 (lactose permease from *Kluyveromyces lactis*), NmneuA (CMP-sialic acid synthase from *Neisseria meningitides*) and Pdbst (sialyltransferase *Photobacterium damselae*) are expressed.

Plasmids were maintained in the host *E. coli* DH5alpha (F, phi80dlacZdeltaM15, delta(lacZYA-argF)U169, deoR, recA1, endA1, hsdR17(rk⁻, mk⁺), phoA, supE44, lambda, thi-1, gyrA96, relA1). Bought from Invitrogen.

Gene Expression Promoters

Genes are expressed using synthetic constitutive promoters, as described in by Blazeck (Biotechnology and Bioengineering, Vol. 109, No. 11, 2012).

Heterologous and Homologous Expression

Genes that needed to be expressed, be it from a plasmid or from the genome were synthetically synthetized with one of the following companies: DNA2.0, Gen9 or IDT Expression could be further facilitated by optimizing the codon usage to the codon usage of the expression host. Gene were optimized using the tools of the supplier.

Cultivations Conditions

In general, yeast strains were initially grown on SD CSM plates to obtain single colonies. These plates were grown for 2-3 days at 30° C.

Starting from a single colony, a preculture was grown over night in 5 mL at 30° C., shaking at 200 rpm. Subsequent 500 mL shake flask experiments were inoculated with 2% of this preculture, in 100 mL media. These shake flasks were incubated at 30° C. with an orbital shaking of 200 rpm. The use of an inducer is not required as all genes are constitutively expressed.

Material and Methods *Bacillus subtilis*

Media

Two different media are used, namely a rich Luria Broth (LB), a minimal medium for shake flask (MMsf). The minimal medium uses a trace element mix.

Trace element mix consisted of 0.735 g/L CaCl2.2H20, 0.1 g/L MnCl2.2H20, 0.033 g/L CuCl2.2H20, 0.06 g/L CoCl2.6H20, 0.17 g/L ZnCl2, XX g/L H3B04, XX g/L Na2EDTA.2H20 and 0.06 g/L Na2Mo04. The Fe-citrate solution contained 0.135 g/L FeCl3.6H20, 1 g/L Na-Citrate (Hoch 1973 PMC1212887).

The Luria Broth (LB) medium consisted of 1% tryptone peptone (Difco, Erembodegem, Belgium), 0.5% yeast extract (Difco) and 0.5% sodium chloride (VWR, Leuven, Belgium).

Luria Broth agar (LBA) plates consisted of the LB media, with 12 g/L agar (Difco, Erembodegem, Belgium) added.

Minimal medium for shake flask experiments (MMsf) contains 2 g/L (NH4)2S04, 7.5 g/L KH2P04, 17.5 g/L K2HP04, 1.25 g/L Na-Citrate, 0.25 g/L MgS04.7H20, 0.05 g/L tryptophan, from 10 up to 30 g/L glucose or another carbon source including but not limited to glucose, fructose, maltose, glycerol and maltotriose, 10 mL/L trace element mix, and 10 mL/L Fe-citrate solution. The medium was set to a pH of 7 with 1M KOH.

Complex medium, e.g. LB, was sterilized by autoclaving (121° C., 21) and minimal medium (MMsf) by filtration (0.22 μm Sartorius). If necessary, the medium was made selective by adding an antibiotic (e.g. zeocin (20 mg/L)).

Strains

*Bacillus subtilis* 168, available at *Bacillus* Genetic Stock Center (Ohio, USA).

Plasmids and Gene Overexpression

Plasmids for gene deletion via Cre/lox are constructed as described by Yan et al. (Appl & environm microbial, sept 2008, p5556-5562).

Expression vectors can be found at Mobitec (Germany), or at ATCC (ATCC® number 87056). The genes BsglmS, ScGNA1 and CjneuB are cloned in these expression vectors. A suitable promoter for expression can be derived from the part repository (iGem): sequence id: BBa_K143012, BBa_K823000, BBa_K823002 or BBa_K823003. Cloning can be performed using Gibson Assembly, Golden Gate assembly, Cliva assembly, LCR or restriction ligation.

Plasmids are maintained in the host *E. coli* DH5alpha (F⁻, phi 80dlacZdeltaM15, delta(lacZYA-argF)U169, deoR, recA1, endA1, hsdR17(rk⁻, mk⁺), phoA, supE44, lambda, thi-1, gyrA96, re/A1). Bought from Invitrogen.

Gene Disruptions

Disrupting of genes is done via homologous recombination with linear DNA and transformation via the electroporation as described by Xue et al. (*J. microb. Meth*. 34 (1999) 183-191). The method of gene knock-outs is described by Liu et al. (*Metab. Engine*. 24 (2014) 61-69). This method uses 1000 bp homologies up- and downstream of the target gene. The homologies to be used in this invention, are listed in table D. After the modification, the mutants are verified using primers upstream and downstream of the modified region. These primers are given in table E. Next, the modification is confirmed by sequencing (performed at LGC Genomics (LGC group, Germany)).

TABLE D

| Gene to be disrupted | Upstream homology | Downstream homology |
|---|---|---|
| nagA-nagB | Gactgcaagatttcggcctgggcggacgggaat | Aaggaacatgctgacttatgaatatcaataaaca |
| | cgtcagttttgtaatttctgtatcaatgattttcat | atcgcctattccgatttactatcagattatggagca |
| | ggtctcttcctcaagtccgagccggtcgtattgct | attaaaaacccaaattaagaacggagagctgcag |
| | tgccctgctcccagagttcaagattcatgacaat | ccggatatgcctcttccttctgagcgcgaatatgcc |
| | cgtgattcgtttattgcttctgaccgcgccagcgc | gaacaattcgggatcagccggatgacagttcgcc |
| | caaatagcgtcatcacattgataatgccaaggcc | aggcgctttctaatttagttaatgaaggcttgctct |
| | cctgatcctcaagaaggtgctcaattaattccgga | atcgcctgaaagggcggggcacctttgtcagcaa |
| | gcgtttcccacaagagtatcctgatcctcctgccg | gccaaaaatggaacaagcacttcaagggctgaca |
| | tatttcaacgcaatcatcggcaacaaggcgatgc | agctttaccgaggatatgaaaagccgcgggatga |
| | cctcttttcacaagctctagcgctgtttcgcttttc | caccgggcagcaggctcattgattatcagcttatt |
| | cgacgccgcttttttcctgtgatcagcacgccgac | gattcaactgaggagctcgcggctatattaggctg |
| | accatatatatcgacaagaacgccatgaattgct | cgggcacccctcctctatccataaaatcactcggg |
| | gtggtaggcgccagcctgctctcaaggaagttgg | tgcggctggcaaatgatattccgatggcgattgag |
| | ttaaacggcttgacagtcttgtcgttttcagcggc | tcctcacatattccgtttgagcttgcgggtgaattg |

TABLE D-continued

| Gene to be disrupted | Upstream homology | Downstream homology |
|---|---|---|
| | gatctgaggacaggcaccccattttctcggagg<br>cgtcaatcagctcctgcgggatgggcatatctct<br>agaaagaataatagctggtgttacatcagtgcac<br>agagaatccattcgctgcttttctcctcttcagga<br>agctgttcaaagaaagaaagctctgttttccga<br>gaagctgcacgcgctccctcgggtaatatgtaaa<br>atatccggcaatttcaatacctggtcttgataggt<br>cactcattgtaatcgggcggttaattccttcttctc<br>cgctgattaattccaaattgaactgttccattacg<br>tcttttgtgcgaaccttttgccacgatatgttcctcc<br>tgttccgggctgccccgagcttgctcacaatactt<br>tcattttatcactttcgggcttgaacctaaaacag<br>attttataaaaggggggaaaacacctcagctggt<br>ctagatcactagtctgaaaaagagtaaaataaa<br>ggtattcaaattccagaaaggcggatcatct<br>(SEQ ID NO: 33) | aacgaatcgcattttcagtcgtcgatctatgatcat<br>attgaaaggtacaacagcataccgatttcccgtgc<br>aaaacaggagcttgagccaagcgctgccaccacg<br>gaagaagcgaatattcttggtattcaaaagggag<br>cgcctgtcctattaattaaacgaacaacatatctgc<br>agaacggaactgcttttgagcatgcaaaatccgta<br>tacagaggcgaccgttatacatttgtccactatatg<br>gatcgtctttcataaaaaaagcctccaaccctttt<br>aaggattggagacatggcgaaaatcaaactggtc<br>tggtgccggacgatatgtttcttttttcgtcttgaac<br>ttccagatcggtgatttcgttttgccgttaaaactgt<br>cttccactataatgtaccaataataaacagactgc<br>ggttcaagatgatcccagcggaattcagctgtgtc<br>cccgctcttcacttgctcccgttttccgagctcttca<br>ttggtatatacgtta (SEQ ID NO: 34) |
| gamA | Tggcggacatggaataaatcacaaacgacaaa<br>gatgacgccggcaagaatagagttaatcaaata<br>gagcacgggcgcaacgaacaagaaagaaaact<br>caaccggttctgtaattccggtcagcatagatgt<br>gagcgccgcagaaatcatcacgccggagatcat<br>ttttttcttttccggacgcgcggtatggataatggc<br>aagagcaacggccggcagacagaaaatcatgt<br>aagggaaatcccccatcataaagcgcccggctg<br>tcgggtctcccgcgaaaaaccttgtcaggtcgcc<br>ggttacggtgttgcctgttgatgggtctgtgtattc<br>tcccatcataaaatagaaaggcgtataaaaaat<br>atgatgcaggccaaaaggaatcagcaaacgat<br>agatcgttgcataaaagaacaggccgactgttg<br>aatcggcaattaaactgctggctgcgttaattcc<br>gttttggatcagcggccaaacgaatgagaaaat<br>gacgccgatcaccaatgaactgacggaagtaat<br>gatcgggacaaagcgttttccagagaaaaatcc<br>aaggaccggatgcagctcgattgatgaaaatcg<br>cttatataaataggcggcgagaagcccgataat<br>gattcctccgaaaaccccccatatcaatcaggtgc<br>tcggctccttcatacggaggctgaaggccgagta<br>attttcccatattgtcgagggtgacggttaaaatt<br>aagtatccgatgacagcggcaagtccggctaca<br>ccttctccgccggctaatccgatcgcgaccccca<br>cggcgaaaatcagcggaaggttatcgaatacaa<br>cgccgcccgcatccttataataagggatgttcagt<br>aaatccttgtctccgaaacggagcaaaagacct<br>gctgccggcaggacggcaaccggagtcatcaac<br>gcgcggccaagctgctgcagaatttgaaatgcct<br>ttttaaacatgacagtctccttttattgtg (SEQ ID NO: 35) | Gtgacacccccctcaaagagatagacaagcaccat<br>atttgttatgaccaatttatgatacttgtcattacga<br>atttagcaccgcccttatcaaactgtcaatattaat<br>ttctgaaaatttgttataaaagaaggatacaaatc<br>tttcatattgggagggcaaatggtattatggtctca<br>atgaaaaagaacggattgcatacagaatgggga<br>gaatgaaatgacagctttatattctgttatcaagtt<br>taaatcattgagttaattaaatcgggcaaatatc<br>aggcgaatgatcagctgccgacggagagtgagtt<br>ttgcgaacaatatgatgtcagcagaacaactgtga<br>gactggctctgcagcagctagagcttgagggatat<br>attaaaagaattcaaggaaaagggacatttgtat<br>cggcggccaaaatacaaacgccgattccgcataa<br>gattacgagcttttgcagaacaaatgagaggacttc<br>gttctgaatcaaaagtgcttgagcttgtggtgattc<br>ctgccgatcattccatcgccgagcttttgaaaatga<br>aagagaatgaacctgtcaacaagcttgtcagagt<br>cagatacgccgagggggaacctttgcagtatcat<br>acctcatatattccctggaaggcggcaccggggct<br>ggcgcaggaggaatgcaccggctcgctgtttgaat<br>tgttaaggacaaaatacaatattgaaatcagcag<br>gggcaggaatcgatcgaaccgattttaacggat<br>gaaacgatcagcggacacttattaaccaatgtcg<br>gagcgcctgcgtttttatcagaatcccttacctatg<br>ataaaaatgaagaagtggtggaatatgcgcaaat<br>tattaccagggggagaccgaacgaaattcaccgta<br>gaacagtcatatcattcataaagcaatgtgttttaa<br>gaagggaatggtggttctatgttttttatttacgaat<br>ggaaaagtgctgtggggagcagt (SEQ ID NO: 36) |

TABLE E

| Target gene | Fw primer | Rv primer |
|---|---|---|
| nagA-nagB | Tgtaatcgggcggttaattc (SEQ ID NO: 37) | Gcccttcaggcgatagag (SEQ ID NO: 38) |
| gamA | Acggcgaaaatcagcggaag (SEQ ID NO: 39) | Tcactctccgtcggcagctg (SEQ ID NO: 40) |

Heterologous and Homologous Expression

Genes that needed to be expressed, be it from a plasmid or from the genome were synthetically synthetized with one of the following companies: DNA2.0, Gen9 or IDT.

Expression could be further facilitated by optimizing the codon usage to the codon usage of the expression host. Gene were optimized using the tools of the supplier.

Cultivations Conditions

A preculture, from a single colony on a LB-plate, in 5 mL LB medium was incubated for 8 h at 37° C. on an orbital shaker at 200 rpm. From this culture, 1 mL was transferred to 100 mL minimal medium (MMsf) in a 500 mL shake flask and incubated at 37° C. on an orbital shaker at 200 rpm. This setup is used for shake flask experiments. The use of an inducer is not required as all genes are constitutively expressed.

Analytical Methods

Optical Density

Cell density of the culture was frequently monitored by measuring optical density at 600 nm (Implen Nanophotometer NP80, Westburg, Belgium). Cell dry weight was obtained by centrifugation (10 min, 5000 g, Legend X1R Thermo Scientific, Belgium) of 20 g reactor broth in pre-dried and weighted falcons. The pellets were subsequently washed once with 20 mL physiological solution (9 g/L NaCl) and dried at 70° C. to a constant weight. To be able to convert $OD_{600nm}$ measurements to biomass concentrations, a correlation curve of the $OD_{600nm}$ to the biomass concentration was made.

Measurement of Cell Dry Weight

From a broth sample, 4×10 g was transferred to centrifuge tubes, the cells were spun down (5000 g, 4° C., 5 min), and the cells were washed twice with 0.9% NaCl solution. The centrifuge tubes containing the cell pellets were dried in an oven at 70° C. for 48 h until constant weight. The cell dry weight was obtained gravimetrically; the tubes were cooled in a desiccator prior to weighing.

Liquid Chromatography

The concentration of carbohydrates like, but not limited to, glucose, fructose and lactose were determined with a Waters Acquity UPLC H-class system with an ELSD detector, using a Acquity UPLC BEH amide, 130 A, 1.7 µm, 2.1 mm×50 mm heated at 35° C., using a 75/25 acetonitrile/water solution with 0.2% triethylamine (0.130 mL/min) as mobile phase.

Sialyllactose was quantified on the same machine, with the same column. The eluent however was modified to 75/25 acetonitrile/water solution with 1% formic acid. The flow rate was set to 0.130 mL/min and the column temperature to 35° C.

Sialic acid was quantified on the same machine, using the REZEX ROA column (300×7.8 mm ID). The eluent is 0.08% acetic acid in water. The flow rate was set to 0.5 mL/min and the column temperature to 65° C. GlcNAc and ManNAc were also measured using this method.

Growth Rate Measurement

The maximal growth rate (µMax) was calculated based on the observed optical densities at 600 nm using the R package grofit.

Example 2: Production of Sialic Acid in Escherichia coli

Figure 1B:
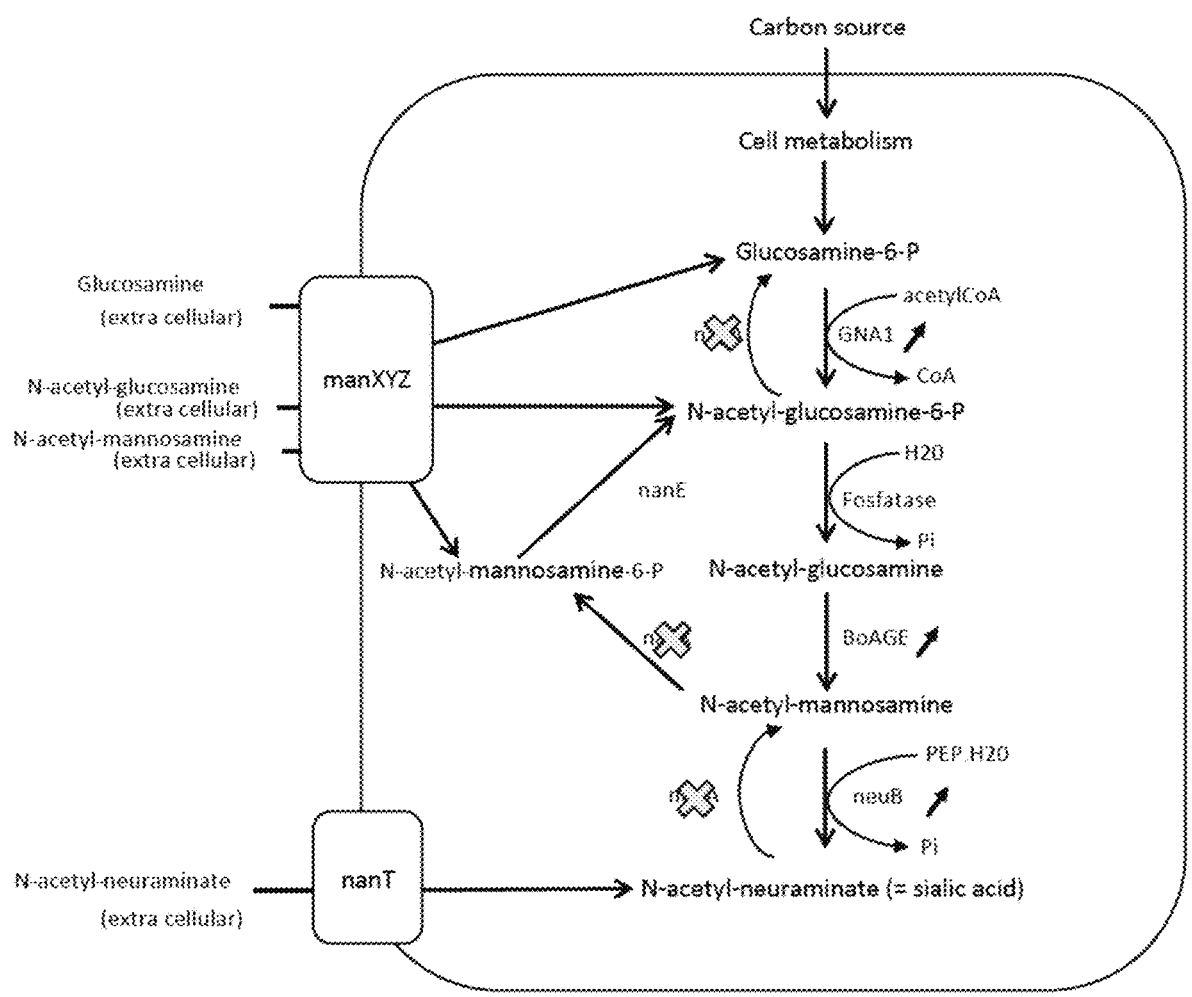
FIG. 1B shows the pathway as used in example 2 with the knock-out indicated with a cross and overexpression with an upgoing arrow next to the indicated enzyme.

A first example provides an Escherichia coli strain capable of producing N-acetylneuraminate (sialic acid) (see FIG. 1B).

A strain capable of accumulating glucosamine-6-phosphate using sucrose as a carbon source was further engineered to allow for N-acetylneuraminate production. The base strain overexpresses a sucrose phosphorylase from Bifidobacterium adolescentis (BaSP), a fructokinase from Zymomonas mobilis (Zmfrk), a mutant fructose-6-P-aminotransferase (EcglmS*54, as described by Deng et al. (Biochimie 88, 419-429 (2006))). To allow for gene sialic acid production the operons nagABCDE, nanATEK and manXYZ were disrupted. BaSP and Zmfrk were introduced at the location of nagABCDE and EcglmS*54 was introduced at the location of nanATEK. These modifications were done as described in example 1 and are based on the principle of Datsenko & Wanner (PNAS USA 97, 6640-6645 (2000)).

In this strain, the biosynthetic pathway for producing sialic acid as described in this invention, was implemented by overexpressing a glucosamine-6-P-aminotransferase from Saccharomyces cerevisiae (ScGNA1), a N-acetylglucosamine-2-epimerase from Bacteroides ovatus (BoAGE) and a sialic acid synthase from Campylobacter jejuni (CjneuB). ScGNA1 and BoAGE were expressed on locations nagABCDE and manXYZ, respectively. CjneuB was expressed using the high copy plasmid pCX-CjneuB.

Figure 2:
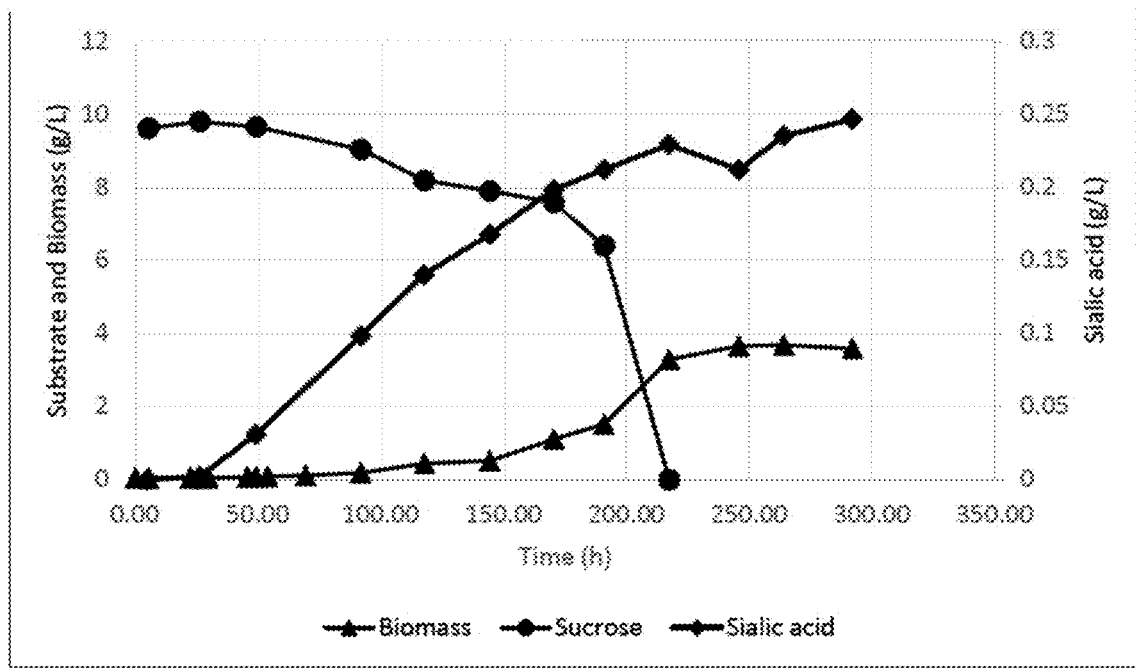
FIG. 2 shows the production results of the *Escherichia coli* strain capable of producing sialic acid as described in example 2.
Figure 3:
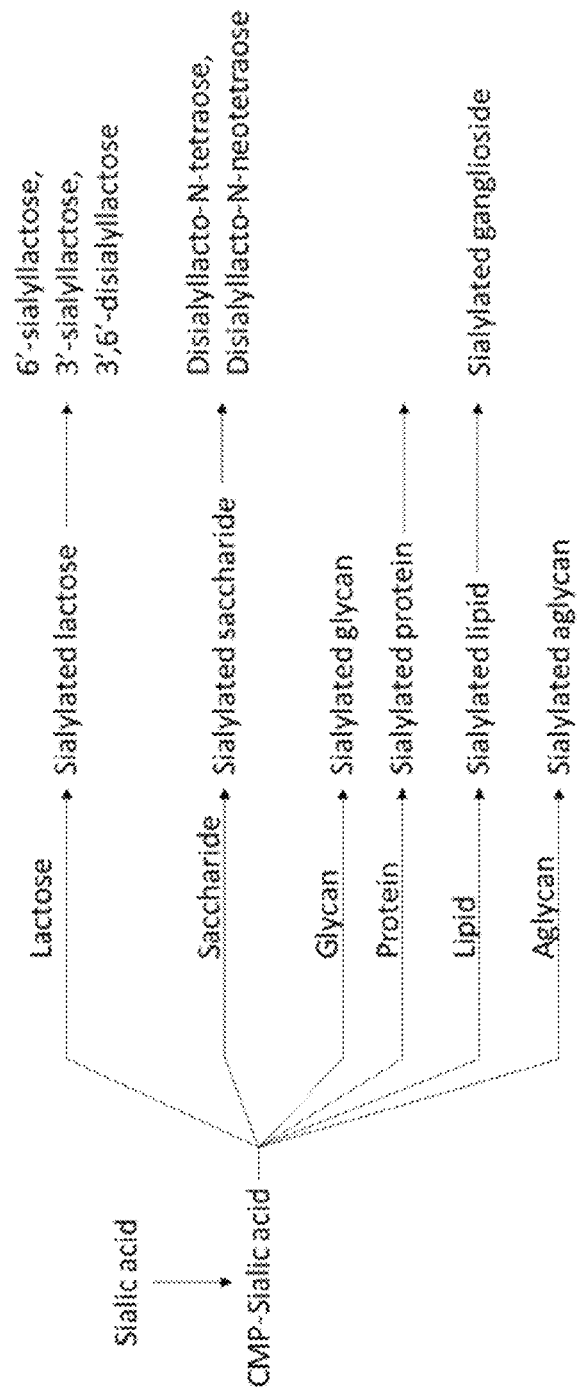
FIG. 3 shows examples of different sialylated compounds which can be produced in the method of the present invention.

The strain was cultured as described in example 1 (materials and methods). Briefly, a 5 mL LB preculture was inoculated and grown overnight at 37° C. This culture was used as inoculum in a shake flask experiment with 100 mL medium which contains 10 g/L sucrose and was made as described in example 1. Regular samples were taken and analyzed as described in example 1. The evolutions of the concentrations of biomass, sucrose and sialic acid are easily followed and an end concentration of 0.22 g/L N-acetylneuraminate was produced extracellularly, as can be seen in FIG. 2.

The same organism also produces N-acetylneuraminate based on glucose, maltose or glycerol as carbon source.

Example 3: Production of 6-Sialyllactose in Escherichia coli

Another example according to present invention is the use of the method and strains for the production of 6-sialyllactose.

The strain of example 3 is a daughter strain of the strain used in example 2. The strain is further modified by overexpressing a lactose permease EclacY from Escherichia coli (as described and demonstrated in example 1 of WO 2016/075243 which is here also incorporated by reference), a CMP-sialic acid synthethase from Neisseria meningitides (NmneuA) and a sialyltransferase from Photobacterium damselae (Pdbst). On top of that lacZ is disrupted.

The genes NmneuA and Pdbst, are expressed from a plasmid, together with CjneuB. This plasmid is pCX-CjneuB-NmneuA-Pdbst, and is made as described in example 1.

Said strain is inoculated as a preculture consisting of 5 ml LB medium as described in example 1. After growing overnight at 37° C. in an incubator. 1% of this preculture is inoculated in a shake flask containing 100 ml medium (MMsf) containing 10 g/l sucrose as carbon source and 10 g/l lactose as precursor. The strain is grown for 300 h at 37° C.

This strain produces quantities of 6-sialyllactose.

Example 4: Production of Sialic Acid in Saccharomyces cerevisiae Using Heterologous Fructose-6-P-aminotransferase Another example provides use of an eukaryotic organism, in the form of Saccharomyces cerevisae, for the invention. This method utilizing the pathway of the invention shall be obtained in Saccharomyces cerevisiae by introducing and expressing a N-acetylglucosamine-2-epimerase (for example from Bacteroides ovatus (BoAGE)) and a sialic acid synthase (for example from Campylobacter jejuni (CjneuB)).

As starting point, a strain with increased metabolic flux towards N-acetylglucosamine-6-phosphate is needed. This is achieved by overexpressing the fructose-6-P-aminotransferase mutant from Escherichia coli (EcglmS*54).

To create a N-acetylneuraminate producing Saccharomyces cerevisiae according to this invention, the genes are introduced via a 2-micron plasmid (Chan 2013 (Plasmid 70 (2013) 2-17)) and the genes are expressed using synthetic constitutive promoters (Blazeck 2012 (Biotechnology and Bioengineering, Vol. 109, No. 11)) as also described in example 1. The specific plasmid used in this embodiment is p2a_21_sia_glmS. This plasmid is introduced into Saccharomyces cerevisae using the transformation technique described by Gietz and Woods (2002, PMID 12073338) and a mutant strain is obtained Said strain is capable of converting fructose-6-phosphate into glucosamine-6-phosphate, followed by glucosamine-6-phosphate conversion in N-acetylglucosamine-6-phosphate. This N-acetylglucosamine-6-phosphate moiety is further converted to N-acetylglucosamine, said N-acetylglucosamine into N-acetylmannosamine and finally this N-acetylmannosamine is converted into N-acetylneuraminate.

A preculture of said strain is made in 5 mL of the synthetic defined medium SD-CSM containing 22 g/L glucose and grown at 30° C. as described in example 1. This preculture is inoculated in 100 mL medium in a shakeflask with 10 g/L sucrose as sole carbon source and grown at 30° C. Regular samples are taken and the production of N-acetylneuraminate is measured as described in example 1. This strain and method produces quantities of N-acetylneuraminate.

The same organism also produces N-acetylneuraminate based on glucose, maltose or glycerol as carbon source.

Example 5: Production of 6-Sialyllactose in *Saccharomyces cerevisiae*

Another example provides use of an eukaryotic organism, in the form of *Saccharomyces cerevisae*, for the invention. This method utilizing the pathway of the invention shall be obtained in *Saccharomyces cerevisiae* by introducing and expressing a N-acetylglucosamine-2-epimerase (for example from *Bacteroides ovatus* (BoAGE)) and a sialic acid synthase (for example from *Campylobacter jejuni* (CjneuB)).

On top of that, further modifications are made in order to produce 6sialyllactose. These modifications comprise the addition of a lactose permease, a CMP-sialic acid synthase and a sialyltransferase. The preferred lactose permease is the KlLAC12 gene from *Kluyveromyces lactis* (WO 2016/075243). The preferred CMP-sialic acid synthase and the sialyltransferase are respectively NmneuA from *Neisseria meningitides* and Pdbst from *Photobacterium damselae*, as also described in example 3.

As starting point, a strain with increased metabolic flux towards N-acetylglucosamine-6-phosphate is needed. This is achieved by overexpressing the fructose-6-P-aminotransferase mutant from *Escherichia coli* (EcglmS*54).

To create a N-acetylneuraminate producing *Saccharomyces cerevisiae* according to this invention, the genes are introduced via a 2-micron plasmid (Chan 2013 (Plasmid 70 (2013) 2-17)) and the genes are expressed using synthetic constitutive promoters (Blazeck 2012 (Biotechnology and Bioengineering, Vol. 109, No. 11)) as also described in example 1. The specific plasmid used in this embodiment is p2a_2μ_sia_glmS. This plasmid is introduced into *Saccharomyces cerevisae* using the transformation technique described by Gietz and Woods (2002) and a mutant strain is obtained Said strain is capable of converting fructose-6-phosphate into glucosamine-6-phosphate, said glucosamine-6-phosphate into N-acetylglucosamine-6-phosphate, said N-acetylglucosamine-6-phosphate into N-acetylglucosamine, said N-acetylglucosamine into N-acetylmannosamine and finally said N-acetylmannosamine into N-acetylneuraminate. Said N-acetylmannosamine is then converted to CMP-sialic acid and transferred to lactose to obtain 6sialyllactose.

A preculture of said strain is made in 5 mL of the synthetic defined medium SD-CSM containing 22 g/L glucose and grown at 30° C. as described in example 1. This preculture is inoculated in 100 mL medium in a shakeflask with 10 g/L sucrose as sole carbon source and grown at 30° C. Regular samples are taken and the production of N-acetylneuraminate is measured as described in example 1. This strain and method produces quantities of 6sialyllactose.

The same organism also produces N-acetylneuraminate based on glucose, maltose or glycerol as carbon source.

Example 6: Production of Sialic Acid in *Saccharomyces cerevisiae* Using Autologous Fructose-6-P-Aminotransferase Another example provides use of an eukaryotic organism, in the form of *Saccharomyces cerevisiae*, for the invention. This method utilizing the pathway of the invention shall be obtained in *Saccharomyces cerevisiae* by introducing and expressing a N-acetylglucosamine-2-epimerase (for example from *Bacteroides ovatus* (BoAGE)) and a sialic acid synthase (for example from *Campylobacter jejuni* (CjneuB)).

As starting point, a strain with increased metabolic flux towards N-acetylglucosamine-6-phosphate is needed. This is achieved by overexpressing the native fructose-6-P-aminotransferase ScGFA1.

To create a N-acetylneuraminate producing *Saccharomyces cerevisiae* according to this invention, the genes are introduced via a 2-micron plasmid (Chan 2013 (Plasmid 70 (2013) 2-17)) and the genes are expressed using synthetic constitutive promoters (Blazeck 2012 (Biotechnology and Bioengineering, Vol. 109, No. 11)) as also described in example 1. The specific plasmid used in this embodiment is p2a_2μ_sia_GFA1. This plasmid is introduced into *Saccharomyces cerevisae* using the transformation technique described by Gietz and Woods (2002) and a mutant strain is obtained Said strain is capable of converting fructose-6-phosphate into glucosamine-6-phosphate, said glucosamine-6-phosphate into N-acetylglucosamine-6-phosphate, said N-acetylglucosamine-6-phosphate into N-acetylglucosamine, said N-acetylglucosamine into N-acetylmannosamine and finally said N-acetylmannosamine into N-acetylneuraminate.

A preculture of said strain is made in 5 mL of the synthetic defined medium SD-CSM containing 22 g/L glucose and grown at 30° C. as described in example 1. This preculture is inoculated in 100 mL medium in a shakeflask with 10 g/L sucrose as sole carbon source and grown at 30° C. Regular samples are taken and the production of N-acetylneuraminate is measured as described in example 1. This strain and method produces quantities of N-acetylneuraminate.

The same organism also produces N-acetylneuraminate based on glucose, maltose or glycerol as carbon source.

Example 7: Production of Sialyllactoses and Other Sialylated Compounds

In an alternative embodiment of example 3, the sialyltransferase is changed to another sialyltransferase with different activity. This can be an alpha-2,3-sialyltransferase alpha-2,6-sialyltransferase, an alpha-2,8-sialyltransferase or a combination thereof. These sialyltransferases are widely available in nature and well annotated.

In this way, production of different sialyllactoses like for example 6-sialyllactose, 3-sialyllactose or a mixture thereof can be obtained.

The strains are cultivated as stated in example 1 and example 3.

The pathways created in examples 2 to 7 can also be combined with other pathways for the synthesis of larger oligosaccharides, e.g. sialyl-lacto-N-triose, sialyllacto-N-tetraose, disialyllactose-N-tetraose, sialyllacto-N-neotetraose, and disialyllactose-N-neotetraose. To this end, the transferases to synthetized these glycosidic bonds are co-expressed with the pathway genes to form CMP-sialic acid and the transferase (as described above) to sialylate said oligosaccharide.

Examples of such sialyltransferases are ST6GalI, ST6GalII, ST3GalI until VI, ST6GalNAc I until VI and ST8Sia I until VI, as described by Datta (Current Drug Targets, 2009, 10, 483-498) and Harduin-Lepers (Biochimie 83 (2001) 727-737). Further examples originating from marine organisms are described by Yamamoto (Mar. Drugs 2010, 8, 2781-2794).

Example 8: Production of Sialylated Lacto-N-Neotetraose

The aim of this experiment was to demonstrate the functionality of presented invention of the production of other sialylated oligosaccharides, in this case sialyltated lacto-N-neotetraose.

A lacto-N-neotetraose producing strain was developed following the protocol described in example 1. For production, the expression of a N-acetylglucosaminyltransferase and a galactosyltransferase are needed, this is achieved by introduction of the genes NmlgtA and NmlgtB respectively, both from *Neisseria meningitides*. Next, the lactose importer EclacY from *Escherichia coli* is (as described and demonstrated in example 1 of WO 2016/075243 which is here also incorporated by reference). Finally, the genes ushA and galT are knocked out. In this way, a lacto-N-neotetraose producing strain is obtained.

To be able to grow on lactose and produce N-acetylglucosamine-6-phosphate, a sucrose phosphorylase from *Bifidobacterium adolescentis* (BaSP), a fructokinase from *Zymomonas mobilis* (frk) and a mutant fructose-6-P-aminotransferase (EcglmS*54, as described by Deng et al (Biochimie 88, 419-429 (2006))) were overexpressed as described in example 1.

In this strain, the method for producing sialic acid as described in this invention, was implemented by overexpressing a glucosamine-6-P-aminotransferase from *Saccharomyces cerevisiae* (ScGNA1), a N-acetylglucosamine-2-epimerase from *Bacteroides ovatus* (BoAGE) and a sialic acid synthase from *Campylobacter jejuni* (CjneuB). ScGNA1 and BoAGE are expressed on locations nagABCDE and manXYZ, respectively. CjneuB is expressed from plasmid pCX-CjneuB-NmneuA-Pdbst.

Sialylation of the lacto-N-neotetraose moiety is performed by the conversion of sialic acid to CMP-sialic acid by a CMP sialic acid synthethase, e.g. NmneuA from *Neisseria meningtides*, subsequently followed by a sialyl transferase, e.g. Pdbst, from *Photobacterium damselae*. These genes (NmneuA and Pdbst) are expressed from the high copy plasmid pCX-CjneuB-NmneuA-Pdbst.

The strain is cultured as described in example 1 (materials and methods). Briefly, a 5 mL LB preculture is inoculated and grown overnight at 37° C. This culture was used as inoculum in a shake flask experiment with 100 mL medium which contains 10 g/L sucrose as carbon and energy source, 10 g/L lactose as precursor and was made according to the description in example 1. Regular samples are taken and analyzed. This strain produces quantities of sialylated lacto-N-neotetraose.

Alternative glycosyltransferases are possible. If EcWgbO (from *Escherichia coli* O55:H7) is expressed instead of NmlgtB for example, production of sialylated lacto-N-tetraose is obtained.

Example 9: Production of Sialic Acid with *Bacillus subtilis*

In another embodiment, this invention can be used for production of N-acetylneuraminate in *Bacillus subtilis*, yet another bacterial production host.

A N-acetylneuraminate producing strain is obtained through this invention by starting with a strain, capable of overproducing glucosamine-6-phosphate intracellularly. For this, the native fructose-6-P-aminotransferase (BsglmS) is overexpressed. The following enzymatic activities are disrupted by knocking out the genes nagA, nagB and gamA: N-acetylglucosamine-6-phosphate deacetylase and glucosamine-6-phosphate isomerase.

In this strain, the method for producing sialic acid as described in this invention, is implemented by overexpressing a glucosamine-6-P-aminotransferase from *Saccharomyces cerevisiae* (ScGNA1), a N-acetylglucosamine-2-epimerase from *Bacteroides ovatus* (BoAGE) and a sialic acid synthase from *Campylobacter jejuni* (CjneuB). These genes are introduced via a plasmid, as described in example 1.

The strain is cultured as described in example 1 (materials and methods). Briefly, a 5 mL LB preculture is inoculated and grown overnight at 30° C. This culture is used as inoculum in a shake flask experiment with 100 mL medium which contains 10 g/L sucrose and is made according to the description in example 1. This strain produces quantities of N-acetylneuraminic acid.

Example 10: Fermentations of 6-Sialyllactose Producing Strain with No Excretion of GlcNAc, ManNAc or Sialic Acid Another example according to the present invention provides use of the method and strains for the production of 6-sialyllactose.

An *Escherichia coli* strain capable of accumulating glucosamine-6-phosphate using sucrose as a carbon source was further engineered to allow for N-acetylneuraminate production. This base strain overexpresses a sucrose phosphorylase from *Bifidobacterium adolescentis* (BaSP), a fructokinase from *Zymomonas mobilis* (Zmfrk), a mutant fructose-6-P-aminotransferase (EcglmS*54, as described by Deng et al. (Biochimie 88, 419-429 (2006)). To allow for 6-sialyllactose production the operons nagABCDE, nanATEK and manXYZ were disrupted. BaSP and Zmfrk were introduced at the location of nagABCDE, EcglmS*54 was introduced at the location of nanATEK. These modifications were done as described in example 1 and are based on the principle of Datsenko & Wanner (PNAS USA 97, 6640-6645 (2000)).

In this strain, the biosynthetic pathway for producing 6-sialyllactose as described in this invention, was implemented by overexpressing a glucosamine-6-P-aminotransferase from *Saccharomyces cerevisiae* (ScGNA1), a N-acetylglucosamine-2-epimerase from *Bacteroides ovatus* (BoAGE) and a sialic acid synthase from *Neisseria meningitides* (NmneuB). ScGNA1 and BoAGE were expressed on locations nagABCDE and manXYZ, respectively. NmNeuB was expressed using the high copy plasmid pBR322-NmNeuB. The strain is further modified by overexpressing a lactose permease EclacY from *Escherichia coli* (as described and demonstrated in example 1 of WO 2016/075243 which is here also incorporated by reference), a CMP-sialic acid synthethase from *Neisseria meningitides* (NmNeuA) and a sialyltransferase from *Photobacterium damselae* (Pdbst). On top of that, lacZ is disrupted. NmNeuA and Pdbst were expressed using the low copy plasmid pSC101-NmneuA-Pdbst.

The strain was cultured in a bioreactor as described in example 1 (materials and methods). Briefly, a 5 mL LB preculture was inoculated and grown overnight at 37° C. This culture was used as inoculum in a shake flask experiment with 500 mL medium which contains 10 g/L sucrose and was made as described in example 1. This culture was used as inoculum in a 2 L bioreactor experiment. Regular samples were taken and analyzed as described in example 1. The final concentration of 6-sialyllactose was 30.5 g/L. No extracellular GlcNAc, ManNAc and sialic acid was detected during the fermentation and in the final broth.

The same organism also produces 6-sialyllactose based on glucose, maltose or glycerol as carbon source.

Example 11: Effect of Phosphatase on Growth and Production of Sialic Acid

A further example provides growth results and sialic acid production of several *Escherichia coli* strains capable of producing N-acetylneuraminate (sialic acid) wherein the strains are expressing an extra phosphatase as indicated hereunder.

The base strain overexpresses a mutant fructose-6-P-aminotransferase (EcglmS*54, as described by Deng et al. (Biochimie 88, 419-429 (2006)), a glucosamine-6-P-aminotransferase from *Saccharomyces cerevisiae* (ScGNA1), a N-acetylglucosamine-2-epimerase from *Bacteroides ovatus* (BoAGE) and a sialic acid synthase from *Campylobacter jejuni* (CjneuB). To allow for gene sialic acid production the operons nagABCDE and nanATEK. The lacYZA operon was replaced by only a single gene operon, the native lacY, which is required for the production of sialyllactose as described in example 10. These modifications were done as described in example 1 and are based on the principle of Datsenko & Wanner (PNAS USA 97, 6640-6645 (2000)).

This base strain was then supplemented with different phosphatase bearing plasmids for comparing the effect of the phosphatase on growth and sialic acid production. The base strain was used as blank in the comparison. These plasmids consisted of, besides the phosphatase and a promoter driving expression of the phosphatase, a pSC101 ori and a spectomycin resistance marker. The following phosphatases were expressed: EcAphA (SEQ ID NO: 42), EcCof (SEQ ID NO: 43), EcHisB (SEQ ID NO: 44), EcOtsB (SEQ ID NO: 45), EcSurE (SEQ ID NO: 46), EcYaed (SEQ ID NO: 47), EcYcjU (SEQ ID NO: 48), EcYedP (SEQ ID NO: 49), EcYfbT (SEQ ID NO: 50), EcYidA (SEQ ID NO: 51), EcYigB (SEQ ID NO: 52), EcYihX (SEQ ID NO: 53), EcYniC (SEQ ID NO: 54), EcYqaB (SEQ ID NO: 55), EcYrbL (SEQ ID NO: 56) and PsMupP (SEQ ID NO: 57). Other phosphatases that are expressed are EcAppA (SEQ ID NO: 58), EcGph (SEQ ID NO: 59), EcSerB (SEQ ID NO: 60), EcNagD (SEQ ID NO: 61), EcYbhA (SEQ ID NO: 62), EcYbiV (SEQ ID NO: 63), EcYbjL (SEQ ID NO: 64), EcYfbR (SEQ ID NO: 65), EcYieH (SEQ ID NO: 66), EcYjgL (SEQ ID NO: 67), Ec YjjG (SEQ ID NO: 68), EcYrfG (SEQ ID NO: 69), EcYbiU (SEQ ID NO: 70), ScDOG1 (SEQ ID NO: 71) and BsAraL (SEQ ID NO: 72).

In a first experiment a subset of the above described strains was used. In a second experiment a second subset of the above described strains were tested.

Each strain was cultured as described in example 1 (materials and methods). Briefly, the workflow consists of 3 growth steps: first growth on LB, followed by growth on MMsf with 15 g/L glycerol, and finally a growth stage using 15 g/L glycerol MMsf. The first step is performed in a 96 well plate, using 175 µL LB per well, and incubated overnight at 37° C. The second step is performed in a 96 well plate using 175 µL medium, incubated for 24 h at 37° C. The final growth step was performed in: i) in a 96 well plate using 175 µL medium, incubated at 37° C. to determine the µMax for the first experiment (see FIG. 5) and ii) in a 24 well deepwell plates using 3 mL do determine sialic acid production and optical densities for the second experiment (see FIG. 4).

Figure 4:
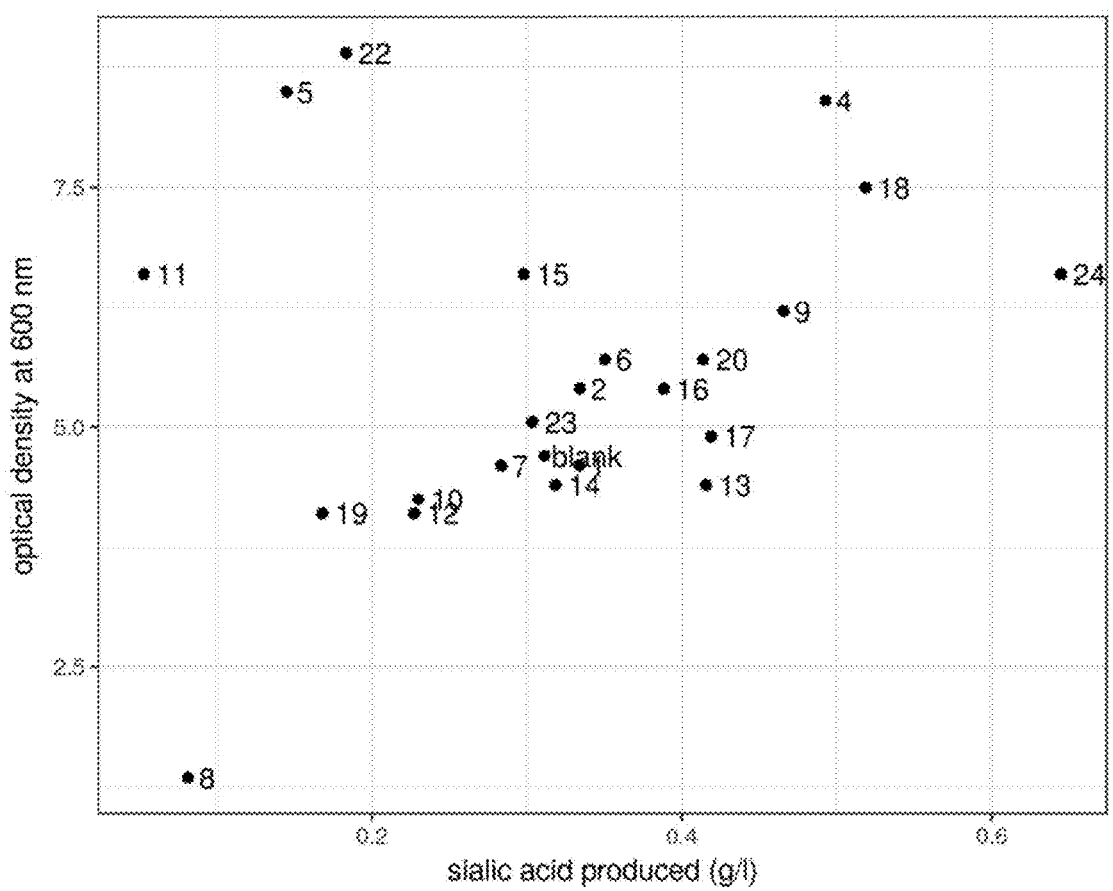
FIG. 4 shows the optical density and sialic acid production of strains supplemented with the indicated phosphatases.
Figure 5:
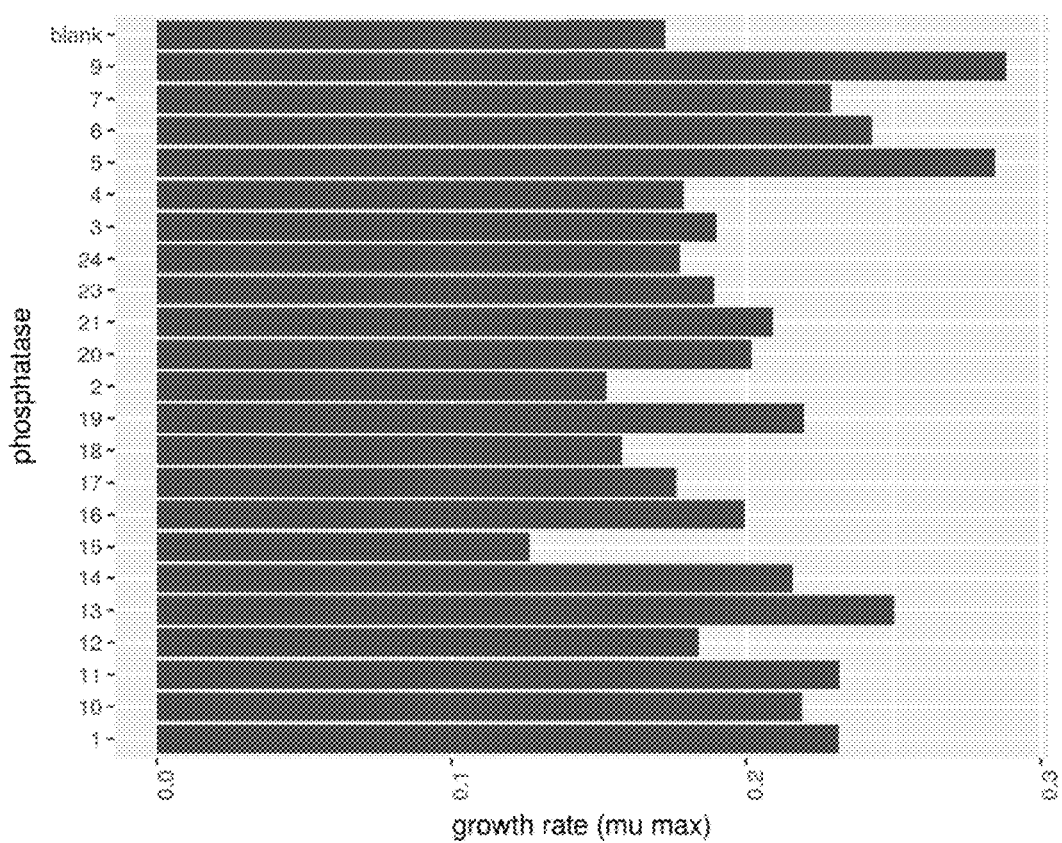
FIG. 5 shows the growth rates of strains supplemented with the indicated phosphatases.

Reference table for FIGS. 4 and 5:

| label | phosphatase | SEQ ID NO | Promotor |
| --- | --- | --- | --- |
| blank | NA | NA | NA |
| 1 | EcAphA | 42 | apFAB346 |
| 2 | EcAphA | 42 | apFAB87 |
| 3 | EcCof | 43 | apFAB87 |
| 4 | EcCof | 43 | apFAB346 |
| 5 | EcHisB | 44 | apFAB346 |
| 6 | EcOtsB | 45 | apFAB346 |
| 7 | EcSurE | 46 | apFAB346 |
| 8 | EcSurE | 46 | apFAB87 |
| 9 | EcYaed | 47 | apFAB346 |
| 10 | EcYaed | 47 | apFAB87 |
| 11 | EcYcjU | 48 | apFAB87 |
| 12 | EcYedP | 49 | apFAB87 |
| 13 | EcYfbT | 50 | apFAB87 |
| 14 | EcYidA | 51 | apFAB346 |
| 15 | EcYidA | 51 | apFAB87 |
| 16 | EcYigB | 52 | apFAB346 |
| 17 | EcYihX | 53 | apFAB346 |
| 18 | EcYihX | 53 | apFAB87 |
| 19 | EcYniC | 54 | apFAB346 |
| 20 | EcYniC | 54 | apFAB87 |
| 21 | EcYqaB | 55 | apFAB87 |
| 22 | EcYqaB | 55 | apFAB346 |
| 23 | EcYrbL | 56 | apFAB87 |
| 24 | PsMupP | 57 | apFAB87 |

Based on FIGS. 4 and 5 phosphatases enabling strains to grow better than the blank strain (no crippled growth) and producing more sialic acid than the blank strain, can be chosen.

Based on the above, it was found that phosphatases comprising at least Motif 1 and Motif 2 provide a strain which is not crippled and produces more sialic acid than the blank strain.

Example 12: Identification of Further Sequences Related to the Phosphatases Used in the Methods of the Invention Sequences (polypeptides) related to SEQ ID NOs: 43, 44, 45, 47, 48, 49, 50, 51, 52, 54, 55 and 57 were identified amongst those maintained in the Entrez Nucleotides database at the National Center for Biotechnology Information (NCBI) using database sequence search tools, such as the Basic Local Alignment Tool (BLAST) (Altschul et al. (1990) J. Mol. Biol. 215:403-410; and Altschul et al. (1997) Nucleic Acids Res. 25:3389-3402). The program is used to find regions of local similarity between sequences by comparing nucleic acid or polypeptide sequences to sequence databases and by calculating the statistical significance of matches. The output of the analysis was viewed by pairwise comparison, and ranked according to the probability score (E-value), where the score reflect the probability that a particular alignment occurs by chance (the lower the E-value, the more significant the hit). In addition to E-values, comparisons were also scored by percentage identity. Percentage identity refers to the number of identical amino acids between the two compared polypeptide sequences over a particular length. In some instances, the default parameters may be adjusted to modify the stringency of the search. For example the E-value may be increased to show less stringent matches. This way, short nearly exact matches may be identified.

Table 1A to 1K provides a list of homologue polypeptide sequences related to SEQ ID NO: 43, 44, 45, 47, 48, 50, 51, 52, 54, 55 and 57, respectively.

TABLE 1A

Examples of polypeptides related to Ec Cof (SEQ ID NO: 43), showing sequence identity to SEQ ID 43:

| % identity (matgat) | short genbank identifier | SEQ ID NO |
|---|---|---|
| 99.6 | Shigella flexneri WP_095762248.1 | 78 |
| 99.3 | Shigella boydii WP_095785299.1 | 79 |
| 98.2 | Escherichia fergusonii WP_024256925.1 | 80 |
| 89.3 | Staphylococcus aureus WP_094409981.1 | 81 |
| 89 | Escherichia albertii WP_000113024.1 | 82 |
| 81.6 | Citrobacter amalonaticus WP_046476411.1 | 83 |
| 81.6 | Salmonella enterica WP_023234244.1 | 84 |
| 80.5 | Escherichia coli WP_088543831.1 | 85 |

TABLE 1B

Examples of polypeptides related to Ec HisB (SEQ ID NO: 44), showing sequence identity to SEQ ID NO: 44:

| % identity (matgat) | short genbank identifier | SEQ ID NO |
|---|---|---|
| 99.4 | Shigella flexneri K-315 EIQ21345.1 | 86 |
| 99.2 | Escherichia albertii WP_059217413.1 | 87 |
| 98.9 | Shigella flexneri WP_094085559.1 | 88 |
| 98.6 | Shigella sonnei WP_077125326.1 | 89 |
| 98.6 | Escherichia coli WP_088129012.1 | 90 |
| 98 | Shigella dysenteriae WP_000080078.1 | 91 |
| 98 | Escherichia marmotae WP_038355110.1 | 92 |
| 94.6 | Salmonella bongori WP_000080052.1 | 93 |

TABLE 1C

Examples of polypeptides related to Ec OtsB (SEQ ID NO: 45), showing sequence identity to SEQ ID 45:

| % identity (matgat) | short genbank identifier | SEQ ID NO |
|---|---|---|
| 99.6 | Shigella sonnei WP_077124555.1 | 94 |
| 99.6 | Escherichia coli WP_032172688.1 | 95 |
| 99.2 | Shigella flexneri WP_064198868.1 | 96 |
| 85.7 | Escherichia albertii WP_059227241.1 | 97 |
| 83.1 | Escherichia fergusonii WP_000165652.1 | 98 |

TABLE 1D

Examples of polypeptides related to Ec Yaed (SEQ ID NO: 47), showing sequence identity to SEQ ID NO: 47:

| % identity (matgat) | short genbank identifier | SEQ ID NO |
|---|---|---|
| 99.5 | Escherichia fergusonii WP_001140180.1 | 99 |
| 99.5 | Shigella sonnei WP_047565591.1 | 100 |
| 99 | Escherichia coli WP_061103769.1 | 101 |
| 95.8 | Escherichia albertii WP_001140171.1 | 102 |
| 93.2 | Kluyvera intermedia WP_047371746.1 | 103 |
| 93.2 | Citrobacter koseri WP_047458784.1 | 104 |
| 89 | Kosakonia arachidis WP_090122712.1 | 105 |
| 85.9 | Kluyvera cryocrescens WP_061282459.1 | 106 |
| 85.9 | Leclercia adecarboxylata WP_039030283.1 | 107 |

TABLE 1E

Examples of polypeptides related to Ec YcjUB (SEQ ID NO: 48), showing sequence identity to SEQ ID NO: 48:

| % identity (matgat) | short genbank identifier | SEQ ID NO |
|---|---|---|
| 99.5 | Shigella sonnei WP_094313132.1 | 108 |
| 97.7 | Escherichia coli WP_000775764.1 | 109 |
| 95.4 | Escherichia coli WP_032302947.1 | 110 |
| 92.7 | Shigella flexneri OUZ88260.1 | 111 |

TABLE 1F

Examples of polypeptides related to Ec YfbT (SEQ ID NO: 50), showing sequence identity to SEQ ID NO: 50:

| % identity (matgat) | short genbank identifier | SEQ ID NO |
|---|---|---|
| 99.1 | Shigella sonnei WP_094323443.1 | 112 |
| 87.5 | Citrobacter werkmanii NBRC 105721 GAL43238.1 | 113 |
| 86.6 | Citrobacter freundii KGZ33467.1 | 114 |
| 86.6 | Citrobacter amalonaticus Y19 AKE59306.1 | 115 |
| 85.6 | Salmonella enterica WP_080095242.1 | 116 |
| 85.6 | Escherichia fergusonii WP_001203376.1 | 117 |
| 85.6 | Salmonella enterica subsp. enterica serovar Hadar KKD79316.1 | 118 |

TABLE 1G

Examples of polypeptides related to Ec YidA (SEQ ID NO: 51), showing sequence identity to SEQ ID NO: 51:

| % identity (matgat) | short genbank identifier | SEQ ID NO |
|---|---|---|
| 99.6 | Escherichia coli WP_053263719.1 | 119 |
| 99.3 | Escherichia fergusonii WP_000985562.1 | 120 |
| 99.3 | Shigella sonnei WP_094337696.1 | 121 |
| 94.4 | Trabulsiella guamensis WP_038161262.1 | 122 |
| 94.1 | Citrobacter amalonaticus WP_061075826.1 | 123 |
| 93.7 | Klebsiella pneumoniae WP_048288968.1 | 124 |
| 93.3 | Trabulsiella odontotermitis WP_054178096.1 | 125 |
| 90 | Enterobacter kobei WP_088221256.1 | 126 |

TABLE 1H

Examples of polypeptides related to Ec YigB (SEQ ID NO: 52), showing sequence identity to SEQ ID NO: 52:

| % identity (matgat) | short genbank identifier | SEQ ID NO |
|---|---|---|
| 99.6 | Shigella sonnei WP_094322240.1 | 127 |
| 93.7 | Shigella sonnei WP_052962467.1 | 128 |
| 87 | Salmonella enterica WP_079797638.1 | 129 |
| 85.7 | Citrobacter braakii WP_080625916.1 | 130 |
| 81.9 | Enterobacter hormaechei WP_047737367.1 | 131 |
| 81.1 | Lelliottia amnigena WP_059180726.1 | 132 |
| 80.3 | Leclercia adecarboxylata WP_039031210.1 | 133 |

TABLE 1I

Examples of polypeptides related to Ec YniC (SEQ ID NO: 54), showing sequence identity to SEQ ID NO: 54:

| % identity (matgat) | short genbank identifier | SEQ ID NO |
|---|---|---|
| 85.6 | Shigella flexneri 1235-66 EIQ75633.1 | 134 |
| 85.1 | Kosakonia sacchari WP_074780431.1 | 135 |
| 85.1 | Enterobacter mori WP_089599104.1 | 136 |

TABLE 1I-continued

Examples of polypeptides related to Ec YniC (SEQ ID NO: 54), showing sequence identity to SEQ ID NO: 54:

| % identity (matgat) | short genbank identifier | SEQ ID NO |
|---|---|---|
| 84.7 | *Lelliottia amnigena* WP_064325804.1 | 137 |
| 84.7 | *Enterobacter* sp. 638 WP_012017112.1 | 138 |
| 84.2 | *Kosakonia radicincitans* WP_071920671.1 | 139 |
| 84.2 | *Salmonella enterica* subsp. *enterica* serovar Newport str. CDC 2010K-2159 AKD18194.1 | 140 |

TABLE 1J

Examples of polypeptides related to Ec YqaB (SEQ ID NO: 55), showing sequence identity to SEQ ID NO: 55:

| % identity (matgat) | short genbank identifier | SEQ ID NO |
|---|---|---|
| 97.9 | *Shigella flexneri* K-315 EIQ18779.1 | 141 |
| 93.6 | *Escherichia albertii* WP_059215906.1 | 142 |
| 88.3 | *Salmonella enterica* WP_079949947.1 | 143 |
| 85.6 | *Kluyvera intermedia* WP_085006827.1 | 144 |
| 85.1 | *Trabulsiella odontotermitis* WP_054177678.1 | 145 |
| 84.6 | *Yokenella regensburgei* WP_006817298.1 | 146 |
| 84.6 | *Raoultella terrigena* WP_045857711.1 | 147 |
| 83.5 | *Klebsiella pneumoniae* WP_064190334.1 | 148 |

TABLE 1K

Examples of polypeptides related to Ps MupP (SEQ ID NO: 57), showing sequence identity to SEQ ID NO: 57:

| % identity (matgat) | short genbank identifier | SEQ ID NO |
|---|---|---|
| 94.6 | *Pseudomonas putida* group WP_062573193.1 | 149 |
| 94.6 | *Pseudomonas* sp. GM84 WP_008090372.1 | 150 |
| 93.3 | *Pseudomonas entomophila* | 151 |
| 92.4 | *Pseudomonas vranovensis* WP_028943668.1 | 152 |
| 83.9 | *Pseudomonas cannabina* WP_055000929.1 | 153 |
| 93.3 | *Pseudomonas monteilii* WP_060480519.1 | 154 |

Sequences have been tentatively assembled and publicly disclosed by research institutions, such as The Institute for Genomic Research (TIGR; beginning with TA). The Eukaryotic Gene Orthologs (EGO) database may be used to identify such related sequences, either by keyword search or by using the BLAST algorithm with the nucleic acid sequence or polypeptide sequence of interest. Special nucleic acid sequence databases have been created for particular organisms, such as by the Joint Genome Institute.

Example 13: Identification of Domains and Motifs Comprised in Polypeptide Sequences Useful in Performing the Methods of the Invention The Integrated Resource of Protein Families, Domains and Sites (InterPro) database is an integrated interface for the commonly used signature databases for text- and sequence-based searches. The InterPro database combines these databases, which use different methodologies and varying degrees of biological information about well-characterized proteins to derive protein signatures. Collaborating databases include SWISS-PROT, PROSITE, TrEMBL, PRINTS, ProDom and Pfam, Smart and TIGRFAMs. Pfam is a large collection of multiple sequence alignments and hidden Markov models covering many common protein domains and families. Pfam is hosted at the Sanger Institute server in the United Kingdom. Interpro is hosted at the European Bioinformatics Institute in the United Kingdom.

The results of the InterPro scan of the polypeptide sequences as represented by SEQ ID NOs: 43, 44, 45, 47, 48, 49, 50, 51, 52, 54 and 55 are presented in Table 2.

TABLE 2

InterPro scan results (major accession numbers) of the polypeptide sequence as represented by SEQ ID NOs: 43, 44, 45, 47, 48, 49, 50, 51, 52, 54 and 55.

| Database | Accession number | Accession name |
|---|---|---|
| Interpro | IPR023214 | HAD superfamily |

Alignment of the tested phosphatase polypeptides was done and FIG. 6 shows part of the alignment. Motif 1 and motif 2 are indicated with boxes. Alignment was made using clustalomega.

Example 14: Effect of Phosphatase on Growth and Production of Sialic Acid in *Saccharomyces cerevisiae*

A further example of sialic acid production of several *Saccharomyces cerevisiae* strains capable of producing N-acetylneuraminate (sialic acid) wherein the strains are expressing an extra phosphatase as indicated hereunder.

The strain used here is derived from the strain described in example 4. To enhance growth and production of sialic acid in *Saccharomyces cerevisiae* according to this invention, the phosphatase genes are introduced via a 2-micron plasmid (Chan 2013 (Plasmid 70 (2013) 2-17)) and the genes are expressed using synthetic constitutive promoters (Blazeck 2012 (Biotechnology and Bioengineering, Vol. 109, No. 11)) as also described in example 1. The specific plasmids used in this embodiment is p2a_2µ_sia_glmS-phospha. This plasmid based on the plasmid p2a_2µ_sia_glmS plasmid is described in example 1. It is introduced into *Saccharomyces cerevisae* using the transformation technique described by Gietz and Woods (2002, PMID 12073338) and a mutant strain is obtained. The effect of phosphatase expression on growth and production of sialic acid of these mutants are evaluated as described in example 11.

Example 15: Effect of Phosphatase on Growth and Production of Sialic Acid in *Bacillus subtilis*

In another embodiment, this invention can be used to enhance growth and production of sialic acid in *Bacillus subtilis*, yet another bacterial production host.

The strain used here is derived from the strain described in example 9. Additionally to the alterations described in example 9, phosphatase genes EcAphA (SEQ ID NO: 42), EcCof (SEQ ID NO: 43), EcHisB (SEQ ID NO: 44), EcOtsB (SEQ ID NO: 45), EcSurE (SEQ ID NO: 46), EcYaed (SEQ ID NO: 47), EcYcjU (SEQ ID NO: 48), EcYedP (SEQ ID NO: 49), EcYfbT (SEQ ID NO: 50), EcYidA (SEQ ID NO: 51), EcYigB (SEQ ID NO: 52), EcYihX (SEQ ID NO: 53), EcYniC (SEQ ID NO: 54), EcYqaB (SEQ ID NO: 55), EcYrbL (SEQ ID NO: 56), PsMupP (SEQ ID NO: 57), EcAppA (SEQ ID NO: 58), EcGph (SEQ ID NO: 59), EcSerB (SEQ ID NO: 60), EcNagD (SEQ ID NO: 61), EcYbhA (SEQ ID NO: 62), EcYbiV (SEQ ID NO: 63), EcYbjL (SEQ ID NO: 64), EcYfbR (SEQ ID NO: 65), EcYieH (SEQ ID NO: 66), EcYjgL (SEQ ID NO: 67), Ec YjjG (SEQ ID NO: 68), EcYrfG (SEQ ID NO: 69), EcYbiU (SEQ ID NO: 70), ScDOG1 (SEQ ID NO: 71) and BsAraL (SEQ ID NO: 72) are overexpressed on a plasmid, as described in example 1. Subsequently, this plasmid is introduced in *Bacillus subtilis*. The effect of phosphatase expression on growth and production of sialic acid of the created mutants are evaluated as described in example 11.

The invention claimed is:

1. A method for the production of a sialylated compound in a microorganism, the method consisting essentially of: culturing a microorganism in a culture medium, said culture medium comprising an exogenous precursor, wherein said microorganism comprises at least one nucleic acid encoding a phosphatase, at least one nucleic acid encoding an N-acetylmannosamine epimerase; and at least one nucleic acid encoding a sialic acid synthase, and wherein said microorganism is unable to i) convert N-acetylglucosamine-6-P to glucosamine-6-P, ii) convert N-acetyl-glucosamine to N-acetyl-glucosamine-6-P, and iii) convert N-acetyl-neuraminate to N-acetyl-mannosamine; and increasing expression in said microorganism of a nucleic acid encoding a HAD-alike phosphatase, wherein said HAD-alike phosphatase comprises: at least one of the following motifs: Motif 1: hDxDx[TV] (SEQ ID NO: 73], or Motif 2: [GSTDE] [DSEN]x(1-2)[hP]x(1-2)[DGTS] (SEQ ID NOs: 74, 75, 76, 77) wherein h means a hydrophobic amino acid (A, I, L, M, F, V, P, G) and x can be any distinct amino acid; or any one of SEQ ID NOs: 43, 44, 45, 46, 47, 48, 50, 51, 52, 54, 55, or 57.

2. The method according to claim 1, wherein said expression is effected by the action of a constitutive promoter.

3. The method according to claim 1, wherein said sialylated compound is selected from the group consisting of N-acetylneuramic acid, sialylated oligosaccharide, sialylated lipid, sialylated protein, and sialylated aglycon.

4. The method according to claim 3, wherein said sialylated compound is N-acetylneuraminic acid or is a sialylated oligosaccharide selected from the group consisting of sialyllactose and disialyl lacto-N-tetrose.

5. The method according to claim 1 wherein said sialylated compound is a sialylated lacto-N-triose, lacto-N-tetraose or a lacto-N-neotetraose, and wherein said microorganism further comprises the activity of a galactosyltransferase.

6. The method according to claim 5 wherein said microorganism is unable to express the genes coding for either of UDP sugar hydrolase or galactose-1-phosphate uridylyltransferase.

7. The method according to claim 1, wherein said microorganism produces less than 50% of an amount of extracellular N-acetylglucosamine than sialylated compound.

8. The method according to claim 1 for producing a sialylated oligosaccharide, comprising: a) culturing a microorganism wherein said microorganism produces internally, activated N-acetylneuraminate as a donor substrate for a sialyltransferase; and b) culturing said microorganism in a culture medium wherein said exogenous precursor is selected from the group consisting of lactose, N-acetyllactosamine, lacto-N-biose, galactose, beta-galactoside, and alpha-galactoside, wherein active uptake into the microorganism of said exogenous precursor occurs and wherein said exogenous precursor is the acceptor substrate for said sialyltransferase for producing the sialylated oligosaccharide.

9. The method according to claim 1, wherein any one or more of the N-acetylmannosamine epimerase and the sialic acid synthase is overexpressed in the microorganism.

10. The method according to claim 1, wherein any one or more of the N-acetylmannosamine epimerase and the sialic acid synthase is introduced and expressed in the microorganism.

11. The method according to claim 1, wherein said microorganism is an *Escherichia coli* strain.

12. The method according to claim 1, wherein said microorganism is a yeast.

* * * * *

```
                        SEQUENCE LISTING

<160> NUMBER OF SEQ ID NOS: 154

<210> SEQ ID NO 1
<211> LENGTH: 69
<212> TYPE: DNA
<213> ORGANISM: Artificial Sequence
<220> FEATURE:
<223> OTHER INFORMATION: Synthetic DNA

<400> SEQUENCE: 1
gctgaacttg taggcctgat aagcgcagcg tatcaggcaa tttttataat cttcatttaa      60
atggcgcgc                                                             69

<210> SEQ ID NO 2
<211> LENGTH: 69
<212> TYPE: DNA
<213> ORGANISM: Artificial Sequence
<220> FEATURE:
<223> OTHER INFORMATION: Synthetic DNA

<400> SEQUENCE: 2
gcgcaacgca attaatgtga gttagctcac tcattaggca ccccaggctt cgcctacctg      60
tgacggaag                                                             69

<210> SEQ ID NO 3
<211> LENGTH: 75
<212> TYPE: DNA
<213> ORGANISM: Artificial Sequence
<220> FEATURE:
<223> OTHER INFORMATION: Synthetic DNA

<400> SEQUENCE: 3
cgcttaaaga tgcctaatcc gccaacggct tacattttac ttattgaggt gaatagtgta      60
ggctggagct gcttc                                                      75

<210> SEQ ID NO 4
<211> LENGTH: 66
<212> TYPE: DNA
<213> ORGANISM: Artificial Sequence
<220> FEATURE:
<223> OTHER INFORMATION: synthetic DNA

<400> SEQUENCE: 4
ggcgtttgtc atcagagcca accacgtccg cagacgtggt tgctatcata tgaatatcct      60
ccttag                                                                66

<210> SEQ ID NO 5
<211> LENGTH: 62
<212> TYPE: DNA
<213> ORGANISM: Artificial Sequence
<220> FEATURE:
<223> OTHER INFORMATION: synthetic DNA

<400> SEQUENCE: 5
taatgcgccg ccagtaaatc aacatgaaat gccgctggct ccgtgtaggc tggagctgct      60
tc                                                                    62
```

<210> SEQ ID NO 6
<211> LENGTH: 70
<212> TYPE: DNA
<213> ORGANISM: Artificial Sequence
<220> FEATURE:
<223> OTHER INFORMATION: synthetic DNA

<400> SEQUENCE: 6

```
ccaacaacaa gcactggata aagcgagtct gcgtcgcctg gttcagttca catatgaata    60
tcctccttag                                                          70
```

<210> SEQ ID NO 7
<211> LENGTH: 70
<212> TYPE: DNA
<213> ORGANISM: Artificial Sequence
<220> FEATURE:
<223> OTHER INFORMATION: synthetic DNA

<400> SEQUENCE: 7

```
aaaatacatc tggcacgttg aggtgttaac gataataaag gaggtagcaa gtgtaggctg    60
gagctgcttc                                                          70
```

<210> SEQ ID NO 8
<211> LENGTH: 70
<212> TYPE: DNA
<213> ORGANISM: Artificial Sequence
<220> FEATURE:
<223> OTHER INFORMATION: synthetic DNA

<400> SEQUENCE: 8

```
cctccagata aaaaacggg gccaaaaggc cccggtagtg tacaacagtc catatgaata     60
tcctccttag                                                          70
```

<210> SEQ ID NO 9
<211> LENGTH: 70
<212> TYPE: DNA
<213> ORGANISM: Artificial Sequence
<220> FEATURE:
<223> OTHER INFORMATION: synthetic DNA

<400> SEQUENCE: 9

```
gtttggcgtt tgtcatcaga gccaaccacg tccgcagacg tggttgctat gtgtaggctg    60
gagctgcttc                                                          70
```

<210> SEQ ID NO 10
<211> LENGTH: 70
<212> TYPE: DNA
<213> ORGANISM: Artificial Sequence
<220> FEATURE:
<223> OTHER INFORMATION: Synthetic DNA

<400> SEQUENCE: 10

```
ttgtcattgt tggatgcgac gctcaagcgt cgcatcaggc ataaagcaga cttaagcgac    60
ttcattcacc                                                          70
```

<210> SEQ ID NO 11
<211> LENGTH: 70
<212> TYPE: DNA
<213> ORGANISM: Artificial Sequence
<220> FEATURE:
<223> OTHER INFORMATION: Synthetic DNA

<400> SEQUENCE: 11

```
catggcggta atgcgccgcc agtaaatcaa catgaaatgc cgctggctcc gtgtaggctg    60
gagctgcttc                                                            70
```

<210> SEQ ID NO 12
<211> LENGTH: 70
<212> TYPE: DNA
<213> ORGANISM: Artificial Sequence
<220> FEATURE:
<223> OTHER INFORMATION: synthetic DNA

<400> SEQUENCE: 12

```
ccaacaacaa gcactggata aagcgagtct gcgtcgcctg gttcagttca cttaagcgac    60
ttcattcacc                                                            70
```

<210> SEQ ID NO 13
<211> LENGTH: 70
<212> TYPE: DNA
<213> ORGANISM: Artificial Sequence
<220> FEATURE:
<223> OTHER INFORMATION: synthetic DNA

<400> SEQUENCE: 13

```
aaaatacatc tggcacgttg aggtgttaac gataataaag gaggtagcaa gtgtaggctg    60
gagctgcttc                                                            70
```

<210> SEQ ID NO 14
<211> LENGTH: 70
<212> TYPE: DNA
<213> ORGANISM: Artificial Sequence
<220> FEATURE:
<223> OTHER INFORMATION: synthetic DNA

<400> SEQUENCE: 14

```
cctccagata aaaaacggg gccaaaaggc cccggtagtg tacaacagtc cttaagcgac     60
ttcattcacc                                                            70
```

<210> SEQ ID NO 15
<211> LENGTH: 70
<212> TYPE: DNA
<213> ORGANISM: Artificial Sequence
<220> FEATURE:
<223> OTHER INFORMATION: synthetic DNA

<400> SEQUENCE: 15

```
gcgcaacgca attaatgtga gttagctcac tcattaggca ccccaggctt gtgtaggctg    60
gagctgcttc                                                            70
```

<210> SEQ ID NO 16
<211> LENGTH: 70
<212> TYPE: DNA
<213> ORGANISM: Artificial Sequence
<220> FEATURE:
<223> OTHER INFORMATION: synthetic DNA

<400> SEQUENCE: 16

```
gctgaacttg taggcctgat aagcgcagcg tatcaggcaa ttttataat cttaagcgac     60 ttcattcacc                                                            70
```

<210> SEQ ID NO 17
<211> LENGTH: 70
<212> TYPE: DNA
<213> ORGANISM: Artificial Sequence

```
<220> FEATURE:
<223> OTHER INFORMATION: synthetic DNA

<400> SEQUENCE: 17
caaaaagcgg tcaaattata cggtgcgccc ccgtgatttc aaacaataag gtgtaggctg    60
gagctgcttc                                                          70

<210> SEQ ID NO 18
<211> LENGTH: 70
<212> TYPE: DNA
<213> ORGANISM: Artificial Sequence
<220> FEATURE:
<223> OTHER INFORMATION: synthetic DNA

<400> SEQUENCE: 18
ataacgtggc ttttttggt aagcagaaaa taagtcatta gtgaaaatat cttaagcgac     60
ttcattcacc                                                          70

<210> SEQ ID NO 19
<211> LENGTH: 20
<212> TYPE: DNA
<213> ORGANISM: Artificial Sequence
<220> FEATURE:
<223> OTHER INFORMATION: synthetic DNA

<400> SEQUENCE: 19
caggtttccc gactggaaag                                               20

<210> SEQ ID NO 20
<211> LENGTH: 20
<212> TYPE: DNA
<213> ORGANISM: Artificial Sequence
<220> FEATURE:
<223> OTHER INFORMATION: synthetic DNA

<400> SEQUENCE: 20
tgtgcgtcgt tgggctgatg                                               20

<210> SEQ ID NO 21
<211> LENGTH: 20
<212> TYPE: DNA
<213> ORGANISM: Artificial Sequence
<220> FEATURE:
<223> OTHER INFORMATION: synthetic DNA

<400> SEQUENCE: 21
cgcttgtcat tgttggatgc                                               20

<210> SEQ ID NO 22
<211> LENGTH: 22
<212> TYPE: DNA
<213> ORGANISM: Artificial Sequence
<220> FEATURE:
<223> OTHER INFORMATION: synthetic DNA

<400> SEQUENCE: 22
gctgacaaag tgcgatttgt tc                                            22

<210> SEQ ID NO 23
<211> LENGTH: 20
<212> TYPE: DNA
<213> ORGANISM: Artificial Sequence
<220> FEATURE:
<223> OTHER INFORMATION: synthetic DNA
```

```
<400> SEQUENCE: 23
gtcgccctgt aattcgtaac                                                 20

<210> SEQ ID NO 24
<211> LENGTH: 20
<212> TYPE: DNA
<213> ORGANISM: Artificial Sequence
<220> FEATURE:
<223> OTHER INFORMATION: synthetic DNA

<400> SEQUENCE: 24
ctttcggtca gaccaccaac                                                 20

<210> SEQ ID NO 25
<211> LENGTH: 20
<212> TYPE: DNA
<213> ORGANISM: Artificial Sequence
<220> FEATURE:
<223> OTHER INFORMATION: synthetic DNA

<400> SEQUENCE: 25
acgcctctga tttggcaaag                                                 20

<210> SEQ ID NO 26
<211> LENGTH: 20
<212> TYPE: DNA
<213> ORGANISM: Artificial Sequence
<220> FEATURE:
<223> OTHER INFORMATION: synthetic DNA

<400> SEQUENCE: 26
agccagtgcg cttaataacc                                                 20

<210> SEQ ID NO 27
<211> LENGTH: 20
<212> TYPE: DNA
<213> ORGANISM: Artificial Sequence
<220> FEATURE:
<223> OTHER INFORMATION: synthetic DNA

<400> SEQUENCE: 27
gctgaacagc aatccacttg                                                 20

<210> SEQ ID NO 28
<211> LENGTH: 20
<212> TYPE: DNA
<213> ORGANISM: Artificial Sequence
<220> FEATURE:
<223> OTHER INFORMATION: synthetic DNA

<400> SEQUENCE: 28
tgaacgatat ggtgagctgg                                                 20

<210> SEQ ID NO 29
<211> LENGTH: 500
<212> TYPE: DNA
<213> ORGANISM: Artificial Sequence
<220> FEATURE:
<223> OTHER INFORMATION: synthetic DNA

<400> SEQUENCE: 29
agatggaatg gcgattttca ctctaaattt taaaaattgc ctctttacaa tagcgaattt      60 cctaacccctt tttttttttt gttgattgcc tattgctcgt tcacttccca tttattttct   120
ctcgaatttc accaaaagtt gatgtggata atcaatcatc gggcctattc ctgcgggtaa   180
```

```
aacgcagggc ccaactcagg atagggttta atattatttt agaggactta caagaaggaa      240
gttatatggt ttaaaaattg taacaaagtt agaacacatt tatttagcag gtctaattta      300
gggctgcaac tatcttttg gttattcata taaaatataa ttttttattt atatagagaa       360
tacaagtgga atcatcttta acgccagctt gtagtgcgca ttgcagaata atggaagttc      420
aaaaattaaa agcgaaggag aagtgatagt agaaagacgg atgggaggct gggggacgaa      480
gagaaagtaa aagggttaat                                                  500
```

<210> SEQ ID NO 30
<211> LENGTH: 500
<212> TYPE: DNA
<213> ORGANISM: Artificial Sequence
<220> FEATURE:
<223> OTHER INFORMATION: synthetic DNA

<400> SEQUENCE: 30

```
ttttttataa aagttgctgt tgatttgctc gagaacttat tgcttatttg gccctgataa      60
ctatataaga aagaaatac agttattcct tgtttatgct ggcttttgt ccacttttc        120 tcaactatat aactatgatg ttggaaagga caccggttct gtaactttgc agtgaaaata     180
agtgtgatgg atgactgaga atgctttctt gtaagcgaaa agaagtacgt gttccaaaaa     240
taaagcagaa aggcgaaaag ggtcgaatgt aagcacactaa ataaatattt taagaagagg    300
aaaagtcgcc tcagaaacgc taaaatgcat ccgatttccc aaagaggaag tctaatgttt    360
tcgatttgtg aaaaaaagat aaaaatcgaa gaaaatgtag ggagccgcgc gttacccgga    420
ttgatatttg agtgatcgac ggcgtcacaa agaaagaat gcttggctaa tcaagaaaag    480
tatgtggttt gtttcatcta                                                  500
```

<210> SEQ ID NO 31
<211> LENGTH: 20
<212> TYPE: DNA
<213> ORGANISM: Artificial Sequence
<220> FEATURE:
<223> OTHER INFORMATION: synthetic DNA

<400> SEQUENCE: 31

```
gcaggtctaa tttagggctg                                                  20
```

<210> SEQ ID NO 32
<211> LENGTH: 20
<212> TYPE: DNA
<213> ORGANISM: Artificial Sequence
<220> FEATURE:
<223> OTHER INFORMATION: synthetic DNA

<400> SEQUENCE: 32

```
agaaagcatt ctcagtcatc                                                  20
```

<210> SEQ ID NO 33
<211> LENGTH: 1000
<212> TYPE: DNA
<213> ORGANISM: Artificial Sequence
<220> FEATURE:
<223> OTHER INFORMATION: synthetic DNA

<400> SEQUENCE: 33

```
gactgcaaga tttcggcctg ggcggacggg aatcgtcagt tttgtaattt ctgtatcaat      60
gattttcatg gtctcttcct caagtccgag ccggtcgtat tgcttgccct gctcccagag     120
```

| | |
|---|---|
| ttcaagattc atgacaatcg tgattcgttt attgcttctg accgcgccag cgccaaatag | 180 |
| cgtcatcaca ttgataatgc caaggcccct gatctcaaga aggtgctcaa ttaattccgg | 240 |
| agcgtttccc acaagagtat cctgatcctc ctgccgtatt tcaacgcaat catcggcaac | 300 |
| aaggcgatgc cctcttttca caagctctag cgctgtttcg cttttccga cgccgctttt | 360 |
| tcctgtgatc agcacgccga caccatatat atcgacaaga acgccatgaa ttgctgtggt | 420 |
| aggcgccagc ctgctctcaa ggaagttggt taaacggctt gacagtcttg tcgttttcag | 480 |
| cggcgatctg aggacaggca ccccattttt ctcggaggcg tcaatcagct cctgcgggat | 540 |
| gggcatatct ctagaaagaa taatagctgg tgttacatca gtgcacagag aatccattcg | 600 |
| ctgcttttc tcctcttcag gaagctgttc aaagaaagaa agctctgttt ttccgagaag | 660 |
| ctgcacgcgc tccctcgggt aatatgtaaa atatccggca atttcaatac ctggtcttga | 720 |
| taggtcactc attgtaatcg ggcggttaat tccttcttct ccgctgatta attccaaatt | 780 |
| gaactgttcc attacgtctt ttgtgcgaac ctttgccacg atatgttcct cctgttccgg | 840 |
| gctgccccga gcttgctcac aatactttca ttttatcact ttcgggcttg aacctaaaac | 900 |
| agattttata aagggggga aaacacctca gctggtctag atcactagtc tgaaaagag | 960 |
| taaaataaag gtattcaaat tccagaaagg cggatcatct | 1000 |

<210> SEQ ID NO 34
<211> LENGTH: 1000
<212> TYPE: DNA
<213> ORGANISM: Artificial Sequence
<220> FEATURE:
<223> OTHER INFORMATION: synthetic DNA

<400> SEQUENCE: 34

| | |
|---|---|
| aaggaacatg ctgacttatg aatatcaata acaatcgcc tattccgatt tactatcaga | 60 |
| ttatggagca attaaaaacc caaattaaga acggagagct gcagccggat atgcctcttc | 120 |
| cttctgagcg cgaatatgcc gaacaattcg ggatcagccg gatgacagtt cgccaggcgc | 180 |
| tttctaattt agttaatgaa ggcttgctct atcgcctgaa agggcggggc acctttgtca | 240 |
| gcaagccaaa aatggaacaa gcacttcaag ggctgacaag ctttaccgag gatatgaaaa | 300 |
| gccgcgggat gacaccgggc agcaggctca ttgattatca gcttattgat tcaactgagg | 360 |
| agctcgcggc tatattaggc tgcgggcacc cctcctctat ccataaaatc actcgggtgc | 420 |
| ggctggcaaa tgatattccg atggcgattg agtcctcaca tattccgttt gagcttgcgg | 480 |
| gtgaattgaa cgaatcgcat tttcagtcgt cgatctatga tcatattgaa aggtacaaca | 540 |
| gcataccgat ttcccgtgca aaacaggagc ttgagccaag cgctgccacc acggaagaag | 600 |
| cgaatattct tggtattcaa aagggagcgc ctgtcctatt aattaaacga acaacatatc | 660 |
| tgcagaacgg aactgctttt gagcatgcaa aatccgtata cagaggcgac cgttatacat | 720 |
| tgtccacta tatggatcgt ctttcataaa aaaagcctcc aacccttttt aaggattgga | 780 |
| gacatggcga aaatcaaact ggtctggtgc cggacgatat gtttcttttt tcgtcttgaa | 840 |
| cttccagatc ggtgatttcg ttttgccgtt aaaactgtct tccactataa tgtaccaata | 900 |
| ataaacagac tgcggttcaa gatgatccca gcggaattca gctgtgtccc cgctcttcac | 960 |
| ttgctcccgt tttccgagct cttcattggt atatacgtta | 1000 |

<210> SEQ ID NO 35
<211> LENGTH: 1000
<212> TYPE: DNA
<213> ORGANISM: Artificial Sequence
<220> FEATURE:
<223> OTHER INFORMATION: synthetic DNA

<400> SEQUENCE: 35

```
tggcggacat ggaataaatc acaaacgaca aagatgacgc cggcaagaat agagttaatc        60
aaatagagca cgggcgcaac gaacaagaaa gaaaactcaa ccggttctgt aattccggtc       120
agcatagatg tgagcgccgc agaaatcatc acgccggaga tcatttttt cttttccgga        180
cgcgcggtat ggataatggc aagagcaacg gccggcagac agaaaatcat gtaagggaaa       240
tccccatca taaagcgccc ggctgtcggg tctcccgcga aaaccttgt caggtcgccg         300
gttacggtgt tgcctgttga tgggtctgtg tattctccca tcataaaata gaaaggcgta       360
taaaaaatat gatgcaggcc aaaaggaatc agcaaacgat agatcgttgc ataaaagaac       420
aggccgactt tgaatcggca aattaaactg ctggctgcgt taattccgtt ttggatcagc       480
ggccaaacga atgagaaaat gacgccgatc accaatgaac tgacggaagt aatgatcggg       540
acaaagcgtt ttccagagaa aaatccaagg accggatgca gctcgattga tgaaaatcgc       600
ttatataaat aggcggcgag aagcccgata atgattcctc cgaaaacccc catatcaatc       660
aggtgctcgg ctccttcata cggaggctga aggccgagta attttcccat attgtcgagg       720
gtgacggtta aaattaagta tccgatgaca gcggcaagtc cggctacacc ttctccgccg       780
gctaatccga tcgcgacccc cacggcgaaa atcagcggaa ggttatcgaa tacaacgccg       840
cccgcatcct ttataatagg gatgttcagt aaatccttgt ctccgaaacg gagcaaaaga       900
cctgctgccg gcaggacggc aaccggagtc atcaacgcgc ggccaagctg ctgcagaatt       960
tgaaatgcct ttttaaacat gacagtctcc ttttattgtg                            1000
```

<210> SEQ ID NO 36
<211> LENGTH: 1000
<212> TYPE: DNA
<213> ORGANISM: Artificial Sequence
<220> FEATURE:
<223> OTHER INFORMATION: synthetic DNA

<400> SEQUENCE: 36

```
gtgacacccc ctcaaagaga tagacaagca ccatatttgt tatgaccaat ttatgatact        60
tgtcattacg aatttagcac cgcccttatc aaactgtcaa tattaatttc tgaaaatttg       120
ttataaaaga aggatacaaa tctttcatat tgggagggca aatggtatta tggtctcaat       180
gaaaagaac ggattgcata cagaatgggg agaatgaaat gacagcttta tattctgtta        240
tcaagtttaa aatcattgag ttaattaaat cgggcaaata tcaggcgaat gatcagctgc       300
cgacggagag tgagttttgc gaacaatatg atgtcagcag aacaactgtg agactggctc       360
tgcagcagct agagcttgag ggatatatta aagaattca aggaaaaggg acatttgtat        420
cggcggccaa aatacaaacg ccgattccgc ataagattac gagctttgca gaacaaatga       480
gaggacttcg ttctgaatca aaagtgcttg agcttgtggt gattcctgcc gatcattcca       540
tcgccgagct tttgaaaatg aaagagaatg aacctgtcaa caagcttgtc agagtcagat       600
acgccgaggg ggaacctttg cagtatcata cctcatatat tccctggaag gcggcaccgg       660
ggctggcgca ggaggaatgc accggctcgc tgtttgaatt gttaaggaca aaatacaata       720
ttgaaatcag caggggcacg gaatcgatcg aaccgatttt aacggatgaa acgatcagcg       780
gacacttatt aaccaatgtc ggagcgcctg cgttttatc agaatccctt acctatgata        840
aaaatgaaga agtggtggaa tatgcgcaaa ttattacacg gggagaccga acgaaattca       900
```

```
ccgtagaaca gtcatatcat tcataaagca atgtgtttta agaagggaat ggtggttcta    960
tgtttttatt tacgaatgga aaagtgctgt ggggagcagt                          1000
```

<210> SEQ ID NO 37
<211> LENGTH: 20
<212> TYPE: DNA
<213> ORGANISM: Artificial Sequence
<220> FEATURE:
<223> OTHER INFORMATION: synthetic DNA

<400> SEQUENCE: 37

```
tgtaatcggg cggttaattc                                                20
```

<210> SEQ ID NO 38
<211> LENGTH: 19
<212> TYPE: DNA
<213> ORGANISM: Artificial Sequence
<220> FEATURE:
<223> OTHER INFORMATION: synthetic DNA

<400> SEQUENCE: 38

```
gccctttcag gcgatagag                                                 19
```

<210> SEQ ID NO 39
<211> LENGTH: 20
<212> TYPE: DNA
<213> ORGANISM: Artificial Sequence
<220> FEATURE:
<223> OTHER INFORMATION: synthetic DNA

<400> SEQUENCE: 39

```
acggcgaaaa tcagcggaag                                                20
```

<210> SEQ ID NO 40
<211> LENGTH: 20
<212> TYPE: DNA
<213> ORGANISM: Artificial Sequence
<220> FEATURE:
<223> OTHER INFORMATION: synthetic DNA

<400> SEQUENCE: 40

```
tcactctccg tcggcagctg                                                20
```

<210> SEQ ID NO 41
<211> LENGTH: 72
<212> TYPE: DNA
<213> ORGANISM: artificial
<220> FEATURE:
<223> OTHER INFORMATION: UTR1

<400> SEQUENCE: 41

```
aattcgccgg agggatatta aaatgaatgg aaaattgaaa catcttaatc atgctaagga    60
ggttttctaa tg                                                        72
```

<210> SEQ ID NO 42
<211> LENGTH: 237
<212> TYPE: PRT
<213> ORGANISM: Escherichia coli

<400> SEQUENCE: 42

Met Arg Lys Ile Thr Gln Ala Ile Ser Ala Val Cys Leu Leu Phe Ala
1               5                   10                  15

Leu Asn Ser Ser Ala Val Ala Leu Ala Ser Ser Pro Ser Pro Leu Asn
            20                  25                  30

```
Pro Gly Thr Asn Val Ala Arg Leu Ala Glu Gln Ala Pro Ile His Trp
        35                  40                  45

Val Ser Val Ala Gln Ile Glu Asn Ser Leu Ala Gly Arg Pro Pro Met
 50                  55                  60

Ala Val Gly Phe Asp Ile Asp Asp Thr Val Leu Phe Ser Ser Pro Gly
 65                  70                  75                  80

Phe Trp Arg Gly Lys Lys Thr Phe Ser Pro Glu Ser Glu Asp Tyr Leu
                 85                  90                  95

Lys Asn Pro Val Phe Trp Glu Lys Met Asn Asn Gly Trp Asp Glu Phe
            100                 105                 110

Ser Ile Pro Lys Glu Val Ala Arg Gln Leu Ile Asp Met His Val Arg
        115                 120                 125

Arg Gly Asp Ala Ile Phe Phe Val Thr Gly Arg Ser Pro Thr Lys Thr
130                 135                 140

Glu Thr Val Ser Lys Thr Leu Ala Asp Asn Phe His Ile Pro Ala Thr
145                 150                 155                 160

Asn Met Asn Pro Val Ile Phe Ala Gly Asp Lys Pro Gly Gln Asn Thr
                165                 170                 175

Lys Ser Gln Trp Leu Gln Asp Lys Asn Ile Arg Ile Phe Tyr Gly Asp
            180                 185                 190

Ser Asp Asn Asp Ile Thr Ala Ala Arg Asp Val Gly Ala Arg Gly Ile
        195                 200                 205

Arg Ile Leu Arg Ala Ser Asn Ser Thr Tyr Lys Pro Leu Pro Gln Ala
210                 215                 220

Gly Ala Phe Gly Glu Glu Val Ile Val Asn Ser Glu Tyr
225                 230                 235

<210> SEQ ID NO 43
<211> LENGTH: 272
<212> TYPE: PRT
<213> ORGANISM: Escherichia coli

<400> SEQUENCE: 43

Met Ala Arg Leu Ala Ala Phe Asp Met Asp Gly Thr Leu Leu Met Pro
 1               5                  10                  15

Asp His His Leu Gly Glu Lys Thr Leu Ser Thr Leu Ala Arg Leu Arg
            20                  25                  30

Glu Arg Asp Ile Thr Leu Thr Phe Ala Thr Gly Arg His Ala Leu Glu
        35                  40                  45

Met Gln His Ile Leu Gly Ala Leu Ser Leu Asp Ala Tyr Leu Ile Thr
 50                  55                  60

Gly Asn Gly Thr Arg Val His Ser Leu Glu Gly Glu Leu Leu His Arg
 65                  70                  75                  80

Asp Asp Leu Pro Ala Asp Val Ala Glu Leu Val Leu Tyr Gln Gln Trp
                 85                  90                  95

Asp Thr Arg Ala Ser Met His Ile Phe Asn Asp Asp Gly Trp Phe Thr
            100                 105                 110

Gly Lys Glu Ile Pro Ala Leu Leu Gln Ala Phe Val Tyr Ser Gly Phe
        115                 120                 125

Arg Tyr Gln Ile Ile Asp Val Lys Lys Met Pro Leu Gly Ser Val Thr
130                 135                 140

Lys Ile Cys Phe Cys Gly Asp His Asp Asp Leu Thr Arg Leu Gln Ile
145                 150                 155                 160

Gln Leu Tyr Glu Ala Leu Gly Glu Arg Ala His Leu Cys Phe Ser Ala
```

```
                165                 170                 175
Thr Asp Cys Leu Glu Val Leu Pro Val Gly Cys Asn Lys Gly Ala Ala
                180                 185                 190

Leu Thr Val Leu Thr Gln His Leu Gly Leu Ser Leu Arg Asp Cys Met
                195                 200                 205

Ala Phe Gly Asp Ala Met Asn Asp Arg Glu Met Leu Val Ser Val Gly
                210                 215                 220

Ser Gly Phe Ile Met Gly Asn Ala Met Pro Gln Leu Arg Ala Glu Leu
225                 230                 235                 240

Pro His Leu Pro Val Ile Gly His Cys Arg Asn Gln Ala Val Ser His
                245                 250                 255

Tyr Leu Thr His Trp Leu Asp Tyr Pro His Leu Pro Tyr Ser Pro Glu
                260                 265                 270

<210> SEQ ID NO 44
<211> LENGTH: 355
<212> TYPE: PRT
<213> ORGANISM: Escherichia coli

<400> SEQUENCE: 44

Met Ser Gln Lys Tyr Leu Phe Ile Asp Arg Asp Gly Thr Leu Ile Ser
1               5                   10                  15

Glu Pro Pro Ser Asp Phe Gln Val Asp Arg Phe Asp Lys Leu Ala Phe
                20                  25                  30

Glu Pro Gly Val Ile Pro Glu Leu Leu Lys Leu Gln Lys Ala Gly Tyr
                35                  40                  45

Lys Leu Val Met Ile Thr Asn Gln Asp Gly Leu Gly Thr Gln Ser Phe
            50                  55                  60

Pro Gln Ala Asp Phe Asp Gly Pro His Asn Leu Met Met Gln Ile Phe
65              70                  75                  80

Thr Ser Gln Gly Val Gln Phe Asp Glu Val Leu Ile Cys Pro His Leu
                85                  90                  95

Pro Ala Asp Glu Cys Asp Cys Arg Lys Pro Lys Val Lys Leu Val Glu
                100                 105                 110

Arg Tyr Leu Ala Glu Gln Ala Met Asp Arg Ala Asn Ser Tyr Val Ile
            115                 120                 125

Gly Asp Arg Ala Thr Asp Ile Gln Leu Ala Glu Asn Met Gly Ile Thr
130                 135                 140

Gly Leu Arg Tyr Asp Arg Glu Thr Leu Asn Trp Pro Met Ile Gly Glu
145                 150                 155                 160

Gln Leu Thr Arg Arg Asp Arg Tyr Ala His Val Val Arg Asn Thr Lys
                165                 170                 175

Glu Thr Gln Ile Asp Val Gln Val Trp Leu Asp Arg Glu Gly Gly Ser
                180                 185                 190

Lys Ile Asn Thr Gly Val Gly Phe Phe Asp His Met Leu Asp Gln Ile
            195                 200                 205

Ala Thr His Gly Gly Phe Arg Met Glu Ile Asn Val Lys Gly Asp Leu
            210                 215                 220

Tyr Ile Asp Asp His His Thr Val Glu Asp Thr Gly Leu Ala Leu Gly
225                 230                 235                 240

Glu Ala Leu Lys Ile Ala Leu Gly Asp Lys Arg Gly Ile Cys Arg Phe
                245                 250                 255

Gly Phe Val Leu Pro Met Asp Glu Cys Leu Ala Arg Cys Ala Leu Asp
                260                 265                 270
```

```
Ile Ser Gly Arg Pro His Leu Glu Tyr Lys Ala Glu Phe Thr Tyr Gln
            275                 280                 285

Arg Val Gly Asp Leu Ser Thr Glu Met Ile Glu His Phe Phe Arg Ser
        290                 295                 300

Leu Ser Tyr Thr Met Gly Val Thr Leu His Leu Lys Thr Lys Gly Lys
305                 310                 315                 320

Asn Asp His His Arg Val Glu Ser Leu Phe Lys Ala Phe Gly Arg Thr
                325                 330                 335

Leu Arg Gln Ala Ile Arg Val Glu Gly Asp Thr Leu Pro Ser Ser Lys
            340                 345                 350

Gly Val Leu
        355

<210> SEQ ID NO 45
<211> LENGTH: 266
<212> TYPE: PRT
<213> ORGANISM: Escherichia coli

<400> SEQUENCE: 45

Met Thr Glu Pro Leu Thr Glu Thr Pro Glu Leu Ser Ala Lys Tyr Ala
1               5                   10                  15

Trp Phe Phe Asp Leu Asp Gly Thr Leu Ala Glu Ile Lys Pro His Pro
            20                  25                  30

Asp Gln Val Val Val Pro Asp Asn Ile Leu Gln Gly Leu Gln Leu Leu
        35                  40                  45

Ala Thr Ala Ser Asp Gly Ala Leu Ala Leu Ile Ser Gly Arg Ser Met
    50                  55                  60

Val Glu Leu Asp Ala Leu Ala Lys Pro Tyr Arg Phe Pro Leu Ala Gly
65                  70                  75                  80

Val His Gly Ala Glu Arg Arg Asp Ile Asn Gly Lys Thr His Ile Val
                85                  90                  95

His Leu Pro Asp Ala Ile Ala Arg Asp Ile Ser Val Gln Leu His Thr
            100                 105                 110

Val Ile Ala Gln Tyr Pro Gly Ala Glu Leu Glu Ala Lys Gly Met Ala
        115                 120                 125

Phe Ala Leu His Tyr Arg Gln Ala Pro Gln His Glu Asp Ala Leu Met
    130                 135                 140

Thr Leu Ala Gln Arg Ile Thr Gln Ile Trp Pro Gln Met Ala Leu Gln
145                 150                 155                 160

Gln Gly Lys Cys Val Val Glu Ile Lys Pro Arg Gly Thr Ser Lys Gly
                165                 170                 175

Glu Ala Ile Ala Ala Phe Met Gln Glu Ala Pro Phe Ile Gly Arg Thr
            180                 185                 190

Pro Val Phe Leu Gly Asp Asp Leu Thr Asp Glu Ser Gly Phe Ala Val
        195                 200                 205

Val Asn Arg Leu Gly Gly Met Ser Val Lys Ile Gly Thr Gly Ala Thr
    210                 215                 220

Gln Ala Ser Trp Arg Leu Ala Gly Val Pro Asp Val Trp Ser Trp Leu
225                 230                 235                 240

Glu Met Ile Thr Thr Ala Leu Gln Gln Lys Arg Glu Asn Asn Arg Ser
                245                 250                 255

Asp Asp Tyr Glu Ser Phe Ser Arg Ser Ile
            260                 265

<210> SEQ ID NO 46
```

```
<211> LENGTH: 253
<212> TYPE: PRT
<213> ORGANISM: Escherichia coli

<400> SEQUENCE: 46

Met Arg Ile Leu Leu Ser Asn Asp Asp Gly Val His Ala Pro Gly Ile
1               5                   10                  15

Gln Thr Leu Ala Lys Ala Leu Arg Glu Phe Ala Asp Val Gln Val Val
            20                  25                  30

Ala Pro Asp Arg Asn Arg Ser Gly Ala Ser Asn Ser Leu Thr Leu Glu
        35                  40                  45

Ser Ser Leu Arg Thr Phe Thr Phe Glu Asn Gly Asp Ile Ala Val Gln
50                  55                  60

Met Gly Thr Pro Thr Asp Cys Val Tyr Leu Gly Val Asn Ala Leu Met
65                  70                  75                  80

Arg Pro Arg Pro Asp Ile Val Val Ser Gly Ile Asn Ala Gly Pro Asn
                85                  90                  95

Leu Gly Asp Asp Val Ile Tyr Ser Gly Thr Val Ala Ala Ala Met Glu
            100                 105                 110

Gly Arg His Leu Gly Phe Pro Ala Leu Ala Val Ser Leu Asp Gly His
        115                 120                 125

Lys His Tyr Asp Thr Ala Ala Ala Val Thr Cys Ser Ile Leu Arg Ala
130                 135                 140

Leu Cys Lys Glu Pro Leu Arg Thr Gly Arg Ile Leu Asn Ile Asn Val
145                 150                 155                 160

Pro Asp Leu Pro Leu Asp Gln Ile Lys Gly Ile Arg Val Thr Arg Cys
                165                 170                 175

Gly Thr Arg His Pro Ala Asp Gln Val Ile Pro Gln Gln Asp Pro Arg
            180                 185                 190

Gly Asn Thr Leu Tyr Trp Ile Gly Pro Pro Gly Gly Lys Cys Asp Ala
        195                 200                 205

Gly Pro Gly Thr Asp Phe Ala Ala Val Asp Glu Gly Tyr Val Ser Ile
    210                 215                 220

Thr Pro Leu His Val Asp Leu Thr Ala His Ser Ala Gln Asp Val Val
225                 230                 235                 240

Ser Asp Trp Leu Asn Ser Val Gly Val Gly Thr Gln Trp
                245                 250

<210> SEQ ID NO 47
<211> LENGTH: 191
<212> TYPE: PRT
<213> ORGANISM: Escherichia coli

<400> SEQUENCE: 47

Met Ala Lys Ser Val Pro Ala Ile Phe Leu Asp Arg Asp Gly Thr Ile
1               5                   10                  15

Asn Val Asp His Gly Tyr Val His Glu Ile Asp Asn Phe Glu Phe Ile
            20                  25                  30

Asp Gly Val Ile Asp Ala Met Arg Glu Leu Lys Lys Met Gly Phe Ala
        35                  40                  45

Leu Val Val Val Thr Asn Gln Ser Gly Ile Ala Arg Gly Lys Phe Thr
    50                  55                  60

Glu Ala Gln Phe Glu Thr Leu Thr Glu Trp Met Asp Trp Ser Leu Ala
65                  70                  75                  80

Asp Arg Asp Val Asp Leu Asp Gly Ile Tyr Tyr Cys Pro His His Pro
                85                  90                  95
```

Gln Gly Ser Val Glu Glu Phe Arg Gln Val Cys Asp Cys Arg Lys Pro
            100                 105                 110

His Pro Gly Met Leu Leu Ser Ala Arg Asp Tyr Leu His Ile Asp Met
            115                 120                 125

Ala Ala Ser Tyr Met Val Gly Asp Lys Leu Glu Asp Met Gln Ala Ala
        130                 135                 140

Val Ala Ala Asn Val Gly Thr Lys Val Leu Val Arg Thr Gly Lys Pro
145                 150                 155                 160

Ile Thr Pro Glu Ala Glu Asn Ala Ala Asp Trp Val Leu Asn Ser Leu
                165                 170                 175

Ala Asp Leu Pro Gln Ala Ile Lys Lys Gln Gln Lys Pro Ala Gln
            180                 185                 190

<210> SEQ ID NO 48
<211> LENGTH: 219
<212> TYPE: PRT
<213> ORGANISM: Escherichia coli

<400> SEQUENCE: 48

Met Lys Leu Gln Gly Val Ile Phe Asp Leu Asp Gly Val Ile Thr Asp
1               5                   10                  15

Thr Ala His Leu His Phe Gln Ala Trp Gln Gln Ile Ala Ala Glu Ile
            20                  25                  30

Gly Ile Ser Ile Asp Ala Gln Phe Asn Glu Ser Leu Lys Gly Ile Ser
        35                  40                  45

Arg Asp Glu Ser Leu Arg Arg Ile Leu Gln His Gly Gly Lys Glu Gly
    50                  55                  60

Asp Phe Asn Ser Gln Glu Arg Ala Gln Leu Ala Tyr Arg Lys Asn Leu
65                  70                  75                  80

Leu Tyr Val His Ser Leu Arg Glu Leu Thr Val Asn Ala Val Leu Pro
                85                  90                  95

Gly Ile Arg Ser Leu Leu Ala Asp Leu Arg Ala Gln Gln Ile Ser Val
            100                 105                 110

Gly Leu Ala Ser Val Ser Leu Asn Ala Pro Thr Ile Leu Ala Ala Leu
        115                 120                 125

Glu Leu Arg Glu Phe Phe Thr Phe Cys Ala Asp Ala Ser Gln Leu Lys
    130                 135                 140

Asn Ser Lys Pro Asp Pro Glu Ile Phe Leu Ala Ala Cys Ala Gly Leu
145                 150                 155                 160

Gly Val Pro Pro Gln Ala Cys Ile Gly Ile Glu Asp Ala Gln Ala Gly
                165                 170                 175

Ile Asp Ala Ile Asn Ala Ser Gly Met Arg Ser Val Gly Ile Gly Ala
            180                 185                 190

Gly Leu Thr Gly Ala Gln Leu Leu Leu Pro Ser Thr Glu Ser Leu Thr
        195                 200                 205

Trp Pro Arg Leu Ser Ala Phe Trp Gln Asn Val
    210                 215

<210> SEQ ID NO 49
<211> LENGTH: 271
<212> TYPE: PRT
<213> ORGANISM: Escherichia coli

<400> SEQUENCE: 49

Met Phe Ser Ile Gln Gln Pro Leu Leu Val Phe Ser Asp Leu Asp Gly
1               5                   10                  15

Thr Leu Leu Asp Ser His Ser Tyr Asp Trp Gln Pro Ala Ala Pro Trp
            20                  25                  30

Leu Thr Arg Leu Arg Glu Ala Asn Val Pro Val Ile Leu Cys Ser Ser
            35                  40                  45

Lys Thr Ser Ala Glu Met Leu Tyr Leu Gln Lys Thr Leu Gly Leu Gln
50                  55                  60

Gly Leu Pro Leu Ile Ala Glu Asn Gly Ala Val Ile Gln Leu Ala Glu
65                  70                  75                  80

Gln Trp Gln Glu Ile Asp Gly Phe Pro Arg Ile Ile Ser Gly Ile Ser
                85                  90                  95

His Gly Glu Ile Ser Leu Val Leu Asn Thr Leu Arg Glu Lys Glu His
            100                 105                 110

Phe Lys Phe Thr Thr Phe Asp Asp Val Asp Asp Ala Thr Ile Ala Glu
            115                 120                 125

Trp Thr Gly Leu Ser Arg Ser Gln Ala Ala Leu Thr Gln Leu His Glu
        130                 135                 140

Ala Ser Val Thr Leu Ile Trp Arg Asp Ser Asp Glu Arg Met Ala Gln
145                 150                 155                 160

Phe Thr Ala Arg Leu Asn Glu Leu Gly Leu Gln Phe Met Gln Gly Ala
                165                 170                 175

Arg Phe Trp His Val Leu Asp Ala Ser Ala Gly Lys Asp Gln Ala Ala
            180                 185                 190

Asn Trp Ile Ile Ala Thr Tyr Gln Gln Leu Ser Gly Lys Arg Pro Thr
        195                 200                 205

Thr Leu Gly Leu Gly Asp Gly Pro Asn Asp Ala Pro Leu Leu Glu Val
210                 215                 220

Met Asp Tyr Ala Val Ile Val Lys Gly Leu Asn Arg Glu Gly Val His
225                 230                 235                 240

Leu His Asp Glu Asp Pro Ala Arg Val Trp Arg Thr Gln Arg Glu Gly
                245                 250                 255

Pro Glu Gly Trp Arg Glu Gly Leu Asp His Phe Ser Ala Arg
            260                 265                 270

<210> SEQ ID NO 50
<211> LENGTH: 216
<212> TYPE: PRT
<213> ORGANISM: Escherichia coli

<400> SEQUENCE: 50

Met Arg Cys Lys Gly Phe Leu Phe Asp Leu Asp Gly Thr Leu Val Asp
1               5                   10                  15

Ser Leu Pro Ala Val Glu Arg Ala Trp Ser Asn Trp Ala Arg Arg His
            20                  25                  30

Gly Leu Ala Pro Glu Glu Val Leu Ala Phe Ile His Gly Lys Gln Ala
            35                  40                  45

Ile Thr Ser Leu Arg His Phe Met Ala Gly Lys Ser Glu Ala Asp Ile
        50                  55                  60

Ala Ala Glu Phe Thr Arg Leu Glu His Ile Glu Ala Thr Glu Thr Glu
65                  70                  75                  80

Gly Ile Thr Ala Leu Pro Gly Ala Ile Ala Leu Leu Ser His Leu Asn
                85                  90                  95

Lys Ala Gly Ile Pro Trp Ala Ile Val Thr Ser Gly Ser Met Pro Val
            100                 105                 110

Ala Arg Ala Arg His Lys Ile Ala Gly Leu Pro Ala Pro Glu Val Phe

```
                 115                 120                 125
Val Thr Ala Glu Arg Val Lys Arg Gly Lys Pro Glu Pro Asp Ala Tyr
            130                 135                 140

Leu Leu Gly Ala Gln Leu Leu Gly Leu Ala Pro Gln Glu Cys Val Val
145                 150                 155                 160

Val Glu Asp Ala Pro Ala Gly Val Leu Ser Gly Leu Ala Ala Gly Cys
                165                 170                 175

His Val Ile Ala Val Asn Ala Pro Ala Asp Thr Pro Arg Leu Asn Glu
            180                 185                 190

Val Asp Leu Val Leu His Ser Leu Glu Gln Ile Thr Val Thr Lys Gln
                195                 200                 205

Pro Asn Gly Asp Val Ile Ile Gln
            210                 215
```

<210> SEQ ID NO 51
<211> LENGTH: 270
<212> TYPE: PRT
<213> ORGANISM: Escherichia coli

<400> SEQUENCE: 51

```
Met Ala Ile Lys Leu Ile Ala Ile Asp Met Asp Gly Thr Leu Leu Leu
1               5                   10                  15

Pro Asp His Thr Ile Ser Pro Ala Val Lys Asn Ala Ile Ala Ala Ala
            20                  25                  30

Arg Ala Arg Gly Val Asn Val Val Leu Thr Thr Gly Arg Pro Tyr Ala
        35                  40                  45

Gly Val His Asn Tyr Leu Lys Glu Leu His Met Glu Gln Pro Gly Asp
    50                  55                  60

Tyr Cys Ile Thr Tyr Asn Gly Ala Leu Val Gln Lys Ala Ala Asp Gly
65                  70                  75                  80

Ser Thr Val Ala Gln Thr Ala Leu Ser Tyr Asp Asp Tyr Arg Phe Leu
                85                  90                  95

Glu Lys Leu Ser Arg Glu Val Gly Ser His Phe His Ala Leu Asp Arg
            100                 105                 110

Thr Thr Leu Tyr Thr Ala Asn Arg Asp Ile Ser Tyr Tyr Thr Val His
        115                 120                 125

Glu Ser Phe Val Ala Thr Ile Pro Leu Val Phe Cys Glu Ala Glu Lys
    130                 135                 140

Met Asp Pro Asn Thr Gln Phe Leu Lys Val Met Met Ile Asp Glu Pro
145                 150                 155                 160

Ala Ile Leu Asp Gln Ala Ile Ala Arg Ile Pro Gln Glu Val Lys Glu
                165                 170                 175

Lys Tyr Thr Val Leu Lys Ser Ala Pro Tyr Phe Leu Glu Ile Leu Asp
            180                 185                 190

Lys Arg Val Asn Lys Gly Thr Gly Val Lys Ser Leu Ala Asp Val Leu
        195                 200                 205

Gly Ile Lys Pro Glu Glu Ile Met Ala Ile Gly Asp Gln Glu Asn Asp
    210                 215                 220

Ile Ala Met Ile Glu Tyr Ala Gly Val Gly Val Ala Met Asp Asn Ala
225                 230                 235                 240

Ile Pro Ser Val Lys Glu Val Ala Asn Phe Val Thr Lys Ser Asn Leu
                245                 250                 255

Glu Asp Gly Val Ala Phe Ala Ile Glu Lys Tyr Val Leu Asn
            260                 265                 270
```

<210> SEQ ID NO 52
<211> LENGTH: 238
<212> TYPE: PRT
<213> ORGANISM: Escherichia coli

<400> SEQUENCE: 52

Met Arg Phe Tyr Arg Pro Leu Gly Arg Ile Ser Ala Leu Thr Phe Asp
1               5                   10                  15

Leu Asp Asp Thr Leu Tyr Asp Asn Arg Pro Val Ile Leu Arg Thr Glu
            20                  25                  30

Arg Glu Ala Leu Thr Phe Val Gln Asn Tyr His Pro Ala Leu Arg Ser
        35                  40                  45

Phe Gln Asn Glu Asp Leu Gln Arg Leu Arg Gln Ala Val Arg Glu Ala
    50                  55                  60

Glu Pro Glu Ile Tyr His Asp Val Thr Arg Trp Arg Phe Arg Ser Ile
65                  70                  75                  80

Glu Gln Ala Met Leu Asp Ala Gly Leu Ser Ala Glu Ala Ser Ala
                85                  90                  95

Gly Ala His Ala Ala Met Ile Asn Phe Ala Lys Trp Arg Ser Arg Ile
                100                 105                 110

Asp Val Pro Gln Gln Thr His Asp Thr Leu Lys Gln Leu Ala Lys Lys
            115                 120                 125

Trp Pro Leu Val Ala Ile Thr Asn Gly Asn Ala Gln Pro Glu Leu Phe
130                 135                 140

Gly Leu Gly Asp Tyr Phe Glu Phe Val Leu Arg Ala Gly Pro His Gly
145                 150                 155                 160

Arg Ser Lys Pro Phe Ser Asp Met Tyr Phe Leu Ala Ala Glu Lys Leu
                165                 170                 175

Asn Val Pro Ile Gly Glu Ile Leu His Val Gly Asp Asp Leu Thr Thr
            180                 185                 190

Asp Val Gly Gly Ala Ile Arg Ser Gly Met Gln Ala Cys Trp Ile Arg
        195                 200                 205

Pro Glu Asn Gly Asp Leu Met Gln Thr Trp Asp Ser Arg Leu Leu Pro
210                 215                 220

His Leu Glu Ile Ser Arg Leu Ala Ser Leu Thr Ser Leu Ile
225                 230                 235

<210> SEQ ID NO 53
<211> LENGTH: 199
<212> TYPE: PRT
<213> ORGANISM: Escherichia coli

<400> SEQUENCE: 53

Met Leu Tyr Ile Phe Asp Leu Gly Asn Val Ile Val Asp Ile Asp Phe
1               5                   10                  15

Asn Arg Val Leu Gly Ala Trp Ser Asp Leu Thr Arg Ile Pro Leu Ala
            20                  25                  30

Ser Leu Lys Lys Ser Phe His Met Gly Glu Ala Phe His Gln His Glu
        35                  40                  45

Arg Gly Glu Ile Ser Asp Glu Ala Phe Ala Glu Ala Leu Cys His Glu
    50                  55                  60

Met Ala Leu Pro Leu Ser Tyr Glu Gln Phe Ser His Gly Trp Gln Ala
65                  70                  75                  80

Val Phe Val Ala Leu Arg Pro Glu Val Ile Ala Ile Met His Lys Leu
                85                  90                  95

```
Arg Glu Gln Gly His Arg Val Val Leu Ser Asn Thr Asn Arg Leu
                100                 105                 110

His Thr Thr Phe Trp Pro Glu Glu Tyr Pro Glu Ile Arg Asp Ala Ala
        115                 120                 125

Asp His Ile Tyr Leu Ser Gln Asp Leu Gly Met Arg Lys Pro Glu Ala
    130                 135                 140

Arg Ile Tyr Gln His Val Leu Gln Ala Glu Gly Phe Ser Pro Ser Asp
145                 150                 155                 160

Thr Val Phe Phe Asp Asp Asn Ala Asp Asn Ile Glu Gly Ala Asn Gln
                165                 170                 175

Leu Gly Ile Thr Ser Ile Leu Val Lys Asp Lys Thr Thr Ile Pro Asp
            180                 185                 190

Tyr Phe Ala Lys Val Leu Cys
            195

<210> SEQ ID NO 54
<211> LENGTH: 222
<212> TYPE: PRT
<213> ORGANISM: Escherichia coli

<400> SEQUENCE: 54

Met Ser Thr Pro Arg Gln Ile Leu Ala Ala Ile Phe Asp Met Asp Gly
1               5                   10                  15

Leu Leu Ile Asp Ser Glu Pro Leu Trp Asp Arg Ala Glu Leu Asp Val
            20                  25                  30

Met Ala Ser Leu Gly Val Asp Ile Ser Arg Arg Asn Glu Leu Pro Asp
        35                  40                  45

Thr Leu Gly Leu Arg Ile Asp Met Val Val Asp Leu Trp Tyr Ala Arg
    50                  55                  60

Gln Pro Trp Asn Gly Pro Ser Arg Gln Glu Val Val Glu Arg Val Ile
65                  70                  75                  80

Ala Arg Ala Ile Ser Leu Val Glu Glu Thr Arg Pro Leu Leu Pro Gly
                85                  90                  95

Val Arg Glu Ala Val Ala Leu Cys Lys Glu Gln Gly Leu Leu Val Gly
                100                 105                 110

Leu Ala Ser Ala Ser Pro Leu His Met Leu Glu Lys Val Leu Thr Met
            115                 120                 125

Phe Asp Leu Arg Asp Ser Phe Asp Ala Leu Ala Ser Ala Glu Lys Leu
    130                 135                 140

Pro Tyr Ser Lys Pro His Pro Gln Val Tyr Leu Asp Cys Ala Ala Lys
145                 150                 155                 160

Leu Gly Val Asp Pro Leu Thr Cys Val Ala Leu Glu Asp Ser Val Asn
                165                 170                 175

Gly Met Ile Ala Ser Lys Ala Ala Arg Met Arg Ser Ile Val Val Pro
            180                 185                 190

Ala Pro Glu Ala Gln Asn Asp Pro Arg Phe Val Leu Ala Asp Val Lys
        195                 200                 205

Leu Ser Ser Leu Thr Glu Leu Thr Ala Lys Asp Leu Leu Gly
    210                 215                 220

<210> SEQ ID NO 55
<211> LENGTH: 188
<212> TYPE: PRT
<213> ORGANISM: Escherichia coli

<400> SEQUENCE: 55
```

Met Tyr Glu Arg Tyr Ala Gly Leu Ile Phe Asp Met Asp Gly Thr Ile
1               5                   10                  15

Leu Asp Thr Glu Pro Thr His Arg Lys Ala Trp Arg Glu Val Leu Gly
            20                  25                  30

His Tyr Gly Leu Gln Tyr Asp Ile Gln Ala Met Ile Ala Leu Asn Gly
            35                  40                  45

Ser Pro Thr Trp Arg Ile Ala Gln Ala Ile Ile Glu Leu Asn Gln Ala
50                  55                  60

Asp Leu Asp Pro His Ala Leu Ala Arg Glu Lys Thr Glu Ala Val Arg
65                  70                  75                  80

Ser Met Leu Leu Asp Ser Val Glu Pro Leu Pro Leu Val Asp Val Val
            85                  90                  95

Lys Ser Trp His Gly Arg Arg Pro Met Ala Val Gly Thr Gly Ser Glu
            100                 105                 110

Ser Ala Ile Ala Glu Ala Leu Leu Ala His Leu Gly Leu Arg His Tyr
            115                 120                 125

Phe Asp Ala Val Val Ala Ala Asp His Val Lys His His Lys Pro Ala
            130                 135                 140

Pro Asp Thr Phe Leu Leu Cys Ala Gln Arg Met Gly Val Gln Pro Thr
145                 150                 155                 160

Gln Cys Val Val Phe Glu Asp Ala Asp Phe Gly Ile Gln Ala Ala Arg
            165                 170                 175

Ala Ala Gly Met Asp Ala Val Asp Val Arg Leu Leu
            180                 185

<210> SEQ ID NO 56
<211> LENGTH: 188
<212> TYPE: PRT
<213> ORGANISM: Escherichia coli

<400> SEQUENCE: 56

Met Ser Lys Ala Gly Ala Ser Leu Ala Thr Cys Tyr Gly Pro Val Ser
1               5                   10                  15

Ala Asp Val Ile Ala Lys Ala Glu Asn Ile Arg Leu Leu Ile Leu Asp
            20                  25                  30

Val Asp Gly Val Leu Ser Asp Gly Leu Ile Tyr Met Gly Asn Asn Gly
            35                  40                  45

Glu Glu Leu Lys Ala Phe Asn Val Arg Asp Gly Tyr Gly Ile Arg Cys
50                  55                  60

Ala Leu Thr Ser Asp Ile Glu Val Ala Ile Ile Thr Gly Arg Lys Ala
65                  70                  75                  80

Lys Leu Val Glu Asp Arg Cys Ala Thr Leu Gly Ile Thr His Leu Tyr
            85                  90                  95

Gln Gly Gln Ser Asn Lys Leu Ile Ala Phe Ser Asp Leu Leu Glu Lys
            100                 105                 110

Leu Ala Ile Ala Pro Glu Asn Val Ala Tyr Val Gly Asp Asp Leu Ile
            115                 120                 125

Asp Trp Pro Val Met Glu Lys Val Gly Leu Ser Val Ala Val Ala Asp
130                 135                 140

Ala His Pro Leu Leu Ile Pro Arg Ala Asp Tyr Val Thr Arg Ile Ala
145                 150                 155                 160

Gly Gly Arg Gly Ala Val Arg Glu Val Cys Asp Leu Leu Leu Leu Ala
            165                 170                 175

Gln Gly Lys Leu Asp Glu Ala Lys Gly Gln Ser Ile
            180                 185

<210> SEQ ID NO 57
<211> LENGTH: 223
<212> TYPE: PRT
<213> ORGANISM: Pseudomonas putida

<400> SEQUENCE: 57

Met Arg Leu Arg Ala Val Leu Phe Asp Met Asp Gly Thr Leu Leu Asp
1               5                   10                  15

Thr Ala Pro Asp Phe Ile Ala Ile Cys Gln Ala Met Leu Ala Glu Arg
            20                  25                  30

Gly Leu Pro Ala Val Asp Asp Asn Leu Ile Arg Gly Val Ile Ser Gly
        35                  40                  45

Gly Ala Arg Ala Met Val Ala Thr Ala Phe Ala Met Asp Pro Glu Ala
    50                  55                  60

Asp Gly Phe Glu Ala Leu Arg Leu Glu Phe Leu Glu Arg Tyr Gln Arg
65                  70                  75                  80

Asp Cys Ala Val His Ser Lys Leu Phe Glu Gly Met Ala Glu Leu Leu
                85                  90                  95

Ala Asp Ile Glu Lys Gly Asn Leu Leu Trp Gly Val Val Thr Asn Lys
            100                 105                 110

Pro Val Arg Phe Ala Glu Pro Ile Met Gln Gln Leu Gly Leu Ala Glu
        115                 120                 125

Arg Ser Ala Leu Leu Ile Cys Pro Asp His Val Lys Asn Ser Lys Pro
    130                 135                 140

Asp Pro Glu Pro Leu Ile Leu Ala Cys Lys Thr Leu Asn Leu Asp Pro
145                 150                 155                 160

Ala Ser Val Leu Phe Val Gly Asp Asp Leu Arg Asp Ile Glu Ser Gly
                165                 170                 175

Arg Asp Ala Gly Thr Arg Thr Ala Ala Val Arg Tyr Gly Tyr Ile His
            180                 185                 190

Pro Glu Asp Asn Pro Asn Asn Trp Gly Ala Asp Val Val Val Asp His
        195                 200                 205

Pro Leu Glu Leu Arg Lys Val Ile Asp Ser Ala Leu Cys Gly Cys
    210                 215                 220

<210> SEQ ID NO 58
<211> LENGTH: 432
<212> TYPE: PRT
<213> ORGANISM: Escherichia coli

<400> SEQUENCE: 58

Met Lys Ala Ile Leu Ile Pro Phe Leu Ser Leu Leu Ile Pro Leu Thr
1               5                   10                  15

Pro Gln Ser Ala Phe Ala Gln Ser Glu Pro Glu Leu Lys Leu Glu Ser
            20                  25                  30

Val Val Ile Val Ser Arg His Gly Val Arg Ala Pro Thr Lys Ala Thr
        35                  40                  45

Gln Leu Met Gln Asp Val Thr Pro Asp Ala Trp Pro Thr Trp Pro Val
    50                  55                  60

Lys Leu Gly Trp Leu Thr Pro Arg Gly Gly Glu Leu Ile Ala Tyr Leu
65                  70                  75                  80

Gly His Tyr Gln Arg Gln Arg Leu Val Ala Asp Gly Leu Leu Ala Lys
                85                  90                  95

Lys Gly Cys Pro Gln Ser Gly Gln Val Ala Ile Ile Ala Asp Val Asp
            100                 105                 110

Glu Arg Thr Arg Lys Thr Gly Glu Ala Phe Ala Ala Gly Leu Ala Pro
            115                 120                 125

Asp Cys Ala Ile Thr Val His Thr Gln Ala Asp Thr Ser Ser Pro Asp
        130                 135                 140

Pro Leu Phe Asn Pro Leu Lys Thr Gly Val Cys Gln Leu Asp Asn Ala
145                 150                 155                 160

Asn Val Thr Asp Ala Ile Leu Ser Arg Ala Gly Ser Ile Ala Asp
                165                 170                 175

Phe Thr Gly His Arg Gln Thr Ala Phe Arg Glu Leu Glu Arg Val Leu
                180                 185                 190

Asn Phe Pro Gln Ser Asn Leu Cys Leu Lys Arg Glu Lys Gln Asp Glu
            195                 200                 205

Ser Cys Ser Leu Thr Gln Ala Leu Pro Ser Glu Leu Lys Val Ser Ala
        210                 215                 220

Asp Asn Val Ser Leu Thr Gly Ala Val Ser Leu Ala Ser Met Leu Thr
225                 230                 235                 240

Glu Ile Phe Leu Leu Gln Gln Ala Gln Gly Met Pro Glu Pro Gly Trp
                245                 250                 255

Gly Arg Ile Thr Asp Ser His Gln Trp Asn Thr Leu Leu Ser Leu His
            260                 265                 270

Asn Ala Gln Phe Tyr Leu Leu Gln Arg Thr Pro Glu Val Ala Arg Ser
        275                 280                 285

Arg Ala Thr Pro Leu Leu Asp Leu Ile Lys Thr Ala Leu Thr Pro His
        290                 295                 300

Pro Pro Gln Lys Gln Ala Tyr Gly Val Thr Leu Pro Thr Ser Val Leu
305                 310                 315                 320

Phe Ile Ala Gly His Asp Thr Asn Leu Ala Asn Leu Gly Gly Ala Leu
                325                 330                 335

Glu Leu Asn Trp Thr Leu Pro Gly Gln Pro Asp Asn Thr Pro Pro Gly
            340                 345                 350

Gly Glu Leu Val Phe Glu Arg Trp Arg Leu Ser Asp Asn Ser Gln
        355                 360                 365

Trp Ile Gln Val Ser Leu Val Phe Gln Thr Leu Gln Gln Met Arg Asp
        370                 375                 380

Lys Thr Pro Leu Ser Leu Asn Thr Pro Pro Gly Glu Val Lys Leu Thr
385                 390                 395                 400

Leu Ala Gly Cys Glu Glu Arg Asn Ala Gln Gly Met Cys Ser Leu Ala
                405                 410                 415

Gly Phe Thr Gln Ile Val Asn Glu Ala Arg Ile Pro Ala Cys Ser Leu
                420                 425                 430

<210> SEQ ID NO 59
<211> LENGTH: 252
<212> TYPE: PRT
<213> ORGANISM: Escherichia coli

<400> SEQUENCE: 59

Met Asn Lys Phe Glu Asp Ile Arg Gly Val Ala Phe Asp Leu Asp Gly
1               5                   10                  15

Thr Leu Val Asp Ser Ala Pro Gly Leu Ala Ala Ala Val Asp Met Ala
                20                  25                  30

Leu Tyr Ala Leu Glu Leu Pro Val Ala Gly Glu Glu Arg Val Ile Thr
            35                  40                  45

Trp Ile Gly Asn Gly Ala Asp Val Leu Met Glu Arg Ala Leu Thr Trp

```
                 50                  55                  60
Ala Arg Gln Glu Arg Ala Thr Gln Arg Lys Thr Met Gly Lys Pro Pro
 65                  70                  75                  80

Val Asp Asp Ile Pro Ala Glu Glu Gln Val Arg Ile Leu Arg Lys
                 85                  90                  95

Leu Phe Asp Arg Tyr Tyr Gly Glu Val Ala Glu Gly Thr Phe Leu
                100                 105                 110

Phe Pro His Val Ala Asp Thr Leu Gly Ala Leu Gln Ala Lys Gly Leu
                115                 120                 125

Pro Leu Gly Leu Val Thr Asn Lys Pro Thr Pro Phe Val Ala Pro Leu
    130                 135                 140

Leu Glu Ala Leu Asp Ile Ala Lys Tyr Phe Ser Val Val Ile Gly Gly
145                 150                 155                 160

Asp Asp Val Gln Asn Lys Lys Pro His Pro Asp Pro Leu Leu Leu Val
                165                 170                 175

Ala Glu Arg Met Gly Ile Ala Pro Gln Gln Met Leu Phe Val Gly Asp
                180                 185                 190

Ser Arg Asn Asp Ile Gln Ala Ala Lys Ala Ala Gly Cys Pro Ser Val
                195                 200                 205

Gly Leu Thr Tyr Gly Tyr Asn Tyr Gly Glu Ala Ile Asp Leu Ser Gln
    210                 215                 220

Pro Asp Val Ile Tyr Gln Ser Ile Asn Asp Leu Leu Pro Ala Leu Gly
225                 230                 235                 240

Leu Pro His Ser Glu Asn Gln Glu Ser Lys Asn Asp
                245                 250

<210> SEQ ID NO 60
<211> LENGTH: 322
<212> TYPE: PRT
<213> ORGANISM: Escherichia coli

<400> SEQUENCE: 60

Met Pro Asn Ile Thr Trp Cys Asp Leu Pro Glu Asp Val Ser Leu Trp
 1               5                  10                  15

Pro Gly Leu Pro Leu Ser Leu Ser Gly Asp Glu Val Met Pro Leu Asp
                20                  25                  30

Tyr His Ala Gly Arg Ser Gly Trp Leu Leu Tyr Gly Arg Gly Leu Asp
                35                  40                  45

Lys Gln Arg Leu Thr Gln Tyr Gln Ser Lys Leu Gly Ala Ala Met Val
     50                  55                  60

Ile Val Ala Ala Trp Cys Val Glu Asp Tyr Gln Val Ile Arg Leu Ala
 65                  70                  75                  80

Gly Ser Leu Thr Ala Arg Ala Thr Arg Leu Ala His Glu Ala Gln Leu
                 85                  90                  95

Asp Val Ala Pro Leu Gly Lys Ile Pro His Leu Arg Thr Pro Gly Leu
                100                 105                 110

Leu Val Met Asp Met Asp Ser Thr Ala Ile Gln Ile Glu Cys Ile Asp
                115                 120                 125

Glu Ile Ala Lys Leu Ala Gly Thr Gly Glu Met Val Ala Glu Val Thr
    130                 135                 140

Glu Arg Ala Met Arg Gly Glu Leu Asp Phe Thr Ala Ser Leu Arg Ser
145                 150                 155                 160

Arg Val Ala Thr Leu Lys Gly Ala Asp Ala Asn Ile Leu Gln Gln Val
                165                 170                 175
```

Arg Glu Asn Leu Pro Leu Met Pro Gly Leu Thr Gln Leu Val Leu Lys
            180                 185                 190

Leu Glu Thr Leu Gly Trp Lys Val Ala Ile Ala Ser Gly Gly Phe Thr
        195                 200                 205

Phe Phe Ala Glu Tyr Leu Arg Asp Lys Leu Arg Leu Thr Ala Val Val
    210                 215                 220

Ala Asn Glu Leu Glu Ile Met Asp Gly Lys Phe Thr Gly Asn Val Ile
225                 230                 235                 240

Gly Asp Ile Val Asp Ala Gln Tyr Lys Ala Lys Thr Leu Thr Arg Leu
                245                 250                 255

Ala Gln Glu Tyr Glu Ile Pro Leu Ala Gln Thr Val Ala Ile Gly Asp
            260                 265                 270

Gly Ala Asn Asp Leu Pro Met Ile Lys Ala Ala Gly Leu Gly Ile Ala
    275                 280                 285

Tyr His Ala Lys Pro Lys Val Asn Glu Lys Ala Glu Val Thr Ile Arg
            290                 295                 300

His Ala Asp Leu Met Gly Val Phe Cys Ile Leu Ser Gly Ser Leu Asn
305                 310                 315                 320

Gln Lys

<210> SEQ ID NO 61
<211> LENGTH: 250
<212> TYPE: PRT
<213> ORGANISM: Escherichia coli

<400> SEQUENCE: 61

Met Thr Ile Lys Asn Val Ile Cys Asp Ile Asp Gly Val Leu Met His
1               5                   10                  15

Asp Asn Val Ala Val Pro Gly Ala Ala Glu Phe Leu His Gly Ile Met
            20                  25                  30

Asp Lys Gly Leu Pro Leu Val Leu Leu Thr Asn Tyr Pro Ser Gln Thr
        35                  40                  45

Gly Gln Asp Leu Ala Asn Arg Phe Ala Thr Ala Gly Val Asp Val Pro
    50                  55                  60

Asp Ser Val Phe Tyr Thr Ser Ala Met Ala Thr Ala Asp Phe Leu Arg
65                  70                  75                  80

Arg Gln Glu Gly Lys Lys Ala Tyr Val Val Gly Glu Gly Ala Leu Ile
                85                  90                  95

His Glu Leu Tyr Lys Ala Gly Phe Thr Ile Thr Asp Val Asn Pro Asp
            100                 105                 110

Phe Val Ile Val Gly Glu Thr Arg Ser Tyr Asn Trp Asp Met Met His
        115                 120                 125

Lys Ala Ala Tyr Phe Val Ala Asn Gly Ala Arg Phe Ile Ala Thr Asn
    130                 135                 140

Pro Asp Thr His Gly Arg Gly Phe Tyr Pro Ala Cys Gly Ala Leu Cys
145                 150                 155                 160

Ala Gly Ile Glu Lys Ile Ser Gly Arg Lys Pro Phe Tyr Val Gly Lys
                165                 170                 175

Pro Ser Pro Trp Ile Ile Arg Ala Ala Leu Asn Lys Met Gln Ala His
            180                 185                 190

Ser Glu Glu Thr Val Ile Val Gly Asp Asn Leu Arg Thr Asp Ile Leu
        195                 200                 205

Ala Gly Phe Gln Ala Gly Leu Glu Thr Ile Leu Val Leu Ser Gly Val
    210                 215                 220

```
Ser Ser Leu Asp Asp Ile Asp Ser Met Pro Phe Arg Pro Ser Trp Ile
225                 230                 235                 240

Tyr Pro Ser Val Ala Glu Ile Asp Val Ile
                245                 250
```

<210> SEQ ID NO 62
<211> LENGTH: 272
<212> TYPE: PRT
<213> ORGANISM: Escherichia coli

<400> SEQUENCE: 62

```
Met Thr Thr Arg Val Ile Ala Leu Asp Leu Asp Gly Thr Leu Leu Thr
1               5                   10                  15

Pro Lys Lys Thr Leu Leu Pro Ser Ser Ile Glu Ala Leu Ala Arg Ala
            20                  25                  30

Arg Glu Ala Gly Tyr Gln Leu Ile Ile Val Thr Gly Arg His His Val
        35                  40                  45

Ala Ile His Pro Phe Tyr Gln Ala Leu Ala Leu Asp Thr Pro Ala Ile
    50                  55                  60

Cys Cys Asn Gly Thr Tyr Leu Tyr Asp Tyr His Ala Lys Thr Val Leu
65                  70                  75                  80

Glu Ala Asp Pro Met Pro Val Ile Lys Ala Leu Gln Leu Ile Glu Met
                85                  90                  95

Leu Asn Glu His His Ile His Gly Leu Met Tyr Val Asp Asp Ala Met
            100                 105                 110

Val Tyr Glu His Pro Thr Gly His Val Ile Arg Thr Ser Asn Trp Ala
        115                 120                 125

Gln Thr Leu Pro Pro Glu Gln Arg Pro Thr Phe Thr Gln Val Ala Ser
    130                 135                 140

Leu Ala Glu Thr Ala Gln Gln Val Asn Ala Val Trp Lys Phe Ala Leu
145                 150                 155                 160

Thr His Asp Asp Leu Pro Gln Leu Gln His Phe Gly Lys His Val Glu
                165                 170                 175

His Glu Leu Gly Leu Glu Cys Glu Trp Ser Trp His Asp Gln Val Asp
            180                 185                 190

Ile Ala Arg Gly Gly Asn Ser Lys Gly Lys Arg Leu Thr Lys Trp Val
        195                 200                 205

Glu Ala Gln Gly Trp Ser Met Glu Asn Val Val Ala Phe Gly Asp Asn
    210                 215                 220

Phe Asn Asp Ile Ser Met Leu Glu Ala Ala Gly Thr Gly Val Ala Met
225                 230                 235                 240

Gly Asn Ala Asp Asp Ala Val Lys Ala Arg Ala Asn Ile Val Ile Gly
                245                 250                 255

Asp Asn Thr Thr Asp Ser Ile Ala Gln Phe Ile Tyr Ser His Leu Ile
            260                 265                 270
```

<210> SEQ ID NO 63
<211> LENGTH: 271
<212> TYPE: PRT
<213> ORGANISM: Escherichia coli

<400> SEQUENCE: 63

```
Met Ser Val Lys Val Ile Val Thr Asp Met Asp Gly Thr Phe Leu Asn
1               5                   10                  15

Asp Ala Lys Thr Tyr Asn Gln Pro Arg Phe Met Ala Gln Tyr Gln Glu
            20                  25                  30
```

```
Leu Lys Lys Arg Gly Ile Lys Phe Val Val Ala Ser Gly Asn Gln Tyr
         35                  40                  45

Tyr Gln Leu Ile Ser Phe Phe Pro Glu Leu Lys Asp Glu Ile Ser Phe
    50                  55                  60

Val Ala Glu Asn Gly Ala Leu Val Tyr Glu His Gly Lys Gln Leu Phe
65                  70                  75                  80

His Gly Glu Leu Thr Arg His Glu Ser Arg Ile Val Ile Gly Glu Leu
                85                  90                  95

Leu Lys Asp Lys Gln Leu Asn Phe Val Ala Cys Gly Leu Gln Ser Ala
            100                 105                 110

Tyr Val Ser Glu Asn Ala Pro Glu Ala Phe Val Ala Leu Met Ala Lys
        115                 120                 125

His Tyr His Arg Leu Lys Pro Val Lys Asp Tyr Gln Glu Ile Asp Asp
    130                 135                 140

Val Leu Phe Lys Phe Ser Leu Asn Leu Pro Asp Glu Gln Ile Pro Leu
145                 150                 155                 160

Val Ile Asp Lys Leu His Val Ala Leu Asp Gly Ile Met Lys Pro Val
                165                 170                 175

Thr Ser Gly Phe Gly Phe Ile Asp Leu Ile Ile Pro Gly Leu His Lys
            180                 185                 190

Ala Asn Gly Ile Ser Arg Leu Leu Lys Arg Trp Asp Leu Ser Pro Gln
        195                 200                 205

Asn Val Val Ala Ile Gly Asp Ser Gly Asn Asp Ala Glu Met Leu Lys
    210                 215                 220

Met Ala Arg Tyr Ser Phe Ala Met Gly Asn Ala Ala Glu Asn Ile Lys
225                 230                 235                 240

Gln Ile Ala Arg Tyr Ala Thr Asp Asp Asn Asn His Glu Gly Ala Leu
                245                 250                 255

Asn Val Ile Gln Ala Val Leu Asp Asn Thr Ser Pro Phe Asn Ser
            260                 265                 270

<210> SEQ ID NO 64
<211> LENGTH: 561
<212> TYPE: PRT
<213> ORGANISM: Escherichia coli

<400> SEQUENCE: 64

Met Asn Ile Asn Val Ala Glu Leu Leu Asn Gly Asn Tyr Ile Leu Leu
1               5                   10                  15

Leu Phe Val Val Leu Ala Leu Gly Leu Cys Leu Gly Lys Leu Arg Leu
                20                  25                  30

Gly Ser Ile Gln Leu Gly Asn Ser Ile Gly Val Leu Val Ser Leu
            35                  40                  45

Leu Leu Gly Gln Gln His Phe Ser Ile Asn Thr Asp Ala Leu Asn Leu
        50                  55                  60

Gly Phe Met Leu Phe Ile Phe Cys Val Gly Val Glu Ala Gly Pro Asn
65                  70                  75                  80

Phe Phe Ser Ile Phe Phe Arg Asp Gly Lys Asn Tyr Leu Met Leu Ala
                85                  90                  95

Leu Val Met Val Gly Ser Ala Leu Val Ile Ala Leu Gly Leu Gly Lys
            100                 105                 110

Leu Phe Gly Trp Asp Ile Gly Leu Thr Ala Gly Met Leu Ala Gly Ser
        115                 120                 125

Met Thr Ser Thr Pro Val Leu Val Gly Ala Gly Asp Thr Leu Arg His
    130                 135                 140
```

```
Ser Gly Met Glu Ser Arg Gln Leu Ser Leu Ala Leu Asp Asn Leu Ser
145                 150                 155                 160

Leu Gly Tyr Ala Leu Thr Tyr Leu Ile Gly Leu Val Ser Leu Ile Val
            165                 170                 175

Gly Ala Arg Tyr Leu Pro Lys Leu Gln His Gln Asp Leu Gln Thr Ser
            180                 185                 190

Ala Gln Gln Ile Ala Arg Glu Arg Gly Leu Asp Thr Asp Ala Asn Arg
            195                 200                 205

Lys Val Tyr Leu Pro Val Ile Arg Ala Tyr Arg Val Gly Pro Glu Leu
            210                 215                 220

Val Ala Trp Thr Asp Gly Lys Asn Leu Arg Glu Leu Gly Ile Tyr Arg
225                 230                 235                 240

Gln Thr Gly Cys Tyr Ile Glu Arg Ile Arg Arg Asn Gly Ile Leu Ala
            245                 250                 255

Asn Pro Asp Gly Asp Ala Val Leu Gln Met Gly Asp Glu Ile Ala Leu
            260                 265                 270

Val Gly Tyr Pro Asp Ala His Ala Arg Leu Asp Pro Ser Phe Arg Asn
            275                 280                 285

Gly Lys Glu Val Phe Asp Arg Asp Leu Leu Asp Met Arg Ile Val Thr
            290                 295                 300

Glu Glu Val Val Val Lys Asn His Asn Ala Val Gly Lys Arg Leu Ala
305                 310                 315                 320

Gln Leu Lys Leu Thr Asp His Gly Cys Phe Leu Asn Arg Val Ile Arg
            325                 330                 335

Ser Gln Ile Glu Met Pro Ile Asp Asn Val Val Leu Asn Lys Gly
            340                 345                 350

Asp Val Leu Gln Val Ser Gly Asp Ala Arg Arg Val Lys Thr Ile Ala
            355                 360                 365

Asp Arg Ile Gly Phe Ile Ser Ile His Ser Gln Val Thr Asp Leu Leu
            370                 375                 380

Ala Phe Cys Ala Phe Phe Val Ile Gly Leu Met Ile Gly Met Ile Thr
385                 390                 395                 400

Phe Gln Phe Ser Thr Phe Ser Phe Gly Met Gly Asn Ala Ala Gly Leu
            405                 410                 415

Leu Phe Ala Gly Ile Met Leu Gly Phe Met Arg Ala Asn His Pro Thr
            420                 425                 430

Phe Gly Tyr Ile Pro Gln Gly Ala Leu Ser Met Val Lys Glu Phe Gly
            435                 440                 445

Leu Met Val Phe Met Ala Gly Val Gly Leu Ser Ala Gly Ser Gly Ile
            450                 455                 460

Asn Asn Gly Leu Gly Ala Ile Gly Gly Gln Met Leu Ile Ala Gly Leu
465                 470                 475                 480

Ile Val Ser Leu Val Pro Val Ile Cys Phe Leu Phe Gly Ala Tyr
            485                 490                 495

Val Leu Arg Met Asn Arg Ala Leu Leu Phe Gly Ala Met Met Gly Ala
            500                 505                 510

Arg Thr Cys Ala Pro Ala Met Glu Ile Ile Ser Asp Thr Ala Arg Ser
            515                 520                 525

Asn Ile Pro Ala Leu Gly Tyr Ala Gly Thr Tyr Ala Ile Ala Asn Val
            530                 535                 540

Leu Leu Thr Leu Ala Gly Thr Ile Ile Val Met Val Trp Pro Gly Leu
545                 550                 555                 560
```

Gly

```
<210> SEQ ID NO 65
<211> LENGTH: 199
<212> TYPE: PRT
<213> ORGANISM: Escherichia coli

<400> SEQUENCE: 65
```

Met Lys Gln Ser His Phe Phe Ala His Leu Ser Arg Leu Lys Leu Ile
1               5                   10                  15

Asn Arg Trp Pro Leu Met Arg Asn Val Arg Thr Glu Asn Val Ser Glu
            20                  25                  30

His Ser Leu Gln Val Ala Met Val Ala His Ala Leu Ala Ala Ile Lys
        35                  40                  45

Asn Arg Lys Phe Gly Gly Asn Val Asn Ala Glu Arg Ile Ala Leu Leu
    50                  55                  60

Ala Met Tyr His Asp Ala Ser Glu Val Leu Thr Gly Asp Leu Pro Thr
65                  70                  75                  80

Pro Val Lys Tyr Phe Asn Ser Gln Ile Ala Gln Glu Tyr Lys Ala Ile
                85                  90                  95

Glu Lys Ile Ala Gln Gln Lys Leu Val Asp Met Val Pro Glu Glu Leu
            100                 105                 110

Arg Asp Ile Phe Ala Pro Leu Ile Asp Glu His Ala Tyr Ser Asp Glu
        115                 120                 125

Glu Lys Ser Leu Val Lys Gln Ala Asp Ala Leu Cys Ala Tyr Leu Lys
    130                 135                 140

Cys Leu Glu Glu Leu Ala Ala Gly Asn Asn Glu Phe Leu Leu Ala Lys
145                 150                 155                 160

Thr Arg Leu Glu Ala Thr Leu Glu Ala Arg Arg Ser Gln Glu Met Asp
                165                 170                 175

Tyr Phe Met Glu Ile Phe Val Pro Ser Phe His Leu Ser Leu Asp Glu
            180                 185                 190

Ile Ser Gln Asp Ser Pro Leu
        195

```
<210> SEQ ID NO 66
<211> LENGTH: 221
<212> TYPE: PRT
<213> ORGANISM: Escherichia coli

<400> SEQUENCE: 66
```

Met Ser Arg Ile Glu Ala Val Phe Phe Asp Cys Asp Gly Thr Leu Val
1               5                   10                  15

Asp Ser Glu Val Ile Cys Ser Arg Ala Tyr Val Thr Met Phe Gln Glu
            20                  25                  30

Phe Gly Ile Thr Leu Asp Pro Glu Glu Val Phe Lys Arg Phe Lys Gly
        35                  40                  45

Val Lys Leu Tyr Glu Ile Ile Asp Ile Val Ser Leu Glu His Gly Val
    50                  55                  60

Thr Leu Ala Lys Thr Glu Ala Glu His Val Tyr Arg Ala Glu Val Ala
65                  70                  75                  80

Arg Leu Phe Asp Ser Glu Leu Glu Ala Ile Glu Gly Ala Gly Ala Leu
                85                  90                  95

Leu Ser Ala Ile Thr Ala Pro Met Cys Val Val Ser Asn Gly Pro Asn
            100                 105                 110

Asn Lys Met Gln His Ser Met Gly Lys Leu Asn Met Leu His Tyr Phe 115                 120                 125
Pro Asp Lys Leu Phe Ser Gly Tyr Asp Ile Gln Arg Trp Lys Pro Asp
    130                 135                 140

Pro Ala Leu Met Phe His Ala Ala Lys Ala Met Asn Val Asn Val Glu
145                 150                 155                 160

Asn Cys Ile Leu Val Asp Asp Ser Val Ala Gly Ala Gln Ser Gly Ile
                    165                 170                 175

Asp Ala Gly Met Glu Val Phe Tyr Phe Cys Ala Asp Pro His Asn Lys
                180                 185                 190

Pro Ile Val His Pro Lys Val Thr Thr Phe Thr His Leu Ser Gln Leu
            195                 200                 205

Pro Glu Leu Trp Lys Ala Arg Gly Trp Asp Ile Thr Ala
        210                 215                 220

<210> SEQ ID NO 67
<211> LENGTH: 604
<212> TYPE: PRT
<213> ORGANISM: Escherichia coli

<400> SEQUENCE: 67

Met Ser Lys Ile Ser Asp Leu Asn Tyr Ser Gln His Ile Thr Leu Ala
1               5                   10                  15

Asp Asn Phe Lys Gln Lys Ser Glu Val Leu Asn Thr Trp Arg Val Gly
            20                  25                  30

Met Asn Asp Phe Ala Arg Ile Ala Gly Gly Gln Asp Asn Arg Arg Asn
        35                  40                  45

Ile Leu Ser Pro Gly Ala Phe Leu Glu Phe Leu Ala Lys Ile Phe Thr
    50                  55                  60

Leu Gly Tyr Val Asp Phe Ser Lys Arg Ser Asn Glu Ala Gly Arg Asn
65                  70                  75                  80

Met Met Ala His Ile Lys Ser Ser Tyr Ser Lys Asp Thr Asn Gly
                85                  90                  95

Asn Glu Lys Met Lys Phe Tyr Met Asn Asn Pro Val Gly Glu Arg Ala
            100                 105                 110

Asp Ser Pro Lys Val Ile Ile Glu Ile Ser Leu Ser Thr Ile Thr Thr
        115                 120                 125

Met Gly Thr Arg Gln Gly His Thr Ala Ile Ile Phe Pro Gln Pro Asp
    130                 135                 140

Gly Ser Thr Asn Arg Tyr Glu Gly Lys Ser Phe Glu Arg Lys Asp Glu
145                 150                 155                 160

Ser Ser Leu His Leu Ile Thr Asn Lys Val Leu Ala Cys Tyr Gln Ser
                165                 170                 175

Glu Ala Asn Lys Lys Ile Ala Arg Leu Leu Asn Asn Gln Glu Leu
                180                 185                 190

Asn Asn Leu Gln Lys Leu Asn Asn Leu Gln Lys Leu Asn Asn Leu Leu
            195                 200                 205

Lys Leu Asn Asn Ile Gln Gly Leu Asn Asn Pro Gln Glu Leu Asn Asn
        210                 215                 220

Pro Gln Asn Leu Asn Asp Ser Gln Glu Leu Asn Asn Ser Gln Glu Leu
225                 230                 235                 240

Asn Ser Pro Gln Glu Leu Asn Asp Pro Gln Glu Leu Asn Asn Ser Gln
                245                 250                 255

Asp Leu Asn Asn Ser Lys Val Ser Cys Thr Val Ser Val Asp Ser Thr
                260                 265                 270

```
Ile Thr Gly Leu Leu Lys Glu Pro Leu Asn Asn Ala Leu Leu Ala Ile
            275                 280                 285

Arg Asn Glu His Leu Leu Leu Met Pro His Val Cys Asp Glu Ser Ile
290                 295                 300

Ser Tyr Leu Leu Gly Glu Lys Gly Ile Leu Glu Glu Ile Asp Lys Leu
305                 310                 315                 320

Tyr Ala Leu Asn Asp His Gly Ile Asp Asn Asp Lys Val Gly Asn Asn
                325                 330                 335

Glu Ile Asn Asp Ile Lys Val Asn Leu Ser His Ile Leu Ile Asp Ser
                340                 345                 350

Leu Asp Asp Ala Lys Val Asn Leu Thr Pro Val Ile Asp Ser Ile Leu
                355                 360                 365

Glu Thr Phe Ser Lys Ser Pro Tyr Ile Asn Asp Val Arg Ile Leu Asp
            370                 375                 380

Trp Cys Phe Asn Lys Ser Met Gln Tyr Phe Asp Asp Thr Lys Lys Ile
385                 390                 395                 400

Lys His Ala Cys Ser Val Ile Asn His Ile Asn Leu Arg Ser Asp Gln
                405                 410                 415

Ser Lys Ile Ala Glu Thr Leu Phe Phe Asn Leu Asp Lys Glu Pro Tyr
            420                 425                 430

Lys Asn Ser Pro Glu Leu Gln Gly Leu Ile Trp Asn Lys Leu Val Val
            435                 440                 445

Tyr Val Asn Glu Phe Asn Leu Ser Asn Arg Glu Lys Thr Asn Leu Ile
            450                 455                 460

Gln Arg Leu Phe Asp Asn Val Glu Ser Ile Phe Asn Glu Val Pro Val
465                 470                 475                 480

Ser Ile Leu Val Asn Asp Ile Phe Met Asn Asp Phe Phe Met Lys Asn
                485                 490                 495

Pro Glu Met Ile Asn Trp Tyr Phe Pro Gln Leu Leu Lys Ser Tyr Glu
            500                 505                 510

Gly Glu Lys Ile Tyr Phe Asp Asn Leu Lys Tyr Asp Leu Asn Asp Asn
            515                 520                 525

Asp Lys Glu Ser Asn Lys Glu Ile Leu Lys Asn Gln Pro Asp Asn Val
530                 535                 540

Ile Lys Glu Lys Leu Asn Asn Glu Tyr Lys Leu Arg Phe Arg Met Met
545                 550                 555                 560

Gln Thr Ile Leu Gln Ser Arg Val Asn Val Leu Pro Tyr Ile Asn Glu
                565                 570                 575

Gln Arg Leu Asn Lys Leu Asn Pro Pro Glu Asn Leu Arg Ile Ala Ile
                580                 585                 590

Glu His Phe Gly Trp Lys Asn Arg Pro Ile Thr Ala
            595                 600

<210> SEQ ID NO 68
<211> LENGTH: 225
<212> TYPE: PRT
<213> ORGANISM: Escherichia coli

<400> SEQUENCE: 68

Met Lys Trp Asp Trp Ile Phe Phe Asp Ala Asp Glu Thr Leu Phe Thr
1               5                   10                  15

Phe Asp Ser Phe Thr Gly Leu Gln Arg Met Phe Leu Asp Tyr Ser Val
                20                  25                  30

Thr Phe Thr Ala Glu Asp Phe Gln Asp Tyr Gln Ala Val Asn Lys Pro
            35                  40                  45
```

```
Leu Trp Val Asp Tyr Gln Asn Gly Ala Ile Thr Ser Leu Gln Leu Gln
 50                  55                  60

His Gly Arg Phe Glu Ser Trp Ala Glu Arg Leu Asn Val Glu Pro Gly
 65                  70                  75                  80

Lys Leu Asn Glu Ala Phe Ile Asn Ala Met Ala Glu Ile Cys Thr Pro
                 85                  90                  95

Leu Pro Gly Ala Val Ser Leu Leu Asn Ala Ile Arg Gly Asn Ala Lys
            100                 105                 110

Ile Gly Ile Ile Thr Asn Gly Phe Ser Ala Leu Gln Gln Val Arg Leu
        115                 120                 125

Glu Arg Thr Gly Leu Arg Asp Tyr Phe Asp Leu Val Ile Ser Glu
130                 135                 140

Glu Val Gly Val Ala Lys Pro Asn Lys Lys Ile Phe Asp Tyr Ala Leu
145                 150                 155                 160

Glu Gln Ala Gly Asn Pro Asp Arg Ser Arg Val Leu Met Val Gly Asp
                165                 170                 175

Thr Ala Glu Ser Asp Ile Leu Gly Gly Ile Asn Ala Gly Leu Ala Thr
            180                 185                 190

Cys Trp Leu Asn Ala His His Arg Glu Gln Pro Glu Gly Ile Ala Pro
        195                 200                 205

Thr Trp Thr Val Ser Ser Leu His Glu Leu Glu Gln Leu Leu Cys Lys
210                 215                 220

His
225

<210> SEQ ID NO 69
<211> LENGTH: 222
<212> TYPE: PRT
<213> ORGANISM: Escherichia coli

<400> SEQUENCE: 69

Met His Ile Asn Ile Ala Trp Gln Asp Val Asp Thr Val Leu Leu Asp
 1               5                  10                  15

Met Asp Gly Thr Leu Leu Asp Leu Ala Phe Asp Asn Tyr Phe Trp Gln
            20                  25                  30

Lys Leu Val Pro Glu Thr Trp Gly Ala Lys Asn Gly Val Thr Pro Gln
        35                  40                  45

Glu Ala Met Glu Tyr Met Arg Gln Gln Tyr His Asp Val Gln His Thr
 50                  55                  60

Leu Asn Trp Tyr Cys Leu Asp Tyr Trp Ser Glu Gln Leu Gly Leu Asp
 65                  70                  75                  80

Ile Cys Ala Met Thr Thr Glu Met Gly Pro Arg Ala Val Leu Arg Glu
                 85                  90                  95

Asp Thr Ile Pro Phe Leu Glu Ala Leu Lys Ala Ser Gly Lys Gln Arg
            100                 105                 110

Ile Leu Leu Thr Asn Ala His Pro His Asn Leu Ala Val Lys Leu Glu
        115                 120                 125

His Thr Gly Leu Asp Ala His Leu Asp Leu Leu Leu Ser Thr His Thr
130                 135                 140

Phe Gly Tyr Pro Lys Glu Asp Gln Arg Leu Trp His Ala Val Ala Glu
145                 150                 155                 160

Ala Thr Gly Leu Lys Ala Glu Arg Thr Leu Phe Ile Asp Asp Ser Glu
                165                 170                 175

Ala Ile Leu Asp Ala Ala Ala Gln Phe Gly Ile Arg Tyr Cys Leu Gly
```

```
                    180                 185                 190
Val Thr Asn Pro Asp Ser Gly Ile Ala Glu Lys Gln Tyr Gln Arg His
                195                 200                 205

Pro Ser Leu Asn Asp Tyr Arg Arg Leu Ile Pro Ser Leu Met
    210                 215                 220

<210> SEQ ID NO 70
<211> LENGTH: 421
<212> TYPE: PRT
<213> ORGANISM: Escherichia coli

<400> SEQUENCE: 70

Met Ala Ser Thr Phe Thr Ser Asp Thr Leu Pro Ala Asp His Lys Ala
1               5                   10                  15

Ala Ile Arg Gln Met Lys His Ala Leu Arg Ala Gln Leu Gly Asp Val
            20                  25                  30

Gln Gln Ile Phe Asn Gln Leu Ser Asp Asp Ile Ala Thr Arg Val Ala
        35                  40                  45

Glu Ile Asn Ala Leu Lys Ala Gln Gly Asp Ala Val Trp Pro Val Leu
    50                  55                  60

Ser Tyr Ala Asp Ile Lys Ala Gly His Val Thr Ala Glu Gln Arg Glu
65                  70                  75                  80

Gln Ile Lys Arg Arg Gly Cys Ala Val Ile Lys Gly His Phe Pro Arg
                85                  90                  95

Glu Gln Ala Leu Gly Trp Asp Gln Ser Met Leu Asp Tyr Leu Asp Arg
            100                 105                 110

Asn Arg Phe Asp Glu Val Tyr Lys Gly Pro Gly Asp Asn Phe Phe Gly
        115                 120                 125

Thr Leu Ser Ala Ser Arg Pro Glu Ile Tyr Pro Ile Tyr Trp Ser Gln
    130                 135                 140

Ala Gln Met Gln Ala Arg Gln Ser Glu Glu Met Ala Asn Ala Gln Ser
145                 150                 155                 160

Phe Leu Asn Arg Leu Trp Thr Phe Glu Ser Asp Gly Lys Gln Trp Phe
                165                 170                 175

Asn Pro Asp Val Ser Val Ile Tyr Pro Asp Arg Ile Arg Arg Arg Pro
            180                 185                 190

Pro Gly Thr Thr Ser Lys Gly Leu Gly Ala His Thr Asp Ser Gly Ala
        195                 200                 205

Leu Glu Arg Trp Leu Leu Pro Ala Tyr Gln Arg Val Phe Ala Asn Val
    210                 215                 220

Phe Asn Gly Asn Leu Ala Gln Tyr Asp Pro Trp His Ala Ala His Arg
225                 230                 235                 240

Thr Glu Val Glu Tyr Thr Val Asp Asn Thr Thr Lys Cys Ser Val
                245                 250                 255

Phe Arg Thr Phe Gln Gly Trp Thr Ala Leu Ser Asp Met Leu Pro Gly
            260                 265                 270

Gln Gly Leu Leu His Val Val Pro Ile Pro Glu Ala Met Ala Tyr Val
        275                 280                 285

Leu Leu Arg Pro Leu Leu Asp Asp Val Pro Glu Asp Glu Leu Cys Gly
    290                 295                 300

Val Ala Pro Gly Arg Val Leu Pro Val Ser Glu Gln Trp His Pro Leu
305                 310                 315                 320

Leu Ile Glu Ala Leu Thr Ser Ile Pro Lys Leu Glu Ala Gly Asp Ser
                325                 330                 335
```

Val Trp Trp His Cys Asp Val Ile His Ser Val Ala Pro Val Glu Asn
            340                 345                 350

Gln Gln Gly Trp Gly Asn Val Met Tyr Ile Pro Ala Ala Pro Met Cys
        355                 360                 365

Glu Lys Asn Leu Ala Tyr Ala His Lys Val Lys Ala Ala Leu Glu Lys
    370                 375                 380

Gly Ala Ser Pro Gly Asp Phe Pro Arg Glu Asp Tyr Glu Thr Asn Trp
385                 390                 395                 400

Glu Gly Arg Phe Thr Leu Ala Asp Leu Asn Ile His Gly Lys Arg Ala
                405                 410                 415

Leu Gly Met Asp Val
            420

<210> SEQ ID NO 71
<211> LENGTH: 246
<212> TYPE: PRT
<213> ORGANISM: Saccharomyces cerevisiae

<400> SEQUENCE: 71

Met Ala Glu Phe Ser Ala Asp Leu Cys Leu Phe Asp Leu Asp Gly Thr
1               5                   10                  15

Ile Val Ser Thr Thr Val Ala Ala Glu Lys Ala Trp Thr Lys Leu Cys
            20                  25                  30

Tyr Glu Tyr Gly Val Asp Pro Ser Glu Leu Phe Lys His Ser His Gly
        35                  40                  45

Ala Arg Thr Gln Glu Val Leu Arg Arg Phe Phe Pro Lys Leu Asp Asp
    50                  55                  60

Thr Asp Asn Lys Gly Val Leu Ala Leu Glu Lys Asp Ile Ala His Ser
65                  70                  75                  80

Tyr Leu Asp Thr Val Ser Leu Ile Pro Gly Ala Glu Asn Leu Leu Leu
                85                  90                  95

Ser Leu Asp Val Asp Thr Glu Thr Gln Lys Lys Leu Pro Glu Arg Lys
            100                 105                 110

Trp Ala Ile Val Thr Ser Gly Ser Pro Tyr Leu Ala Phe Ser Trp Phe
        115                 120                 125

Glu Thr Ile Leu Lys Asn Val Gly Lys Pro Lys Val Phe Ile Thr Gly
    130                 135                 140

Phe Asp Val Lys Asn Gly Lys Pro Asp Pro Glu Gly Tyr Ser Arg Ala
145                 150                 155                 160

Arg Asp Leu Leu Arg Gln Asp Leu Gln Leu Thr Gly Lys Gln Asp Leu
                165                 170                 175

Lys Tyr Val Val Phe Glu Asp Ala Pro Val Gly Ile Lys Ala Gly Lys
            180                 185                 190

Ala Met Gly Ala Ile Thr Val Gly Ile Thr Ser Ser Tyr Asp Lys Ser
        195                 200                 205

Val Leu Phe Asp Ala Gly Ala Asp Tyr Val Val Cys Asp Leu Thr Gln
    210                 215                 220

Val Ser Val Val Lys Asn Asn Glu Asn Gly Ile Val Ile Gln Val Asn
225                 230                 235                 240

Asn Pro Leu Thr Arg Ala
                245

<210> SEQ ID NO 72
<211> LENGTH: 272
<212> TYPE: PRT
<213> ORGANISM: Bacillus subtilis

<400> SEQUENCE: 72

Met Arg Ile Met Ala Ser His Asp Thr Pro Val Ser Pro Ala Gly Ile
1               5                   10                  15

Leu Ile Asp Leu Asp Gly Thr Val Phe Arg Gly Asn Glu Leu Ile Glu
            20                  25                  30

Gly Ala Arg Glu Ala Ile Lys Thr Leu Arg Arg Met Gly Lys Lys Ile
        35                  40                  45

Val Phe Leu Ser Asn Arg Gly Asn Ile Ser Arg Ala Met Cys Arg Lys
50                  55                  60

Lys Leu Leu Gly Ala Gly Ile Glu Thr Asp Val Asn Asp Ile Val Leu
65                  70                  75                  80

Ser Ser Ser Val Thr Ala Ala Phe Leu Lys Lys His Tyr Arg Phe Ser
                85                  90                  95

Lys Val Trp Val Leu Gly Glu Gln Gly Leu Val Asp Glu Leu Arg Leu
            100                 105                 110

Ala Gly Val Gln Asn Ala Ser Glu Pro Lys Glu Ala Asp Trp Leu Val
        115                 120                 125

Ile Ser Leu His Glu Thr Leu Thr Tyr Asp Asp Leu Asn Gln Ala Phe
130                 135                 140

Gln Ala Ala Gly Gly Ala Arg Ile Ile Ala Thr Asn Lys Asp Arg
145                 150                 155                 160

Ser Phe Pro Asn Glu Asp Gly Asn Ala Ile Asp Val Ala Gly Met Ile
                165                 170                 175

Gly Ala Ile Glu Thr Ser Ala Gln Ala Lys Thr Glu Leu Val Val Gly
            180                 185                 190

Lys Pro Ser Trp Leu Met Ala Glu Ala Ala Cys Thr Ala Met Gly Leu
        195                 200                 205

Ser Ala His Glu Cys Met Ile Ile Gly Asp Ser Ile Glu Ser Asp Ile
210                 215                 220

Ala Met Gly Lys Leu Tyr Gly Met Lys Ser Ala Leu Val Leu Thr Gly
225                 230                 235                 240

Ser Ala Lys Gln Gly Glu Gln Arg Leu Tyr Thr Pro Asp Tyr Val Leu
                245                 250                 255

Asp Ser Ile Lys Asp Val Thr Lys Leu Ala Glu Glu Gly Ile Leu Ile
            260                 265                 270

<210> SEQ ID NO 73
<211> LENGTH: 6
<212> TYPE: PRT
<213> ORGANISM: Artificial Sequence
<220> FEATURE:
<223> OTHER INFORMATION: Motif 1: hDxDx[TV]
<220> FEATURE:
<221> NAME/KEY: MISC_FEATURE
<222> LOCATION: (1)..(1)
<223> OTHER INFORMATION: X is an hydrophobic amino acid (A, I, L, M, F,
      V, P or G)
<220> FEATURE:
<221> NAME/KEY: MISC_FEATURE
<222> LOCATION: (3)..(3)
<223> OTHER INFORMATION: X can be any amino acid
<220> FEATURE:
<221> NAME/KEY: MISC_FEATURE
<222> LOCATION: (5)..(5)
<223> OTHER INFORMATION: X can be any amino acid
<220> FEATURE:
<221> NAME/KEY: MISC_FEATURE
<222> LOCATION: (6)..(6)
<223> OTHER INFORMATION: X can be T or V

```
<400> SEQUENCE: 73

Xaa Asp Xaa Asp Xaa Xaa
1               5

<210> SEQ ID NO 74
<211> LENGTH: 6
<212> TYPE: PRT
<213> ORGANISM: Artificial Sequence
<220> FEATURE:
<223> OTHER INFORMATION: Motif 2: [GSTDE][DSEN]x[hP]x[DGTS]
<220> FEATURE:
<221> NAME/KEY: MISC_FEATURE
<222> LOCATION: (1)..(1)
<223> OTHER INFORMATION: X can be G, S, T, D or E
<220> FEATURE:
<221> NAME/KEY: MISC_FEATURE
<222> LOCATION: (2)..(2)
<223> OTHER INFORMATION: X can be D, S, E or N
<220> FEATURE:
<221> NAME/KEY: MISC_FEATURE
<222> LOCATION: (3)..(3)
<223> OTHER INFORMATION: X can be any amino acid
<220> FEATURE:
<221> NAME/KEY: MISC_FEATURE
<222> LOCATION: (4)..(4)
<223> OTHER INFORMATION: X can be a hydrophobic amino acid (A, I, L, M,
      F, V, P or G) or P
<220> FEATURE:
<221> NAME/KEY: MISC_FEATURE
<222> LOCATION: (5)..(5)
<223> OTHER INFORMATION: X can be any amino acid
<220> FEATURE:
<221> NAME/KEY: MISC_FEATURE
<222> LOCATION: (6)..(6)
<223> OTHER INFORMATION: X can be D, G, T or S

<400> SEQUENCE: 74

Xaa Xaa Xaa Xaa Xaa Xaa
1               5

<210> SEQ ID NO 75
<211> LENGTH: 7
<212> TYPE: PRT
<213> ORGANISM: Artificial Sequence
<220> FEATURE:
<223> OTHER INFORMATION: [GSTDE][DSEN]xx[hP]x[DGTS]
<220> FEATURE:
<221> NAME/KEY: MISC_FEATURE
<222> LOCATION: (1)..(1)
<223> OTHER INFORMATION: X can be G, S, T, D or E
<220> FEATURE:
<221> NAME/KEY: MISC_FEATURE
<222> LOCATION: (2)..(2)
<223> OTHER INFORMATION: X can be D, S, E or N
<220> FEATURE:
<221> NAME/KEY: MISC_FEATURE
<222> LOCATION: (3)..(4)
<223> OTHER INFORMATION: X can be any amino acid
<220> FEATURE:
<221> NAME/KEY: MISC_FEATURE
<222> LOCATION: (5)..(5)
<223> OTHER INFORMATION: X can be a hydrophobic amino acid (A, I, L, M,
      F, V, P or G) or P
<220> FEATURE:
<221> NAME/KEY: MISC_FEATURE
<222> LOCATION: (6)..(6)
<223> OTHER INFORMATION: X can be any amino acid
<220> FEATURE:
<221> NAME/KEY: MISC_FEATURE
<222> LOCATION: (7)..(7)
<223> OTHER INFORMATION: X can be D, G, T or S

<400> SEQUENCE: 75

Xaa Xaa Xaa Xaa Xaa Xaa Xaa
```

```
<210> SEQ ID NO 76
<211> LENGTH: 7
<212> TYPE: PRT
<213> ORGANISM: Artificial Sequence
<220> FEATURE:
<223> OTHER INFORMATION: [GSTDE][DSEN]x[hP]xx[DGTS]
<220> FEATURE:
<221> NAME/KEY: MISC_FEATURE
<222> LOCATION: (1)..(1)
<223> OTHER INFORMATION: X can be G, S, T, D or E
<220> FEATURE:
<221> NAME/KEY: MISC_FEATURE
<222> LOCATION: (2)..(2)
<223> OTHER INFORMATION: X can be D, S, E or N
<220> FEATURE:
<221> NAME/KEY: MISC_FEATURE
<222> LOCATION: (3)..(3)
<223> OTHER INFORMATION: X can be any amino acid
<220> FEATURE:
<221> NAME/KEY: MISC_FEATURE
<222> LOCATION: (4)..(4)
<223> OTHER INFORMATION: X can be a hydrophobic amino acid (A, I, L, M,
      F, V, P or G) or P
<220> FEATURE:
<221> NAME/KEY: MISC_FEATURE
<222> LOCATION: (5)..(6)
<223> OTHER INFORMATION: X can be any amino acid
<220> FEATURE:
<221> NAME/KEY: MISC_FEATURE
<222> LOCATION: (7)..(7)
<223> OTHER INFORMATION: X can be D, G, T or S

<400> SEQUENCE: 76

Xaa Xaa Xaa Xaa Xaa Xaa Xaa
1               5

<210> SEQ ID NO 77
<211> LENGTH: 8
<212> TYPE: PRT
<213> ORGANISM: Artificial Sequence
<220> FEATURE:
<223> OTHER INFORMATION: [GSTDE][DSEN]xx[hP]xx[DGTS]
<220> FEATURE:
<221> NAME/KEY: MISC_FEATURE
<222> LOCATION: (1)..(1)
<223> OTHER INFORMATION: X can be G, S, T, D or E
<220> FEATURE:
<221> NAME/KEY: MISC_FEATURE
<222> LOCATION: (2)..(2)
<223> OTHER INFORMATION: X can be D, S, E or N
<220> FEATURE:
<221> NAME/KEY: MISC_FEATURE
<222> LOCATION: (3)..(4)
<223> OTHER INFORMATION: X can be any amino acid
<220> FEATURE:
<221> NAME/KEY: MISC_FEATURE
<222> LOCATION: (5)..(5)
<223> OTHER INFORMATION: X can be a hydrophobic amino acid (A, I, L, M,
      F, V, P or G) or P
<220> FEATURE:
<221> NAME/KEY: MISC_FEATURE
<222> LOCATION: (6)..(7)
<223> OTHER INFORMATION: X can be any amino acid
<220> FEATURE:
<221> NAME/KEY: MISC_FEATURE
<222> LOCATION: (8)..(8)
<223> OTHER INFORMATION: X can be a D, G, T or S

<400> SEQUENCE: 77

Xaa Xaa Xaa Xaa Xaa Xaa Xaa Xaa
1               5
```

-continued

```
<210> SEQ ID NO 78
<211> LENGTH: 272
<212> TYPE: PRT
<213> ORGANISM: Shigella flexneri

<400> SEQUENCE: 78
```

| Met | Ala | Arg | Leu | Ala | Ala | Phe | Asp | Met | Asp | Gly | Thr | Leu | Leu | Met | Pro |
|---|---|---|---|---|---|---|---|---|---|---|---|---|---|---|---|
| 1 | | | | 5 | | | | | 10 | | | | | 15 | |

| Asp | His | His | Leu | Gly | Glu | Lys | Thr | Leu | Ser | Thr | Leu | Ala | Arg | Leu | Arg |
|---|---|---|---|---|---|---|---|---|---|---|---|---|---|---|---|
| | | | 20 | | | | | 25 | | | | | 30 | | |

| Glu | Arg | Asp | Ile | Thr | Leu | Thr | Phe | Ala | Thr | Gly | Arg | His | Ala | Leu | Glu |
|---|---|---|---|---|---|---|---|---|---|---|---|---|---|---|---|
| | | 35 | | | | | 40 | | | | | 45 | | | |

| Met | Gln | His | Ile | Leu | Gly | Ala | Leu | Ser | Leu | Asp | Ala | Tyr | Leu | Ile | Thr |
|---|---|---|---|---|---|---|---|---|---|---|---|---|---|---|---|
| | 50 | | | | | 55 | | | | | 60 | | | | |

| Gly | Asn | Gly | Thr | Arg | Val | His | Ser | Leu | Glu | Gly | Glu | Leu | Leu | His | Arg |
|---|---|---|---|---|---|---|---|---|---|---|---|---|---|---|---|
| 65 | | | | | 70 | | | | | 75 | | | | | 80 |

| Asp | Asp | Leu | Pro | Ala | Asp | Val | Ala | Glu | Leu | Val | Leu | Tyr | Gln | Gln | Trp |
|---|---|---|---|---|---|---|---|---|---|---|---|---|---|---|---|
| | | | | 85 | | | | | 90 | | | | | 95 | |

| Asp | Thr | Arg | Ala | Ser | Met | His | Ile | Phe | Asn | Asp | Asp | Gly | Trp | Phe | Thr |
|---|---|---|---|---|---|---|---|---|---|---|---|---|---|---|---|
| | | | 100 | | | | | 105 | | | | | 110 | | |

| Gly | Lys | Glu | Ile | Pro | Ala | Leu | Leu | Gln | Ala | Phe | Val | Tyr | Ser | Gly | Phe |
|---|---|---|---|---|---|---|---|---|---|---|---|---|---|---|---|
| | | 115 | | | | | 120 | | | | | 125 | | | |

| Arg | Tyr | Gln | Ile | Ile | Asp | Val | Lys | Lys | Met | Pro | Leu | Gly | Ser | Val | Thr |
|---|---|---|---|---|---|---|---|---|---|---|---|---|---|---|---|
| | 130 | | | | | 135 | | | | | 140 | | | | |

| Lys | Ile | Cys | Phe | Cys | Gly | Asp | His | Asp | Asp | Leu | Thr | Arg | Leu | Gln | Ile |
|---|---|---|---|---|---|---|---|---|---|---|---|---|---|---|---|
| 145 | | | | | 150 | | | | | 155 | | | | | 160 |

| Gln | Leu | Tyr | Glu | Ala | Leu | Gly | Glu | Arg | Ala | His | Leu | Cys | Phe | Ser | Ala |
|---|---|---|---|---|---|---|---|---|---|---|---|---|---|---|---|
| | | | | 165 | | | | | 170 | | | | | 175 | |

| Thr | Asp | Cys | Leu | Glu | Val | Leu | Pro | Val | Gly | Cys | Asn | Lys | Gly | Ala | Ala |
|---|---|---|---|---|---|---|---|---|---|---|---|---|---|---|---|
| | | | 180 | | | | | 185 | | | | | 190 | | |

| Leu | Thr | Val | Leu | Thr | Gln | His | Leu | Asp | Leu | Ser | Leu | Arg | Asp | Cys | Met |
|---|---|---|---|---|---|---|---|---|---|---|---|---|---|---|---|
| | | 195 | | | | | 200 | | | | | 205 | | | |

| Ala | Phe | Gly | Asp | Ala | Met | Asn | Asp | Arg | Glu | Met | Leu | Val | Ser | Val | Gly |
|---|---|---|---|---|---|---|---|---|---|---|---|---|---|---|---|
| | 210 | | | | | 215 | | | | | 220 | | | | |

| Ser | Gly | Phe | Ile | Met | Gly | Asn | Ala | Met | Pro | Gln | Leu | Arg | Ala | Glu | Leu |
|---|---|---|---|---|---|---|---|---|---|---|---|---|---|---|---|
| 225 | | | | | 230 | | | | | 235 | | | | | 240 |

| Pro | His | Leu | Pro | Val | Ile | Gly | His | Cys | Arg | Asn | Gln | Ala | Val | Ser | His |
|---|---|---|---|---|---|---|---|---|---|---|---|---|---|---|---|
| | | | | 245 | | | | | 250 | | | | | 255 | |

| Tyr | Leu | Thr | His | Trp | Leu | Asp | Tyr | Pro | His | Leu | Pro | Tyr | Ser | Pro | Glu |
|---|---|---|---|---|---|---|---|---|---|---|---|---|---|---|---|
| | | | 260 | | | | | 265 | | | | | 270 | | |

```
<210> SEQ ID NO 79
<211> LENGTH: 272
<212> TYPE: PRT
<213> ORGANISM: Shigella boydii

<400> SEQUENCE: 79
```

| Met | Ala | Arg | Leu | Ala | Ala | Phe | Asp | Met | Asp | Gly | Thr | Leu | Leu | Met | Pro |
|---|---|---|---|---|---|---|---|---|---|---|---|---|---|---|---|
| 1 | | | | 5 | | | | | 10 | | | | | 15 | |

| Asp | His | His | Leu | Gly | Glu | Lys | Thr | Leu | Ser | Thr | Leu | Ala | Arg | Leu | Arg |
|---|---|---|---|---|---|---|---|---|---|---|---|---|---|---|---|
| | | | 20 | | | | | 25 | | | | | 30 | | |

| Glu | Arg | Asp | Ile | Thr | Leu | Thr | Phe | Ala | Thr | Gly | Arg | His | Ala | Leu | Glu |
|---|---|---|---|---|---|---|---|---|---|---|---|---|---|---|---|
| | | 35 | | | | | 40 | | | | | 45 | | | |

| Met | Gln | His | Ile | Leu | Gly | Ala | Leu | Ser | Leu | Asp | Ala | Tyr | Leu | Ile | Thr |
|---|---|---|---|---|---|---|---|---|---|---|---|---|---|---|---|
| | 50 | | | | | 55 | | | | | 60 | | | | |

| Gly | Asn | Gly | Thr | Arg | Val | His | Ser | Leu | Glu | Gly | Glu | Leu | Leu | His | Arg |
|---|---|---|---|---|---|---|---|---|---|---|---|---|---|---|---|

```
                65                  70                  75                  80
Asp Asp Leu Pro Ala Asp Val Ala Glu Leu Val Leu Tyr Gln Gln Trp
                    85                  90                  95

Asp Thr Arg Ala Ser Met His Ile Phe Asn Asp Asp Gly Trp Phe Thr
                    100                 105                 110

Gly Lys Glu Ile Pro Ala Leu Leu Gln Ala Phe Val Tyr Asn Gly Phe
                    115                 120                 125

Arg Tyr Gln Ile Ile Asp Val Lys Lys Met Pro Leu Gly Ser Val Thr
                    130                 135                 140

Lys Ile Cys Phe Cys Gly Asp His Asp Asp Leu Thr Arg Leu Gln Ile
145                 150                 155                 160

Gln Leu Tyr Glu Ala Leu Gly Glu Arg Ala His Leu Cys Phe Ser Ala
                    165                 170                 175

Thr Asp Cys Leu Glu Val Leu Pro Val Gly Cys Asn Lys Gly Ala Ala
                    180                 185                 190

Leu Thr Val Leu Thr Gln His Leu Gly Leu Ser Leu Arg Asp Cys Met
                    195                 200                 205

Ala Phe Gly Asp Ala Met Asn Asp Arg Glu Met Leu Gly Ser Val Gly
                    210                 215                 220

Ser Gly Phe Ile Met Gly Asn Ala Met Pro Gln Leu Arg Ala Glu Leu
225                 230                 235                 240

Pro His Leu Pro Val Ile Gly His Cys Arg Asn Gln Ala Val Ser His
                    245                 250                 255

Tyr Leu Thr His Trp Leu Asp Tyr Pro His Leu Pro Tyr Ser Pro Glu
                    260                 265                 270

<210> SEQ ID NO 80
<211> LENGTH: 272
<212> TYPE: PRT
<213> ORGANISM: Escherichia fergusonii

<400> SEQUENCE: 80

Met Ala Arg Leu Ala Ala Phe Asp Met Asp Gly Thr Leu Leu Met Pro
1               5                   10                  15

Asp His His Leu Gly Glu Lys Thr Leu Ser Thr Leu Ala Arg Leu Arg
                    20                  25                  30

Glu Arg Asp Ile Thr Leu Thr Phe Ala Thr Gly Arg His Ala Leu Glu
                35                  40                  45

Met Gln His Ile Leu Gly Ala Leu Ser Leu Asp Ala Tyr Leu Ile Thr
            50                  55                  60

Gly Asn Gly Thr Arg Val His Ser Leu Glu Gly Glu Leu Leu His Arg
65                  70                  75                  80

Asp Asp Leu Pro Ala Asp Val Ala Glu Leu Val Leu Tyr Gln Gln Trp
                    85                  90                  95

Asp Thr Arg Ala Ser Met His Ile Phe Asn Asp Asp Gly Trp Phe Thr
                    100                 105                 110

Gly Lys Glu Ile Pro Ala Leu Leu Gln Ala Phe Val Tyr Ser Gly Phe
                    115                 120                 125

Arg Tyr Gln Ile Ile Asp Val Lys Lys Met Pro Leu Asp Arg Val Thr
                    130                 135                 140

Lys Ile Cys Phe Cys Gly Asp His Asp Asp Leu Thr Arg Leu Gln Ile
145                 150                 155                 160

Gln Leu His Glu Ala Leu Gly Glu Arg Ala His Leu Cys Phe Ser Ala
                    165                 170                 175
```

```
Thr Asp Cys Leu Glu Val Leu Pro Val Gly Cys Asn Lys Gly Ala Ala
            180                 185                 190

Leu Thr Val Leu Thr Gln His Leu Gly Leu Ser Leu Arg Glu Cys Met
        195                 200                 205

Ala Phe Gly Asp Ala Met Asn Asp Arg Glu Met Leu Gly Ser Val Gly
    210                 215                 220

Ser Gly Phe Ile Met Gly Asn Ala Met Pro Gln Leu Arg Ala Glu Leu
225                 230                 235                 240

Pro His Leu Pro Val Ile Gly His Cys Arg Asn Gln Ala Val Ser His
                245                 250                 255

Tyr Leu Thr His Trp Leu Asp Tyr Pro His Leu Pro Tyr Ser Pro Glu
            260                 265                 270

<210> SEQ ID NO 81
<211> LENGTH: 245
<212> TYPE: PRT
<213> ORGANISM: Staphylococcus aureus

<400> SEQUENCE: 81

Met Ala Arg Leu Ala Ala Phe Asp Met Asp Gly Thr Leu Leu Val Pro
1               5                   10                  15

Asp His His Leu Gly Glu Lys Thr Leu Ser Thr Leu Ala Arg Leu Arg
            20                  25                  30

Glu Arg Asp Ile Thr Leu Thr Phe Ala Thr Gly Arg His Ala Leu Glu
        35                  40                  45

Met Gln His Ile Leu Gly Ala Leu Ser Leu Asp Ala Tyr Leu Ile Thr
    50                  55                  60

Gly Asn Gly Thr Arg Val His Ser Leu Glu Gly Glu Leu Leu His Arg
65                  70                  75                  80

Asp Asp Leu Pro Ala Asp Val Ala Glu Leu Val Leu Tyr Gln Gln Trp
                85                  90                  95

Asp Thr Arg Ala Ser Met His Ile Phe Asn Asp Asp Gly Trp Phe Thr
            100                 105                 110

Gly Lys Glu Ile Pro Ala Leu Leu Gln Ala Phe Val Tyr Ser Gly Phe
        115                 120                 125

Arg Tyr Gln Ile Ile Asp Val Lys Lys Met Pro Leu Gly Ser Val Thr
    130                 135                 140

Lys Ile Cys Phe Cys Gly Asp His Asp Asp Leu Thr Arg Leu Gln Ile
145                 150                 155                 160

Gln Leu Tyr Glu Ala Leu Gly Glu Arg Ala His Leu Cys Phe Ser Ala
                165                 170                 175

Thr Asp Cys Leu Glu Val Leu Pro Val Gly Cys Asn Lys Gly Ala Ala
            180                 185                 190

Leu Thr Val Leu Thr Gln His Leu Gly Leu Ser Leu Arg Asp Cys Thr
        195                 200                 205

Ala Phe Gly Asp Ala Met Asn Asp Arg Glu Met Leu Val Ser Val Gly
    210                 215                 220

Ser Gly Phe Ile Met Gly Asn Ala Met Pro Gln Leu Arg Ala Glu Leu
225                 230                 235                 240

Pro His Leu Pro Val
                245

<210> SEQ ID NO 82
<211> LENGTH: 272
<212> TYPE: PRT
<213> ORGANISM: unknown
```

<220> FEATURE:
<223> OTHER INFORMATION: Escherichia albertii

<400> SEQUENCE: 82

Met Ala Arg Leu Ala Ala Phe Asp Met Asp Gly Thr Leu Leu Met Pro
1               5                   10                  15

Asp His His Leu Gly Glu Lys Thr Leu Ser Thr Leu Ala Arg Leu Arg
            20                  25                  30

Asp Arg Asp Ile Thr Leu Thr Phe Ala Thr Gly Arg His Ala Leu Glu
        35                  40                  45

Met Arg His Ile Leu Gly Thr Phe Ala Leu Asp Ala Tyr Leu Ile Thr
    50                  55                  60

Gly Asn Gly Thr Arg Val His Ser Gln Glu Gly Asp Leu Leu Tyr Arg
65                  70                  75                  80

Asp Asp Leu Pro Ala Asp Val Ala Glu Arg Val Leu His Gln Lys Trp
                85                  90                  95

Asp Thr Gln Ala Ser Met His Ile Phe Asn Asp Asp Gly Trp Phe Thr
            100                 105                 110

Gly Gln Glu Met Pro Ser Leu Leu Gln Ala Phe Val Tyr Ser Gly Phe
        115                 120                 125

Arg Tyr Gln Ile Ile Asp Val Lys Lys Met Pro Leu Asp Arg Val Thr
    130                 135                 140

Lys Ile Cys Phe Cys Gly Asp His Asp Leu Thr Arg Leu Gln Ile
145                 150                 155                 160

Gln Leu Asn Glu Ala Leu Gly Asp Arg Ala His Leu Cys Phe Ser Ala
                165                 170                 175

Ile Asn Cys Leu Glu Val Leu Pro Val Gly Cys Asn Lys Gly Ala Ala
            180                 185                 190

Leu Ala Val Leu Ala Asp Tyr Leu Gly Phe Ser Leu Arg Asp Cys Met
        195                 200                 205

Ala Phe Gly Asp Ala Met Asn Asp Arg Glu Met Leu Gly Ser Val Gly
    210                 215                 220

Asn Gly Phe Ile Met Gly Asn Ala Met Pro Gln Leu Leu Ala Glu Leu
225                 230                 235                 240

Pro His Leu Pro Val Ile Gly His Cys Arg Asn Gln Ala Val Ser His
                245                 250                 255

Tyr Leu Thr His Trp Leu Asp Asn Pro His Leu Pro Tyr Ser Pro Glu
            260                 265                 270

<210> SEQ ID NO 83
<211> LENGTH: 272
<212> TYPE: PRT
<213> ORGANISM: Citrobacter amalonaticus

<400> SEQUENCE: 83

Met Ala Arg Leu Ala Ala Phe Asp Met Asp Gly Thr Leu Leu Met Pro
1               5                   10                  15

Asn His Leu Leu Gly Asp Glu Thr Leu Ser Thr Leu Ala Arg Leu Arg
            20                  25                  30

Glu Arg Asp Ile Thr Leu Thr Phe Ala Thr Gly Arg His Val Leu Glu
        35                  40                  45

Met Arg His Ile Leu Gly Thr Phe Ser Leu Asp Ala Phe Leu Ile Thr
    50                  55                  60

Gly Asn Gly Thr Arg Ile His Ser Leu Glu Gly Glu Val Leu His Arg
65                  70                  75                  80

Gln Asp Leu Glu Pro Ala Val Ala Glu Ile Val Leu His Gln Arg Trp
                85                  90                  95

Asp Thr Gln Ala Ser Met His Ile Phe Asn Asp Asn Gly Trp Phe Thr
            100                 105                 110

Gly Gln Glu Ile Pro Glu Met Leu His Ala His Val Tyr Ser Gly Phe
        115                 120                 125

Arg Tyr Gln Ile Val Asp Val Ala Arg Ile Pro Ala Asp Arg Val Thr
    130                 135                 140

Lys Val Cys Phe Cys Gly Asp His Asp Leu Thr Arg Leu Lys Ile
145                 150                 155                 160

Gln Leu Glu Glu Val Leu Gly Ala Arg Ala His Leu Cys Phe Ser Ala
                165                 170                 175

Val Asp Cys Leu Glu Val Leu Pro Val Gly Cys Asn Lys Gly Ser Ala
            180                 185                 190

Leu Glu Val Leu Ser Gly His Leu Gly Leu Ser Leu Ala Glu Cys Met
        195                 200                 205

Ala Phe Gly Asp Ala Met Asn Asp Arg Glu Met Leu Gly Ser Val Gly
    210                 215                 220

Arg Gly Leu Ile Met Gly Asn Ala Met Pro Gln Leu Ile Ala Glu Leu
225                 230                 235                 240

Pro His Leu Pro Val Ile Gly His Cys Arg Asn Gln Ala Val Ser His
                245                 250                 255

Phe Leu Thr His Trp Leu Asp Tyr Pro Asn Leu Pro Tyr Ser Pro Glu
            260                 265                 270

<210> SEQ ID NO 84
<211> LENGTH: 272
<212> TYPE: PRT
<213> ORGANISM: Salmonella enterica

<400> SEQUENCE: 84

Met Ala Arg Leu Ala Ala Phe Asp Met Asp Gly Thr Leu Leu Met Pro
1               5                   10                  15

Asp His His Leu Gly Lys Glu Thr Leu Ala Thr Leu Ala Arg Leu Arg
            20                  25                  30

Glu Arg Asp Ile Thr Leu Thr Phe Ala Thr Gly Arg His Val Leu Glu
        35                  40                  45

Met Arg His Ile Leu Gly Thr Leu Ser Leu Asp Ala Tyr Leu Ile Thr
    50                  55                  60

Gly Asn Gly Thr Arg Ile His Ser Leu Glu Gly Asp Val Leu His Arg
65                  70                  75                  80

Gln Asp Leu Asp Pro Gln Val Ala Asp Thr Val Met His His Ala Trp
                85                  90                  95

Asp Thr Arg Ala Ser Met His Val Phe Asn Asp Asn Gly Trp Phe Thr
            100                 105                 110

Gly Gln Glu Ile Pro Ala Leu Leu Gln Ala His Val Tyr Ser Gly Phe
        115                 120                 125

Arg Tyr Gln Val Ile Asp Ile Lys Ser Ile Pro Ala His Gln Val Thr
    130                 135                 140

Lys Ile Cys Phe Cys Gly Asp His Asp Leu Ile Arg Leu Arg Ile
145                 150                 155                 160

Gln Leu Asn Glu Ala Leu Glu Glu Arg Ala His Leu Cys Phe Ser Ala
                165                 170                 175

Val Asp Cys Leu Glu Val Leu Pro Leu Gly Cys Asn Lys Gly Ser Ala
            180                 185                 190

```
Leu Ala Val Leu Ser Asn His Leu Gly Leu Ser Leu Ala Asp Cys Met
        195                 200                 205

Ala Phe Gly Asp Ala Met Asn Asp Arg Glu Met Leu Gly Ser Val Gly
        210                 215                 220

Arg Gly Leu Ile Met Gly Asn Ala Met Pro Gln Leu Ile Ala Ala Leu
225                 230                 235                 240

Pro His Leu Ser Val Ile Gly His Cys Gly Asn Gln Ala Val Ser His
                245                 250                 255

Phe Leu Thr His Trp Leu Asp Asn Pro His Leu Pro Tyr Ser Pro Glu
                260                 265                 270
```

<210> SEQ ID NO 85
<211> LENGTH: 220
<212> TYPE: PRT
<213> ORGANISM: Escherichia coli

<400> SEQUENCE: 85

```
Leu Gly Ala Leu Ser Leu Asp Ala Tyr Leu Ile Thr Gly Asn Gly Thr
1               5                   10                  15

Arg Val His Ser Leu Glu Gly Glu Leu Leu His Arg Asp Asp Leu Pro
            20                  25                  30

Ala Asp Val Ala Glu Leu Val Leu Tyr Gln Gln Trp Asp Thr Arg Ala
        35                  40                  45

Ser Met His Ile Phe Asn Asp Gly Trp Phe Thr Gly Lys Glu Ile
    50                  55                  60

Pro Ala Leu Leu Gln Ala Phe Val Tyr Ser Gly Phe Arg Tyr Gln Ile
65                  70                  75                  80

Ile Asp Val Lys Lys Met Pro Leu Gly Ser Val Thr Lys Ile Cys Phe
                85                  90                  95

Cys Gly Asp His Asp Asp Leu Thr Arg Leu Gln Ile Gln Leu Tyr Glu
                100                 105                 110

Ala Leu Gly Glu Arg Ala His Leu Cys Phe Ser Ala Thr Asp Cys Leu
            115                 120                 125

Glu Val Leu Pro Val Gly Cys Asn Lys Gly Ala Ala Leu Thr Val Leu
        130                 135                 140

Thr Gln His Leu Gly Leu Ser Leu Arg Asp Cys Met Ala Phe Gly Asp
145                 150                 155                 160

Ala Met Asn Asp Arg Glu Met Leu Gly Ser Val Gly Ser Gly Phe Ile
                165                 170                 175

Met Gly Asn Ala Met Pro Gln Leu Arg Ala Glu Leu Pro His Leu Pro
            180                 185                 190

Val Ile Gly His Cys Arg Asn Gln Ala Val Ser His Tyr Leu Thr His
        195                 200                 205

Trp Leu Asp Tyr Pro His Leu Pro Tyr Ser Pro Glu
    210                 215                 220
```

<210> SEQ ID NO 86
<211> LENGTH: 355
<212> TYPE: PRT
<213> ORGANISM: Shigella flexneri

<400> SEQUENCE: 86

```
Met Ser Gln Lys Tyr Leu Phe Ile Asp Arg Asp Gly Thr Leu Ile Ser
1               5                   10                  15

Glu Pro Pro Ser Asp Phe Gln Val Asp Arg Phe Asp Lys Leu Ala Phe
            20                  25                  30
```

Glu Pro Gly Val Ile Pro Glu Leu Leu Lys Leu Gln Lys Ala Gly Tyr
                35                  40                  45

Lys Leu Val Met Ile Thr Asn Gln Asp Gly Leu Gly Thr Gln Ser Phe
 50                  55                  60

Pro Gln Ala Asp Phe Asp Gly Pro His Asn Leu Met Met Gln Ile Phe
 65                  70                  75                  80

Thr Ser Gln Gly Val Gln Phe Asp Glu Val Leu Ile Cys Pro His Leu
                85                  90                  95

Pro Ala Asp Glu Cys Asp Cys Arg Lys Pro Lys Val Lys Leu Val Glu
                100                 105                 110

Arg Tyr Leu Ala Glu Gln Ala Met Asp Arg Ala Asn Ser Tyr Val Ile
                115                 120                 125

Gly Asp Arg Ala Thr Asp Ile Gln Leu Ala Glu Asn Met Gly Ile Thr
130                 135                 140

Gly Leu Arg Tyr Asp Arg Glu Thr Leu Asn Trp Pro Met Ile Gly Glu
145                 150                 155                 160

Gln Leu Thr Lys Arg Asp Arg Tyr Ala His Val Val Arg Asn Thr Lys
                165                 170                 175

Glu Thr Gln Ile Asp Val Gln Val Trp Leu Asp Arg Glu Gly Gly Ser
                180                 185                 190

Lys Ile Asn Thr Gly Val Gly Phe Phe Asp His Met Leu Asp Gln Ile
                195                 200                 205

Ala Thr His Gly Gly Phe Arg Met Glu Ile Asn Val Lys Gly Asp Leu
                210                 215                 220

Tyr Ile Asp Asp His His Thr Val Glu Asp Thr Gly Leu Ala Leu Gly
225                 230                 235                 240

Glu Ala Leu Lys Ile Ala Leu Gly Asp Lys Arg Gly Ile Cys Arg Phe
                245                 250                 255

Gly Phe Val Leu Pro Met Asp Glu Cys Leu Ala Arg Cys Ala Leu Asp
                260                 265                 270

Ile Ser Gly Arg Pro His Leu Glu Tyr Lys Ala Glu Phe Thr Tyr Gln
                275                 280                 285

Arg Val Gly Asp Leu Ser Thr Glu Met Ile Glu His Phe Phe Arg Ser
                290                 295                 300

Leu Ser Tyr Thr Met Gly Val Thr Leu His Leu Lys Thr Lys Gly Lys
305                 310                 315                 320

Asn Asp His His Arg Val Glu Ser Leu Phe Lys Ala Phe Gly Arg Thr
                325                 330                 335

Leu Arg Gln Ala Met Arg Val Glu Gly Asp Thr Leu Pro Ser Ser Lys
                340                 345                 350

Gly Val Leu
        355

<210> SEQ ID NO 87
<211> LENGTH: 355
<212> TYPE: PRT
<213> ORGANISM: Escherichia albertii

<400> SEQUENCE: 87

Met Ser Gln Lys Tyr Leu Phe Ile Asp Arg Asp Gly Thr Leu Ile Ser
 1               5                  10                  15

Glu Pro Pro Ser Asp Phe Gln Val Asp Arg Phe Asp Lys Leu Ala Phe
                20                  25                  30

Glu Pro Gly Val Ile Pro Glu Leu Leu Lys Leu Gln Lys Ala Gly Tyr

```
            35                  40                  45
Lys Leu Val Met Ile Thr Asn Gln Asp Gly Leu Gly Thr Gln Ser Phe
 50                  55                  60

Pro Gln Ala Asp Phe Asp Gly Pro His Asn Leu Met Met Gln Ile Phe
 65                  70                  75                  80

Thr Ser Gln Gly Val Gln Phe Asp Glu Val Leu Ile Cys Pro His Leu
                 85                  90                  95

Pro Ala Asp Glu Cys Asp Cys Arg Lys Pro Lys Val Lys Leu Val Glu
                100                 105                 110

Arg Tyr Leu Ala Glu Gln Ala Met Asp Arg Ala Asn Ser Tyr Val Ile
                115                 120                 125

Gly Asp Arg Ala Thr Asp Ile Gln Leu Ala Glu Asn Met Gly Ile Thr
130                 135                 140

Gly Leu Arg Tyr Asp Arg Glu Thr Leu Asn Trp Pro Met Ile Gly Glu
145                 150                 155                 160

Gln Leu Thr Lys Arg Asp Arg Tyr Ala His Val Val Arg Asn Thr Lys
                165                 170                 175

Glu Thr Gln Ile Asp Val Gln Val Trp Leu Asp Arg Glu Gly Asp Ser
                180                 185                 190

Lys Ile Asn Thr Gly Val Gly Phe Asp His Met Leu Asp Gln Ile
                195                 200                 205

Ala Thr His Gly Gly Phe Arg Met Glu Ile Asn Val Lys Gly Asp Leu
210                 215                 220

Tyr Ile Asp Asp His His Thr Val Glu Asp Thr Gly Leu Ala Leu Gly
225                 230                 235                 240

Glu Ala Leu Lys Ile Ala Leu Gly Asp Lys Arg Gly Ile Cys Arg Phe
                245                 250                 255

Gly Phe Val Leu Pro Met Asp Glu Cys Leu Ala Arg Cys Ala Met Asp
                260                 265                 270

Ile Ser Gly Arg Pro His Leu Glu Tyr Lys Ala Glu Phe Thr Tyr Gln
                275                 280                 285

Arg Val Gly Asp Leu Ser Thr Glu Met Ile Glu His Phe Phe Arg Ser
290                 295                 300

Leu Ser Tyr Thr Met Gly Val Thr Leu His Leu Lys Thr Lys Gly Lys
305                 310                 315                 320

Asn Asp His His Arg Val Glu Ser Leu Phe Lys Ala Phe Gly Arg Thr
                325                 330                 335

Leu Arg Gln Ala Ile Arg Val Gly Asp Thr Leu Pro Ser Ser Lys
                340                 345                 350

Gly Val Leu
    355

<210> SEQ ID NO 88
<211> LENGTH: 355
<212> TYPE: PRT
<213> ORGANISM: Shigella flexneri

<400> SEQUENCE: 88

Met Ser Gln Lys Tyr Leu Phe Ile Asp Arg Asp Gly Thr Leu Ile Ser
 1               5                  10                  15

Glu Pro Pro Ser Asp Phe Gln Val Asp Arg Phe Asp Lys Leu Ala Phe
                20                  25                  30

Glu Pro Gly Val Ile Pro Glu Leu Leu Lys Leu Gln Lys Ala Gly Tyr
            35                  40                  45
```

```
Lys Leu Val Met Ile Thr Asn Gln Asp Gly Leu Gly Thr Gln Ser Phe
 50                  55                  60

Pro Gln Ala Asp Phe Asp Gly Pro His Asn Leu Met Met Gln Ile Phe
 65                  70                  75                  80

Thr Ser Gln Gly Val Gln Phe Asp Glu Val Leu Ile Cys Pro His Leu
                 85                  90                  95

Pro Ala Asp Glu Cys Asp Cys Arg Lys Pro Lys Val Lys Leu Val Glu
            100                 105                 110

Gly Tyr Leu Ala Glu Gln Ala Met Asp Arg Ala Asn Ser Tyr Val Ile
        115                 120                 125

Gly Asp Arg Ala Thr Asp Ile Gln Leu Ala Glu Asn Met Gly Ile Asn
130                 135                 140

Gly Leu Arg Tyr Asp Arg Glu Thr Leu Asn Trp Pro Met Ile Gly Glu
145                 150                 155                 160

Gln Leu Thr Lys Arg Asp Arg Tyr Ala His Val Val Arg Asn Thr Lys
                165                 170                 175

Glu Thr Gln Ile Asp Val Gln Val Trp Leu Asp Arg Glu Gly Gly Ser
            180                 185                 190

Lys Ile Asn Thr Gly Val Gly Phe Phe Asp His Met Leu Asp Gln Ile
        195                 200                 205

Ala Thr His Gly Gly Phe Arg Met Glu Ile Asn Val Lys Gly Asp Leu
210                 215                 220

Tyr Ile Asp Asp His His Thr Val Glu Asp Thr Gly Leu Ala Leu Gly
225                 230                 235                 240

Glu Ala Leu Lys Ile Ala Leu Gly Asp Lys Arg Gly Ile Cys Arg Phe
                245                 250                 255

Gly Phe Val Leu Pro Met Asp Glu Cys Leu Ala Arg Cys Ala Leu Asp
            260                 265                 270

Ile Ser Gly Arg Pro His Leu Glu Tyr Lys Ala Glu Phe Thr Tyr Gln
        275                 280                 285

Arg Val Gly Asp Leu Ser Thr Glu Met Ile Glu His Phe Phe Arg Ser
290                 295                 300

Leu Ser Tyr Thr Met Gly Val Thr Leu His Leu Lys Thr Lys Gly Lys
305                 310                 315                 320

Asn Asp His His Arg Val Glu Ser Leu Phe Lys Ala Phe Gly Arg Thr
                325                 330                 335

Leu Arg Gln Ala Leu Arg Val Glu Gly Asp Thr Leu Pro Ser Ser Lys
            340                 345                 350

Gly Val Leu
    355

<210> SEQ ID NO 89
<211> LENGTH: 355
<212> TYPE: PRT
<213> ORGANISM: Shigella sonnei

<400> SEQUENCE: 89

Met Ser Gln Lys Tyr Leu Phe Ile Asp Arg Asp Gly Thr Leu Ile Ser
 1               5                  10                  15

Glu Pro Pro Ser Asp Phe Gln Val Asp Arg Phe Asp Lys Leu Ala Phe
                 20                  25                  30

Glu Pro Gly Val Ile Pro Glu Leu Leu Lys Leu Gln Lys Ala Gly Tyr
             35                  40                  45

Lys Leu Val Met Ile Thr Asn Gln Asp Gly Leu Gly Thr Gln Ser Phe
 50                  55                  60
```

```
Pro Gln Ala Asp Phe Asp Gly Pro His Asn Leu Met Met Gln Ile Phe
 65                  70                  75                  80

Thr Ser Gln Gly Val Gln Phe Asp Glu Val Leu Ile Cys Pro Pro Leu
             85                   90                  95

Pro Ala Asp Glu Cys Asp Cys Arg Lys Pro Lys Val Lys Leu Val Glu
            100                 105                 110

Arg Tyr Leu Ala Glu Gln Ala Met Asp Arg Ala Asn Ser Tyr Val Ile
            115                 120                 125

Gly Asp Arg Ala Thr Asp Ile Gln Leu Ala Glu Asn Met Gly Ile Asn
130                 135                 140

Gly Leu Arg Tyr Asp Arg Glu Ile Leu Asn Trp Pro Met Ile Gly Glu
145                 150                 155                 160

Gln Leu Thr Lys Arg Asp Arg Tyr Ala His Val Val Arg Asn Thr Lys
                165                 170                 175

Glu Thr Gln Ile Asp Val Gln Val Trp Leu Asp Arg Glu Gly Gly Ser
            180                 185                 190

Lys Ile Asn Thr Gly Val Gly Phe Phe Asp His Met Leu Asp Gln Ile
            195                 200                 205

Ala Thr His Gly Gly Phe Arg Met Glu Ile Asn Val Lys Gly Asp Leu
210                 215                 220

Tyr Ile Asp Asp His His Thr Val Glu Asp Thr Gly Leu Ala Leu Gly
225                 230                 235                 240

Glu Ala Leu Lys Met Ala Leu Gly Asp Lys Arg Gly Ile Cys Arg Phe
                245                 250                 255

Gly Phe Val Leu Pro Met Asp Glu Cys Leu Ala Arg Cys Ala Leu Asp
            260                 265                 270

Ile Ser Gly Arg Pro His Leu Glu Tyr Lys Ala Glu Phe Thr Tyr Gln
            275                 280                 285

Arg Val Gly Asp Leu Ser Thr Glu Met Ile Glu His Phe Phe Arg Ser
290                 295                 300

Leu Ser Tyr Thr Met Gly Val Thr Leu His Leu Lys Thr Lys Gly Lys
305                 310                 315                 320

Asn Asp His His Arg Val Glu Ser Leu Phe Lys Ala Phe Gly Arg Thr
                325                 330                 335

Leu Arg Gln Ala Ile Arg Val Glu Gly Asp Thr Leu Pro Ser Ser Lys
            340                 345                 350

Gly Val Leu
        355

<210> SEQ ID NO 90
<211> LENGTH: 355
<212> TYPE: PRT
<213> ORGANISM: Escherichia coli

<400> SEQUENCE: 90

Met Ser Gln Lys Tyr Leu Phe Ile Asp Arg Asp Gly Thr Leu Ile Ser
 1               5                  10                  15

Glu Pro Pro Ser Asp Phe Gln Val Asp Arg Phe Asp Lys Leu Ala Phe
             20                  25                  30

Glu Pro Gly Val Ile Pro Gln Leu Lys Leu Gln Lys Ala Gly Tyr
            35                  40                  45

Lys Leu Val Met Ile Thr Asn Gln Asp Gly Leu Gly Thr Gln Ser Phe
 50                  55                  60

Pro Gln Ala Asp Phe Asp Gly Pro His Asn Leu Met Met Gln Ile Phe
```

```
            65                  70                  75                  80
        Thr Ser Gln Gly Val Gln Phe Asp Glu Val Leu Ile Cys Pro His Leu
                        85                  90                  95

Pro Ser Asp Glu Cys Asp Cys Arg Lys Pro Lys Val Lys Leu Val Glu
                        100                 105                 110

Arg Tyr Leu Ala Glu Gln Ala Met Asp Arg Ala Asn Ser Tyr Val Ile
                        115                 120                 125

Gly Asp Arg Ala Thr Asp Ile Gln Leu Ala Glu Asn Met Gly Ile Asn
                        130                 135                 140

Gly Leu Arg Tyr Asp Arg Glu Thr Leu Asn Trp Pro Met Ile Gly Glu
        145                 150                 155                 160

Gln Leu Ile Lys Arg Asp Arg Tyr Ala His Val Val Arg Asn Thr Lys
                        165                 170                 175

Glu Thr Gln Ile Asp Val Gln Val Trp Leu Asp Arg Glu Gly Gly Ser
                        180                 185                 190

Lys Ile Asn Thr Gly Val Gly Phe Phe Asp His Met Leu Asp Gln Ile
                        195                 200                 205

Ala Thr His Gly Gly Phe Arg Met Glu Ile Asn Val Lys Gly Asp Leu
                        210                 215                 220

Tyr Ile Asp Asp His His Thr Val Glu Asp Thr Gly Leu Ala Leu Gly
        225                 230                 235                 240

Glu Ala Leu Lys Ile Ala Leu Gly Asp Lys Arg Gly Ile Cys Arg Phe
                        245                 250                 255

Gly Phe Val Leu Pro Met Asp Glu Cys Leu Ala Arg Cys Ala Leu Asp
                        260                 265                 270

Ile Ser Gly Arg Pro His Leu Glu Tyr Lys Ala Glu Phe Thr Tyr Gln
                        275                 280                 285

Arg Val Gly Asp Leu Ser Thr Glu Met Ile Glu His Phe Phe Arg Ser
                        290                 295                 300

Leu Ser Tyr Thr Met Gly Val Thr Leu His Leu Lys Thr Lys Gly Lys
        305                 310                 315                 320

Asn Asp His His Arg Val Glu Ser Leu Phe Lys Ala Phe Gly Arg Thr
                        325                 330                 335

Leu Arg Gln Ala Ile Arg Val Glu Gly Asp Thr Leu Pro Ser Ser Lys
                        340                 345                 350

Gly Val Leu
                355

<210> SEQ ID NO 91
<211> LENGTH: 355
<212> TYPE: PRT
<213> ORGANISM: Shigella dysenteriae

<400> SEQUENCE: 91

Met Ser Gln Lys Tyr Leu Phe Ile Asp Arg Asp Gly Thr Leu Ile Ser
1               5                   10                  15

Glu Pro Pro Ser Asp Phe Gln Val Asp Arg Phe Asp Lys Leu Ala Phe
                20                  25                  30

Glu Pro Gly Val Ile Pro Glu Leu Leu Lys Leu Gln Lys Ala Gly Tyr
                35                  40                  45

Lys Leu Val Met

Thr Ser Gln Gly Val Gln Phe Asp Glu Val Leu Ile Cys Pro His Leu
                85                  90                  95

Pro Ala Asp Glu Cys Asp Cys Arg Lys Pro Lys Val Lys Leu Val Glu
            100                 105                 110

Arg Tyr Leu Ala Glu Gln Ala Met Asp Arg Ala Asn Ser Tyr Val Ile
        115                 120                 125

Gly Asp Arg Ala Thr Asp Ile Gln Leu Ala Glu Asn Met Gly Ile Asn
    130                 135                 140

Gly Leu Arg Tyr Asp Cys Glu Ile Leu Ser Trp Pro Met Ile Gly Glu
145                 150                 155                 160

Gln Leu Thr Lys Arg Asp Arg Tyr Ala His Val Val Arg Asn Thr Lys
                165                 170                 175

Glu Thr Gln Ile Asp Val Arg Val Trp Leu Asp Arg Glu Gly Gly Ser
            180                 185                 190

Lys Ile Asn Thr Gly Val Gly Phe Phe Asp His Met Leu Asp Gln Ile
        195                 200                 205

Ala Thr His Gly Gly Phe Arg Met Glu Ile Asn Val Lys Gly Asp Leu
    210                 215                 220

Tyr Ile Asp Asp His His Thr Val Glu Asp Thr Gly Leu Ala Leu Gly
225                 230                 235                 240

Glu Ala Leu Lys Met Ala Leu Gly Asp Lys Arg Gly Ile Cys Arg Phe
                245                 250                 255

Gly Phe Val Leu Pro Met Asp Glu Cys Leu Ala Arg Cys Ala Leu Asp
            260                 265                 270

Ile Ser Gly Arg Pro His Leu Glu Tyr Lys Ala Glu Phe Thr Tyr Gln
        275                 280                 285

Arg Val Gly Asp Leu Ser Thr Glu Met Ile Glu His Phe Phe Arg Ser
    290                 295                 300

Leu Ser Tyr Thr Met Gly Val Thr Leu His Leu Lys Thr Lys Gly Lys
305                 310                 315                 320

Asn Asp His His Arg Val Glu Ser Leu Phe Lys Ala Phe Gly Arg Thr
                325                 330                 335

Leu Arg Gln Ala Ile Arg Val Glu Gly Asp Thr Leu Pro Ser Ser Lys
            340                 345                 350

Gly Val Leu
        355

<210> SEQ ID NO 92
<211> LENGTH: 355
<212> TYPE: PRT
<213> ORGANISM: Escherichia marmotae

<400> SEQUENCE: 92

Met Ser Gln Lys Tyr Leu Phe Ile Asp Arg Asp Gly Thr Leu Ile Ser
1               5                   10                  15

Glu Pro Pro Ser Asp Phe Gln Val Asp Arg Phe Asp Lys Leu Ala Phe
            20                  25                  30

Glu Pro Gly Val Ile Pro Glu Leu Leu Lys Leu Gln Lys Ala Gly Tyr
        35                  40                  45

Lys Leu Val Met Ile Thr Asn Gln Asp Gly Leu Gly Thr Gln Arg Phe
    50                  55                  60

Pro Gln Ala Asp Phe Asp Gly Pro His Asn Leu Met Met Gln Ile Phe
65                  70                  75                  80

Thr Ser Gln Gly Val Gln Phe Asp Glu Val Leu Ile Cys Pro His Leu
                85                  90                  95

Pro Asp Asp Glu Cys Asp Cys Arg Lys Pro Lys Val Lys Leu Val Glu
                100                 105                 110

Arg Tyr Leu Ala Glu Gln Ala Met Asp Arg Ala Ser Ser Tyr Val Ile
            115                 120                 125

Gly Asp Arg Ala Thr Asp Ile Gln Leu Ala Glu Asn Met Gly Ile Asn
        130                 135                 140

Gly Leu Arg Tyr Asn Arg Glu Thr Leu Asn Trp Pro Met Ile Gly Glu
145                 150                 155                 160

Gln Leu Thr Lys Arg Asn Arg Tyr Ala His Val Val Arg Asn Thr Lys
                165                 170                 175

Glu Thr Gln Ile Asp Val Gln Val Trp Leu Asp Arg Glu Gly Gly Ser
            180                 185                 190

Lys Ile Asn Thr Gly Val Gly Phe Phe Asp His Met Leu Asp Gln Ile
        195                 200                 205

Ala Thr His Gly Gly Phe Arg Met Glu Ile Asn Val Lys Gly Asp Leu
    210                 215                 220

Tyr Ile Asp Asp His His Thr Val Glu Asp Thr Gly Leu Ala Leu Gly
225                 230                 235                 240

Glu Ala Leu Lys Ile Ala Leu Gly Asp Lys Arg Gly Ile Cys Arg Phe
                245                 250                 255

Gly Phe Val Leu Pro Met Asp Glu Cys Leu Ala Arg Cys Ala Leu Asp
            260                 265                 270

Ile Ser Gly Arg Pro His Leu Glu Tyr Lys Ala Glu Phe Thr Tyr Gln
        275                 280                 285

Arg Val Gly Asp Leu Ser Thr Glu Met Ile Glu His Phe Phe Arg Ser
    290                 295                 300

Leu Ser Tyr Thr Met Gly Val Thr Leu His Leu Lys Thr Lys Gly Lys
305                 310                 315                 320

Asn Asp His His Arg Val Glu Ser Leu Phe Lys Ala Phe Gly Arg Thr
                325                 330                 335

Leu Arg Gln Ala Ile Arg Val Glu Gly Asp Thr Leu Pro Ser Ser Lys
            340                 345                 350

Gly Val Leu
        355

<210> SEQ ID NO 93
<211> LENGTH: 355
<212> TYPE: PRT
<213> ORGANISM: Salmonella bongori

<400> SEQUENCE: 93

Met Ser Gln Lys Tyr Leu Phe Ile Asp Arg Asp Gly Thr Leu Ile Ser
1               5                   10                  15

Glu Pro Pro Ser Asp Phe Gln Val Asp Arg Phe Asp Lys Leu Ala Phe
            20                  25                  30

Glu Pro Glu Val Ile Pro Val Leu Leu Lys Leu Gln Lys Ala Gly Phe
        35                  40                  45

Lys Leu Val Met Ile Thr Asn Gln Asp Gly Leu Gly Thr Gln Ser Phe
    50                  55                  60

Pro Gln Ala Asp Phe Asp Gly Pro His Asn Leu Met Met Gln Val Phe
65                  70                  75                  80

Thr Ser Gln Gly Val His Phe Asp Glu Val Leu Ile Cys Pro His Leu
                85                  90                  95

Pro Ala Asp Glu Cys Asp Cys Arg Lys Pro Lys Ile Lys Leu Val Glu

```
            100                 105                 110

Arg Tyr Leu Ala Glu Gln Ala Met Asp Ser Ala Asn Ser Tyr Val Ile
            115                 120                 125

Gly Asp Arg Ala Thr Asp Val Gln Leu Ala Asp Asn Met Gly Ile Thr
        130                 135                 140

Gly Leu Arg Tyr His Arg Glu Thr Leu Asn Trp Ser Met Ile Gly Glu
145                 150                 155                 160

Gln Leu Thr Lys Arg Asp Arg Tyr Ala His Val Ile Arg Asn Thr Lys
                165                 170                 175

Glu Thr Gln Ile Asp Val Arg Val Trp Leu Asp Arg Glu Gly Asn Ser
            180                 185                 190

Lys Ile Asn Thr Gly Val Gly Phe Asp His Met Leu Asp Gln Ile
        195                 200                 205

Ala Thr His Gly Gly Phe Arg Met Asp Val Thr Val Lys Gly Asp Leu
    210                 215                 220

Tyr Ile Asp Asp His His Thr Val Glu Asp Thr Gly Leu Ala Leu Gly
225                 230                 235                 240

Glu Ala Leu Lys Leu Ala Leu Gly Asp Lys Arg Gly Ile Cys Arg Phe
                245                 250                 255

Gly Phe Val Leu Pro Met Asp Glu Cys Leu Ala Arg Cys Ala Leu Asp
            260                 265                 270

Ile Ser Gly Arg Pro His Leu Glu Tyr Lys Ala Glu Phe Thr Tyr Gln
        275                 280                 285

Arg Val Gly Asp Leu Ser Thr Glu Met Ile Glu His Phe Phe Arg Ser
    290                 295                 300

Leu Ser Tyr Thr Met Gly Val Thr Leu His Leu Lys Thr Lys Gly Lys
305                 310                 315                 320

Asn Asp His His Arg Val Glu Ser Leu Phe Lys Ala Phe Gly Arg Thr
                325                 330                 335

Leu Arg Gln Ala Ile Arg Val Glu Gly Asp Thr Leu Pro Ser Ser Lys
            340                 345                 350

Gly Val Leu
        355

<210> SEQ ID NO 94
<211> LENGTH: 266
<212> TYPE: PRT
<213> ORGANISM: Shigella sonnei

<400> SEQUENCE: 94

Met Thr Glu Pro Leu Thr Glu Thr Pro Glu Leu Ser Ala Lys Tyr Ala
1               5                   10                  15

Trp Phe Phe Asp Leu Asp Gly Thr Leu Ala Glu Ile Lys Pro His Pro
            20                  25                  30

Asp Gln Val Val Pro Asp Asn Ile Leu Gln Gly Leu Gln Leu Leu
        35                  40                  45

Ala Thr Ala Ser Asp Gly Ala Leu Ala Leu Ile Ser Gly Arg Ser Met
    50                  55                  60

Val Glu Leu Asp Ala Leu Ala Lys Pro Tyr Arg Phe Pro Leu Ala Gly
65                  70                  75                  80

Val His Gly Ala Glu Arg Arg Asp Ile Asn Gly Lys Thr His Ile Val
                85                  90                  95

His Leu Pro Asp Ala Ile Ala Arg Asp Ile Ser Val Gln Leu His Thr
            100                 105                 110
```

Val Ile Ala Gln Tyr Pro Gly Ala Glu Leu Glu Ala Lys Gly Met Ala
            115                 120                 125

Phe Ala Leu His Tyr Arg Gln Ala Pro Gln His Glu Asp Ala Leu Met
        130                 135                 140

Thr Leu Ala Gln Arg Ile Thr Gln Ile Trp Pro Gln Met Ala Leu Gln
145                 150                 155                 160

Gln Gly Lys Cys Val Val Glu Ile Lys Pro Arg Gly Thr Ser Lys Gly
                165                 170                 175

Glu Ala Ile Ala Ala Phe Met Gln Glu Ala Pro Phe Ile Gly Arg Thr
            180                 185                 190

Pro Val Phe Leu Gly Asp Asp Leu Thr Asp Glu Ser Gly Phe Ala Val
        195                 200                 205

Val Asn Arg Leu Gly Gly Met Ser Val Lys Ile Gly Thr Gly Ala Thr
210                 215                 220

Gln Ala Ser Trp Arg Leu Ala Gly Val Pro Asp Val Trp Ser Trp Leu
225                 230                 235                 240

Glu Met Ile Ser Thr Ala Leu Gln Gln Lys Arg Glu Asn Asn Arg Ser
                245                 250                 255

Asp Asp Tyr Glu Ser Phe Ser Arg Ser Ile
            260                 265

<210> SEQ ID NO 95
<211> LENGTH: 266
<212> TYPE: PRT
<213> ORGANISM: Escherichia coli

<400> SEQUENCE: 95

Met Thr Glu Pro Leu Thr Glu Thr Pro Glu Leu Ser Ala Lys Tyr Ala
1               5                   10                  15

Trp Phe Phe Asp Leu Asp Gly Thr Leu Ala Glu Ile Lys Pro His Pro
            20                  25                  30

Asp Gln Val Val Val Pro Asp Asn Ile Leu Gln Gly Leu Gln Leu Leu
        35                  40                  45

Ala Thr Ala Ser Asp Gly Ala Leu Ala Leu Ile Ser Gly Arg Ser Met
    50                  55                  60

Val Glu Leu Asp Ala Leu Ala Lys Pro Tyr Arg Phe Pro Leu Ala Gly
65                  70                  75                  80

Val His Gly Ala Glu Arg Arg Asp Ile Asn Gly Lys Thr His Ile Val
                85                  90                  95

His Leu Pro Asp Ala Ile Ala Arg Asp Ile Ser Val Gln Leu His Thr
            100                 105                 110

Val Ile Ala Gln Tyr Pro Gly Ala Glu Leu Glu Ala Lys Gly Met Ala
        115                 120                 125

Phe Ala Leu His Tyr Arg Gln Ala Pro Gln His Glu Asp Ala Leu Met
    130                 135                 140

Thr Leu Ala Gln Arg Ile Thr Gln Ile Trp Pro Gln Met Ala Leu Gln
145                 150                 155                 160

Gln Gly Lys Cys Val Val Glu Ile Lys Pro Arg Gly Thr Ser Lys Gly
                165                 170                 175

Glu Ala Ile Ala Ala Phe Met Gln Glu Ala Pro Phe Ile Gly Arg Thr
            180                 185                 190

Pro Val Phe Leu Gly Asp Asp Leu Thr Asp Glu Ser Gly Phe Ala Val
        195                 200                 205

Val Asn Arg Leu Gly Gly Met Ser Ile Lys Ile Gly Thr Gly Ala Thr
    210                 215                 220

```
Gln Ala Ser Trp Arg Leu Ala Gly Val Pro Asp Val Trp Ser Trp Leu
225                 230                 235                 240

Glu Met Ile Thr Thr Ala Leu Gln Gln Lys Arg Glu Asn Asn Arg Ser
            245                 250                 255

Asp Asp Tyr Glu Ser Phe Ser Arg Ser Ile
            260                 265

<210> SEQ ID NO 96
<211> LENGTH: 266
<212> TYPE: PRT
<213> ORGANISM: Shigella flexneri

<400> SEQUENCE: 96

Met Thr Glu Pro Leu Thr Glu Thr Pro Glu Leu Ser Ala Lys Tyr Ala
1               5                   10                  15

Trp Phe Phe Asp Leu Asp Gly Thr Leu Ala Glu Ile Lys Pro His Pro
            20                  25                  30

Asp Gln Val Val Val Pro Asp Asn Ile Leu Gln Gly Leu Gln Leu Leu
        35                  40                  45

Ala Thr Ala Ser Asp Gly Ala Leu Ala Leu Ile Ser Gly Arg Ser Met
    50                  55                  60

Val Glu Leu Asp Ala Leu Ala Lys Pro Tyr Arg Phe Pro Leu Ala Gly
65                  70                  75                  80

Val His Gly Ala Glu Arg Arg Asp Ile Asn Gly Lys Thr His Ile Val
                85                  90                  95

His Leu Pro Asp Ala Ile Ala Arg Asp Ile Ser Val Gln Leu His Thr
            100                 105                 110

Val Ile Ala Gln Tyr Pro Gly Ala Glu Leu Glu Ala Lys Gly Met Ala
        115                 120                 125

Phe Ala Leu His Tyr Arg Gln Ala Pro Gln His Glu Asp Ala Leu Met
130                 135                 140

Thr Leu Ala Gln Arg Ile Thr Gln Ile Trp Pro Gln Met Ala Leu Gln
145                 150                 155                 160

Gln Gly Lys Cys Val Val Glu Ile Lys Pro Arg Gly Thr Ser Lys Gly
                165                 170                 175

Glu Ala Ile Ala Ala Phe Met Gln Glu Ala Pro Phe Ile Gly Arg Thr
            180                 185                 190

Pro Val Phe Leu Gly Asp Asp Leu Thr Asp Glu Ser Gly Phe Ala Val
        195                 200                 205

Val Asn Arg Leu Gly Gly Met Ser Val Lys Ile Gly Thr Gly Ala Thr
    210                 215                 220

Gln Ala Ser Trp Arg Leu Ala Gly Val Pro Asp Val Trp Ser Trp Leu
225                 230                 235                 240

Lys Met Ile Thr Ala Ala Leu Gln Gln Lys Arg Glu Asn Asn Arg Ser
                245                 250                 255

Asp Asp Tyr Glu Ser Phe Ser Arg Ser Ile
            260                 265

<210> SEQ ID NO 97
<211> LENGTH: 265
<212> TYPE: PRT
<213> ORGANISM: Escherichia albertii

<400> SEQUENCE: 97

Met Thr Glu Pro Leu Thr Ala Leu Pro Glu Leu Ser Ala Lys Tyr Ala
1               5                   10                  15
```

```
Trp Phe Phe Asp Leu Asp Gly Thr Leu Ala Glu Ile Lys Pro His Pro
             20                  25                  30

Asp Gln Val Ala Val Pro Asp Lys Ile Leu Gln Gly Leu Gln Arg Leu
         35                  40                  45

Ala Thr Ile Ser His Gly Ala Leu Ala Leu Ile Ser Gly Arg Ser Met
     50                  55                  60

Val Glu Leu Asp Ala Leu Val Asn Pro Tyr Arg Phe Pro Leu Ala Gly
 65                  70                  75                  80

Val His Gly Ala Glu Arg Arg Asp Ile Asn Gly Lys Thr His Ile Val
                 85                  90                  95

His Leu Pro Lys Ala Met Ala Arg Asp Ile Cys Val Gln Leu His Met
            100                 105                 110

Ala Ile Ala Arg Phe Pro Gly Ala Glu Leu Glu Glu Lys Gly Met Ala
        115                 120                 125

Phe Ala Leu His Tyr Arg Gln Val Pro Gln Tyr Glu Asp Ala Leu Leu
130                 135                 140

Thr Leu Ala Arg His Ile Thr Gln Thr Trp Pro Gln Met Val Leu Gln
145                 150                 155                 160

Gln Gly Lys Cys Val Val Glu Ile Lys Pro Gly Gly Thr Ser Lys Gly
                165                 170                 175

Glu Ala Ile Val Ala Phe Met Gln Glu Thr Pro Phe Ile Gly Arg Lys
            180                 185                 190

Pro Val Phe Leu Gly Asp Asp Leu Thr Asp Glu Ser Gly Phe Ala Val
        195                 200                 205

Val Asn Arg Leu Gly Gly Ile Ser Val Lys Ile Gly Thr Gly Ala Thr
    210                 215                 220

Gln Ala Ser Trp Arg Met Ala Gly Val Pro Asp Val Trp Arg Trp Leu
225                 230                 235                 240

Glu Met Ile Thr His Ala Leu Gln Lys Arg Ala Asn Asp Arg Ser Asp
                245                 250                 255

Asn Asp Glu Pro Phe Ser Arg Ser Ile
            260                 265

<210> SEQ ID NO 98
<211> LENGTH: 267
<212> TYPE: PRT
<213> ORGANISM: Escherichia fergusonii

<400> SEQUENCE: 98

Met Thr Lys Pro Leu Thr Glu Ala Pro Glu Leu Ser Ala Lys Tyr Ala
 1               5                  10                  15

Trp Phe Phe Asp Leu Asp Gly Thr Leu Ala Glu Ile Lys Pro His Pro
             20                  25                  30

Asp Gln Val Ala Ile Pro Asp Ala Ile Leu Gln Gly Leu Gln Gln Leu
         35                  40                  45

Ala Val His Ser Asp Gly Ala Leu Ala Leu Ile Ser Gly Arg Ser Met
     50                  55                  60

Val Glu Leu Asp Thr Leu Ala Lys Pro Tyr Arg Phe Pro Leu Ala Gly
 65                  70                  75                  80

Val His Gly Ala Glu Arg Arg Asp Ile Asn Gly Lys Thr His Ile Val
                 85                  90                  95

Arg Leu Pro Asp Ala Met Val Arg Asp Ile Ser Val Gln Leu His Thr
            100                 105                 110

Thr Leu Ala Gly Leu Thr Gly Val Glu Ile Glu Glu Lys Gly Met Ala
```

```
            115                 120                 125
Phe Ala Leu His Tyr Arg Gln Ala Pro Gln His Glu Ala Leu Leu Phe
    130                 135                 140
Thr Leu Ala Gln Arg Ile Thr Gln Ile Trp Pro Gln Met Ala Leu Gln
145                 150                 155                 160
Gln Gly Lys Cys Val Val Glu Ile Lys Pro Arg Gly Thr Cys Lys Gly
                165                 170                 175
Asp Ala Ile Ala Glu Phe Met Gln Glu Thr Pro Phe Val Gly Arg Ile
            180                 185                 190
Pro Ile Phe Trp Gly Asp Asp Leu Thr Asp Glu Ser Gly Phe Ala Val
                195                 200                 205
Val Asn Gln Ala Gly Gly Ile Ser Val Lys Ile Gly Ala Gly Glu Thr
    210                 215                 220
Gln Ala Lys Trp Arg Leu Ala Gly Val Pro Asp Val Trp Arg Trp Leu
225                 230                 235                 240
Ala Val Ile Thr Asn Ser Leu Gln Glu Gln Lys Leu Glu Glu Asn Arg
                245                 250                 255
Ser Asp Asp Tyr Glu Ser Phe Ser Arg Ser Ile
                260                 265

<210> SEQ ID NO 99
<211> LENGTH: 191
<212> TYPE: PRT
<213> ORGANISM: Escherichia fergusonii

<400> SEQUENCE: 99

Met Ala Lys Ser Val Pro Ala Ile Phe Leu Asp Arg Asp Gly Thr Ile
1               5                   10                  15
Asn Val Asp His Gly Tyr Val His Glu Ile Asp Asn Phe Glu Phe Ile
            20                  25                  30
Asp Gly Val Ile Asp Ala Met Arg Glu Leu Lys Lys Met Gly Phe Ala
        35                  40                  45
Leu Val Val Val Thr Asn Gln Ser Gly Ile Ala Arg Gly Lys Phe Thr
    50                  55                  60
Glu Ala Gln Phe Glu Thr Leu Thr Glu Trp Met Asp Trp Ser Leu Ala
65                  70                  75                  80
Asp Arg Asp Val Asp Leu Asp Gly Ile Tyr Tyr Cys Pro His His Pro
                85                  90                  95
Gln Gly Ser Val Glu Glu Phe Arg Gln Val Cys Asp Cys Arg Lys Pro
                100                 105                 110
His Pro Gly Met Leu Leu Ser Ala Arg Asp Tyr Leu His Ile Asp Met
            115                 120                 125
Ala Ala Ser Tyr Met Val Gly Asp Lys Leu Glu Asp Met Gln Ala Ala
    130                 135                 140
Thr Ala Ala Asn Val Gly Thr Lys Val Leu Val Arg Thr Gly Lys Pro
145                 150                 155                 160
Ile Thr Pro Glu Ala Glu Asn Ala Ala Asp Trp Val Leu Asn Ser Leu
                165                 170                 175
Ala Asp Leu Pro Gln Ala Ile Lys Lys Gln Gln Lys Pro Ala Gln
            180                 185                 190

<210> SEQ ID NO 100
<211> LENGTH: 191
<212> TYPE: PRT
<213> ORGANISM: Shigella sonnei
```

<400> SEQUENCE: 100

```
Met Ala Lys Ser Val Pro Ala Ile Phe Leu Asp Arg Asp Gly Thr Ile
1               5                   10                  15

Asn Val Asp His Gly Tyr Val His Glu Ile Asp Asn Phe Glu Phe Ile
            20                  25                  30

Asp Gly Val Ile Asp Ala Met Arg Glu Leu Lys Lys Met Gly Phe Ala
        35                  40                  45

Leu Val Val Val Thr Asn Gln Ser Gly Ile Ala Arg Gly Lys Phe Thr
    50                  55                  60

Glu Ala Gln Phe Glu Thr Leu Thr Glu Trp Met Asp Trp Ser Leu Ala
65                  70                  75                  80

Asp Arg Asp Val Asp Leu Asp Gly Ile Tyr Tyr Cys Pro His His Pro
                85                  90                  95

Gln Gly Ser Val Glu Glu Phe Arg Gln Val Cys Asp Cys Arg Lys Pro
            100                 105                 110

His Pro Gly Met Leu Leu Ser Ala Arg Asp Tyr Leu His Ile Asp Met
        115                 120                 125

Ala Ala Ser Tyr Met Val Gly Asp Lys Leu Glu Asp Met Gln Ala Ala
    130                 135                 140

Val Ala Ala Asn Val Gly Thr Lys Val Leu Val Arg Thr Gly Lys Pro
145                 150                 155                 160

Ile Thr Pro Glu Ala Glu Asn Ala Ala Asp Trp Met Leu Asn Ser Leu
                165                 170                 175

Ala Asp Leu Pro Gln Ala Ile Lys Lys Gln Gln Lys Pro Ala Gln
            180                 185                 190
```

<210> SEQ ID NO 101
<211> LENGTH: 191
<212> TYPE: PRT
<213> ORGANISM: Escherichia coli

<400> SEQUENCE: 101

```
Met Ala Lys Ser Val Pro Ala Ile Phe Leu Asp Arg Asp Gly Thr Ile
1               5                   10                  15

Asn Val Asp His Gly Tyr Val His Glu Ile Asp Asn Phe Glu Phe Ile
            20                  25                  30

Asp Gly Val Ile Asp Ala Met Arg Glu Leu Lys Lys Met Gly Phe Ala
        35                  40                  45

Leu Val Val Val Thr Asn Gln Ser Gly Ile Ala Arg Gly Lys Phe Thr
    50                  55                  60

Glu Ala Gln Phe Glu Thr Leu Thr Glu Trp Met Asp Trp Ser Leu Ala
65                  70                  75                  80

Asp Arg Asp Val Asp Leu Asp Gly Ile Tyr Tyr Cys Pro His His Pro
                85                  90                  95

Gln Gly Ser Val Glu Glu Phe Arg Gln Leu Cys Asp Cys Arg Lys Pro
            100                 105                 110

His Pro Gly Met Leu Leu Ser Ala Arg Asp Tyr Leu His Ile Asp Met
        115                 120                 125

Ala Ala Ser Tyr Met Val Gly Asp Lys Leu Glu Asp Met Gln Ala Ala
    130                 135                 140

Val Ala Ala Asn Val Gly Thr Lys Val Leu Val Arg Thr Gly Lys Pro
145                 150                 155                 160

Ile Thr Pro Glu Ala Glu Asn Ala Ala Asp Trp Val Leu Asn Ser Leu
                165                 170                 175
```

```
Ala Asp Leu Pro Gln Ala Ile Lys Lys Gln Gln Lys Pro Ala Arg
            180                 185                 190

<210> SEQ ID NO 102
<211> LENGTH: 188
<212> TYPE: PRT
<213> ORGANISM: Escherichia albertii

<400> SEQUENCE: 102

Met Ala Lys Ser Val Pro Ala Ile Phe Leu Asp Arg Asp Gly Thr Ile
1               5                   10                  15

Asn Val Asp His Gly Tyr Val His Glu Ile Asp Asn Phe Glu Phe Ile
            20                  25                  30

Asp Gly Val Ile Asp Ala Met Arg Glu Leu Lys Lys Met Gly Phe Ala
        35                  40                  45

Leu Val Val Val Thr Asn Gln Ser Gly Ile Ala Arg Gly Lys Phe Thr
    50                  55                  60

Glu Ala Gln Phe Glu Thr Leu Thr Glu Trp Met Asp Trp Ser Leu Ala
65                  70                  75                  80

Asp Arg Asp Val Asp Leu Asp Gly Ile Tyr Tyr Cys Pro His His Pro
                85                  90                  95

Gln Gly Ser Val Glu Glu Phe Arg Gln Val Cys Asp Cys Arg Lys Pro
            100                 105                 110

His Pro Gly Met Leu Ile Ser Ala Arg Asp Tyr Leu His Ile Asp Met
        115                 120                 125

Thr Ala Ser Tyr Met Val Gly Asp Lys Leu Glu Asp Met Gln Ala Ala
    130                 135                 140

Ser Ala Ala Asn Val Gly Thr Lys Val Leu Val Arg Thr Gly Lys Pro
145                 150                 155                 160

Val Thr Pro Glu Ala Glu Asp Ala Ala Asp Trp Val Leu Asn Ser Leu
                165                 170                 175

Ala Asp Leu Pro Gln Ala Ile Lys Lys Gln Gln Lys
            180                 185

<210> SEQ ID NO 103
<211> LENGTH: 188
<212> TYPE: PRT
<213> ORGANISM: Kluyvera intermedia

<400> SEQUENCE: 103

Met Ala Lys Ser Val Pro Ala Ile Phe Leu Asp Arg Asp Gly Thr Ile
1               5                   10                  15

Asn Val Asp His Gly Tyr Val His Glu Ile Asp Asn Phe Glu Phe Ile
            20                  25                  30

Glu Gly Val Ile Asp Ala Met Arg Glu Leu Lys Ala Met Gly Phe Ala
        35                  40                  45

Leu Val Val Val Thr Asn Gln Ser Gly Ile Ala Arg Gly Lys Phe Thr
    50                  55                  60

Glu Ala Gln Phe Glu Thr Leu Thr Glu Trp Met Asp Trp Ser Leu Ala
65                  70                  75                  80

Asp Arg Asp Val Asp Leu Asp Gly Ile Tyr Tyr Cys Pro His His Pro
                85                  90                  95

Gln Gly Thr Val Glu Glu Phe Arg Gln Val Cys Asp Cys Arg Lys Pro
            100                 105                 110

His Pro Gly Met Leu Ile Ser Ala Arg Asp Tyr Leu His Ile Asp Met
        115                 120                 125
```

```
Ser Ala Ser Tyr Met Val Gly Asp Lys Leu Glu Asp Met Gln Ala Ala
        130                 135                 140

Ala Ala Ala Asp Val Gly Thr Lys Val Leu Val Arg Thr Gly Lys Pro
145                 150                 155                 160

Val Thr Pro Glu Ala Glu Asn Ala Ala Asp Trp Val Ile Asn Ser Leu
                165                 170                 175

Ala Asp Leu Pro Ala Ala Ile Lys Lys Gln Gln Lys
            180                 185

<210> SEQ ID NO 104
<211> LENGTH: 188
<212> TYPE: PRT
<213> ORGANISM: Citrobacter koseri

<400> SEQUENCE: 104

Met Ala Lys Ser Val Pro Ala Ile Phe Leu Asp Arg Asp Gly Thr Ile
1               5                   10                  15

Asn Val Asp His Gly Tyr Val His Glu Ile Asp Glu Phe Glu Phe Ile
                20                  25                  30

Glu Gly Val Ile Asp Ala Met Arg Glu Leu Lys Lys Met Gly Phe Ala
            35                  40                  45

Leu Val Val Val Thr Asn Gln Ser Gly Ile Ala Arg Gly Lys Phe Thr
50                  55                  60

Glu Ala Gln Phe Glu Thr Leu Thr Glu Trp Met Asp Trp Ser Leu Ala
65                  70                  75                  80

Asp Arg Asp Val Asp Leu Asp Gly Ile Tyr Tyr Cys Pro His His Pro
                85                  90                  95

Gln Gly Ser Val Glu Glu Phe Arg Gln Ala Cys Asp Cys Arg Lys Pro
            100                 105                 110

His Pro Gly Met Leu Ile Ser Ala Arg Asp Phe Leu His Ile Asp Met
        115                 120                 125

Ala Ala Ser Tyr Met Val Gly Asp Lys Ile Glu Asp Met Gln Ala Ala
        130                 135                 140

Ala Ala Ala Asn Val Gly Thr Lys Val Leu Val Arg Thr Gly Lys Pro
145                 150                 155                 160

Val Thr Pro Glu Ala Glu Asn Ala Ala Asp Trp Val Leu Asn Ser Leu
                165                 170                 175

Ala Asp Leu Pro Ser Ala Ile Arg Lys Gln Gln Lys
            180                 185

<210> SEQ ID NO 105
<211> LENGTH: 188
<212> TYPE: PRT
<213> ORGANISM: Kosakonia arachidis

<400> SEQUENCE: 105

Met Thr Lys Ser Val Pro Ala Ile Phe Leu Asp Arg Asp Gly Thr Ile
1               5                   10                  15

Asn Val Asp His Gly Tyr Val His Glu Ile Asp Asn Phe Glu Phe Ile
                20                  25                  30

Asp Gly Val Ile Asp Ala Met Arg Glu Leu Lys Glu Met Gly Tyr Ala
            35                  40                  45

Leu Val Leu Val Thr Asn Gln Ser Gly Ile Ala Arg Gly Lys Phe Thr
50                  55                  60

Glu Ala Gln Phe Glu Thr Leu Thr Glu Trp Met Asp Trp Ser Leu Ala
65                  70                  75                  80
```

```
Asp Arg Gly Val Asp Leu Asp Gly Ile Tyr Tyr Cys Pro His His Pro
            85                  90                  95

Gln Gly Thr Val Glu Glu Phe Arg Gln Val Cys Asp Cys Arg Lys Pro
        100                 105                 110

His Pro Gly Met Leu Ile Ser Ala Arg Asp Phe Leu His Ile Asp Met
            115                 120                 125

Ser Ala Ser Tyr Met Val Gly Asp Lys Ile Glu Asp Met Gln Ala Ala
        130                 135                 140

Gln Ala Ala Gln Val Gly Thr Lys Val Leu Val Arg Thr Gly Lys Pro
145                 150                 155                 160

Ile Thr Pro Glu Ala Glu Lys Ser Ala Asp Trp Val Ile Asn Ser Leu
                165                 170                 175

Ala Glu Leu Pro Leu Ala Ile Lys Lys His Gln Lys
            180                 185

<210> SEQ ID NO 106
<211> LENGTH: 187
<212> TYPE: PRT
<213> ORGANISM: Kluyvera cryocrescens

<400> SEQUENCE: 106

Met Ala Lys Ser Val Pro Ala Ile Phe Leu Asp Arg Asp Gly Thr Ile
1               5                   10                  15

Asn Val Asp His Gly Tyr Val His Glu Ile Asp Phe Glu Phe Ile
            20                  25                  30

Asp Gly Val Ile Asp Ala Met Arg Glu Leu Lys Glu Met Gly Tyr Ala
        35                  40                  45

Leu Val Leu Val Thr Asn Gln Ser Gly Ile Ala Arg Gly Lys Phe Thr
    50                  55                  60

Glu Ala Gln Phe Glu Thr Leu Thr Glu Trp Met Asp Trp Ser Leu Ala
65                  70                  75                  80

Asp Arg Gly Val Asp Leu Asp Gly Ile Tyr Phe Cys Pro His His Pro
            85                  90                  95

Gln Gly Thr Val Glu Glu Tyr Arg Gln Val Cys Asp Cys Arg Lys Pro
        100                 105                 110

His Pro Gly Met Leu Lys Ser Ala Gln Glu Tyr Leu His Ile Asp Met
            115                 120                 125

Ser Ser Ser Tyr Met Val Gly Asp Lys Ile Glu Asp Met Gln Ala Ala
        130                 135                 140

Ala Ala Ala Asn Val Gly Thr Lys Val Leu Val Arg Thr Gly Lys Pro
145                 150                 155                 160

Val Thr Glu Asp Ala Glu Lys Ala Ala Asp Trp Val Ile Asn Ser Leu
                165                 170                 175

Ala Asp Leu Pro Ala Met Ile Lys Lys Gln Lys
            180                 185

<210> SEQ ID NO 107
<211> LENGTH: 188
<212> TYPE: PRT
<213> ORGANISM: Leclercia adecarboxylata

<400> SEQUENCE: 107

Met Ala Lys Ser Val Pro Ala Ile Phe Leu Asp Arg Asp Gly Thr Ile
1               5                   10                  15

Asn Val Asp His Gly Tyr Val His Glu Ile Asp Glu Phe Glu Phe Ile
            20                  25                  30
```

Glu Gly Val Ile Glu Ala Met Arg Glu Leu Lys Glu Met Gly Phe Ala
         35                  40                  45

Leu Val Val Val Thr Asn Gln Ser Gly Ile Ala Arg Gly Lys Phe Thr
 50                  55                  60

Glu Ala Gln Phe Glu Thr Leu Thr Glu Trp Met Asp Trp Ser Leu Ala
65                  70                  75                  80

Asp Arg Gly Val Asp Leu Asp Gly Ile Tyr Tyr Cys Pro His His Pro
                 85                  90                  95

Gln Gly Thr Val Glu Glu Tyr Arg Gln Thr Cys Asp Cys Arg Lys Pro
            100                 105                 110

His Pro Gly Met Phe Ile Ser Ala Gln Glu Phe Leu His Ile Asp Met
        115                 120                 125

Ser Ala Ser Tyr Met Val Gly Asp Lys Leu Glu Asp Met Gln Ala Ala
130                 135                 140

Ala Ala Ala Gly Val Gly His Lys Ile Leu Val Arg Thr Gly Lys Pro
145                 150                 155                 160

Val Thr Pro Glu Ala Glu Asn Ala Ala Asp Cys Val Ile Asn Ser Leu
                165                 170                 175

Ala Ala Leu Pro Glu Thr Ile Lys Lys Gln Gln Lys
            180                 185

<210> SEQ ID NO 108
<211> LENGTH: 219
<212> TYPE: PRT
<213> ORGANISM: Shigella sonnei

<400> SEQUENCE: 108

Met Lys Leu Gln Gly Val Ile Phe Asp Leu Asp Gly Val Ile Thr Asp
1                5                  10                  15

Thr Ala His Leu His Phe Gln Ala Trp Gln Gln Ile Ala Ala Glu Ile
                 20                  25                  30

Gly Ile Ser Ile Asp Ala Gln Phe Asn Glu Ser Leu Lys Gly Ile Ser
             35                  40                  45

Arg Asp Glu Ser Leu Arg Arg Ile Leu Gln His Gly Gly Lys Glu Gly
50                  55                  60

Asp Phe Asn Ser Gln Glu Arg Ala Gln Leu Ala Tyr Arg Lys Asn Leu
65                  70                  75                  80

Leu Tyr Val His Ser Leu Arg Glu Leu Thr Val Asn Ala Val Leu Pro
                 85                  90                  95

Gly Ile Arg Ser Leu Leu Ala Asp Leu Arg Ala Gln Gln Ile Ser Val
            100                 105                 110

Gly Leu Ala Ser Val Ser Leu Asn Ala Pro Thr Ile Leu Ala Ala Leu
        115                 120                 125

Glu Leu Arg Lys Phe Phe Thr Phe Cys Ala Asp Ala Ser Gln Leu Lys
    130                 135                 140

Asn Ser Lys Pro Asp Pro Glu Ile Phe Leu Ala Ala Cys Ala Gly Leu
145                 150                 155                 160

Gly Val Pro Pro Gln Ala Cys Ile Gly Ile Glu Asp Ala Gln Ala Gly
                165                 170                 175

Ile Asp Ala Ile Asn Ala Ser Gly Met Arg Ser Val Gly Ile Gly Ala
            180                 185                 190

Gly Leu Thr Gly Ala Gln Leu Leu Pro Ser Thr Glu Ser Leu Thr
        195                 200                 205

Trp Pro Arg Leu Ser Ala Phe Trp Gln Asn Val
    210                 215

-continued

<210> SEQ ID NO 109
<211> LENGTH: 219
<212> TYPE: PRT
<213> ORGANISM: Escherichia coli

<400> SEQUENCE: 109

Met Lys Leu Gln Gly Val Ile Phe Asp Leu Asp Gly Val Ile Thr Asp
1               5                   10                  15

Thr Ala His Leu His Phe Lys Ala Trp Gln Gln Ile Ala Ala Glu Ile
                20                  25                  30

Gly Ile Ser Ile Asp Ala Gln Phe Asn Glu Ser Leu Lys Gly Ile Ser
            35                  40                  45

Arg Asp Glu Ser Leu Arg Arg Ile Leu Gln His Gly Gly Lys Glu Gly
        50                  55                  60

Asp Phe Asn Pro Gln Glu Arg Ala Gln Leu Ala Tyr Arg Lys Asn Leu
65                  70                  75                  80

Leu Tyr Val His Ser Leu Arg Glu Leu Thr Val Asn Ala Val Leu Pro
                85                  90                  95

Gly Ile Arg Asn Leu Leu Ala Asp Leu Arg Ala Gln Gln Ile Pro Val
            100                 105                 110

Gly Leu Ala Ser Val Ser Leu Asn Ala Pro Thr Ile Leu Ala Ala Leu
            115                 120                 125

Glu Leu Arg Glu Phe Phe Thr Phe Cys Ala Asp Ala Ser Gln Leu Lys
        130                 135                 140

Asn Ser Lys Pro Asp Pro Glu Ile Phe Leu Ala Ala Cys Ala Gly Leu
145                 150                 155                 160

Gly Val Pro Pro Gln Ala Cys Ile Gly Ile Glu Asp Ala Gln Ala Gly
                165                 170                 175

Ile Asp Ala Ile Asn Ala Ser Gly Met Arg Ser Val Gly Ile Gly Ala
            180                 185                 190

Gly Leu Thr Gly Ala Gln Leu Leu Pro Ser Thr Asp Ser Leu Thr
            195                 200                 205

Trp Pro Arg Leu Ser Ala Phe Trp Gln Asn Val
    210                 215

<210> SEQ ID NO 110
<211> LENGTH: 219
<212> TYPE: PRT
<213> ORGANISM: Escherichia coli

<400> SEQUENCE: 110

Met Lys Leu Gln Gly Val Ile Phe Asp Leu Asp Gly Val Ile Thr Asp
1               5                   10                  15

Thr Ala His Leu His Phe Gln Ala Trp Gln Gln Ile Ala Ala Glu Ile
                20                  25                  30

Gly Ile Gly Ile Asp Val Gln Phe Asn Glu Thr Leu Lys Gly Ile Ser
            35                  40                  45

Arg Asp Glu Ser Leu Arg Arg Ile Leu Gln His Gly Gly Lys Glu Gly
        50                  55                  60

Asp Phe Asn Val Gln Glu Arg Ala Gln Leu Ala Tyr Arg Lys Asn Leu
65                  70                  75                  80

Leu Tyr Val His Ser Leu Arg Glu Leu Thr Val Asn Ala Val Leu Pro
                85                  90                  95

Gly Ile Arg Pro Leu Leu Ala Asp Leu Arg Ala Gln Gly Ile Pro Val
            100                 105                 110

```
Gly Leu Ala Ser Val Ser Leu Asn Ala Pro Thr Ile Leu Ala Ala Leu
        115                 120                 125

Glu Leu Arg Glu Phe Phe Thr Phe Cys Ala Asp Ala Ser Gln Leu Lys
    130                 135                 140

His Ser Lys Pro Asp Pro Glu Ile Phe Leu Ala Ala Cys Ala Gly Leu
145                 150                 155                 160

Gly Val Pro Pro Gln Ala Cys Ile Gly Ile Glu Asp Ala Gln Ala Gly
                165                 170                 175

Ile Asp Ala Ile Asn Ala Ser Gly Met Arg Ser Val Gly Ile Gly Thr
            180                 185                 190

Ser Leu Thr Gly Ala Gln Leu Leu Pro Ser Thr Glu Ser Leu Thr
        195                 200                 205

Trp Pro Arg Leu Ser Ala Phe Trp Gln Asn Val
    210                 215
```

<210> SEQ ID NO 111
<211> LENGTH: 208
<212> TYPE: PRT
<213> ORGANISM: Shigella flexneri

<400> SEQUENCE: 111

```
Met Lys Leu Gln Gly Val Ile Phe Asp Leu Asp Gly Val Ile Thr Asp
1               5                   10                  15

Thr Ala His Leu His Phe Gln Ala Trp Gln Ile Ala Ala Glu Ile
                20                  25                  30

Gly Ile Ser Ile Asp Ala Gln Phe Asn Glu Ser Leu Lys Gly Ile Ser
            35                  40                  45

Arg Asp Glu Ser Leu Arg Arg Ile Leu Gln His Gly Gly Lys Glu Gly
    50                  55                  60

Asp Phe Asn Pro Gln Glu Arg Ala Gln Leu Ala Tyr Arg Lys Asn Leu
65                  70                  75                  80

Leu Tyr Val His Ser Leu Arg Glu Leu Thr Val Asn Ala Val Leu Pro
                85                  90                  95

Gly Ile Arg Asn Leu Leu Ala Glu Leu Arg Ala Gln Gln Ile Pro Val
            100                 105                 110

Gly Leu Ala Ser Val Ser Leu Asn Ala Pro Thr Ile Leu Ala Ala Leu
        115                 120                 125

Glu Leu Arg Glu Phe Phe Thr Phe Cys Ala Asp Ala Ser Gln Leu Lys
    130                 135                 140

Asn Ser Lys Pro Asp Pro Glu Ile Phe Leu Ala Ala Cys Ala Gly Leu
145                 150                 155                 160

Gly Val Pro Pro Gln Ala Cys Ile Gly Ile Glu Asp Ala Gln Ala Gly
                165                 170                 175

Ile Asp Ala Ile Asn Ala Ser Gly Met Arg Ser Val Gly Ile Gly Ala
            180                 185                 190

Gly Leu Thr Gly Ala Gln Leu Leu Pro Ser Thr Asp Ser Leu Thr
        195                 200                 205
```

<210> SEQ ID NO 112
<211> LENGTH: 216
<212> TYPE: PRT
<213> ORGANISM: Shigella sonnei

<400> SEQUENCE: 112

```
Met Arg Cys Lys Gly Phe Leu Phe Asp Leu Asp Gly Thr Leu Val Asp
1               5                   10                  15
```

Ser Leu Pro Ala Val Glu Arg Ala Trp Ser Asn Trp Ser Arg Arg His
            20                  25                  30

Gly Leu Ala Pro Glu Val Leu Ala Phe Ile His Gly Lys Gln Ala
        35                  40                  45

Ile Thr Ser Leu Arg His Phe Met Ala Gly Lys Ser Glu Ala Asp Ile
 50                  55                  60

Ala Ala Glu Phe Thr Arg Leu Glu His Ile Glu Ala Thr Glu Thr Glu
 65                  70                  75                  80

Gly Ile Thr Ala Leu Pro Gly Ala Ile Ala Leu Ser His Leu Asn
                 85                  90                  95

Lys Ala Gly Ile Pro Trp Ala Ile Val Thr Ser Gly Ser Met Pro Val
                100                 105                 110

Ala Arg Ala Arg His Lys Ile Ala Gly Leu Pro Ala Pro Glu Val Phe
            115                 120                 125

Val Thr Ala Glu Arg Val Lys Arg Gly Lys Pro Glu Pro Asp Ala Tyr
130                 135                 140

Leu Leu Gly Ala Gln Leu Leu Gly Leu Ala Pro Gln Glu Cys Val Val
145                 150                 155                 160

Val Glu Asp Ala Pro Ala Gly Val Leu Ser Gly Leu Ala Ala Gly Cys
                165                 170                 175

His Val Ile Ala Val Asn Ala Pro Ala Asp Thr Pro Gly Leu Asn Glu
            180                 185                 190

Val Asp Leu Val Leu His Ser Leu Glu Gln Ile Thr Val Thr Lys Gln
        195                 200                 205

Pro Asn Gly Asp Val Ile Ile Gln
    210                 215

<210> SEQ ID NO 113
<211> LENGTH: 215
<212> TYPE: PRT
<213> ORGANISM: Citrobacter werkmanii NBRC 105721

<400> SEQUENCE: 113

Met Gln Cys Lys Gly Phe Leu Phe Asp Leu Asp Gly Thr Leu Val Asp
 1               5                  10                  15

Ser Leu Pro Ala Val Glu Arg Ala Trp Cys Asn Trp Ala Asp Arg Phe
            20                  25                  30

Gly Leu Asp His Ala Glu Val Leu Gly Phe Ile His Gly Lys Gln Ala
        35                  40                  45

Ile Thr Ser Leu Arg His Phe Met Val Gly Lys Ser Glu Ala Glu Ile
 50                  55                  60

Ala Ala Glu Phe Thr Arg Leu Glu Gln Ile Glu Ala Thr Glu Thr Ala
 65                  70                  75                  80

Gly Ile Thr Ala Leu Pro Gly Ala Val Asp Leu Leu Asn His Leu Asn
                 85                  90                  95

Lys Ala Gly Ile Pro Trp Ala Ile Val Thr Ser Gly Ser Met Pro Val
                100                 105                 110

Ala Arg Ala Arg His Arg Val Ala Gly Leu Pro Ala Pro Glu Val Phe
            115                 120                 125

Val Thr Ala Glu Arg Val Lys Arg Gly Lys Pro Glu Pro Asp Ala Tyr
130                 135                 140

Leu Leu Gly Ala Gln Leu Leu Gly Leu Ala Pro Gln Glu Cys Ala Val
145                 150                 155                 160

Val Glu Asp Ala Pro Ala Gly Val Leu Ser Gly Leu Ala Ala Gly Cys

His Val Ile Ala Val Asn Ala Pro Ala Asp Thr Pro Arg Leu Asp Glu
            180                 185                 190

Val Asp Phe Ser Leu Thr Ser Leu Glu Gln Ile Ser Val Thr Lys Gln
            195                 200                 205

Pro Asn Gly Asn Val Val Val
            210             215

<210> SEQ ID NO 114
<211> LENGTH: 215
<212> TYPE: PRT
<213> ORGANISM: Citrobacter freundii

<400> SEQUENCE: 114

Met Gln Cys Lys Gly Phe Leu Phe Asp Leu Asp Gly Thr Leu Val Asp
1               5                   10                  15

Ser Leu Pro Ala Val Glu Arg Ala Trp Cys Asn Trp Ala Asp Arg Phe
            20                  25                  30

Gly Leu Asp His Ala Glu Val Leu Gly Phe Ile His Gly Lys Gln Ala
        35                  40                  45

Ile Thr Ser Leu Arg His Phe Met Val Gly Lys Ser Glu Ala Glu Ile
    50                  55                  60

Ala Ala Glu Phe Thr Arg Leu Glu Gln Ile Glu Ala Thr Glu Thr Ala
65                  70                  75                  80

Gly Ile Thr Ala Leu Pro Gly Ala Val Asp Leu Leu Asn His Leu Asn
                85                  90                  95

Lys Ala Gly Ile Pro Trp Ala Ile Val Thr Ser Gly Ser Met Pro Val
            100                 105                 110

Ala Arg Ala Arg His Arg Val Ala Gly Leu Pro Ala Pro Glu Val Phe
        115                 120                 125

Val Thr Ala Glu Arg Val Lys Arg Gly Lys Pro Glu Pro Asp Ala Tyr
    130                 135                 140

Leu Leu Gly Ala Gln Leu Leu Gly Val Ala Pro Gln Glu Cys Ala Val
145                 150                 155                 160

Val Glu Asp Ala Pro Ala Gly Val Leu Ser Gly Leu Ala Ala Gly Cys
                165                 170                 175

His Val Ile Ala Val Asn Ala Pro Ala Asp Thr Pro Arg Leu Asp Glu
            180                 185                 190

Val Asp Phe Ser Leu Thr Ser Leu Glu His Ile Ser Val Thr Lys Gln
            195                 200                 205

Pro Asn Gly Asn Val Val Val
            210             215

<210> SEQ ID NO 115
<211> LENGTH: 215
<212> TYPE: PRT
<213> ORGANISM: Citrobacter amalonaticus

<400> SEQUENCE: 115

Met Gln Cys Lys Gly Phe Leu Phe Asp Leu Asp Gly Thr Leu Val Asp
1               5                   10                  15

Ser Leu Pro Ala Val Glu Arg Ala Trp Cys Asn Trp Ala Asp Arg Phe
            20                  25                  30

Gly Leu Ala His Asp Asp Val Leu Ser Phe Val His Gly Lys Gln Ala
        35                  40                  45

Ile Thr Ser Leu Arg His Phe Met Ala Gly Lys Pro Glu Ala Glu Ile

```
                50                  55                  60
Val Ala Glu Phe Thr Arg Leu Glu Lys Ile Glu Ala Thr Glu Thr Ala
 65                  70                  75                  80

Gly Ile Thr Ala Leu Pro Gly Ala Val Ala Leu Leu Asn His Leu Asn
                 85                  90                  95

Lys Ala Gly Ile Pro Trp Ala Ile Val Thr Ser Gly Ser Met Pro Val
                100                 105                 110

Ala Arg Ala Arg His Gln Val Ala Asn Leu Pro Ala Pro Glu Val Phe
                115                 120                 125

Val Thr Ala Glu Arg Val Lys Arg Gly Lys Pro Glu Pro Asp Ala Tyr
                130                 135                 140

Leu Leu Gly Ala Gln Leu Leu Gly Leu Ser Pro His Glu Cys Val Val
145                 150                 155                 160

Val Glu Asp Ala Pro Ala Gly Val Leu Ser Gly Leu Ala Ala Gly Cys
                165                 170                 175

His Val Ile Ala Val Asn Ala Pro Ala Asp Thr Pro Arg Leu Asp Glu
                180                 185                 190

Val Asp Phe Val Leu Thr Ser Leu Glu Gln Leu Ser Val Thr Lys Gln
                195                 200                 205

Pro Asn Gly Asp Val Val Val
                210                 215

<210> SEQ ID NO 116
<211> LENGTH: 215
<212> TYPE: PRT
<213> ORGANISM: Salmonella enterica

<400> SEQUENCE: 116

Val Gln Cys Lys Gly Phe Leu Phe Asp Leu Asp Gly Thr Leu Val Asp
  1               5                  10                  15

Ser Leu Pro Ala Val Glu Arg Ala Trp Cys Ser Trp Ala Asp Arg Phe
                 20                  25                  30

Asn Leu Ala His Asp Glu Val Leu Gly Phe Ile His Gly Lys Gln Ala
                 35                  40                  45

Ile Thr Ser Leu Arg His Phe Met Ala Gly Lys Ser Glu Ala Glu Ile
 50                  55                  60

Ala Ala Glu Phe Thr Arg Leu Glu Gln Ile Glu Ala Thr Glu Thr Ala
 65                  70                  75                  80

Gly Ile Thr Ala Leu Pro Gly Ala Val Asp Leu Leu Asn His Leu Asn
                 85                  90                  95

Lys Ala Gly Ile Pro Trp Ala Ile Val Thr Ser Gly Ser Met Pro Val
                100                 105                 110

Ala Arg Ala Arg His Gln Val Ala Gly Leu Pro Ala Pro Glu Val Phe
                115                 120                 125

Val Thr Ala Glu Arg Val Lys Arg Gly Lys Pro Glu Pro Asp Ala Tyr
                130                 135                 140

Leu Leu Gly Ala Gln Leu Leu Gly Leu Val Pro Gln Glu Cys Val Val
145                 150                 155                 160

Val Glu Asp Ala Pro Ala Gly Val Leu Ser Gly Leu Ala Ala Gly Cys
                165                 170                 175

His Val Ile Ala Val Asn Ala Pro Ala Asp Thr Pro Arg Leu Ala Asp
                180                 185                 190

Val Asp Phe Ala Leu Asn Ser Leu Thr Gln Leu Ser Val Ala Lys Gln
                195                 200                 205
```

Pro Asn Gly Asp Val Val Val
    210             215

<210> SEQ ID NO 117
<211> LENGTH: 216
<212> TYPE: PRT
<213> ORGANISM: Escherichia fergusonii

<400> SEQUENCE: 117

Met Arg Cys Lys Gly Phe Leu Phe Asp Leu Asp Gly Thr Leu Val Asp
1               5                   10                  15

Ser Leu Pro Ala Val Glu Arg Ala Trp Cys Asn Trp Ala Asp Arg Phe
            20                  25                  30

Gly Ile Asp His His Glu Leu Leu Ser Phe Ile His Gly Lys Gln Ala
        35                  40                  45

Ile Thr Ser Leu Arg His Phe Met Pro Gly Arg Pro Glu Glu Glu Ile
    50                  55                  60

Leu Ala Glu Phe Thr Arg Leu Glu Gln Ile Glu Ala Thr Gln Thr Glu
65                  70                  75                  80

Gly Ile Thr Ala Leu Pro Gly Ala Ile Glu Leu Leu Thr His Leu Asn
                85                  90                  95

Lys Ser Gly Ile Pro Trp Ala Ile Val Thr Ser Gly Ser Met Pro Val
            100                 105                 110

Ala Arg Ala Arg His Gln Val Ala Gly Leu Pro Phe Pro Glu Val Phe
        115                 120                 125

Val Thr Ala Glu Arg Val Lys Arg Gly Lys Pro Glu Pro Asp Ala Tyr
    130                 135                 140

Leu Leu Gly Ala Gln Leu Leu Gly Leu Glu Pro Lys Glu Cys Val Val
145                 150                 155                 160

Val Glu Asp Ala Pro Ala Gly Val Leu Ser Gly Leu Ala Ala Gly Cys
                165                 170                 175

His Val Ile Ala Val Asn Thr Pro Ala Asp Thr Pro Arg Leu Ser Glu
            180                 185                 190

Val Asp Phe Val Leu Thr Ser Leu Gln Gln Ile Thr Val Thr Lys Gln
        195                 200                 205

Pro Asn Gly Glu Val Ile Ile Gln
    210             215

<210> SEQ ID NO 118
<211> LENGTH: 215
<212> TYPE: PRT
<213> ORGANISM: Salmonella enterica subsp. enterica serovar Hadar

<400> SEQUENCE: 118

Val Gln Cys Lys Gly Phe Leu Phe Asp Leu Asp Gly Thr Leu Val Asp
1               5                   10                  15

Ser Leu Pro Ala Val Glu Arg Ala Trp Cys Ser Trp Ala Asp Arg Phe
            20                  25                  30

Asn Leu Ala His Asp Glu Val Leu Gly Phe Ile His Gly Lys Gln Ala
        35                  40                  45

Ile Thr Ser Leu Arg His Phe Met Ala Gly Lys Ser Glu Ala Glu Ile
    50                  55                  60

Ala Ala Glu Phe Thr Arg Leu Glu Gln Ile Glu Ala Thr Glu Thr Ala
65                  70                  75                  80

Gly Ile Thr Ala Leu Pro Gly Ala Val Asp Leu Leu Asn His Leu Asn
                85                  90                  95

```
Lys Ala Gly Ile Pro Trp Ala Ile Val Thr Ser Gly Ser Met Pro Val
                100                 105                 110

Ala Arg Ala Arg His Gln Val Ala Gly Leu Pro Ala Pro Glu Val Phe
            115                 120                 125

Val Thr Ala Glu Arg Val Lys Arg Gly Lys Pro Glu Pro Asp Ala Tyr
    130                 135                 140

Leu Leu Gly Ala Gln Leu Leu Gly Leu Ser Pro Gln Glu Cys Val Val
145                 150                 155                 160

Val Glu Asp Ala Pro Ala Gly Val Leu Ser Gly Leu Ala Ala Gly Cys
                165                 170                 175

His Val Ile Ala Val Asn Ala Pro Ala Asp Thr Pro Arg Leu Ala Asp
            180                 185                 190

Val Asp Phe Ala Leu Asp Ser Leu Thr Gln Leu Ser Val Ala Lys Gln
    195                 200                 205

Pro Asn Gly Asp Val Val Val
            210                 215

<210> SEQ ID NO 119
<211> LENGTH: 270
<212> TYPE: PRT
<213> ORGANISM: Escherichia coli

<400> SEQUENCE: 119

Met Ala Ile Lys Leu Ile Ala Ile Asp Met Asp Gly Thr Leu Leu Leu
1               5                   10                  15

Pro Asp His Thr Ile Ser Pro Ala Val Lys Asn Ala Ile Ala Ala Ala
            20                  25                  30

Arg Ala Arg Gly Val Asn Val Val Leu Thr Thr Gly Arg Pro Tyr Ala
        35                  40                  45

Gly Val His Asn Tyr Leu Lys Glu Leu His Met Glu Gln Pro Gly Asp
    50                  55                  60

Tyr Cys Ile Thr Tyr Asn Gly Ala Leu Val Gln Lys Ala Ala Asp Gly
65                  70                  75                  80

Ser Thr Val Ala Gln Thr Ala Leu Ser Tyr Asp Asp Tyr Arg Phe Leu
                85                  90                  95

Glu Lys Leu Ser Arg Glu Val Gly Ser His Phe His Ala Leu Asp Arg
            100                 105                 110

Thr Thr Leu Tyr Thr Ala Asn Arg Asp Ile Ser Tyr Tyr Thr Val His
        115                 120                 125

Glu Ser Phe Val Ala Thr Ile Pro Leu Val Phe Cys Glu Ala Glu Lys
    130                 135                 140

Met Asp Pro Asn Thr Gln Phe Leu Lys Val Met Met Ile Asp Glu Pro
145                 150                 155                 160

Ala Ile Leu Asp Gln Ala Ile Ala Arg Ile Pro Gln Glu Val Lys Glu
                165                 170                 175

Lys Tyr Thr Val Leu Lys Ser Ala Pro Tyr Phe Leu Glu Ile Leu Asp
            180                 185                 190

Lys Arg Val Asn Lys Gly Thr Gly Val Lys Ser Leu Ala Asp Val Leu
        195                 200                 205

Gly Ile Lys Pro Glu Glu Ile Met Ala Ile Gly Asp Gln Glu Asn Asp
    210                 215                 220

Ile Ala Met Ile Glu Tyr Ala Gly Ile Gly Val Ala Met Asp Asn Ala
225                 230                 235                 240

Ile Pro Ser Val Lys Glu Val Ala Asn Phe Val Thr Lys Ser Asn Leu
                245                 250                 255
```

Glu Asp Gly Val Ala Phe Ala Ile Glu Lys Tyr Val Leu Asn
          260                 265                 270

<210> SEQ ID NO 120
<211> LENGTH: 270
<212> TYPE: PRT
<213> ORGANISM: Escherichia fergusonii

<400> SEQUENCE: 120

Met Ala Ile Lys Leu Ile Ala Ile Asp Met Asp Gly Thr Leu Leu Leu
1               5                   10                  15

Pro Asp His Thr Ile Ser Pro Ala Val Lys Asn Ala Ile Ala Ala Ala
            20                  25                  30

Arg Ala Arg Gly Val Asn Val Val Leu Thr Thr Gly Arg Pro Tyr Ala
        35                  40                  45

Gly Val His Asn Tyr Leu Lys Glu Leu His Met Glu Gln Pro Gly Asp
    50                  55                  60

Tyr Cys Ile Thr Tyr Asn Gly Ala Leu Val Gln Lys Ala Asp Gly
65                  70                  75                  80

Ser Thr Val Ala Gln Thr Ala Leu Ser Tyr Glu Asp Tyr Arg Phe Leu
                85                  90                  95

Glu Lys Leu Ser Arg Glu Val Gly Ser His Phe His Ala Leu Asp Arg
            100                 105                 110

Thr Thr Leu Tyr Thr Ala Asn Arg Asp Ile Ser Tyr Tyr Thr Val His
        115                 120                 125

Glu Ser Phe Val Ala Thr Ile Pro Leu Val Phe Cys Glu Ala Glu Lys
    130                 135                 140

Met Asp Pro Asn Thr Gln Phe Leu Lys Val Met Met Ile Asp Glu Pro
145                 150                 155                 160

Thr Ile Leu Asp Gln Ala Ile Ala Arg Ile Pro Gln Glu Val Lys Glu
                165                 170                 175

Lys Tyr Thr Val Leu Lys Ser Ala Pro Tyr Phe Leu Glu Ile Leu Asp
            180                 185                 190

Lys Arg Val Asn Lys Gly Thr Gly Val Lys Ser Leu Ala Asp Val Leu
        195                 200                 205

Gly Ile Lys Pro Glu Glu Ile Met Ala Ile Gly Asp Gln Glu Asn Asp
    210                 215                 220

Ile Ala Met Ile Glu Tyr Ala Gly Val Gly Val Ala Met Asp Asn Ala
225                 230                 235                 240

Ile Pro Ser Val Lys Glu Val Ala Asn Phe Val Thr Lys Ser Asn Leu
                245                 250                 255

Glu Asp Gly Val Ala Phe Ala Ile Glu Lys Tyr Val Leu Asn
            260                 265                 270

<210> SEQ ID NO 121
<211> LENGTH: 270
<212> TYPE: PRT
<213> ORGANISM: Shigella sonnei

<400> SEQUENCE: 121

Met Ala Ile Lys Leu Ile Ala Ile Asp Met Asp Gly Thr Leu Leu Leu
1               5                   10                  15

Pro Asp His Thr Ile Ser Pro Ala Val Lys Asn Ala Ile Ala Ala Ala
            20                  25                  30

Arg Ala Arg Gly Val Asn Val Val Leu Thr Thr Gly Arg Pro Tyr Ala
        35                  40                  45

```
Gly Val His Asn Tyr Leu Lys Glu Leu His Met Glu Leu Pro Gly Asp
             50                  55                  60

Tyr Cys Ile Thr Tyr Asn Gly Ala Leu Val Gln Lys Ala Ala Asp Gly
 65                  70                  75                  80

Ser Thr Val Ala Gln Thr Ala Leu Ser Tyr Asp Asp Tyr Arg Phe Leu
                 85                  90                  95

Glu Lys Leu Ser Arg Glu Val Gly Ser His Phe His Ala Leu Asp Arg
                100                 105                 110

Thr Thr Leu Tyr Thr Ala Asn Arg Asp Ile Ser Tyr Tyr Thr Val His
            115                 120                 125

Glu Ser Phe Val Ala Thr Ile Pro Leu Val Phe Cys Glu Ala Glu Lys
            130                 135                 140

Met Asp Pro Asn Thr Gln Phe Leu Lys Val Met Met Ile Asp Glu Pro
145                 150                 155                 160

Ala Ile Leu Asp Gln Ala Ile Ala Arg Ile Pro Gln Glu Val Lys Glu
                165                 170                 175

Lys Tyr Thr Val Leu Lys Ser Ala Pro Tyr Phe Leu Glu Ile Leu Asp
                180                 185                 190

Lys Arg Val Asn Lys Ser Thr Gly Val Lys Ser Leu Ala Asp Val Leu
            195                 200                 205

Gly Ile Lys Pro Glu Glu Ile Met Ala Ile Gly Asp Gln Glu Asn Asp
210                 215                 220

Ile Ala Met Ile Glu Tyr Ala Gly Val Gly Val Ala Met Asp Asn Ala
225                 230                 235                 240

Ile Pro Ser Val Lys Glu Val Ala Asn Phe Val Thr Lys Ser Asn Leu
                245                 250                 255

Glu Asp Gly Val Ala Phe Ala Ile Glu Lys Tyr Val Leu Asn
            260                 265                 270

<210> SEQ ID NO 122
<211> LENGTH: 269
<212> TYPE: PRT
<213> ORGANISM: Trabulsiella guamensis

<400> SEQUENCE: 122

Met Ala Ile Lys Leu Ile Ala Ile Asp Met Asp Gly Thr Leu Leu Leu
1               5                   10                  15

Pro Asp His Thr Ile Ser Pro Ala Val Lys Asn Ala Ile Ala Ala Ala
                20                  25                  30

Arg Met Arg Gly Val Asn Val Val Leu Thr Thr Gly Arg Pro Tyr Ala
            35                  40                  45

Gly Val His His Tyr Leu Lys Glu Leu His Met Glu Gln Pro Gly Asp
        50                  55                  60

Tyr Cys Ile Thr Tyr Asn Gly Ala Leu Val Gln Lys Ala Ser Asp Gly
65                  70                  75                  80

Ser Thr Val Ala Gln Thr Ala Leu Ser Tyr Asp Asp Tyr Arg Phe Leu
                85                  90                  95

Glu Lys Leu Ser Arg Glu Val Gly Ser His Phe His Ala Leu Asp Arg
                100                 105                 110

Asn Thr Leu Tyr Thr Ala Asn Arg Asp Ile Ser Tyr Tyr Thr Val His
            115                 120                 125

Glu Ser Tyr Val Ala Thr Ile Pro Leu Val Phe Cys Glu Ala Glu Lys
            130                 135                 140

Met Asp Pro Ala Thr Gln Phe Leu Lys Val Met Met Ile Asp Glu Pro
```

```
            145                 150                 155                 160
    Val Val Leu Asp Lys Ala Ile Ala Arg Ile Pro Ala Glu Val Lys Glu
                    165                 170                 175

Lys Tyr Thr Val Leu Lys Ser Ala Pro Tyr Phe Leu Glu Ile Leu Asp
                    180                 185                 190

Lys Arg Val Asn Lys Gly Thr Gly Val Lys Ser Leu Ala Asp Val Leu
                    195                 200                 205

Gly Ile Gln Pro Asp Glu Ile Met Ala Ile Gly Asp Gln Glu Asn Asp
                210                 215                 220

Ile Ala Met Ile Glu Tyr Ala Gly Val Gly Val Ala Met Asp Asn Ala
    225                 230                 235                 240

Ile Pro Ser Val Lys Glu Val Ala Asn Phe Ile Thr Lys Ser Asn Leu
                    245                 250                 255

Glu Asp Gly Val Ala Tyr Ala Ile Glu Lys Tyr Val Leu
                    260                 265

<210> SEQ ID NO 123
<211> LENGTH: 270
<212> TYPE: PRT
<213> ORGANISM: Citrobacter amalonaticus

<400> SEQUENCE: 123

Met Ala Ile Lys Leu Ile Ala Ile Asp Met Asp Gly Thr Leu Leu Leu
    1               5                   10                  15

Pro Asp His Thr Ile Ser Pro Ala Val Lys Arg Ala Ile Ala Ala Ala
                    20                  25                  30

Arg Glu Lys Gly Val Asn Val Leu Thr Thr Gly Arg Pro Tyr Ala
                35                  40                  45

Gly Val His Ser Tyr Leu Lys Glu Leu His Met Glu Gln Pro Gly Asp
                50                  55                  60

Tyr Cys Ile Thr Tyr Asn Gly Ala Leu Val Gln Lys Ala Gly Asp Gly
    65                  70                  75                  80

Ser Thr Val Ala Gln Thr Ala Leu Ser Tyr Asp Asp Tyr Arg Tyr Leu
                    85                  90                  95

Glu Lys Leu Ser Arg Glu Val Gly Ser His Phe His Ala Leu Asp Arg
                    100                 105                 110

Thr Thr Leu Tyr Thr Ala Asn Arg Asp Ile Ser Tyr Tyr Thr Val His
                    115                 120                 125

Glu Ser Tyr Val Ala Thr Ile Pro Leu Val Phe Cys Glu Ala Glu Lys
                130                 135                 140

Met Asp Pro Lys Thr Gln Phe Leu Lys Val Met Met Ile Asp Glu Pro
    145                 150                 155                 160

Ala Ile Leu Asp Gln Ala Ile Ala Arg Ile Pro Ala Glu Val Lys Glu
                    165                 170                 175

Lys Tyr Thr Val Leu Lys Ser Ala Pro Tyr Phe Leu Glu Ile Leu Asp
                    180                 185                 190

Lys Arg Val Asn Lys Gly Thr Gly Val Lys Ser Leu Ala Asp Ala Leu
                    195                 200                 205

Gly Ile Lys Pro Glu Glu Ile Met Ala Ile Gly Asp Gln Glu Asn Asp
                210                 215                 220

Ile Ala Met Ile Glu Tyr Ala Gly Leu Gly Val Ala Met Asp Asn Ala
    225                 230                 235                 240

Ile Pro Ser Val Lys Glu Ile Ala Asn Phe Val Thr Lys Ser Asn Leu
                    245                 250                 255
```

Glu Asp Gly Val Ala Tyr Ala Ile Glu Gln His Val Leu Lys
            260                 265                 270

<210> SEQ ID NO 124
<211> LENGTH: 269
<212> TYPE: PRT
<213> ORGANISM: Klebsiella pneumoniae

<400> SEQUENCE: 124

Met Ala Ile Lys Leu Ile Ala Ile Asp Met Asp Gly Thr Leu Leu Leu
1               5                   10                  15

Pro Asp His Thr Ile Ser Pro Ala Val Lys Thr Ala Ile Ala Ala Ala
            20                  25                  30

Arg Glu Arg Gly Val Asn Val Val Leu Thr Thr Gly Arg Pro Tyr Ala
        35                  40                  45

Gly Val His Ser Tyr Leu Lys Glu Leu His Met Glu Gln Pro Gly Asp
    50                  55                  60

Tyr Cys Ile Thr Tyr Asn Gly Ala Leu Val Gln Lys Ala Gly Asp Gly
65                  70                  75                  80

Ser Thr Val Ala Gln Thr Ala Leu Ser Tyr Asp Asp Tyr Arg Phe Leu
                85                  90                  95

Glu Gln Leu Ser Arg Glu Val Gly Ser His Phe His Ala Leu Asp Arg
            100                 105                 110

Asn Thr Leu Tyr Thr Ala Asn Arg Asp Ile Ser Tyr Tyr Thr Val His
        115                 120                 125

Glu Ser Tyr Val Ala Thr Ile Pro Leu Val Phe Cys Glu Ala Glu Lys
    130                 135                 140

Met Asp Pro Glu Ile Gln Leu Leu Lys Val Met Met Ile Asp Glu Pro
145                 150                 155                 160

Ala Ile Leu Asp Gln Ala Ile Ala Arg Ile Pro Ala Glu Val Lys Glu
                165                 170                 175

Lys Tyr Thr Val Leu Lys Ser Ala Pro Tyr Phe Leu Glu Ile Leu Asp
            180                 185                 190

Lys Arg Val Asn Lys Gly Thr Gly Val Lys Ser Leu Ala Asp Ala Leu
        195                 200                 205

Gly Ile Lys Pro Glu Glu Ile Met Ala Ile Gly Asp Gln Glu Asn Asp
    210                 215                 220

Ile Ala Met Ile Glu Phe Ala Gly Val Gly Val Ala Met Asp Asn Ala
225                 230                 235                 240

Ile Pro Ala Val Lys Glu Ala Ala Asn Phe Ile Thr Lys Ser Asn Leu
                245                 250                 255

Glu Asp Gly Val Ala Phe Ala Ile Glu Lys Tyr Val Leu
            260                 265

<210> SEQ ID NO 125
<211> LENGTH: 269
<212> TYPE: PRT
<213> ORGANISM: Trabulsiella odontotermitis

<400> SEQUENCE: 125

Met Ala Ile Lys Leu Ile Ala Ile Asp Met Asp Gly Thr Leu Leu Leu
1               5                   10                  15

Pro Asp His Thr Ile Ser Pro Ala Val Lys Asn Ala Ile Ala Ala Ala
            20                  25                  30

Arg Met Arg Gly Val Asn Val Val Leu Thr Thr Gly Arg Pro Tyr Ala
        35                  40                  45

```
Gly Val His His Tyr Leu Lys Glu Leu His Met Glu Gln Pro Gly Asp
     50                  55                  60
Tyr Cys Ile Thr Tyr Asn Gly Ala Leu Val Gln Lys Ala Ser Asp Gly
 65                  70                  75                  80
Ser Thr Val Ala Gln Thr Ala Leu Ser Tyr Asp Asp Tyr Arg Tyr Leu
                 85                  90                  95
Glu Lys Leu Ser Arg Glu Val Gly Ser His Phe His Ala Leu Asp Arg
            100                 105                 110
Asn Thr Leu Tyr Thr Ala Asn Arg Asp Ile Ser Tyr Tyr Thr Val His
        115                 120                 125
Glu Ser Tyr Val Ala Thr Ile Pro Leu Val Phe Cys Glu Ala Glu Lys
130                 135                 140
Met Asp Pro Ala Thr Gln Phe Leu Lys Val Met Met Ile Asp Glu Pro
145                 150                 155                 160
Val Val Leu Asp Lys Ala Ile Ala Arg Ile Pro Ala Glu Val Lys Glu
                165                 170                 175
Lys Tyr Thr Val Leu Lys Ser Ala Pro Tyr Phe Leu Glu Ile Leu Asp
            180                 185                 190
Lys Arg Val Asn Lys Gly Thr Gly Val Lys Ser Leu Ala Glu Ala Leu
        195                 200                 205
Gly Ile Gln Pro Asp Glu Ile Met Ala Ile Gly Asp Gln Glu Asn Asp
    210                 215                 220
Ile Ala Met Ile Glu Tyr Ala Gly Val Gly Val Ala Met Asp Asn Ala
225                 230                 235                 240
Ile Pro Ser Val Lys Glu Val Ala Asn Phe Ile Thr Lys Ser Asn Leu
                245                 250                 255
Glu Asp Gly Val Ala Tyr Ala Ile Glu Lys Tyr Val Leu
            260                 265

<210> SEQ ID NO 126
<211> LENGTH: 270
<212> TYPE: PRT
<213> ORGANISM: Enterobacter kobei

<400> SEQUENCE: 126

Met Ala Ile Lys Leu Ile Ala Ile Asp Met Asp Gly Thr Leu Leu Leu
 1               5                  10                  15
Pro Asp His Thr Ile Ser Pro Ala Val Lys Lys Ala Ile Ala Ala Ala
                 20                  25                  30
Arg Glu Lys Gly Val Asn Val Val Leu Thr Thr Gly Arg Pro Tyr Ala
             35                  40                  45
Gly Val His Asn Tyr Leu Arg Glu Leu His Met Asp Lys Pro Gly Asp
     50                  55                  60
Tyr Cys Ile Thr Tyr Asn Gly Ala Leu Val Gln Lys Ala Ser Asp Gly
 65                  70                  75                  80
Ser Thr Val Ala Gln Thr Thr Leu Ser Tyr Asp Asp Tyr Arg Tyr Leu
                 85                  90                  95
Glu Gln Leu Ser Arg Glu Val Gly Ser His Phe His Ala Leu Asp Arg
            100                 105                 110
Asn Thr Leu Tyr Thr Ala Asn Arg Asp Ile Ser Tyr Tyr Thr Val His
        115                 120                 125
Glu Ser Tyr Val Ala Thr Ile Pro Leu Val Phe Cys Glu Ala Glu Lys
130                 135                 140
Met Asp Pro Ala Ile Gln Leu Leu Lys Val Met Met Ile Asp Glu Pro
145                 150                 155                 160
```

```
Ala Ile Leu Asp Lys Ala Ile Ala Arg Ile Pro Ala Glu Val Lys Glu
            165                 170                 175

Lys Tyr Thr Val Leu Lys Ser Ala Pro Tyr Phe Leu Glu Ile Leu Asp
        180                 185                 190

Lys Arg Val Asn Lys Gly Thr Gly Val Lys Ser Leu Ala Asp Thr Leu
            195                 200                 205

Gly Ile Thr Pro Asp Glu Ile Met Thr Leu Gly Asp Gln Glu Asn Asp
        210                 215                 220

Ile Ala Met Ile Glu Tyr Ala Gly Leu Gly Val Ala Met Asp Asn Ala
225                 230                 235                 240

Ile Asp Ser Val Lys Glu Val Ala Asp Phe Val Thr Lys Ser Asn Leu
            245                 250                 255

Glu Asp Gly Val Ala Tyr Ala Ile Glu Lys Phe Val Leu Asn
        260                 265                 270

<210> SEQ ID NO 127
<211> LENGTH: 238
<212> TYPE: PRT
<213> ORGANISM: Shigella sonnei

<400> SEQUENCE: 127

Met Arg Phe Tyr Arg Pro Leu Gly Arg Ile Ser Ala Leu Thr Phe Asp
1               5                   10                  15

Leu Asp Asp Thr Leu Tyr Asp Asn Arg Pro Val Ile Leu Arg Thr Glu
            20                  25                  30

Arg Glu Ala Leu Thr Phe Val Gln Asn Tyr His Pro Ala Leu Arg Ser
        35                  40                  45

Phe Gln Asn Glu Asp Leu Gln Arg Leu Arg Gln Ala Val Arg Glu Ala
    50                  55                  60

Glu Pro Glu Ile Tyr His Asp Val Thr Arg Trp Arg Phe Arg Ser Ile
65                  70                  75                  80

Glu Gln Ala Met Leu Asp Ala Gly Leu Ser Ala Glu Glu Ala Ser Ala
                85                  90                  95

Gly Ala His Ala Ala Met Ile Asn Phe Ala Lys Trp Arg Ser Arg Ile
            100                 105                 110

Asp Val Pro Gln Gln Thr His Asp Thr Leu Lys Gln Leu Ala Lys Lys
        115                 120                 125

Trp Pro Leu Val Ala Ile Thr Asn Gly Asn Ala Gln Pro Glu Leu Phe
    130                 135                 140

Gly Leu Gly Asp Tyr Phe Glu Phe Val Leu Arg Ala Gly Pro His Gly
145                 150                 155                 160

Arg Ser Lys Pro Phe Ser Asp Met Tyr Phe Leu Ala Ala Glu Lys Leu
                165                 170                 175

Asn Val Pro Ile Gly Glu Ile Leu His Val Gly Asp Asp Leu Thr Thr
            180                 185                 190

Asp Val Gly Gly Ala Ile Arg Ser Gly Met Gln Ala Cys Trp Ile Lys
        195                 200                 205

Pro Glu Asn Gly Asp Leu Met Gln Thr Trp Asp Ser Arg Leu Leu Pro
    210                 215                 220

His Leu Glu Ile Ser Arg Leu Ala Ser Leu Thr Ser Leu Ile
225                 230                 235

<210> SEQ ID NO 128
<211> LENGTH: 223
<212> TYPE: PRT
```

<213> ORGANISM: Shigella sonnei

<400> SEQUENCE: 128

Met Arg Phe Tyr Arg Pro Leu Gly Arg Ile Ser Ala Leu Thr Phe Asp
1               5                   10                  15

Leu Asp Asp Thr Leu Tyr Asp Asn Arg Pro Val Ile Leu Arg Thr Glu
            20                  25                  30

Arg Glu Ala Leu Thr Phe Val Gln Asn Tyr His Pro Ala Leu Arg Ser
        35                  40                  45

Phe Gln Asn Glu Asp Leu Gln Arg Leu Arg Gln Ala Val Arg Glu Ala
    50                  55                  60

Glu Pro Glu Ile Tyr His Asp Val Thr Arg Trp Arg Phe Arg Ser Ile
65                  70                  75                  80

Glu Gln Ala Met Leu Asp Ala Gly Leu Ser Ala Glu Glu Ala Ser Ala
                85                  90                  95

Gly Ala His Ala Ala Met Ile Asn Phe Ala Lys Trp Arg Ser Arg Ile
            100                 105                 110

Asp Val Pro Gln Gln Thr His Asp Thr Leu Lys Gln Leu Ala Lys Lys
        115                 120                 125

Trp Pro Leu Val Ala Ile Thr Asn Gly Asn Ala Gln Pro Glu Leu Phe
    130                 135                 140

Gly Leu Gly Asp Tyr Phe Glu Phe Val Leu Arg Ala Gly Pro His Gly
145                 150                 155                 160

Arg Ser Lys Pro Phe Ser Asp Met Tyr Phe Leu Ala Ala Glu Lys Leu
                165                 170                 175

Asn Val Pro Ile Gly Glu Ile Leu His Val Gly Asp Asp Leu Thr Thr
            180                 185                 190

Asp Val Gly Gly Ala Ile Arg Ser Gly Met Gln Ala Cys Trp Ile Arg
        195                 200                 205

Pro Glu Asn Gly Asp Leu Met Gln Thr Trp Asp Ser Arg Leu Leu
    210                 215                 220

<210> SEQ ID NO 129
<211> LENGTH: 238
<212> TYPE: PRT
<213> ORGANISM: Salmonella enterica

<400> SEQUENCE: 129

Met Arg Phe Tyr Arg Pro Leu Gly Arg Ile Ala Ala Leu Thr Phe Asp
1               5                   10                  15

Leu Asp Asp Thr Leu Tyr Asp Asn Arg Pro Val Ile Leu Arg Thr Glu
            20                  25                  30

Gln Glu Ala Leu Ala Phe Met Gln Asn Tyr His Pro Ser Leu Arg Ser
        35                  40                  45

Phe Gln Asn Val Asp Leu Gln Arg Ile Arg Gln Ala Val Arg Glu Ala
    50                  55                  60

Glu Pro Glu Ile Tyr His Asp Val Thr Arg Trp Arg His Arg Ala Ile
65                  70                  75                  80

Glu Gln Ala Met Arg Asp Ala Gly Leu Ser Ala Gln Glu Ala Ile Ala
                85                  90                  95

Gly Ala Asn Ala Ala Met Met His Phe Ala Lys Trp Arg Ser Gln Ile
            100                 105                 110

Glu Val Pro Gln Ala Thr His Glu Thr Leu Gln Gln Leu Ala Lys Lys
        115                 120                 125

Trp Pro Leu Val Ala Ile Thr Asn Gly Asn Ala Gln Pro Glu Leu Phe

```
            130                 135                 140
Gly Leu Gly Asp Tyr Phe Lys Phe Val Leu Arg Ala Gly Pro Asp Gly
145                 150                 155                 160

Arg Ser Lys Pro Phe Ser Asp Met Tyr Phe Leu Val Ala Glu Lys Leu
                165                 170                 175

His Val Pro Ile Gly Glu Ile Leu His Val Gly Asp Asp Leu Thr Thr
            180                 185                 190

Asp Val Ala Gly Ala Ile Arg Cys Gly Met Gln Ala Cys Trp Ile Lys
            195                 200                 205

Pro Glu Asn Ala Asp Leu Met Arg Thr Gln Asp Ser Arg Leu Leu Pro
            210                 215                 220

His Ile Glu Ile Ser Arg Leu Ala Ser Leu Thr Ser Leu Ile
225                 230                 235

<210> SEQ ID NO 130
<211> LENGTH: 238
<212> TYPE: PRT
<213> ORGANISM: Citrobacter braakii

<400> SEQUENCE: 130

Met Arg Phe Tyr Arg Pro Leu Gly Arg Ile Ser Ala Leu Thr Phe Asp
1               5                   10                  15

Leu Asp Asp Thr Leu Tyr Asp Asn Arg Pro Val Ile Thr Arg Thr Glu
                20                  25                  30

Gln Glu Ala Leu Ala Phe Val Gln Asn Tyr His Pro Ala Leu Asn Ser
            35                  40                  45

Leu Gln Asn Ser Asp Leu Gln Arg Leu Arg Gln Ala Val Arg Asp Ala
        50                  55                  60

Glu Pro Glu Ile Tyr His Asp Val Thr Gln Trp Arg His Arg Ala Val
65                  70                  75                  80

Glu Arg Ala Met Leu Glu Ala Gly Leu Ser Glu Ala Glu Ala Lys Met
                85                  90                  95

Gly Ala Asn Ala Ala Met Met Asn Phe Ala Lys Trp Arg Ser Arg Ile
            100                 105                 110

Asp Val Pro Gln Ser Thr His Asp Thr Leu Lys Thr Leu Ala Arg Lys
            115                 120                 125

Trp Pro Leu Val Ala Ile Thr Asn Gly Asn Ala Gln Pro Glu Leu Phe
        130                 135                 140

Gly Leu Gly Asp Tyr Phe Glu Phe Val Leu Arg Ala Gly Pro Asp Gly
145                 150                 155                 160

Arg Ser Lys Pro Phe Ser Asp Met Tyr Ala Leu Ala Ala Glu Lys Leu
                165                 170                 175

Lys Met Pro Val Gly Glu Ile Leu His Val Gly Asp Asp Leu Thr Thr
            180                 185                 190

Asp Val Ala Gly Ala Ile Arg Cys Gly Met Gln Ala Cys Trp Ile Lys
            195                 200                 205

Pro Glu Asn Ala Asp Leu Met Gln Thr Ala Asp Ser Arg Leu Leu Pro
            210                 215                 220

His Ile Glu Ile Ser Gln Leu Ala Ser Leu Thr Ser Leu Ile
225                 230                 235

<210> SEQ ID NO 131
<211> LENGTH: 238
<212> TYPE: PRT
<213> ORGANISM: Enterobacter hormaechei
```

```
<400> SEQUENCE: 131

Met Arg Phe Tyr Arg Pro Leu Gly Gln Ile Ser Ala Leu Thr Phe Asp
1               5                   10                  15

Leu Asp Asp Thr Leu Tyr Asp Asn Arg Pro Val Ile Leu Arg Thr Glu
                20                  25                  30

Gln Glu Ser Leu Ala Phe Val Gln Asn Tyr His Pro Ala Leu Lys Thr
            35                  40                  45

Met Gln Asn Lys Asp Phe Gln Lys Leu Arg Gln Ser Leu Arg Glu Thr
        50                  55                  60

Glu Pro Asp Ile Tyr His Asp Val Thr Glu Trp Arg Arg Arg Ala Val
65                  70                  75                  80

Glu Gln Ala Met Leu Asn Val Gly Leu Ser Ser Gln Asp Ala Ala Ile
                85                  90                  95

Gly Ala Glu Ala Ala Met Glu Asn Phe Ala Lys Trp Arg Ser Arg Val
                100                 105                 110

Asp Val Pro Gln Glu Thr His Asp Thr Leu Ala Lys Leu Ala Glu Lys
            115                 120                 125

Trp Pro Leu Val Ala Ile Thr Asn Gly Asn Ala Gln Pro Glu Leu Phe
        130                 135                 140

Gly Leu Gly Asp Tyr Phe Glu Phe Val Leu Arg Ala Gly Pro His Gly
145                 150                 155                 160

Arg Ser Lys Pro Phe Ser Asp Met Tyr His Leu Ala Ala Glu Lys Leu
                165                 170                 175

Asn Leu Pro Leu Gly Glu Ile Leu His Val Gly Asp Asp Leu Thr Thr
            180                 185                 190

Asp Val Ala Gly Ala Ile Arg Cys Gly Met Gln Ala Cys Trp Ile Lys
        195                 200                 205

Pro Glu Asn Ala Ser Leu Met Thr Thr Pro Asp Ser Arg Leu Leu Pro
210                 215                 220

His Leu Glu Ile Ser Arg Leu Ala Ser Leu Thr Thr Leu Ile
225                 230                 235

<210> SEQ ID NO 132
<211> LENGTH: 238
<212> TYPE: PRT
<213> ORGANISM: Lelliottia amnigena

<400> SEQUENCE: 132

Met Arg Phe Tyr Arg Pro Leu Gly Gln Ile Ser Ala Leu Thr Phe Asp
1               5                   10                  15

Leu Asp Asp Thr Leu Tyr Asp Asn Arg Gln Val Ile Leu Arg Thr Glu
                20                  25                  30

Gln Glu Ala Leu Ala Phe Val Gln Asn Tyr His Pro Ser Leu Lys Thr
            35                  40                  45

Leu Gln Asn Thr Asp Phe Gln Arg Leu Arg Gln Ala Leu Arg Glu Thr
        50                  55                  60

Glu Pro Asp Ile Tyr His Asp Val Thr Glu Trp Arg Arg Arg Ala Val
65                  70                  75                  80

Glu Gln Ala Met Ile Asn Ala Gly Leu Thr Ala Ala Glu Ala Ala Leu
                85                  90                  95

Gly Ala Glu Ala Ser Met Ala Asn Phe Ala Lys Trp Arg Ser Arg Ile
                100                 105                 110

Asp Val Pro Gln Glu Thr His Asp Thr Leu Ala Lys Leu Ala Glu Lys
            115                 120                 125
```

```
Trp Pro Leu Val Ala Ile Thr Asn Gly Asn Ala Gln Pro Glu Leu Phe
            130                 135                 140

Gly Leu Gly Asp Tyr Phe Thr Phe Val Phe Arg Ala Gly Pro His Gly
145                 150                 155                 160

Arg Ser Lys Pro Phe Ser Asp Met Tyr His Leu Ala Ala Glu Lys Leu
                165                 170                 175

Asp Leu Pro Leu Gly Glu Ile Leu His Val Gly Gly Asp Leu Thr Thr
            180                 185                 190

Asp Val Ala Gly Ala Ile Arg Cys Gly Met Gln Ala Cys Trp Ile Lys
                195                 200                 205

Pro Glu Asn Ala Asp Leu Met His Thr Ile Asp Ser Arg Leu Leu Pro
210                 215                 220

His Val Glu Ile Ser Arg Leu Ala Ser Leu Thr Thr Leu Ile
225                 230                 235

<210> SEQ ID NO 133
<211> LENGTH: 238
<212> TYPE: PRT
<213> ORGANISM: Leclercia adecarboxylata

<400> SEQUENCE: 133

Met Arg Phe Tyr Arg Pro Leu Gly Gln Ile Ser Ala Leu Thr Phe Asp
1               5                   10                  15

Leu Asp Asp Thr Leu Tyr Asp Asn Arg Gln Val Ile Leu Arg Thr Glu
            20                  25                  30

Gln Glu Ala Leu Thr Phe Val Gln Asn Tyr His Pro Ala Leu Lys Thr
        35                  40                  45

Leu Glu Asn Lys Glu Phe His Arg Leu Arg Gln Ala Leu Arg Gln Thr
50                  55                  60

Glu Pro Glu Ile Tyr His Asp Val Thr Glu Trp Arg Arg Arg Ala Val
65                  70                  75                  80

Glu Leu Ala Met Leu Asn Ala Gly Leu Thr Ala Ala Glu Ala Ala Leu
                85                  90                  95

Gly Ala Glu Ala Ser Met Ala His Phe Ala Gln Trp Arg Ser Arg Ile
            100                 105                 110

Asp Val Pro Gln Glu Thr His Asp Thr Leu Ala Ala Leu Ala Glu Lys
        115                 120                 125

Trp Pro Leu Val Ala Ile Thr Asn Gly Asn Ala Gln Pro Glu Leu Phe
130                 135                 140

Gly Leu Gly Asp Tyr Phe Gln Phe Val Leu Arg Ala Gly Pro His Gly
145                 150                 155                 160

Arg Ser Lys Pro Phe Asn Asp Met Tyr His Leu Ala Ala Glu Lys Leu
                165                 170                 175

Ser Leu Pro Leu Gly Gln Ile Leu His Val Gly Asp Asp Leu Thr Thr
            180                 185                 190

Asp Val Ala Gly Ala Ile Arg Cys Gly Met Gln Ala Cys Trp Ile Lys
                195                 200                 205

Pro Glu Asn Ala Asp Leu Met Gln Thr Ala Asp Ser Arg Leu Leu Pro
210                 215                 220

His Ile Glu Ile Ser Arg Leu Ala Ser Leu Thr Thr Leu Ile
225                 230                 235

<210> SEQ ID NO 134
<211> LENGTH: 190
<212> TYPE: PRT
<213> ORGANISM: Shigella flexneri
```

<400> SEQUENCE: 134

```
Met Ser Thr Pro Arg Gln Ile Leu Ala Ala Ile Phe Asp Met Asp Gly
1               5                   10                  15

Leu Leu Ile Asp Ser Glu Pro Leu Trp Asp Arg Ala Glu Leu Asp Val
            20                  25                  30

Met Ala Ser Leu Gly Val Asp Ile Ser Arg Arg Asn Glu Leu Pro Asp
        35                  40                  45

Thr Leu Gly Leu Arg Ile Asp Met Val Val Asp Leu Trp Tyr Ala Arg
    50                  55                  60

Gln Pro Trp Asn Gly Pro Ser Arg Gln Glu Val Val Glu Arg Val Ile
65                  70                  75                  80

Ala Arg Ala Ile Ser Leu Val Glu Glu Thr Arg Pro Leu Leu Pro Gly
                85                  90                  95

Val Arg Glu Ala Val Ala Leu Cys Lys Glu Gln Gly Leu Leu Val Gly
            100                 105                 110

Leu Ala Ser Ala Ser Pro Leu His Met Leu Glu Lys Val Leu Thr Met
        115                 120                 125

Phe Asp Leu Arg Asp Ser Phe Asp Ala Leu Ala Ser Ala Glu Lys Leu
    130                 135                 140

Pro Tyr Ser Lys Pro His Pro Gln Val Tyr Leu Asp Cys Ala Ala Lys
145                 150                 155                 160

Leu Gly Val Asp Pro Leu Thr Cys Val Ala Leu Glu Asp Ser Val Asn
                165                 170                 175

Gly Met Ile Ala Ser Lys Ala Ala Arg Met Arg Ser Ile Val
            180                 185                 190
```

<210> SEQ ID NO 135
<211> LENGTH: 222
<212> TYPE: PRT
<213> ORGANISM: Kosakonia sacchari

<400> SEQUENCE: 135

```
Met Thr Thr Pro Arg Gln Ile Leu Ala Ala Ile Phe Asp Met Asp Gly
1               5                   10                  15

Leu Leu Ile Asp Ser Glu Pro Leu Trp Asp Arg Ala Glu Leu Glu Val
            20                  25                  30

Val Ala Ser Leu Gly Val Asp Ile Thr Arg Arg His Glu Leu Pro Asp
        35                  40                  45

Thr Leu Gly Leu Arg Ile Asp Met Val Val Glu Leu Trp Tyr Ala Gln
    50                  55                  60

Gln Pro Trp Asn Gly Pro Asp Arg Gln Glu Val Thr Glu Cys Ile Ile
65                  70                  75                  80

Gln Arg Ala Ile Ser Leu Val Glu Glu Lys Arg Pro Leu Leu Pro Gly
                85                  90                  95

Val Arg Glu Ala Ile Ala Leu Cys Lys Ala Asn Gly Leu Leu Val Gly
            100                 105                 110

Leu Ala Ser Ala Ser Pro Leu His Met Leu Glu Lys Val Leu Ala Met
        115                 120                 125

Phe Glu Leu Arg Asp Ser Phe Asp Ala Leu Ala Ser Ala Glu Lys Leu
    130                 135                 140

Pro Tyr Ser Lys Pro His Pro Gln Val Tyr Leu Asp Cys Ala Ala Lys
145                 150                 155                 160

Leu Gly Val Asp Pro Leu Thr Cys Val Ala Leu Glu Asp Ser Val Asn
                165                 170                 175
```

```
Gly Met Ile Ala Ser Lys Ala Ala Arg Met Arg Ser Ile Val Val Pro
            180                 185                 190

Asp Glu Glu His Arg Ala Asp Pro Arg Tyr Val Leu Ala Asn Val Lys
        195                 200                 205

Leu Thr Ser Leu Glu Gln Leu Thr Leu Ala His Pro Ile Gly
    210                 215                 220

<210> SEQ ID NO 136
<211> LENGTH: 222
<212> TYPE: PRT
<213> ORGANISM: Enterobacter mori

<400> SEQUENCE: 136

Met Ser Thr Pro Arg Gln Ile Leu Ala Ala Ile Phe Asp Met Asp Gly
1               5                   10                  15

Leu Leu Ile Asp Ser Glu Pro Leu Trp Asp Arg Ala Glu Leu Asp Val
            20                  25                  30

Met Ala Ser Leu Gly Val Asp Ile Ser Arg Arg Asn Glu Leu Pro Asp
        35                  40                  45

Thr Leu Gly Leu Arg Ile Asp Met Val Val Asp Leu Trp Tyr Ala His
    50                  55                  60

Gln Pro Trp Val Gly Pro Gly Arg Asp Glu Val Ile Ala Arg Ile Ile
65                  70                  75                  80

Asn Arg Ala Ile Thr Leu Val Glu Glu Gln Lys Pro Leu Leu Pro Gly
                85                  90                  95

Val Arg Asp Ala Ile Ala Leu Cys Lys Ala Gln Gly Leu Lys Val Gly
            100                 105                 110

Leu Ala Ser Ala Ser Pro Leu His Met Leu Glu Lys Val Leu Ser Leu
        115                 120                 125

Phe Glu Leu Arg Asp Ser Phe Asp Ala Leu Ala Ser Ala Glu Lys Leu
    130                 135                 140

Pro Tyr Ser Lys Pro His Pro Gln Val Tyr Met Asp Cys Ala Ala Lys
145                 150                 155                 160

Leu Gly Leu Asp Pro Leu Thr Cys Val Ala Leu Glu Asp Ser Val Asn
                165                 170                 175

Gly Met Val Ala Ser Lys Ala Ala Arg Met Arg Ser Ile Val Val Pro
            180                 185                 190

Ala Glu Glu Gly Arg His Asp Pro Arg Phe Ala Leu Ala Asp Val Lys
        195                 200                 205

Leu Ala Ser Leu Glu Asp Leu Thr Val Ala His Leu Arg Gly
    210                 215                 220

<210> SEQ ID NO 137
<211> LENGTH: 222
<212> TYPE: PRT
<213> ORGANISM: Lelliottia amnigena

<400> SEQUENCE: 137

Met Ser Thr Ser Arg Gln Ile Val Ala Ala Ile Phe Asp Met Asp Gly
1               5                   10                  15

Leu Leu Ile Asp Ser Glu Pro Leu Trp Asp Arg Ala Glu Leu Asp Val
            20                  25                  30

Met Glu Ser Leu Gly Val Asp Ile Arg Arg Arg Asn Glu Leu Pro Asp
        35                  40                  45

Thr Leu Gly Leu Arg Ile Asp Met Val Val Glu Leu Trp Tyr Ala His
    50                  55                  60
```

```
Gln Pro Trp Asn Gly Pro Ser Arg Gln Glu Val Thr Asp Arg Ile Ile
 65                  70                  75                  80

Ser Arg Ala Leu Thr Leu Val Glu Ala Ser Arg Pro Leu Leu Pro Gly
                 85                  90                  95

Val Arg Glu Ala Val Ala Leu Cys Lys Ala Gln Gly Leu Lys Val Gly
            100                 105                 110

Leu Ala Ser Ala Ser Pro Leu His Met Leu Glu Lys Val Leu Ala Met
        115                 120                 125

Phe Asp Leu Arg Glu Ser Phe Asp Ala Leu Ala Ser Ala Glu Lys Leu
    130                 135                 140

Pro Tyr Ser Lys Pro His Pro Gln Val Tyr Met Asp Cys Ala Ala Lys
145                 150                 155                 160

Leu Gly Val Asp Thr Leu Ala Cys Val Ala Leu Glu Asp Ser Val Asn
                165                 170                 175

Gly Met Ile Ala Ser Lys Ala Ala Arg Met Arg Ser Val Val Val Pro
            180                 185                 190

Ala Glu Glu Gly Gln His Asp Pro Arg Phe Ala Leu Ala Asp Val Lys
        195                 200                 205

Leu Ala Thr Leu Ala Asp Leu Thr Pro Ala His Leu Arg Gly
    210                 215                 220

<210> SEQ ID NO 138
<211> LENGTH: 222
<212> TYPE: PRT
<213> ORGANISM: Enterobacter sp. 638

<400> SEQUENCE: 138

Met Ser Thr Pro His Gln Ile Val Ala Ala Ile Phe Asp Met Asp Gly
  1               5                  10                  15

Leu Leu Ile Asp Ser Glu Pro Leu Trp Asp Arg Ala Glu Leu Asp Val
                 20                  25                  30

Met Ala Ser Leu Gly Val Asp Ile Ser Arg Arg Gly Glu Leu Pro Asp
             35                  40                  45

Thr Leu Gly Leu Arg Ile Asp Met Val Val Glu Leu Trp Phe Ala His
 50                  55                  60

Gln Pro Trp Ser Gly Pro Ser Arg Glu Glu Val Thr Ala Arg Val Ile
 65                  70                  75                  80

Ser Arg Ala Ile Ala Leu Val Glu Glu Lys Arg Pro Leu Leu Pro Gly
                 85                  90                  95

Ala Arg Glu Ala Ile Ala Leu Cys Lys Ala Gln Gly Leu Lys Val Gly
            100                 105                 110

Leu Ala Ser Ala Ser Pro Leu His Met Leu Glu Lys Val Leu Glu Met
        115                 120                 125

Phe Asp Leu Arg Asp Ser Phe Asp Ala Leu Ala Ser Ala Glu Lys Leu
    130                 135                 140

Pro Tyr Ser Lys Pro His Pro Gln Val Tyr Met Asp Cys Ala Ala Lys
145                 150                 155                 160

Leu Gly Val Asp Pro Leu Ala Cys Val Ala Leu Glu Asp Ser Val Asn
                165                 170                 175

Gly Met Val Ala Ser Lys Ala Ala Arg Met Arg Ser Ile Val Val Pro
            180                 185                 190

Ala Glu Glu Gly Gln His Asp Pro Arg Phe Ala Leu Ala Asn Ala Lys
        195                 200                 205

Leu Thr Ser Leu Val Asp Leu Thr Pro Ala His Leu Phe Gly
```

-continued

<210> SEQ ID NO 139
<211> LENGTH: 222
<212> TYPE: PRT
<213> ORGANISM: Kosakonia radicincitans

<400> SEQUENCE: 139

Met Thr Ala Pro Arg Gln Ile Leu Ala Ala Ile Phe Asp Met Asp Gly
1               5                   10                  15

Leu Leu Ile Asp Ser Glu Pro Leu Trp Asp Arg Ala Glu Leu Glu Val
            20                  25                  30

Val Ala Ser Leu Gly Val Asp Ile Asn Arg Arg His Glu Leu Pro Asp
        35                  40                  45

Thr Leu Gly Leu Arg Ile Asp Met Val Val Glu Leu Trp Tyr Ala Gln
    50                  55                  60

Gln Pro Trp Asn Gly Pro Asp Arg Lys Glu Val Thr Glu Arg Ile Ile
65                  70                  75                  80

Gln Arg Ala Ile Ser Leu Val Glu Glu Lys Arg Pro Leu Leu Pro Gly
                85                  90                  95

Val Arg Glu Ala Ile Ala Leu Cys Lys Ala Asn Gly Leu Leu Val Gly
            100                 105                 110

Leu Ala Ser Ala Ser Pro Leu His Met Leu Glu Lys Val Leu Ala Met
        115                 120                 125

Phe Glu Leu Arg Asp Ser Phe Asp Ala Leu Ala Ser Ala Glu Asn Leu
    130                 135                 140

Pro Tyr Ser Lys Pro His Pro Gln Val Tyr Leu Asp Cys Ala Ala Lys
145                 150                 155                 160

Leu Gly Ile Asp Pro Leu Thr Cys Val Ala Leu Glu Asp Ser Val Asn
                165                 170                 175

Gly Met Ile Ala Ser Lys Ala Ala Arg Met Arg Ser Ile Val Val Pro
            180                 185                 190

Asp Glu Glu His Arg Thr Asp Pro Arg Tyr Val Leu Ala Asn Val Lys
        195                 200                 205

Leu Thr Ser Leu Glu Gln Leu Thr Leu Ala His Leu Ile Gly
    210                 215                 220

<210> SEQ ID NO 140
<211> LENGTH: 209
<212> TYPE: PRT
<213> ORGANISM: Salmonella enterica subsp. enterica serovar Newport str.

<400> SEQUENCE: 140

Met Asp Gly Leu Leu Ile Asp Ser Glu Pro Leu Trp Asp Arg Ala Glu
1               5                   10                  15

Leu Asp Val Met Ala Ser Leu Gly Val Asp Ile Thr Arg Arg His Glu
            20                  25                  30

Leu Pro Asp Thr Leu Gly Leu Arg Ile Asp Met Val Val Asp Leu Trp
        35                  40                  45

Phe Ala Gln Gln Pro Trp Asn Gly Pro Asp Arg Gln Glu Val Thr Asn
    50                  55                  60

Arg Val Ile Ala Arg Ala Ile Thr Leu Ile Glu Thr Arg Pro Leu
65                  70                  75                  80

Leu Pro Gly Val Arg Glu Ala Val Ala Leu Cys Lys Ala Gln Gly Leu
                85                  90                  95

Leu Val Gly Leu Ala Ser Ala Ser Pro Leu His Met Leu Glu Lys Val

```
                100                 105                 110
Leu Thr Met Phe Glu Leu Arg Asp Ser Phe Asp Ala Leu Ala Ser Ala
        115                 120                 125

Glu Lys Leu Pro Tyr Ser Lys Pro His Pro Gln Val Tyr Leu Asp Cys
        130                 135                 140

Ala Ala Lys Leu Gly Val Asp Pro Leu Thr Cys Val Ala Leu Glu Asp
145                 150                 155                 160

Ser Val Asn Gly Leu Ile Ala Ala Lys Ala Arg Met Arg Ala Ile
                165                 170                 175

Val Val Pro Ala Glu Glu Asn Gln His Asp Pro Arg Phe Ala Leu Ala
                180                 185                 190

Asn Val Lys Leu Asn Ser Leu Thr Glu Leu Thr Ala Ala His Leu Leu
                195                 200                 205

Gly

<210> SEQ ID NO 141
<211> LENGTH: 188
<212> TYPE: PRT
<213> ORGANISM: Shigella flexneri

<400> SEQUENCE: 141

Met Tyr Glu Arg Tyr Ala Gly Leu Ile Phe Asp Met Asp Gly Thr Ile
1               5                   10                  15

Leu Asp Thr Glu Pro Thr His Arg Lys Ala Trp Arg Glu Val Leu Gly
                20                  25                  30

His Tyr Gly Leu Gln Tyr Asp Val Gln Ala Met Ile Ala Leu Asn Gly
            35                  40                  45

Ser Pro Thr Trp Arg Ile Ala Gln Ala Ile Ile Glu Leu Asn Gln Ala
    50                  55                  60

Asp Leu Asp Pro His Ala Leu Ala Arg Glu Lys Thr Glu Ala Val Arg
65                  70                  75                  80

Ser Met Leu Leu Asp Ser Val Glu Pro Leu Pro Leu Val Glu Val Val
                85                  90                  95

Lys Ser Trp His Gly Arg Arg Pro Met Ala Val Gly Thr Gly Ser Glu
                100                 105                 110

Ser Ala Ile Ala Glu Ala Leu Leu Ala His Leu Gly Leu Arg Arg Tyr
            115                 120                 125

Phe Asp Ala Val Ala Ala Asp His Val Lys His His Lys Pro Ala
        130                 135                 140

Pro Asp Thr Phe Leu Leu Cys Ala Gln Arg Met Gly Val Gln Pro Thr
145                 150                 155                 160

Gln Cys Val Val Phe Glu Asp Ala Asp Phe Gly Ile Gln Ala Ala Arg
                165                 170                 175

Ala Ala Gly Met Asp Ala Val Asp Ile Arg Leu Leu
            180                 185

<210> SEQ ID NO 142
<211> LENGTH: 188
<212> TYPE: PRT
<213> ORGANISM: Escherichia albertii

<400> SEQUENCE: 142

Met Tyr Glu Arg Tyr Ala Gly Leu Ile Phe Asp Met Asp Gly Thr Ile
1               5                   10                  15

Leu Asp Thr Glu Pro Thr His Arg Lys Ala Trp Arg Glu Val Leu Gly
                20                  25                  30
```

-continued

Arg Tyr Gly Leu Arg Tyr Asn Val Gln Ala Met Ile Ala Leu Asn Gly
            35                  40                  45

Ser Pro Thr Trp Arg Ile Ala Gln Ala Ile Ile Glu Leu Asn Gln Ala
 50                  55                  60

Asp Leu Asp Pro Tyr Ala Leu Ala Arg Glu Lys Thr Glu Ala Val Arg
 65                  70                  75                  80

Ser Met Leu Leu Asp Ser Val Glu Pro Leu Pro Leu Val Glu Val Val
                85                  90                  95

Lys Ser Trp Tyr Gly Arg Arg Pro Met Ala Val Gly Thr Gly Ser Glu
                100                 105                 110

Ser Ala Ile Ala Glu Ala Leu Leu Thr His Leu Gly Leu Arg Arg Tyr
            115                 120                 125

Phe Asp Thr Val Val Ala Ala Asp His Val Lys His His Lys Pro Ala
        130                 135                 140

Pro Asp Thr Phe Leu Leu Cys Ala Gln His Met Gly Val Gln Pro Ala
145                 150                 155                 160

Gln Cys Val Val Phe Glu Asp Ala Asp Phe Gly Ile Gln Ala Ala Arg
                    165                 170                 175

Ala Ala Gly Met Asp Ala Val Asp Val Arg Leu Leu
                180                 185

<210> SEQ ID NO 143
<211> LENGTH: 188
<212> TYPE: PRT
<213> ORGANISM: Salmonella enterica

<400> SEQUENCE: 143

Met Tyr Ala Arg Tyr Ala Gly Leu Ile Phe Asp Met Asp Gly Thr Leu
1               5                   10                  15

Leu Asp Thr Glu Pro Thr His Arg Lys Ala Trp Arg Glu Val Leu Gly
                20                  25                  30

His Tyr Gly Leu Arg Phe Asp Glu Gln Ala Met Val Ala Leu Asn Gly
            35                  40                  45

Ser Pro Thr Trp Leu Ile Ala Gln Ser Ile Ile Glu Leu Asn His Ala
 50                  55                  60

Asp Leu Asp Pro Leu Ser Leu Ala Arg Glu Lys Thr Asp Ala Val Lys
 65                  70                  75                  80

Ser Ile Leu Leu Asp Cys Val Glu Pro Leu Pro Leu Val Glu Val Val
                85                  90                  95

Lys Ala Trp His Gly Arg Arg Pro Met Ser Val Gly Thr Gly Ser Glu
                100                 105                 110

Ser Ala Ile Ala Glu Ala Leu Leu Ala His Leu Gly Leu Arg Arg Tyr
            115                 120                 125

Phe Asp Ala Val Val Ala Ala Asp His Val Gln His His Lys Pro Ala
        130                 135                 140

Pro Asp Thr Phe Leu Leu Cys Ala Gln Arg Met Gly Val Met Pro Thr
145                 150                 155                 160

Gln Cys Val Val Phe Glu Asp Ala Asp Phe Gly Leu Gln Ala Ala Arg
                    165                 170                 175

Ala Ala Gly Met Asp Ala Val Asp Val Arg Leu Leu
                180                 185

<210> SEQ ID NO 144
<211> LENGTH: 188
<212> TYPE: PRT

<213> ORGANISM: Kluyvera intermedia

<400> SEQUENCE: 144

```
Met Tyr Glu Arg Tyr Asp Gly Leu Ile Phe Asp Met Asp Gly Thr Ile
1               5                   10                  15

Leu Asp Thr Glu Pro Thr His Arg Lys Ala Trp His Asp Val Leu Gly
            20                  25                  30

His Tyr Gly Leu Arg Tyr Asp Ile Gln Ala Met Ile Ala Leu Asn Gly
        35                  40                  45

Ser Pro Thr Trp Arg Ile Ala Gln Ser Val Ile Glu Leu Asn Gln Ala
    50                  55                  60

Asp Leu Asp Pro Tyr Ala Leu Ala Arg Glu Lys Thr Glu Ala Val Lys
65                  70                  75                  80

Ala Met Leu Leu Asp Thr Val Arg Pro Leu Pro Leu Ile Asp Val Val
                85                  90                  95

Lys Ala Trp Tyr Gly Arg Arg Pro Leu Ser Val Gly Thr Gly Ser Glu
            100                 105                 110

Ser Ala Ile Ala Glu Ala Leu Leu Ser His Leu Gly Leu Arg His Tyr
        115                 120                 125

Phe Ala Val Val Ala Ala Glu His Val Lys Asn His Lys Pro Ala
    130                 135                 140

Pro Asp Thr Phe Leu Leu Cys Ala Glu Lys Met Gly Val Ala Pro Gln
145                 150                 155                 160

Lys Cys Val Val Phe Glu Asp Ala Asp Phe Gly Leu Gln Ala Ala Arg
                165                 170                 175

Ser Ala Gly Met Asp Ala Val Asp Val Arg Leu Leu
            180                 185
```

<210> SEQ ID NO 145
<211> LENGTH: 188
<212> TYPE: PRT
<213> ORGANISM: Trabulsiella odontotermitis

<400> SEQUENCE: 145

```
Met Tyr Glu Arg Tyr Ala Gly Leu Ile Phe Asp Met Asp Gly Thr Ile
1               5                   10                  15

Leu Asp Thr Glu Pro Thr His Arg Lys Ala Trp His Glu Val Leu Gly
            20                  25                  30

Arg Tyr Gly Ile Arg Phe Asp Glu Gln Ser Ile Ile Ala Leu Asn Gly
        35                  40                  45

Ser Pro Thr Trp Arg Ile Ala Gln Glu Ile Ile Thr Leu Asn Gln Ala
    50                  55                  60

Asp Leu Asp Pro His Ala Leu Ala Arg Glu Lys Thr Asp Ala Val Lys
65                  70                  75                  80

Ile Met Leu Leu Asp Ser Val Gln Pro Leu Pro Leu Ile Asp Val Val
                85                  90                  95

Lys Ala Trp His Gly Arg Arg Pro Met Ser Val Gly Thr Gly Ser Glu
            100                 105                 110

Ser Ala Ile Ala Glu Ala Leu Leu Ala His Leu Gly Leu Arg His Tyr
        115                 120                 125

Phe Ser Ala Val Val Ala Ala Asp His Val Arg His Lys Pro Ala
    130                 135                 140

Pro Asp Thr Phe Leu Leu Cys Ala Glu Arg Met Gly Val Glu Pro Ala
145                 150                 155                 160

Lys Cys Ile Val Phe Glu Asp Ala Asp Phe Gly Leu Gln Ala Ala Ala
```

```
                    165                 170                 175

Ser Ala Gly Met Asp Val Val Asp Val Arg Leu Leu
            180                 185

<210> SEQ ID NO 146
<211> LENGTH: 188
<212> TYPE: PRT
<213> ORGANISM: Yokenella regensburgei

<400> SEQUENCE: 146

Met Tyr Glu Arg Tyr Ala Gly Leu Ile Phe Asp Met Asp Gly Thr Ile
1               5                   10                  15

Leu Asp Thr Glu Pro Thr His Cys Lys Ala Trp His Asp Val Leu Gly
            20                  25                  30

Arg Tyr Gly Met His Phe Asp Glu Gln Ala Met Thr Ala Leu Asn Gly
        35                  40                  45

Ser Pro Thr Trp Arg Ile Ala Gln Ser Ile Ile Glu Leu Asn Gln Ala
    50                  55                  60

Thr Leu Asp Pro His Gln Leu Ala Arg Glu Lys Thr Asp Ala Val Lys
65                  70                  75                  80

Ala Met Leu Leu Asp Thr Val Arg Pro Leu Pro Leu Ile Asp Val Val
                85                  90                  95

Lys Ala Trp His Gly Arg Arg Pro Met Ala Val Gly Thr Gly Ser Glu
            100                 105                 110

Ser Ala Ile Ala Glu Ala Leu Leu Ala His Leu Gly Leu Arg Glu Tyr
        115                 120                 125

Phe Thr Ala Val Val Ala Ala Asp His Val Lys His Lys Pro Ala
    130                 135                 140

Pro Asp Thr Phe Leu Leu Cys Ala Glu Leu Met Gly Val Ala Ala Asn
145                 150                 155                 160

Gln Cys Val Val Phe Glu Asp Ala Asp Phe Gly Leu Gln Ala Ala Arg
                165                 170                 175

Ser Ala Gly Met Asp Val Val Asp Val Arg Leu Leu
            180                 185

<210> SEQ ID NO 147
<211> LENGTH: 188
<212> TYPE: PRT
<213> ORGANISM: Raoultella terrigena

<400> SEQUENCE: 147

Met Tyr Glu Arg Tyr Ala Gly Leu Ile Phe Asp Met Asp Gly Thr Ile
1               5                   10                  15

Leu Asp Thr Glu Pro Thr His Arg Lys Ala Trp His Glu Val Leu Gly
            20                  25                  30

Arg Tyr Gly Met Arg Phe Asp Glu Gln Ala Met Val Ala Leu Asn Gly
        35                  40                  45

Ser Pro Thr Trp Arg Ile Ala Gln Val Ile Ile Glu Leu Asn Gln Ala
    50                  55                  60

Asp Leu Asp Pro His Arg Leu Ala Leu Glu Lys Thr Asn Ala Val Lys
65                  70                  75                  80

Ala Met Leu Leu Asp Ser Val Arg Pro Leu Pro Leu Ile Glu Val Val
                85                  90                  95

Lys Glu Trp His Gly Arg Arg Pro Met Ser Val Gly Thr Gly Ser Glu
            100                 105                 110

Ser Ala Val Ala Glu Ala Leu Leu Ala His Leu Gly Leu Arg His Tyr
```

```
                 115                 120                 125
Phe Ser Ala Val Ile Ala Ala Asp His Val Thr Asn His Lys Pro Ala
    130                 135                 140

Pro Asp Thr Phe Leu Leu Cys Ala Glu Arg Met Gly Val Ala Pro Glu
145                 150                 155                 160

Lys Cys Val Val Phe Glu Asp Ala Asp Phe Gly Leu Gln Ala Ala Arg
                165                 170                 175

Arg Ala Gly Met Asp Ala Asp Val Arg Leu Leu
            180                 185

<210> SEQ ID NO 148
<211> LENGTH: 188
<212> TYPE: PRT
<213> ORGANISM: Klebsiella pneumoniae

<400> SEQUENCE: 148

Met Tyr Glu Gly Tyr Ala Gly Leu Ile Phe Asp Met Asp Gly Thr Ile
1               5                   10                  15

Leu Asp Thr Glu Pro Thr His Arg Gln Ala Trp Asn Glu Val Leu Gly
            20                  25                  30

Arg Tyr Gly Met Arg Phe Asp Glu Gln Ala Met Val Ala Leu Asn Gly
        35                  40                  45

Ser Pro Thr Trp Arg Ile Ala Gln Ala Ile Glu Leu Asn Gln Ala
    50                  55                  60

Asp Leu Asp Pro His Arg Leu Ala Gln Glu Lys Thr Gln Ala Val Lys
65                  70                  75                  80

Ala Met Leu Leu Asp Ser Val Arg Pro Leu Pro Leu Ile Glu Val Val
                85                  90                  95

Lys Ala Trp His Gly Cys Arg Pro Met Ser Val Gly Thr Gly Ser Glu
            100                 105                 110

Ser Ala Val Ala Glu Ala Leu Leu Ala His Leu Gly Leu Arg His Tyr
        115                 120                 125

Phe Ser Ala Val Val Ala Ala Asp His Val Val Asn His Lys Pro Ala
    130                 135                 140

Pro Asp Thr Phe Leu Leu Cys Ala Glu Arg Met Gly Val Ala Pro Glu
145                 150                 155                 160

Lys Cys Val Val Phe Glu Asp Ala Asp Phe Gly Leu Gln Ala Ala Lys
                165                 170                 175

Arg Ala Gly Met Asp Ala Asp Val Arg Leu Leu
            180                 185

<210> SEQ ID NO 149
<211> LENGTH: 223
<212> TYPE: PRT
<213> ORGANISM: Pseudomonas putida

<400> SEQUENCE: 149

Met Arg Leu Arg Ala Val Leu Phe Asp Met Asp Gly Thr Leu Leu Asp
1               5                   10                  15

Thr Ala Pro Asp Phe Ile Ala Ile Cys Gln Ala Met Leu Ala Asp Arg
            20                  25                  30

Gly Leu Pro Ala Ile Asp Asp Ala Arg Ile Arg Glu Val Ile Ser Gly
        35                  40                  45

Gly Ala Arg Ala Met Val Ala Ala Thr Phe Ala Met Asn Pro Glu Ala
    50                  55                  60

Asp Gly Phe Glu Ala Leu Arg Leu Glu Phe Leu Glu Arg Tyr Gln Arg
```

```
                65                  70                  75                  80
Asp Cys Ala Val His Ser Lys Leu Phe Asp Gly Met Pro Glu Leu Leu
                    85                  90                  95

Ala Asp Ile Glu Lys Gly Asn Leu Leu Trp Gly Val Val Thr Asn Lys
                100                 105                 110

Pro Val Arg Phe Ala Glu Pro Ile Met Gln Arg Leu Gly Leu Ala Glu
                115                 120                 125

Arg Ser Ala Leu Leu Ile Cys Pro Asp His Val Lys Asn Ser Lys Pro
            130                 135                 140

Asp Pro Glu Pro Leu Ile Leu Ala Cys Lys Thr Leu Gly Leu Asp Pro
145                 150                 155                 160

Ala Ser Val Leu Phe Val Gly Asp Asp Leu Arg Asp Ile Glu Ser Gly
                165                 170                 175

Arg Asp Ala Gly Thr Arg Thr Ala Ala Val Arg Tyr Gly Tyr Ile His
                180                 185                 190

Pro Glu Asp Asn Pro Asn Asn Trp Gly Ala Asp Val Val Val Asp His
            195                 200                 205

Pro Leu Glu Leu Arg Lys Val Ile Asp Ser Ala Leu Cys Gly Cys
210                 215                 220

<210> SEQ ID NO 150
<211> LENGTH: 223
<212> TYPE: PRT
<213> ORGANISM: Pseudomonas sp. GM84

<400> SEQUENCE: 150

Met Arg Leu Arg Ala Val Leu Phe Asp Met Asp Gly Thr Leu Leu Asp
1               5                   10                  15

Thr Ala Pro Asp Phe Ile Ala Ile Cys Gln Ala Met Leu Ala Glu Arg
                20                  25                  30

Gly Leu Pro Ala Ile Asp Asp Lys Leu Ile Arg Asp Val Ile Ser Gly
            35                  40                  45

Gly Ala Arg Ala Met Val Ala Ala Thr Phe Ala Met Asn Pro Asp Asp
50                  55                  60

Asp Gly Phe Glu Pro Leu Arg Leu Glu Phe Leu Glu Arg Tyr Gln Arg
65                  70                  75                  80

Asp Cys Ala Val His Ser Lys Leu Phe Asp Gly Met Gly Glu Leu Leu
                    85                  90                  95

Ala Asp Ile Glu Lys Gly Asn Leu Leu Trp Gly Val Val Thr Asn Lys
                100                 105                 110

Pro Val Arg Phe Ala Glu Pro Ile Met Gln Arg Leu Gly Leu Ala Glu
                115                 120                 125

Arg Ser Ala Leu Leu Ile Cys Pro Asp His Val Lys Asn Ser Lys Pro
            130                 135                 140

Asp Pro Glu Pro Leu Ile Leu Ala Cys Lys Thr Leu Asn Leu Asp Pro
145                 150                 155                 160

Ala Ser Val Leu Phe Val Gly Asp Asp Leu Arg Asp Ile Glu Ser Gly
                165                 170                 175

Arg Asp Ala Gly Thr Arg Thr Ala Ala Val Arg Tyr Gly Tyr Ile His
                180                 185                 190

Pro Glu Asp Asn Pro Asn Asn Trp Gly Ala Asp Val Val Val Asp His
            195                 200                 205

Pro Leu Glu Leu Arg Lys Val Ile Asp Ser Ala Leu Cys Gly Cys
210                 215                 220
```

<210> SEQ ID NO 151
<211> LENGTH: 223
<212> TYPE: PRT
<213> ORGANISM: Pseudomonas entomophila

<400> SEQUENCE: 151

Met Arg Leu Arg Ala Val Leu Phe Asp Met Asp Gly Thr Leu Leu Asp
1               5                   10                  15

Thr Ala Pro Asp Phe Ile Ala Ile Cys Gln Ala Met Leu Thr Asp Arg
            20                  25                  30

Gly Leu Pro Thr Ile Asp Asp Ala Arg Ile Arg Asp Val Ile Ser Gly
        35                  40                  45

Gly Ala Arg Ala Met Val Ala Ala Thr Phe Ala Met Asp Pro Asp Ala
    50                  55                  60

Glu Gly Phe Glu Ala Leu Arg Leu Glu Phe Leu Glu Arg Tyr Gln Arg
65                  70                  75                  80

Asp Cys Ala Val His Ser Lys Leu Phe Asp Gly Met Pro Glu Leu Leu
                85                  90                  95

Ala Asp Ile Glu Lys Gly Asn Leu Leu Trp Gly Val Val Thr Asn Lys
            100                 105                 110

Pro Val Arg Phe Ala Glu Pro Ile Met Gln Arg Leu Gly Leu Ala Glu
        115                 120                 125

Arg Ser Ala Leu Leu Ile Cys Pro Asp His Val Lys Asn Ser Lys Pro
    130                 135                 140

Asp Pro Glu Pro Leu Ile Leu Ala Cys Lys Thr Leu Asp Leu Asp Pro
145                 150                 155                 160

Ala Ser Val Leu Phe Val Gly Asp Asp Leu Arg Asp Ile Glu Ser Gly
                165                 170                 175

Arg Asp Ala Gly Thr Arg Thr Ala Ala Val Arg Tyr Gly Tyr Ile His
            180                 185                 190

Pro Glu Asp Asn Pro Asn Asn Trp Gly Ala Asp Val Val Val Asp His
        195                 200                 205

Pro Leu Glu Leu Arg Lys Val Ile Asp Ser Ala Leu Cys Gly Cys
    210                 215                 220

<210> SEQ ID NO 152
<211> LENGTH: 223
<212> TYPE: PRT
<213> ORGANISM: Pseudomonas vranovensis

<400> SEQUENCE: 152

Met Arg Leu Arg Ala Val Leu Phe Asp Met Asp Gly Thr Leu Leu Asp
1               5                   10                  15

Thr Ala Pro Asp Phe Ile Ala Ile Cys Gln Ala Met Leu Ala Asp Arg
            20                  25                  30

Gly Leu Pro Ala Ile Asp Asp Gln Arg Ile Arg Asp Val Ile Ser Gly
        35                  40                  45

Gly Ala Arg Ala Met Val Glu Val Thr Phe Gly Ile Thr Pro Glu Val
    50                  55                  60

Ala Glu Phe Glu Ala Leu Arg Leu Glu Phe Leu Glu Arg Tyr Gln Arg
65                  70                  75                  80

Asp Cys Ala Val His Ser Lys Leu Phe Asp Gly Met Ala Glu Leu Leu
                85                  90                  95

Ala Asp Ile Glu Lys Gly Asn Leu Leu Trp Gly Val Val Thr Asn Lys
            100                 105                 110

```
Pro Val Arg Phe Ala Glu Pro Ile Met Gln Arg Leu Gly Leu Ala Glu
        115                 120                 125

Arg Ser Ala Leu Leu Ile Cys Pro Asp His Val Lys Asn Ser Lys Pro
    130                 135                 140

Asp Pro Glu Pro Leu Ile Leu Ala Cys Lys Thr Leu Asn Leu Asp Pro
145                 150                 155                 160

Ala Ser Val Leu Phe Val Gly Asp Asp Leu Arg Asp Ile Glu Ser Gly
                165                 170                 175

Arg Asp Ala Gly Thr Arg Thr Ala Val Arg Tyr Gly Tyr Ile His
                180                 185                 190

Pro Glu Asp Asn Pro Asn Asn Trp Gly Ala Asp Val Val Val Asp His
        195                 200                 205

Pro Leu Glu Leu Arg Lys Val Leu Asp Ser Ala Leu Cys Gly Cys
    210                 215                 220

<210> SEQ ID NO 153
<211> LENGTH: 223
<212> TYPE: PRT
<213> ORGANISM: Pseudomonas cannabina

<400> SEQUENCE: 153

Met Arg Leu Arg Ala Val Leu Phe Asp Met Asp Gly Thr Leu Leu Asp
1               5                   10                  15

Thr Ala Pro Asp Phe Ile Ala Ile Ala Gln Ala Met Leu Ala Asp Arg
                20                  25                  30

Gly Leu Pro Ala Val Ala Asp Lys Leu Ile Arg Asp Glu Ile Ser Gly
            35                  40                  45

Gly Ala Lys Ala Met Val Ala Ala Ala Phe Ala Leu Ser Pro Glu Ala
        50                  55                  60

Pro Glu Phe Glu Ala Leu Arg Leu Glu Phe Leu Glu Arg Tyr Gln Arg
65                  70                  75                  80

Asp Cys Ala Thr His Ser Arg Leu Phe Asn Gly Met Pro Glu Leu Leu
                85                  90                  95

Ala Asp Ile Glu Lys Ala Gly Leu Ile Trp Gly Val Val Thr Asn Lys
                100                 105                 110

Pro Val Arg Phe Ala Gln Pro Ile Met Glu Gln Leu Lys Leu Ala Glu
        115                 120                 125

Arg Ser Ala Val Leu Ile Cys Pro Asp His Val Thr His Ser Lys Pro
    130                 135                 140

His Pro Glu Pro Met Ile Leu Ala Cys Lys Leu Leu Asp Leu Asp Pro
145                 150                 155                 160

Ala Ser Val Leu Phe Val Gly Asp Asp Leu Arg Asp Ile Glu Ser Gly
                165                 170                 175

Arg Asp Ala Gly Thr Lys Thr Ala Val Arg Tyr Gly Tyr Ile His
                180                 185                 190

Pro Asp Asp Asn Pro Asp His Trp Gly Ala Asp Val Val Val Asp His
        195                 200                 205

Pro Leu Glu Leu Arg Lys Val Leu Asp Asn Ala Leu Cys Ser Cys
    210                 215                 220

<210> SEQ ID NO 154
<211> LENGTH: 223
<212> TYPE: PRT
<213> ORGANISM: Pseudomonas monteilii

<400> SEQUENCE: 154
```

```
Met Arg Leu Arg Ala Val Leu Phe Asp Met Asp Gly Thr Leu Leu Asp
1               5               10              15

Thr Ala Pro Asp Phe Ile Ala Ile Cys Gln Ala Met Leu Ala Glu Arg
            20              25              30

Gly Leu Pro Ala Ile Asp Asp Gln Ala Ile Arg Asp Val Ile Ser Gly
            35              40              45

Gly Ala Arg Ala Met Val Ala Ala Thr Phe Ala Met Asn Pro Glu Asp
50              55              60

Glu Gly Phe Glu Ala Leu Arg Leu Glu Phe Leu Glu Arg Tyr Gln Arg
65              70              75              80

Asp Cys Ala Val His Ser Lys Leu Phe Asp Gly Met Gly Glu Leu Leu
                85              90              95

Ala Asp Leu Glu Lys Gly Lys Leu Leu Trp Gly Val Val Thr Asn Lys
            100             105             110

Pro Val Arg Phe Ala Glu Pro Ile Met Gln Gln Leu Gly Leu Ala Glu
            115             120             125

Arg Ser Ala Leu Leu Ile Cys Pro Asp His Val Lys Asn Ser Lys Pro
    130             135             140

Asp Pro Glu Pro Leu Ile Leu Ala Cys Lys Thr Leu Asn Leu Asp Pro
145             150             155             160

Ala Ser Val Leu Phe Val Gly Asp Asp Leu Arg Asp Ile Glu Ser Gly
                165             170             175

Arg Asp Ala Gly Thr Arg Thr Ala Ala Val Arg Tyr Gly Tyr Ile His
            180             185             190

Pro Asp Asp Asn Pro Asn His Trp Gly Ala Asp Val Val Val Asp His
            195             200             205

Pro Leu Glu Leu Arg Lys Val Ile Asp Ser Ala Leu Cys Gly Cys
    210             215             220
```